(12) United States Patent
Suh et al.

(10) Patent No.: US 12,137,609 B2
(45) Date of Patent: Nov. 5, 2024

(54) COMPOUND AND ORGANIC LIGHT EMITTING DEVICE COMPRISING SAME

(71) Applicant: LG CHEM, LTD., Seoul (KR)

(72) Inventors: Sang Duk Suh, Daejeon (KR); Dong Hoon Lee, Daejeon (KR); Boon Jae Jang, Daejeon (KR); Min Woo Jung, Daejeon (KR); Jungha Lee, Daejeon (KR); Su Jin Han, Daejeon (KR); Seulchan Park, Daejeon (KR); Sunghyun Hwang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 789 days.

(21) Appl. No.: 17/292,621

(22) PCT Filed: Jul. 17, 2020

(86) PCT No.: PCT/KR2020/009472
§ 371 (c)(1),
(2) Date: May 10, 2021

(87) PCT Pub. No.: WO2021/025328
PCT Pub. Date: Feb. 11, 2021

(65) Prior Publication Data
US 2022/0006022 A1    Jan. 6, 2022

(30) Foreign Application Priority Data

Aug. 2, 2019    (KR) .......................... 10-2019-0094225

(51) Int. Cl.
*H01L 51/00* (2006.01)
*C07D 487/04* (2006.01)
*H10K 85/60* (2023.01)
*H10K 50/11* (2023.01)

(52) U.S. Cl.
CPC ......... *H10K 85/654* (2023.02); *C07D 487/04* (2013.01); *H10K 85/6572* (2023.02); *H10K 85/6574* (2023.02); *H10K 85/6576* (2023.02); *H10K 50/11* (2023.02)

(58) Field of Classification Search
CPC ............. H01L 51/0067; H01L 51/5012; H01L 51/0073; H01L 51/0074; H01L 51/50; H01L 51/00; C07D 487/04; C07D 333/76; C07D 307/91; C07D 209/82; C09K 11/06
See application file for complete search history.

(56) References Cited

U.S. PATENT DOCUMENTS

| | | | |
|---|---|---|---|
| 11,767,324 B2 * | 9/2023 | Yoon | H10K 85/6576 428/690 |
| 2004/0251816 A1 | 12/2004 | Leo et al. | |
| 2011/0101312 A1 | 5/2011 | Lecloux et al. | |
| 2012/0211701 A1 | 8/2012 | Spreitzer et al. | |
| 2013/0140544 A1 † | 6/2013 | Lecloux | |
| 2013/0248849 A1 | 9/2013 | Feldman et al. | |
| 2014/0070204 A1 | 3/2014 | Nagao et al. | |
| 2015/0025239 A1 | 1/2015 | Ahn et al. | |
| 2016/0233435 A1 | 8/2016 | Zeng et al. | |
| 2016/0276599 A1 | 9/2016 | Park et al. | |
| 2016/0329506 A1 | 11/2016 | Lee et al. | |
| 2017/0025618 A1 | 1/2017 | Zheng et al. | |
| 2017/0256719 A1 | 9/2017 | Jang et al. | |
| 2017/0263869 A1 | 9/2017 | Tada et al. | |
| 2017/0365789 A1 | 12/2017 | Pan et al. | |
| 2018/0138425 A1 | 5/2018 | Ma et al. | |
| 2018/0282295 A1 | 10/2018 | Parham et al. | |
| 2018/0312514 A1 | 11/2018 | Ma et al. | |
| 2020/0176688 A1 | 6/2020 | Cho et al. | |
| 2021/0143340 A1 † | 5/2021 | Ogawa | |

FOREIGN PATENT DOCUMENTS

| | | | | |
|---|---|---|---|---|
| CN | 102596950 A | | 7/2012 | |
| CN | 107078221 A | | 8/2017 | |
| DE | 102016201672 A1 | | 8/2016 | |
| EP | 3522246 A1 | | 8/2019 | |
| JP | 2013-509363 A | | 3/2013 | |
| JP | 2013-509406 A | * | 3/2013 | ........... C07D 487/04 |
| JP | 2014525910 A | | 10/2014 | |
| JP | 2018188421 A | | 11/2018 | |
| KR | 10-2000-0051826 A | | 8/2000 | |
| KR | 10-2010-0094415 A | | 8/2010 | |
| KR | 10-2012-0072785 A | | 7/2012 | |
| KR | 10-2012-0129733 A | | 11/2012 | |

(Continued)

*Primary Examiner* — Robert D Harlan

(74) *Attorney, Agent, or Firm* — Bryan Cave Leighton Paisner LLP

(57) ABSTRACT

A compound represented by Chemical Formula 1 and an organic light emitting device comprising the same, the compound used as a material of an organic material layer of the organic light emitting device and providing improved efficiency, low driving voltage and improved lifetime characteristics.

[Chemical Formula 1]

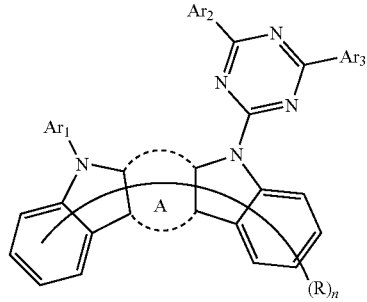

18 Claims, 1 Drawing Sheet

(56) References Cited

FOREIGN PATENT DOCUMENTS

| | | |
|---|---|---|
| KR | 10-2013-0096666 A | 8/2013 |
| KR | 20140009838 A | 1/2014 |
| KR | 10-2014-0124654 A | 10/2014 |
| KR | 10-2016-0045508 A | 4/2016 |
| KR | 10-1788094 B1 | 10/2017 |
| KR | 10-2018-0121835 A | 11/2018 |
| KR | 10-2018-0137772 A | 12/2018 |
| KR | 10-2019-0009211 A | 1/2019 |
| KR | 10-2019-0055122 A | 5/2019 |
| KR | 10-2019-0070064 A | 6/2019 |
| KR | 10-2054806 B1 | 12/2019 |
| NO | 2018198844 A1 | 11/2018 |
| WO | 2003/012890 A3 | 2/2003 |
| WO | 2010/126234 A1 | 11/2010 |
| WO | 2011/059463 A1 | 5/2011 |
| WO | 2012/087955 A1 | 6/2012 |
| WO | 2012153725 A1 | 11/2012 |
| WO | 2013/073896 A1 | 5/2013 |
| WO | 2013/122402 A1 | 8/2013 |
| WO | 2013/157886 A1 | 10/2013 |
| WO | 2015/053524 A1 | 4/2015 |
| WO | 2015/076599 A1 | 5/2015 |
| WO | 2015/084021 A1 | 6/2015 |
| WO | 2015/167199 A1 | 11/2015 |
| WO | 2016/074755 A1 | 5/2016 |
| WO | 2016/112762 A1 | 7/2016 |
| WO | WO-2017142308 A1 * | 8/2017 ........... C07D 209/82 |
| WO | 2018173598 A1 † | 9/2018 |
| WO | 2019/117440 A1 | 6/2019 |
| WO | 2019179497 A1 | 9/2019 |

\* cited by examiner
† cited by third party

【FIG. 1】
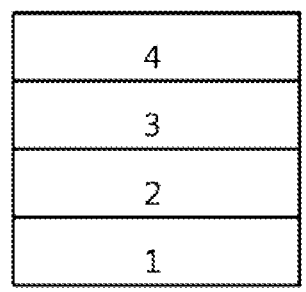
【FIG. 2】
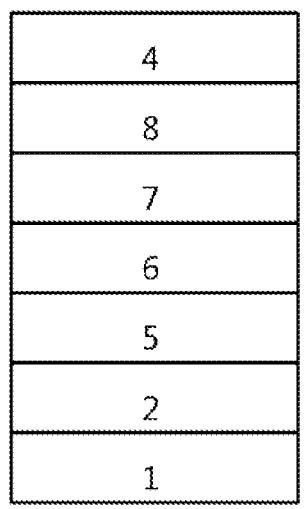

COMPOUND AND ORGANIC LIGHT EMITTING DEVICE COMPRISING SAME

CROSS-REFERENCE TO RELATED APPLICATION(S)

This application is a National Stage Application of International Application No. PCT/KR2020/009472 filed on Jul. 17, 2020, and claims priority to Korean Patent Application No. 10-2019-0094225 filed on Aug. 2, 2019, the disclosure of which is incorporated herein by reference in its entirety.

FIELD OF DISCLOSURE

The present disclosure relates to a novel compound and an organic light emitting device comprising the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for—the organic materials used in the organic light emitting devices as described above.

In this regard, the present disclosure provides novel materials for organic light emitting devices that can be used for an organic light emitting device and at the same time, can be used by a solution process.

RELATED ARTS (Patent Literature 0001) Korean Patent Application Publication No. 10-2000-0051826

SUMMARY

It is an object of the present disclosure to provide a novel compound and an organic light emitting device comprising the same.

According to an object of the present disclosure, there is provided a compound represented by the following Chemical Formula 1:

[Chemical Formula 1]

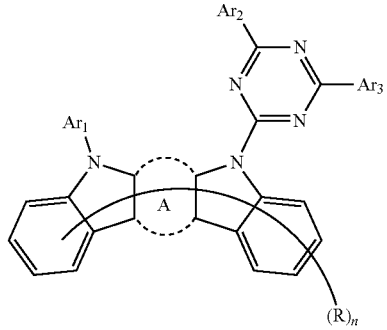

in the Chemical Formula 1,
A is a benzene ring fused with two adjacent pentagonal rings,
at least one of $Ar_1$, $Ar_2$ and $Ar_3$ is a biphenylyl group; a dibenzofuranyl group; a dibenzothiophenyl group; a 9,9-dimethylfluorenyl group; a 9,9-diphenylfluorenyl group; a carbazol-9-yl group; a 9-methyl-carbazolyl group; or a 9-phenyl-carbazolyl group, and the rest are a phenyl group, and $Ar_2$ and $Ar_3$ are not a biphenylyl group at the same time,
at least one of $Ar_1$, $Ar_2$ and $Ar_3$ is substituted with one or more deuterium, and the rest are unsubstituted,
R is hydrogen; deuterium; halogen; cyano; a substituted or unsubstituted $C_{1-60}$ alkyl; a substituted or unsubstituted $C_{1-60}$ alkoxy; a substituted or unsubstituted $C_{2-60}$ alkenyl; a substituted or unsubstituted $C_{2-60}$ alkynyl; a substituted or unsubstituted $C_{3-60}$ cycloalkyl; a substituted or unsubstituted $C_{6-60}$ aryl group; or a substituted or unsubstituted $C_{2-60}$ heteroaryl group containing any one or more heteroatoms selected from the group consisting of N, O and S; a substituted or unsubstituted tri($C_{1-60}$ alkyl)silyl group; or a substituted or unsubstituted tri($C_{6-60}$ aryl)silyl group, and
n is an integer of 0 to 10.

According to another aspect of the present disclosure, there is provided an organic light emitting device comprising: a first electrode; a second electrode that is disposed to face the first electrode; and one or more organic material layers that are disposed between the first electrode and the second electrode, wherein one or more layers of the organic material layers include a compound represented by Chemical Formula 1.

Advantageous Effects

The above-mentioned compound represented by Chemical Formula 1 can be used as a material of an organic material layer of an organic light emitting device, and can improve the efficiency, achieve low driving voltage and/or improve lifetime characteristics in the organic light emitting device.

DESCRIPTION OF DRAWINGS

FIG. 1 depicts an example of an organic light emitting device comprising a substrate 1, an anode 2, a light emitting layer 3, and a cathode 4.

FIG. 2 depicts an example of an organic light emitting device comprising a substrate 1, an anode 2, a hole injection layer 5, a hole transport layer 6, a light emitting layer 7, an electron injection and transport layer 8, and a cathode 4.

DETAILED DESCRIPTION

Hereinafter, embodiments of the present disclosure will be described in more detail to facilitate understanding of the invention.

As used herein, the notation

or | means a bond linked to another substituent group.

As used herein, the term "substituted or unsubstituted" means being unsubstituted or substituted with one or more substituents selected from the group consisting of deuterium; a halogen group; a cyano group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heteroaryl group containing at least one of N, O and S atoms, or being unsubstituted or substituted with a substituent to which two or more substituents of the above-exemplified substituents are connected. For example, "a substituent in which two or more substituents are connected" may be a biphenyl group. Namely, a biphenyl group may be an aryl group, or it may also be interpreted as a substituent in which two phenyl groups are connected.

In the present disclosure, the carbon number of a carbonyl group is not particularly limited, but is preferably 1 to 40. Specifically, the carbonyl group may be a group having the following structural formulas, but is not limited thereto.

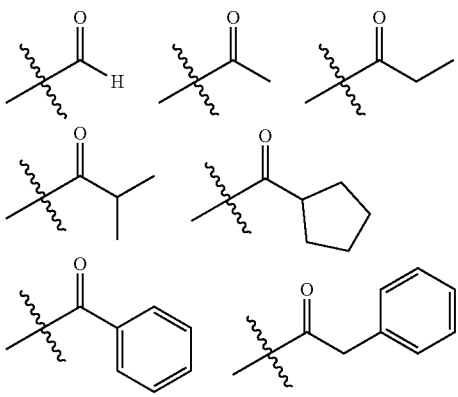

In the present disclosure, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a group having the following structural formulas, but is not limited thereto.

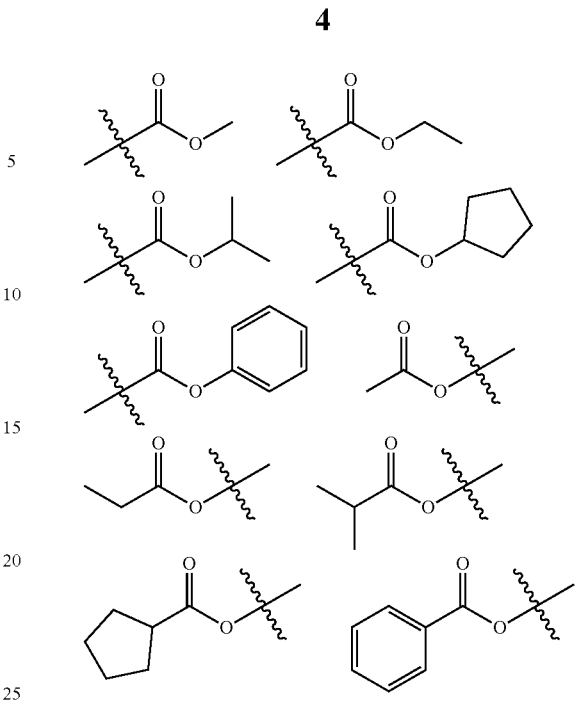

In the present disclosure, the carbon number of an imide group is not particularly limited, but is preferably 1 to 25. Specifically, the imide group may be a group having the following structural formulas, but is not limited thereto.

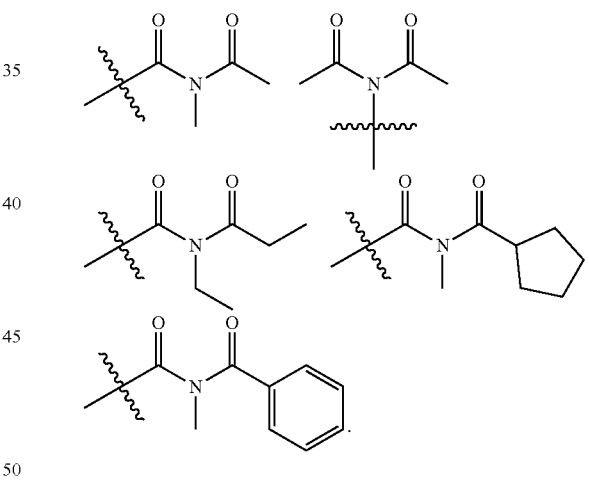

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present disclosure, a boron group specifically includes a trimethylboron group, a triethylboron group, a t-butyldimethylboron group, a triphenylboron group, and a phenylboron group, but is not limited thereto.

In the present disclosure, examples of a halogen group include fluorine, chlorine, bromine, or iodine.

In the present disclosure, the alkyl group may be straight-chain or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 4-methylhexyl, 5-methylhexyl, and the like, but are not limited thereto.

In the present disclosure, the alkenyl group may be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to still another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to still another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it may be a monocyclic aryl group or a polycyclic aryl group. According to one embodiment, the carbon number of the aryl group is 6 to 30. According to one embodiment, the carbon number of the aryl group is 6 to 20. The aryl group may be a phenyl group, a biphenyl group, a terphenyl group or the like as the monocyclic aryl group, but is not limited thereto. The polycyclic aryl group includes a naphthyl group, an anthracenyl group, a phenanthrenyl group, a pyrenyl group, a perylenyl group, a chrysenyl group, or the like, but is not limited thereto.

In the present disclosure, the fluorenyl group may be substituted, and two substituents may be linked with each other to form a spiro structure. In the case where the fluorenyl group is substituted,

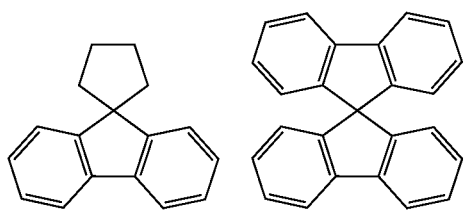

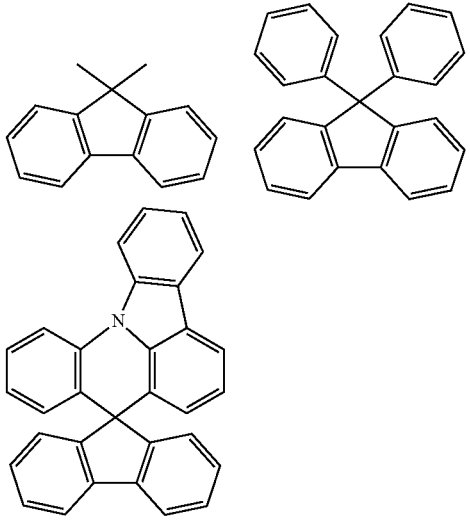

and the like can be formed. However, the structure is not limited thereto.

In the present disclosure, a heteroaryl group is a heteroaryl group containing one or more of O, N, Si and S as a heteroatom, and the carbon number thereof is not particularly limited, but is preferably 2 to 60. Examples of the heteroaryl group include a xanthene group, a thioxanthene group, a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present disclosure, the aryl group in the aralkyl group, the aralkenyl group, the alkylaryl group, the arylamine group and the arylsily group is the same as the aforementioned examples of the aryl group. In the present disclosure, the alkyl group in the aralkyl group, the alkylaryl group and the alkylamine group is the same as the aforementioned examples of the alkyl group. In the present disclosure, the heteroaryl in the heteroarylamine group can be applied to the aforementioned description of the heteroaryl group. In the present disclosure, the alkenyl group in the aralkenyl group is the same as the aforementioned examples of the alkenyl group. In the present disclosure, the aforementioned description of the aryl group may be applied except that the arylene is a divalent group. In the present disclosure, the aforementioned description of the heteroaryl group can be applied except that the heteroarylene is a divalent group. In the present disclosure, the aforementioned description of the aryl group or cycloalkyl group can be applied except that the hydrocarbon ring is not a monovalent group but formed by combining two substituent groups. In the present disclosure, the aforementioned description of the heteroaryl can be applied, except that the heterocycle is not a monovalent group but formed by combining two substituent groups.

The present disclosure provides the compound represented by Chemical Formula 1.

Preferably, the compound is represented by any one of the following Chemical Formulas 1-1 to 1-6:

[Chemical Formula 1-1]

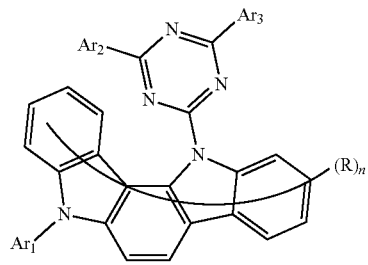

[Chemical Formula 1-2]

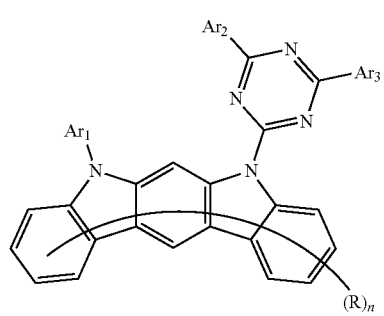

[Chemical Formula 1-3]

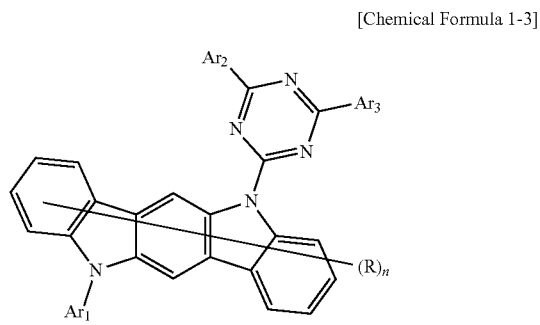

[Chemical Formula 1-4]

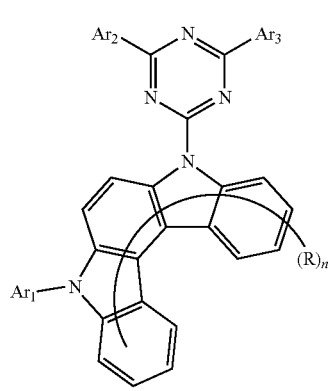

[Chemical Formula 1-5]

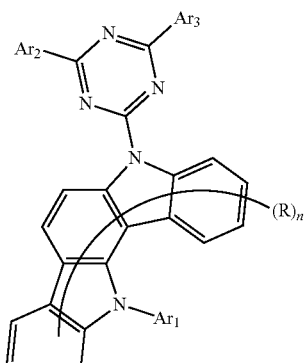

[Chemical Formula 1-6]

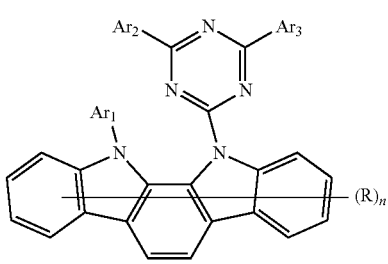

in Chemical Formulas 1-1 to 1-6, $Ar_1$, $Ar_2$, $Ar_3$, R and n are the same as defined in Chemical Formula 1.

Further, when at least one of $Ar_1$, $Ar_2$ and $Ar_3$ is substituted with one or more deuterium, preferably, $Ar_1$, $Ar_2$ or $Ar_3$ is any one selected from the group consisting of the following Chemical Formulas 2-1 to 2-4:

[Chemical Formula 2-1]

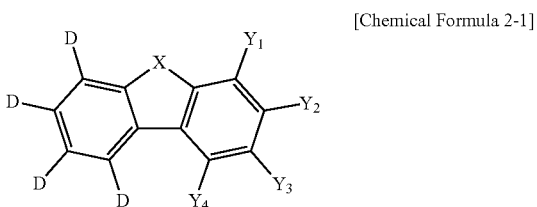

[Chemical Formula 2-2]

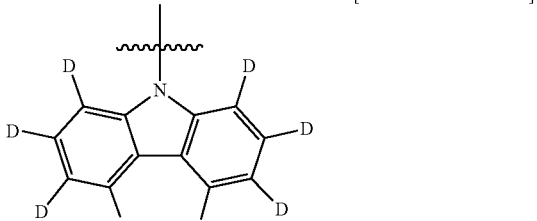

[Chemical Formula 2-3]

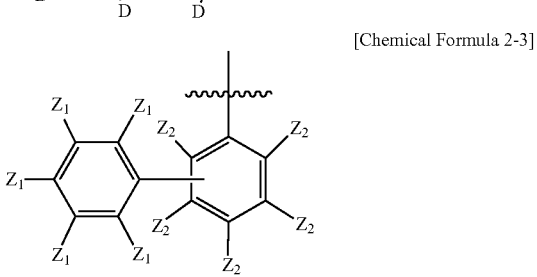

-continued

[Chemical Formula 2-4]

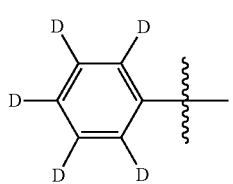

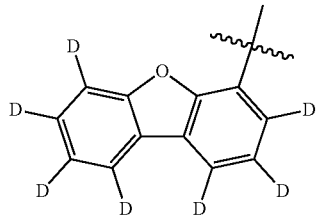

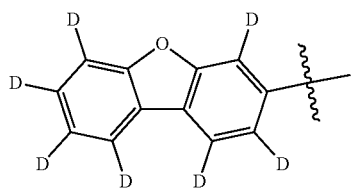

in Chemical Formulas 2-1 to 2-4,

X is O; S; —NR$_1$; or —CR$_2$R$_3$,

R$_1$, R$_2$ and R$_3$ are each independently hydrogen; a methyl group; or a phenyl group, one of Y$_1$, Y$_2$, Y$_3$ and Y$_4$ is a single bond linked to a carbon atom in the triazinyl group or a nitrogen atom in the indolocarbazole group, and the rest are deuterium, all Z$_1$ are hydrogen or all Z$_1$ are deuterium, and all Z$_2$ are hydrogen or all Z$_2$ are deuterium, and all Z$_1$ and all Z$_2$ are not simultaneously hydrogen.

Further, Chemical Formula 2-1 is preferably any one selected from the group consisting of the following Chemical Formulas 2-1-1 to 2-1-4.

[Chemical Formula 2-1-1]

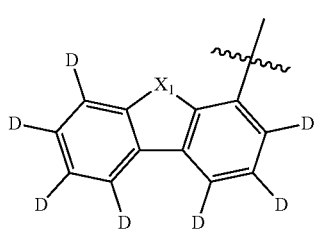

[Chemical Formula 2-1-2]

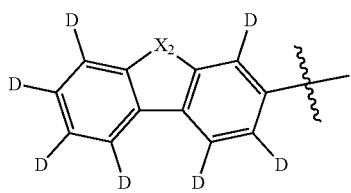

[Chemical Formula 2-1-3]

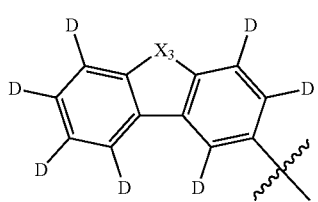

[Chemical Formula 2-1-4]

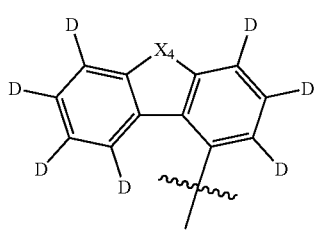

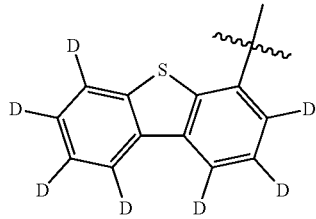

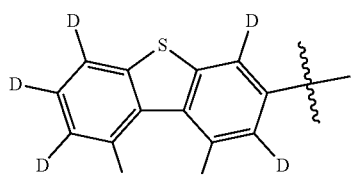

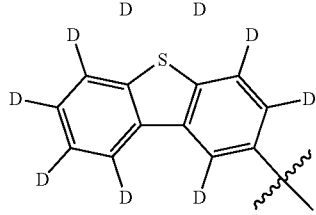

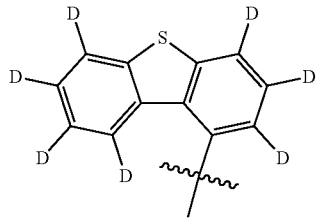

in Chemical Formulas 2-1-1 to 2-1-4, X$_1$ to X$_4$ are each independently O; S; —NR$_1$; or —CR$_2$R$_3$, and R$_1$, R$_2$ and R$_3$ are each independently hydrogen; a methyl group; or a phenyl group.

More preferably, Ar$_1$, Ar$_2$ or Ar$_3$ is any one selected from the group consisting of the following:

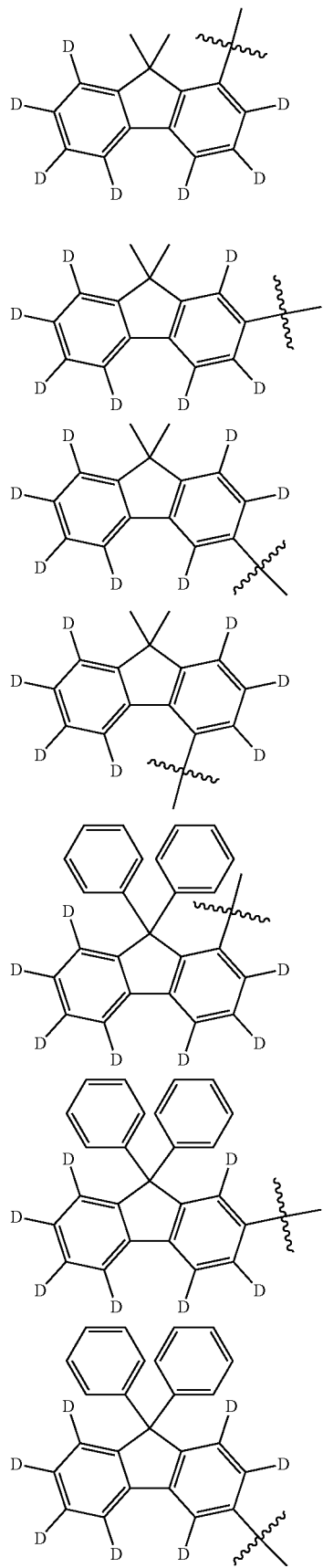
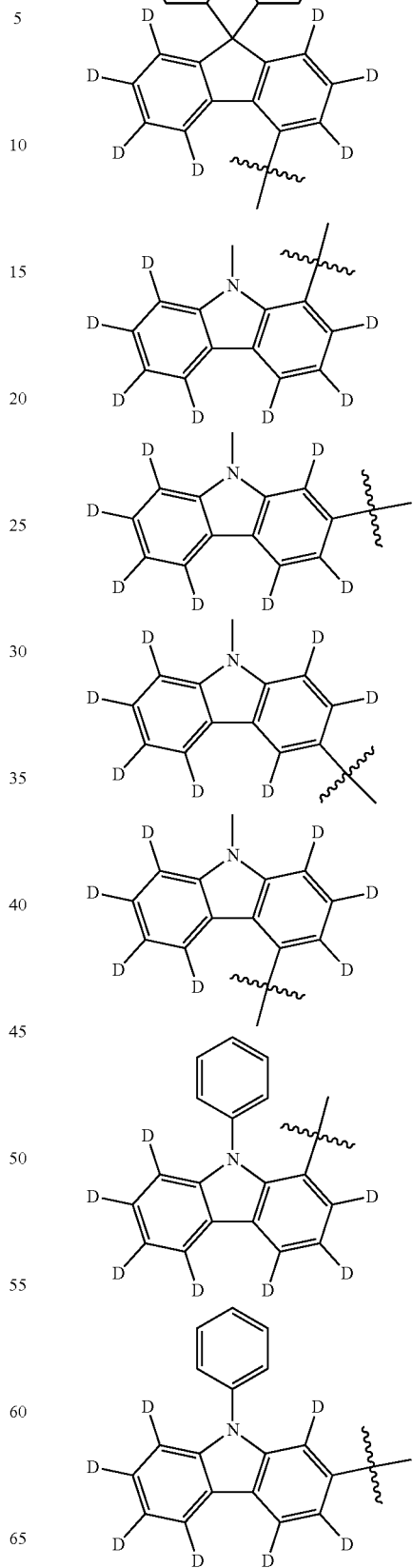

-continued

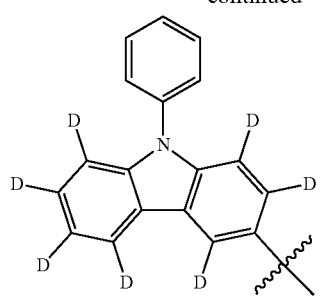

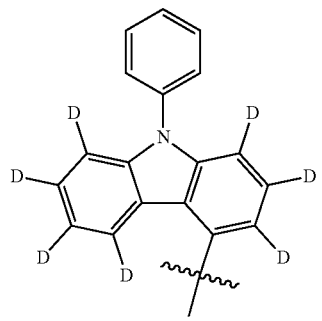

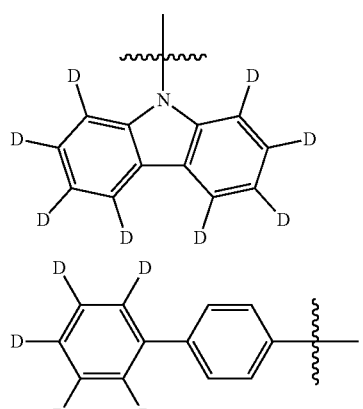

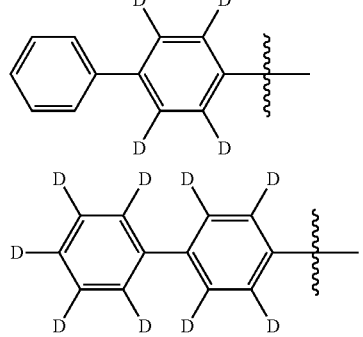

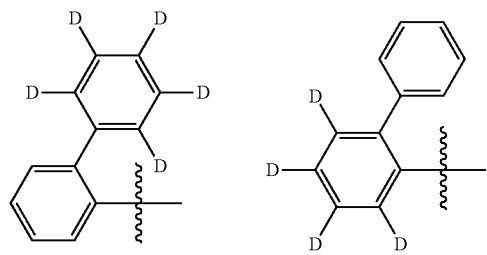

-continued

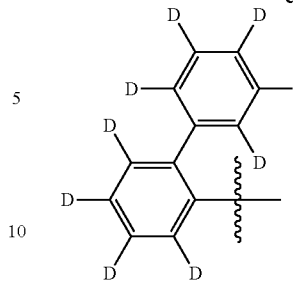

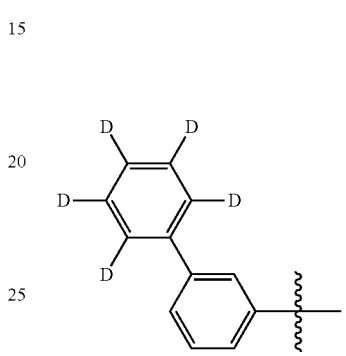

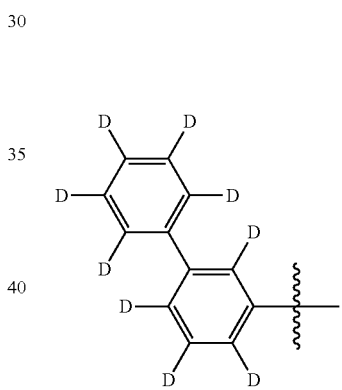

Preferably, in Chemical Formula 1, one of $Ar_1$, $Ar_2$ and $Ar_3$ is a biphenylyl group, and the rest are a phenyl group, and at least one of the $Ar_1$, $Ar_2$ and $Ar_3$ is substituted with one or more deuterium, and the rest are unsubstituted.

Preferably, in Chemical Formula 1, one of $Ar_1$, $Ar_2$ and $Ar_3$ is represented by the following Chemical Formula 2-3, and the rest are an unsubstituted phenyl group:

[Chemical Formula 2-3]

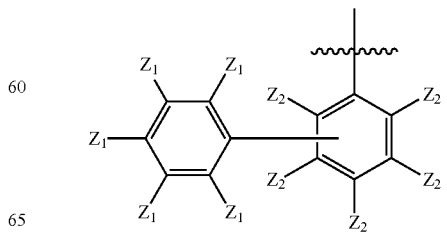

in Chemical Formula 2-3, all $Z_1$ are deuterium and all $Z_2$ are hydrogen.

Preferably, in Chemical Formula 1, one of $Ar_1$, $Ar_2$ and $Ar_3$ is an unsubstituted biphenylyl group, the rest are a phenyl group, and at least one of the rest is represented by the following Chemical Formula 2-4.

[Chemical Formula 2-4]

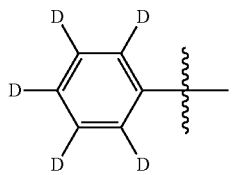

Preferably, in Chemical Formula 1, $Ar_1$ is a biphenylyl group, one of $Ar_2$ and $Ar_3$ is a biphenylyl group, and the other is a phenyl group, and at least one of $Ar_1$, $Ar_2$ and $Ar_3$ is substituted with one or more deuterium, and the rest are unsubstituted.

Preferably, in Chemical Formula 1, one of $Ar_1$, $Ar_2$ and $Ar_3$ is an unsubstituted dibenzofuranyl group; an unsubstituted dibenzothiophenyl group; an unsubstituted 9,9-dimethylfluorenyl group; an unsubstituted carbazol-9-yl group; or an unsubstituted 9-phenyl-carbazolyl group, and the rest are a phenyl group, and at least one of the rest is substituted with deuterium.

Preferably, in Chemical Formula 1, one of $Ar_1$, $Ar_2$ and $Ar_3$ is a dibenzofuranyl group substituted with deuterium; a dibenzothiophenyl group substituted with deuterium; or a 9,9-dimethylfluorenyl group substituted with deuterium, and the rest are an unsubstituted phenyl group.

Preferably, all R are hydrogen, or all R are deuterium. At this time, preferably, n is an integer of 0 to 8.

Representative examples of the compound represented by Chemical Formula 1 are as follows:

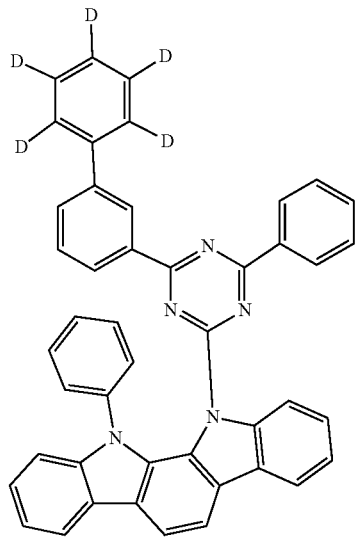

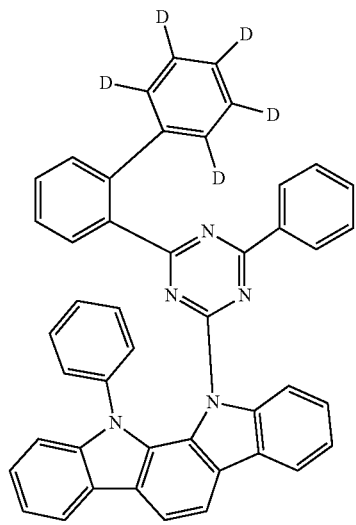

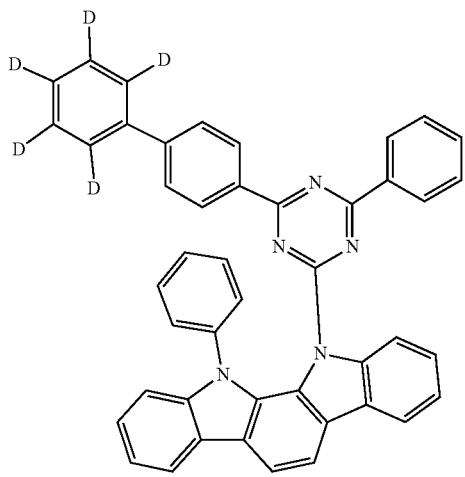

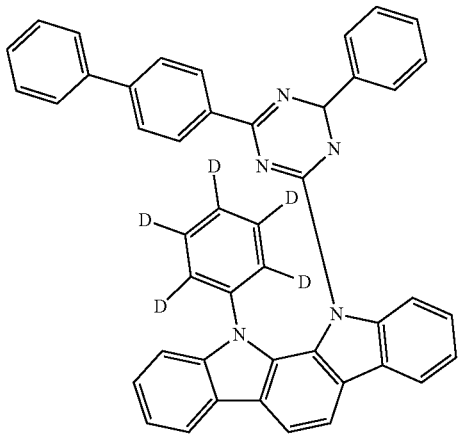

17
-continued
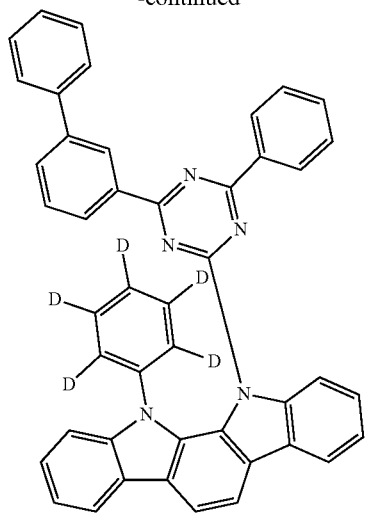
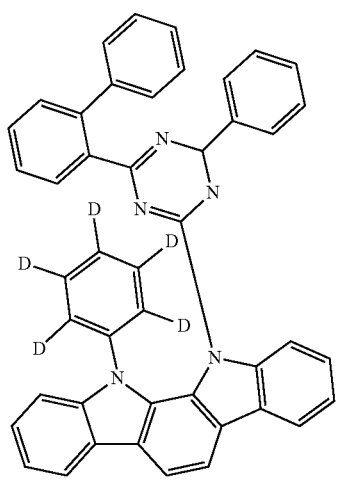
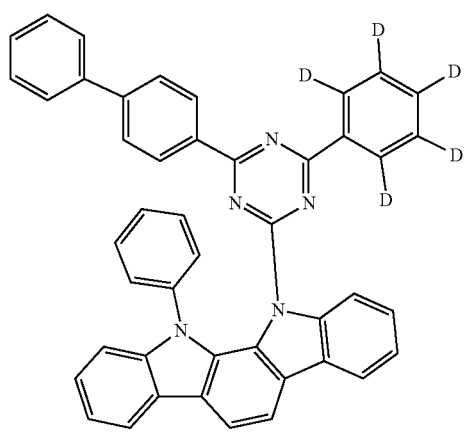
18
-continued
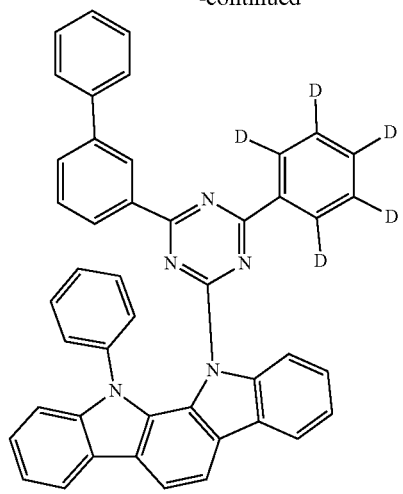
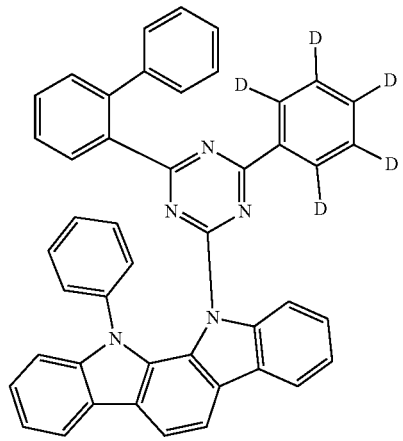
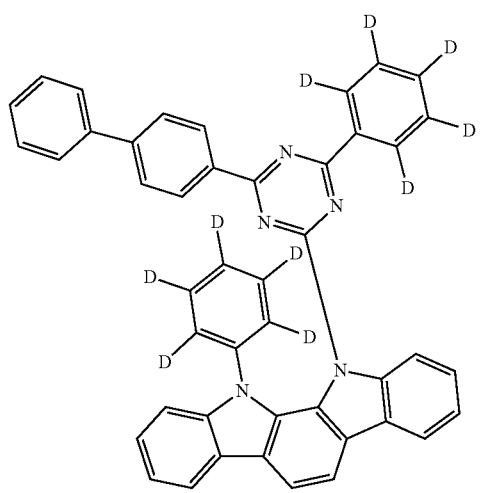

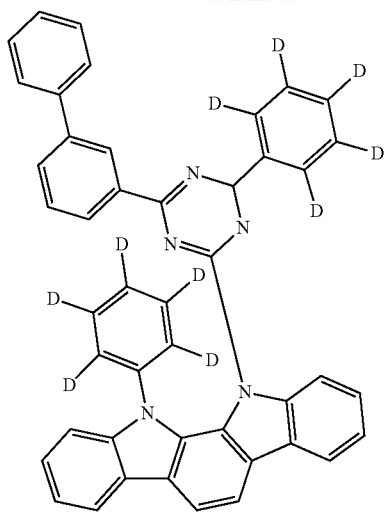
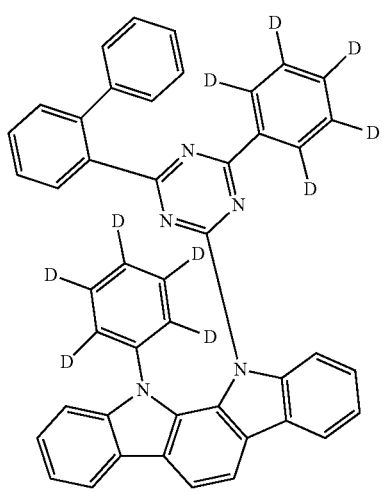
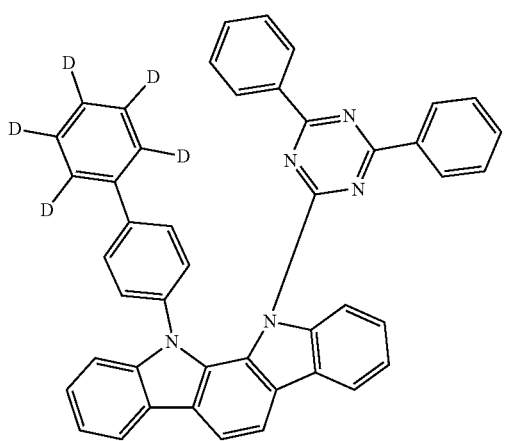
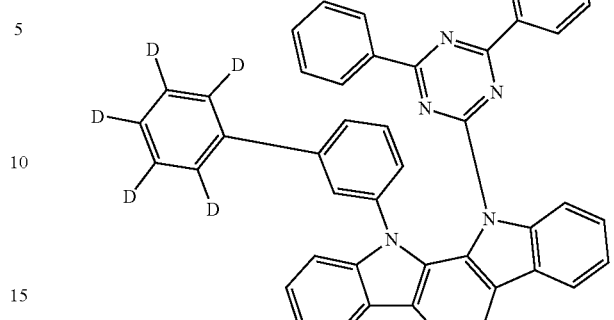
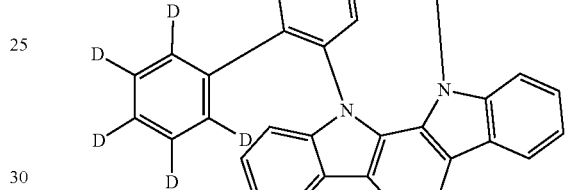
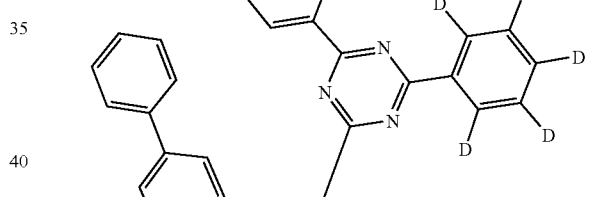
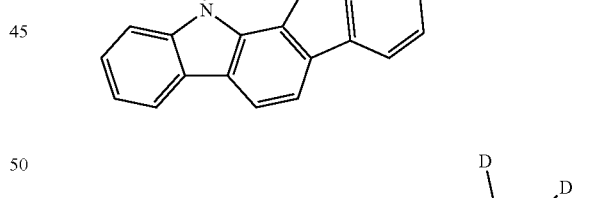

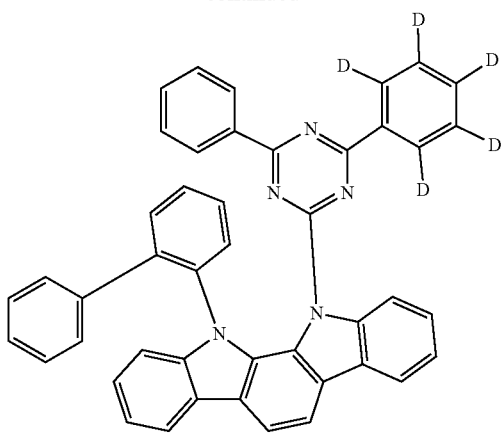
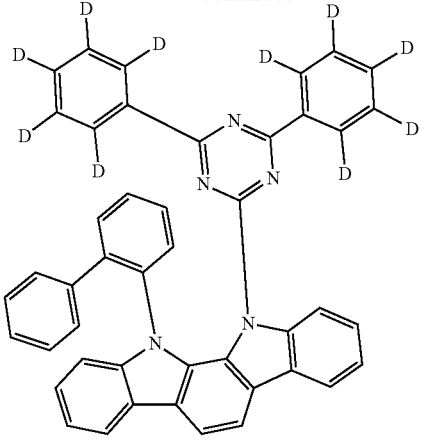
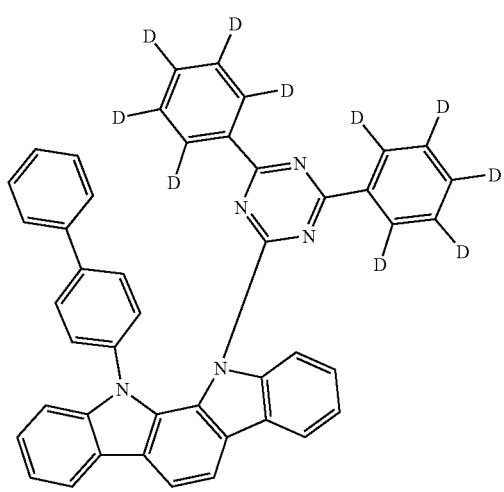
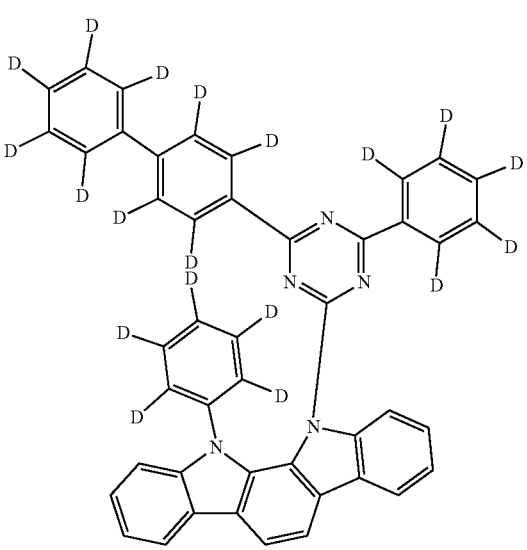
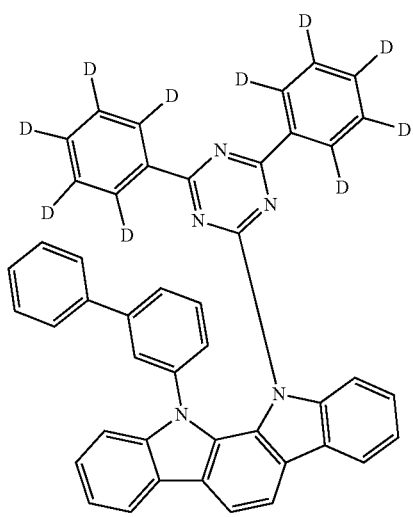
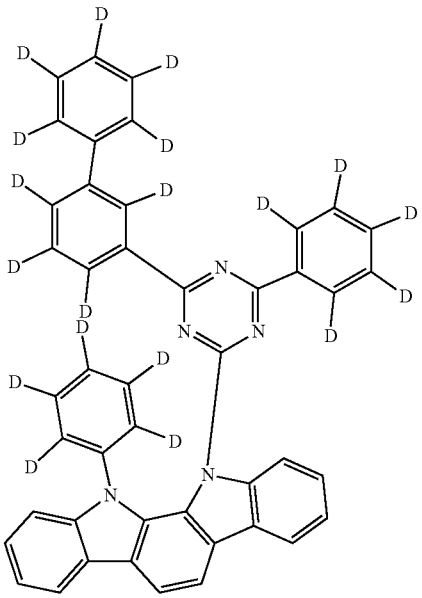

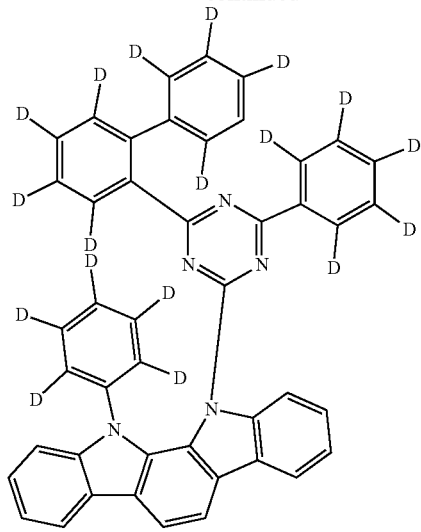
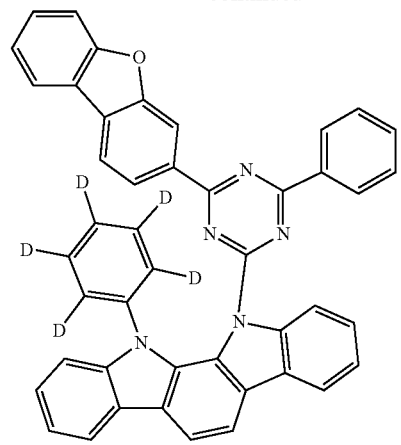
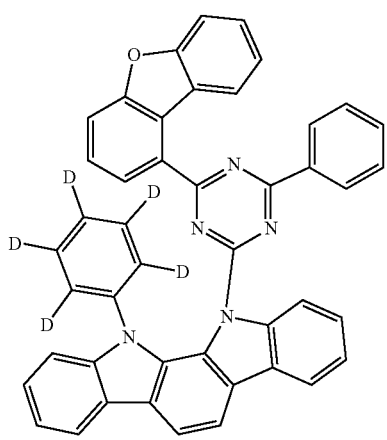
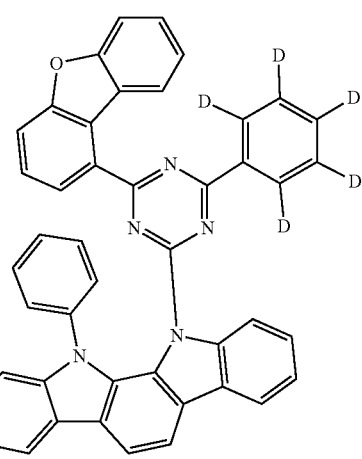
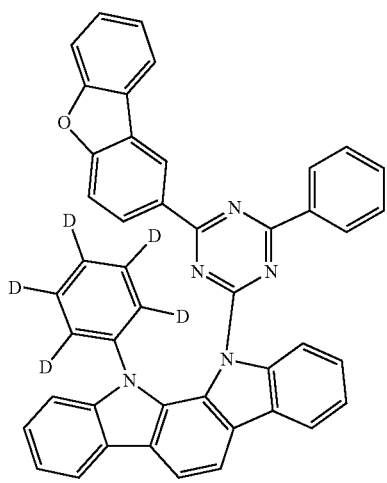
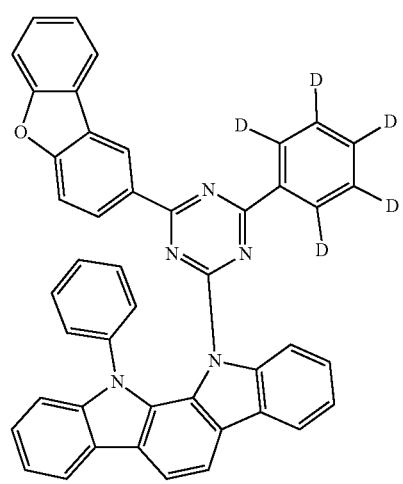

25
-continued
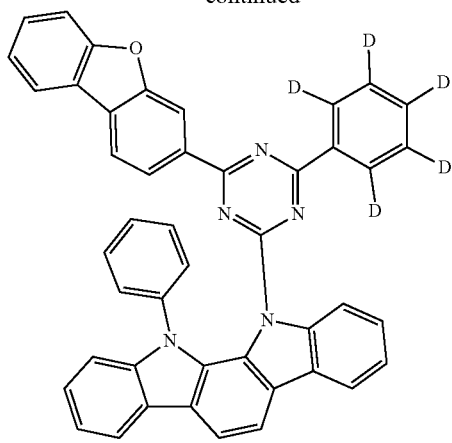
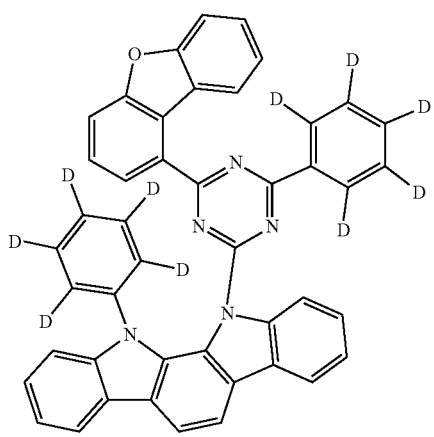
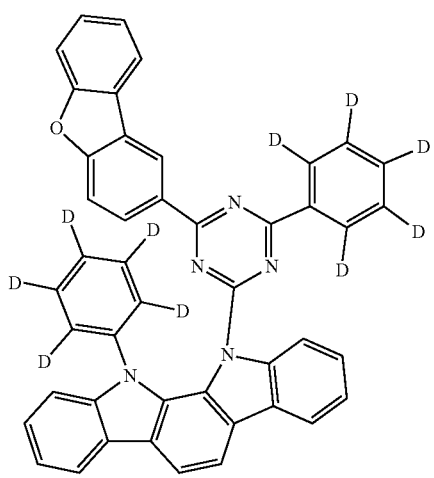
26
-continued
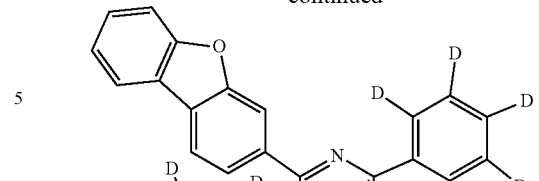
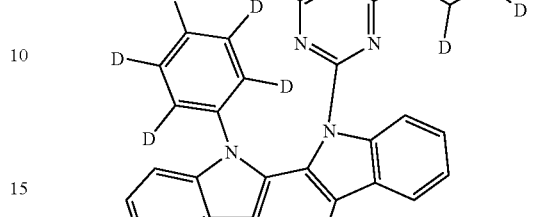
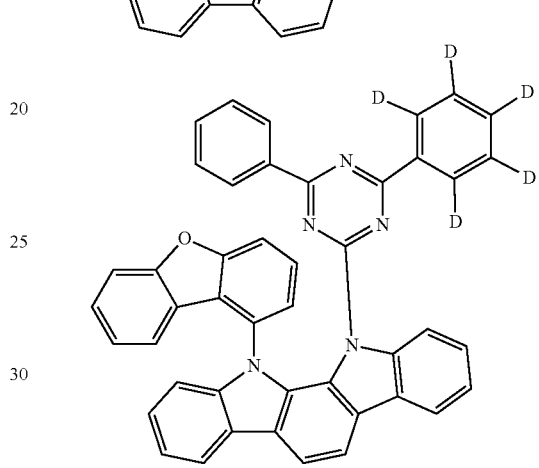
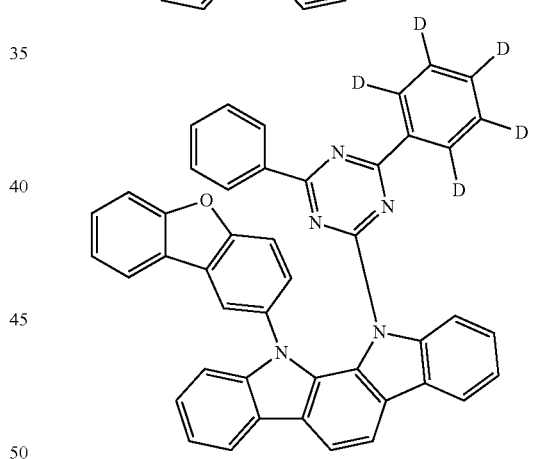
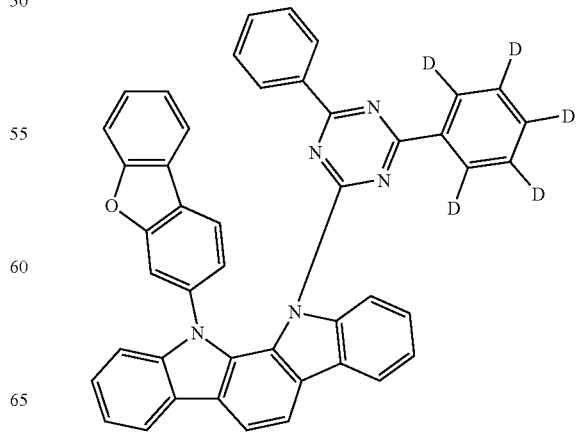

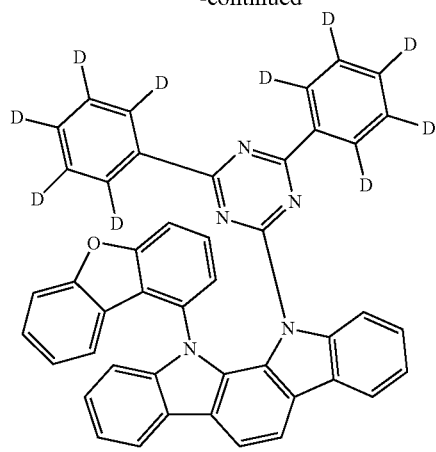
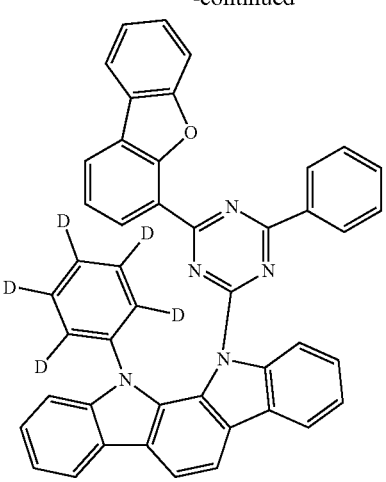
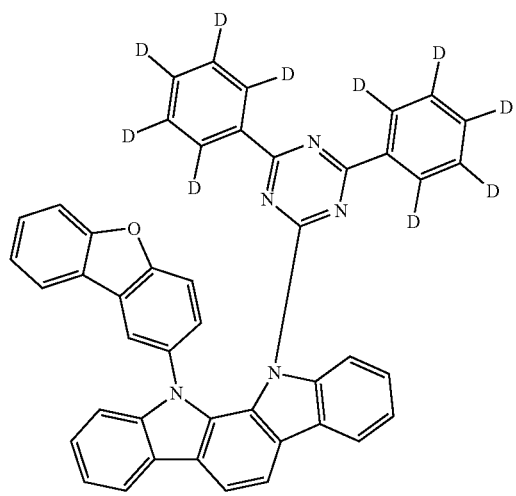
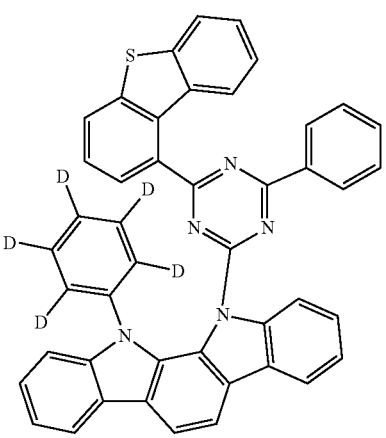
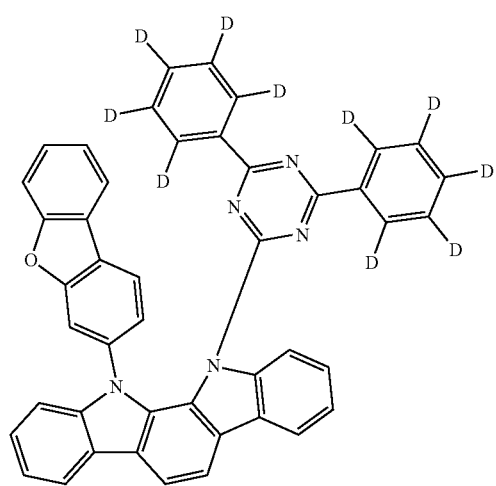
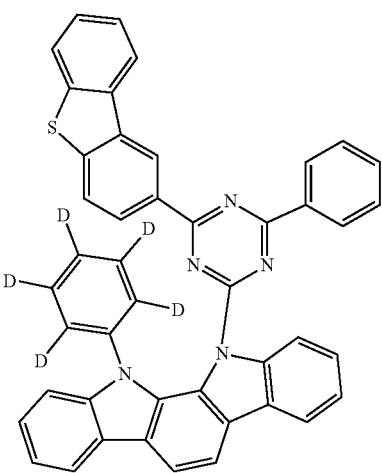

-continued
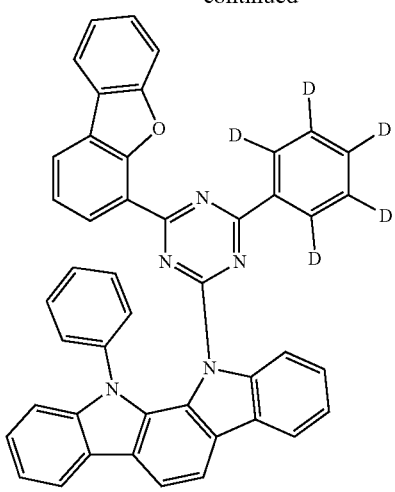
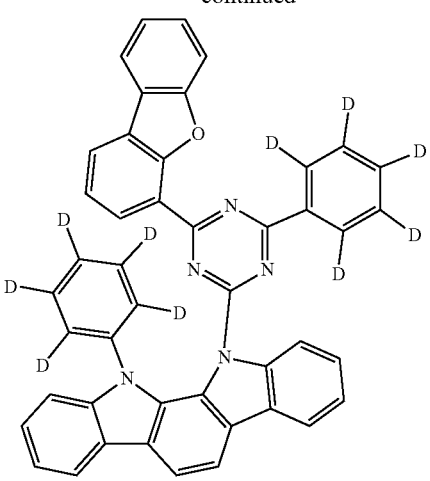
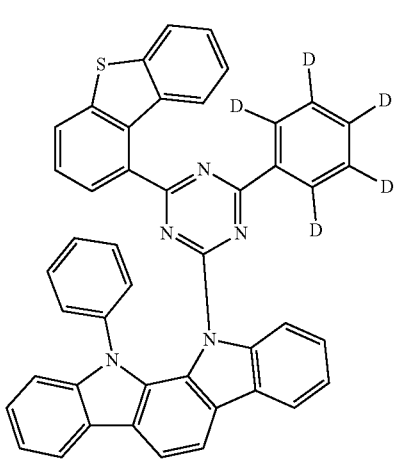
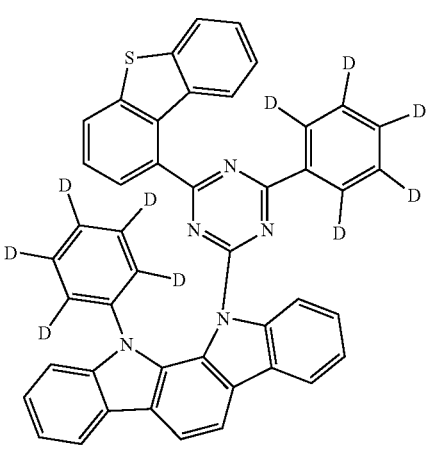
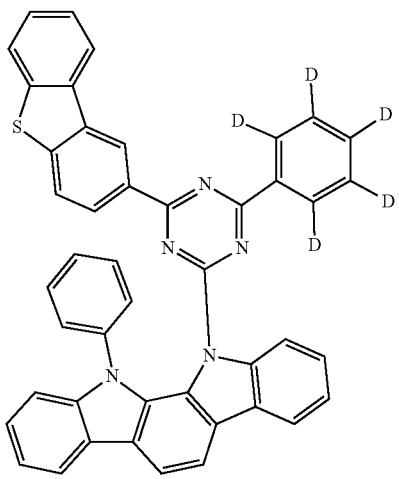
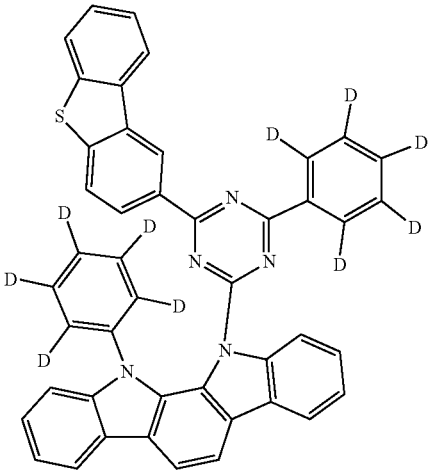

31
-continued
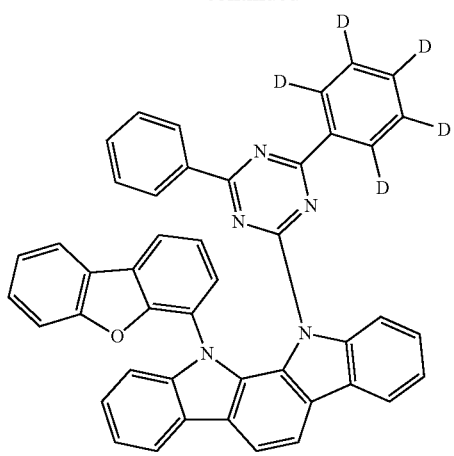
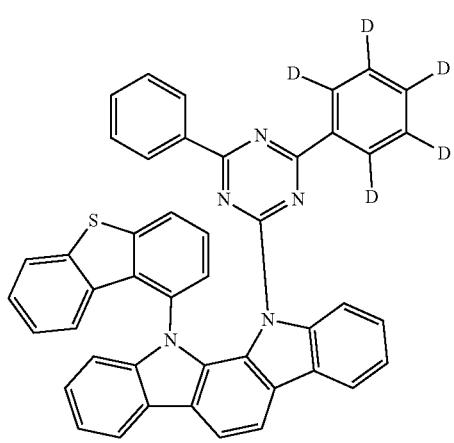
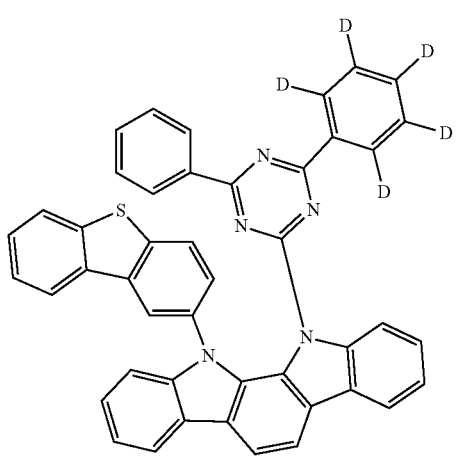
32
-continued
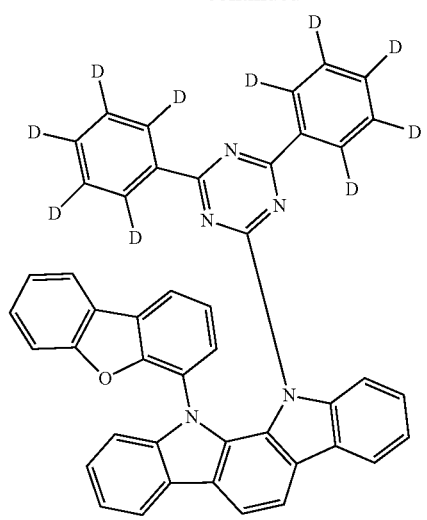
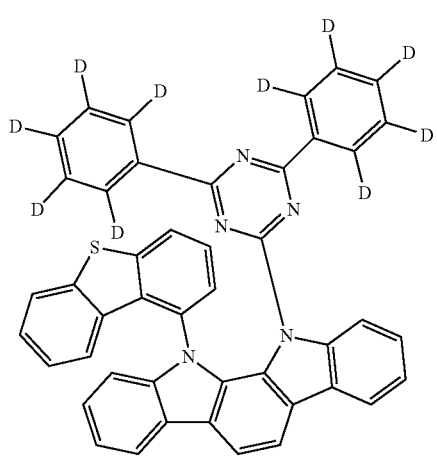
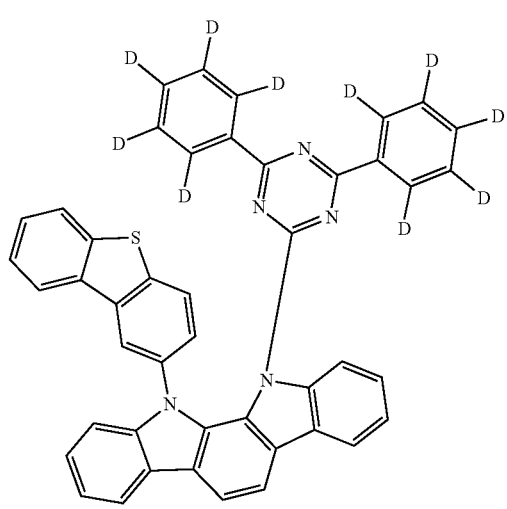

33
-continued
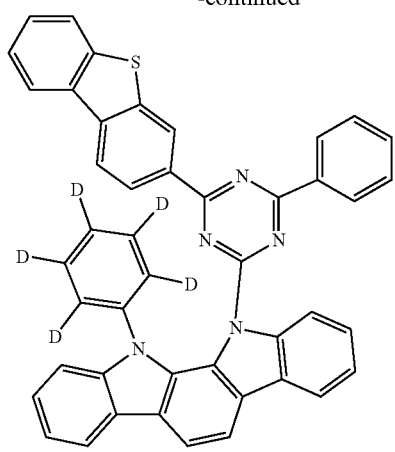
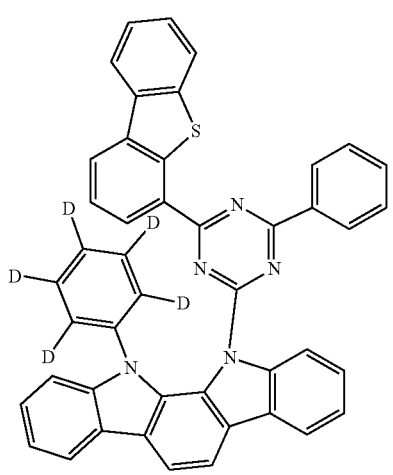
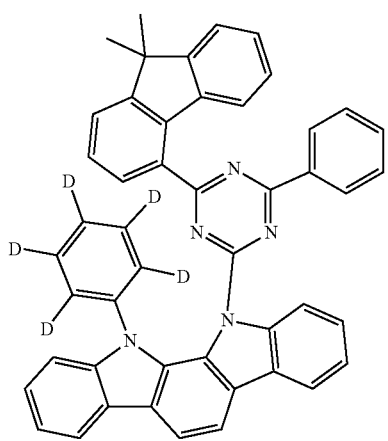
34
-continued
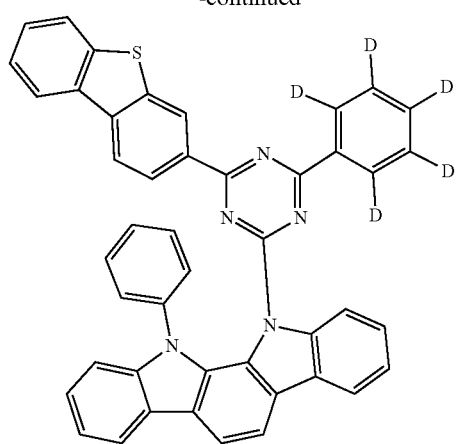
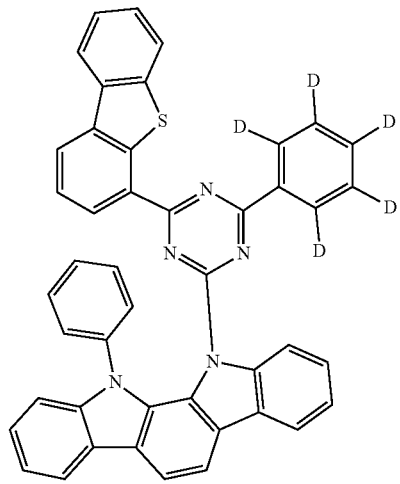
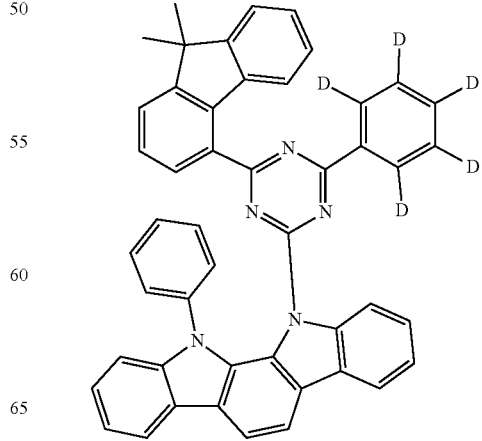

35
-continued
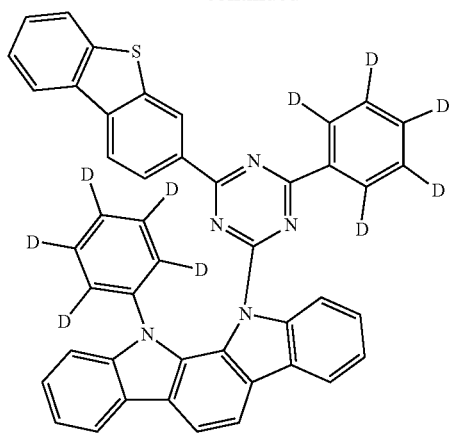
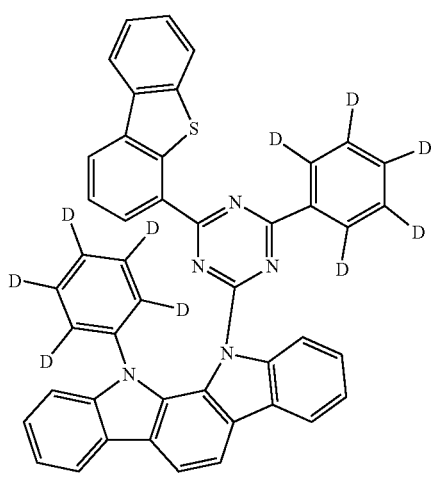
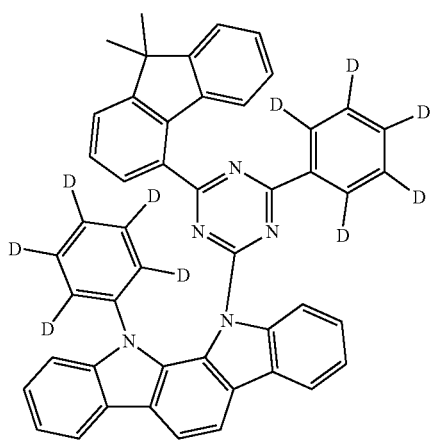
36
-continued
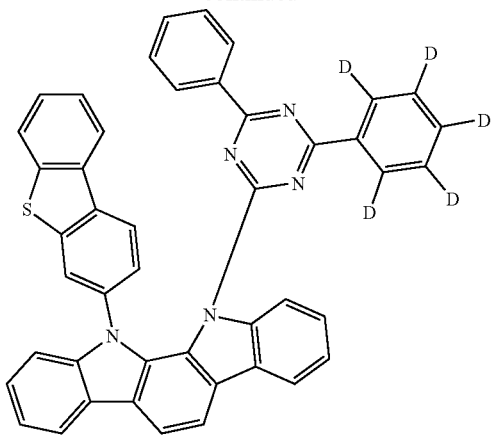
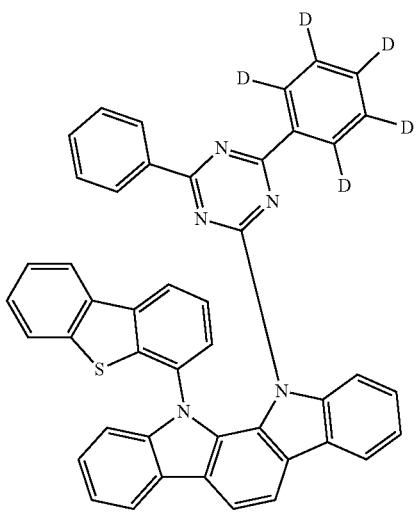
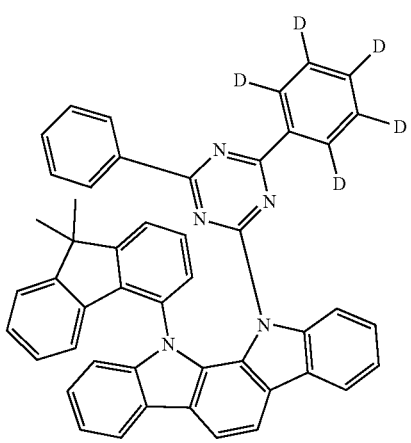

-continued
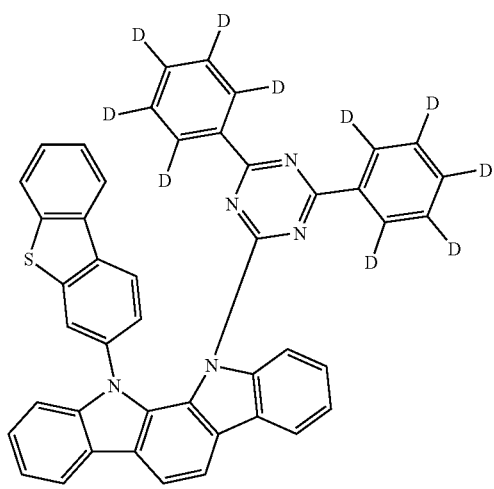
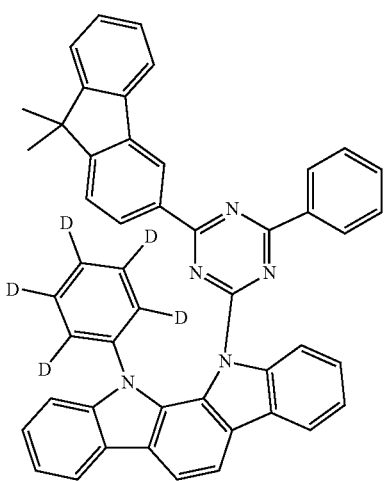
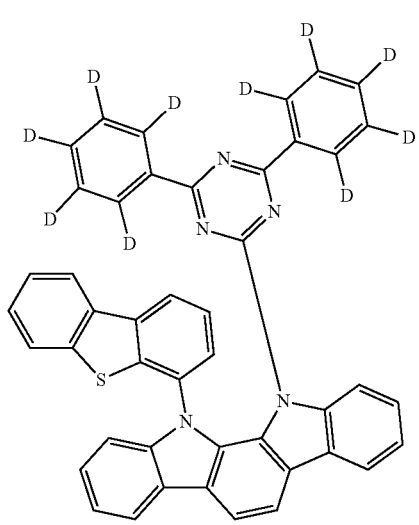
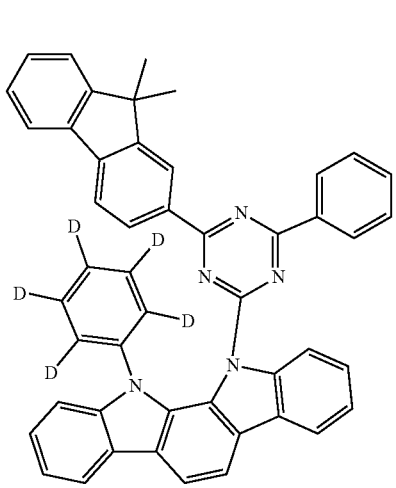
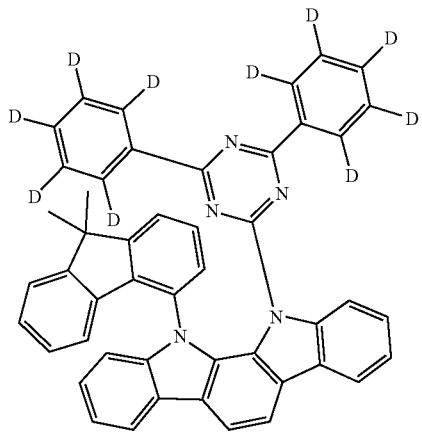
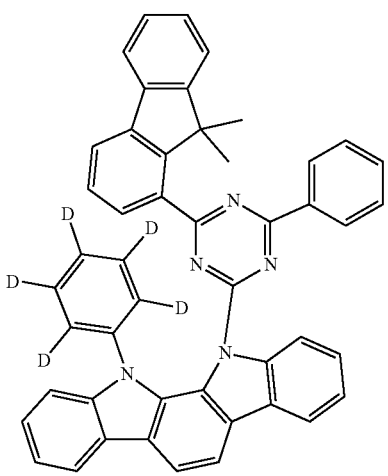

39
-continued
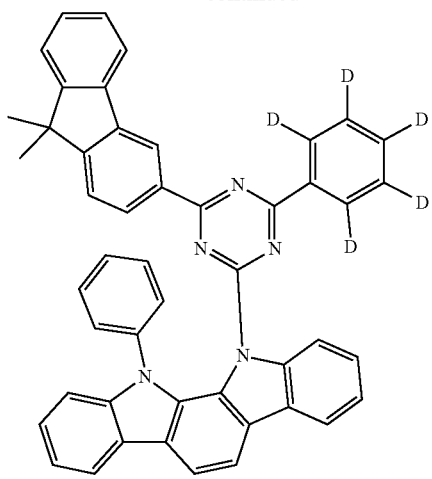
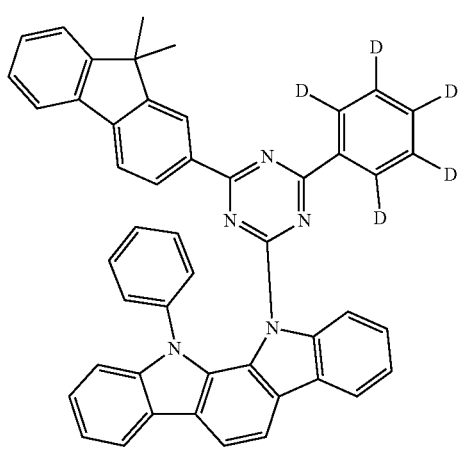
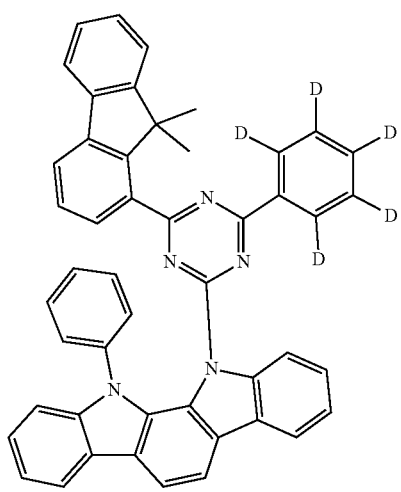
40
-continued
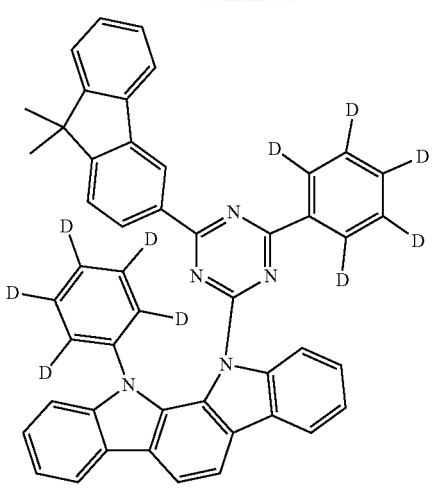
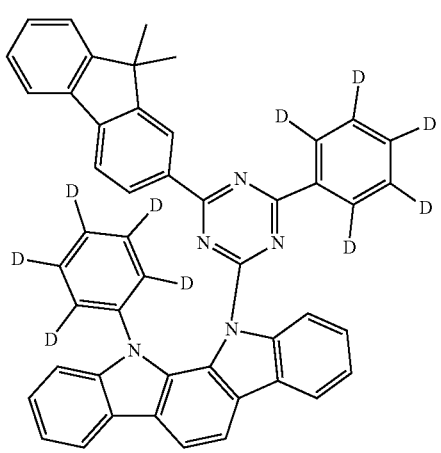
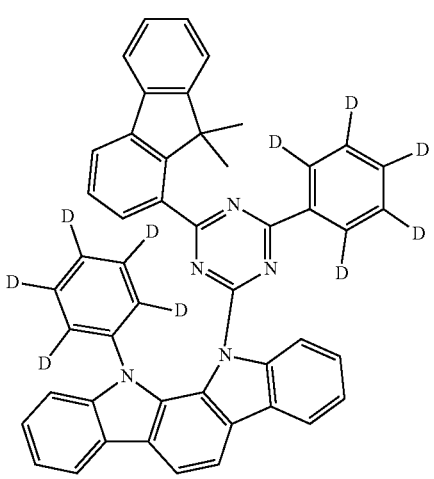

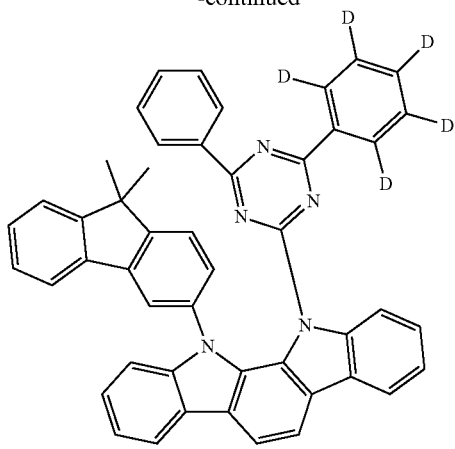
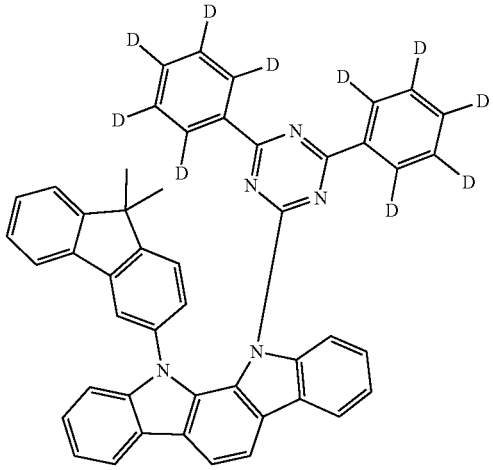
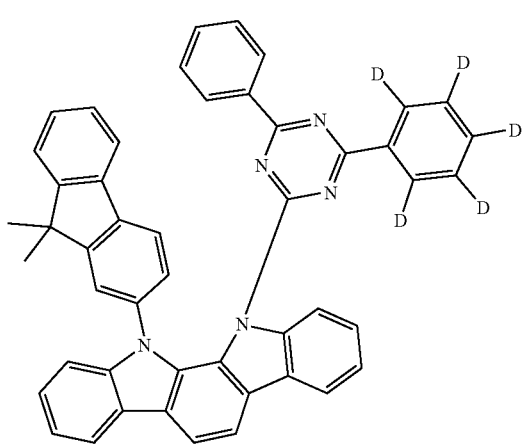
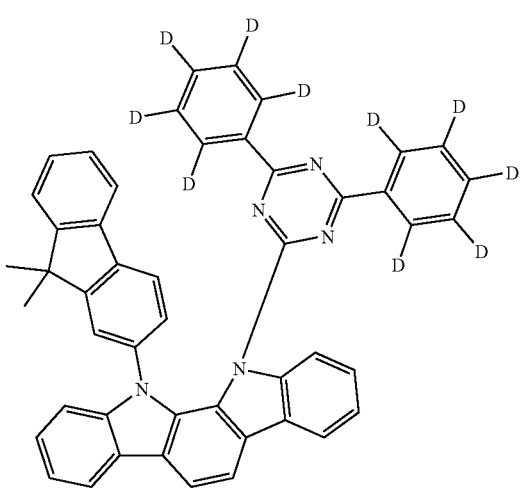
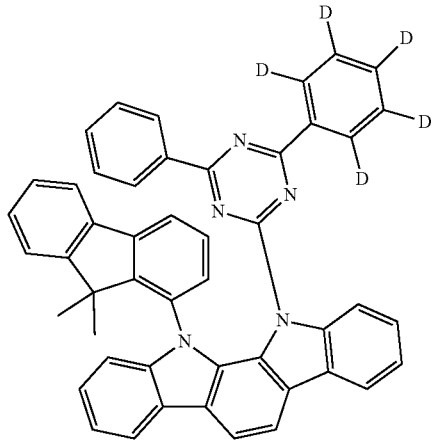
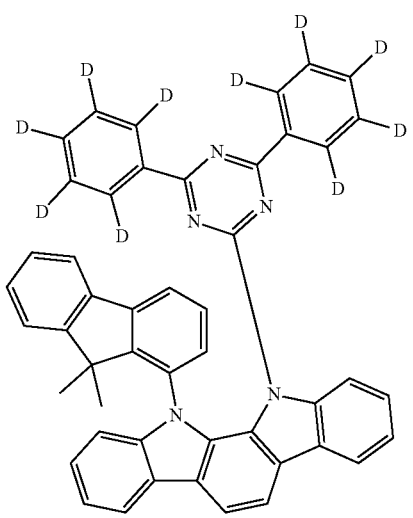

-continued
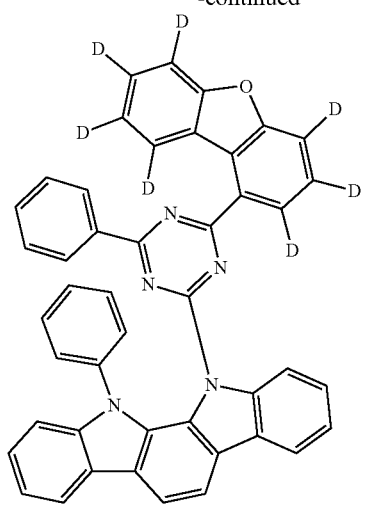
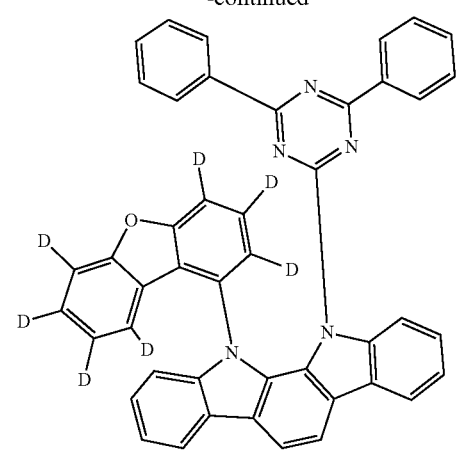
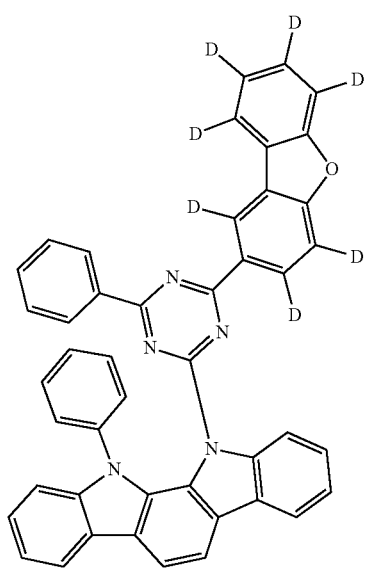
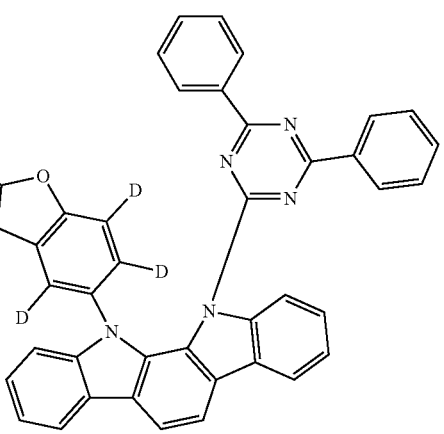
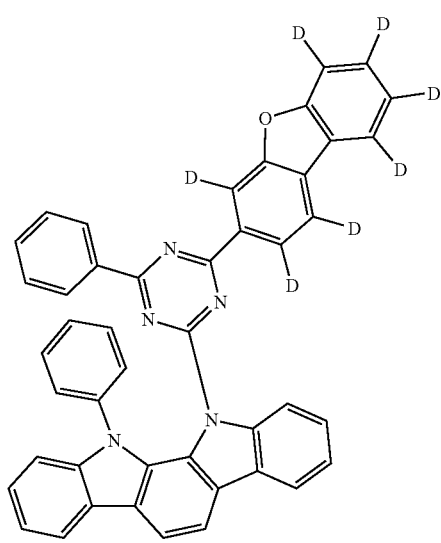
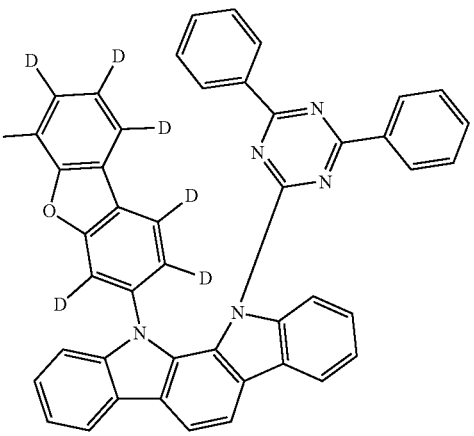

-continued
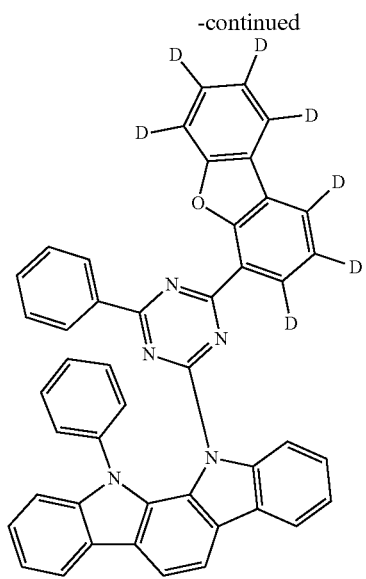
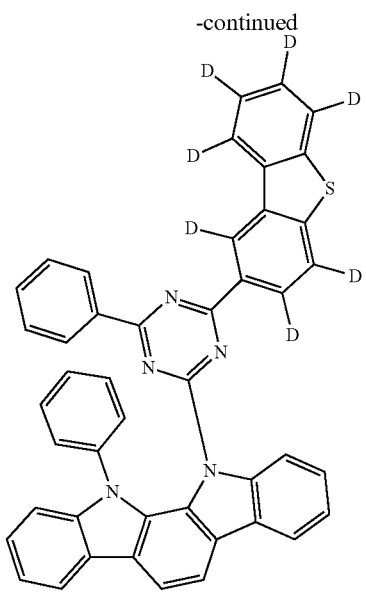
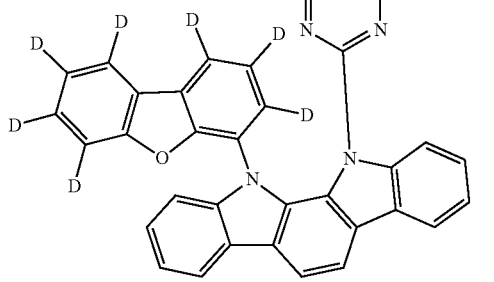
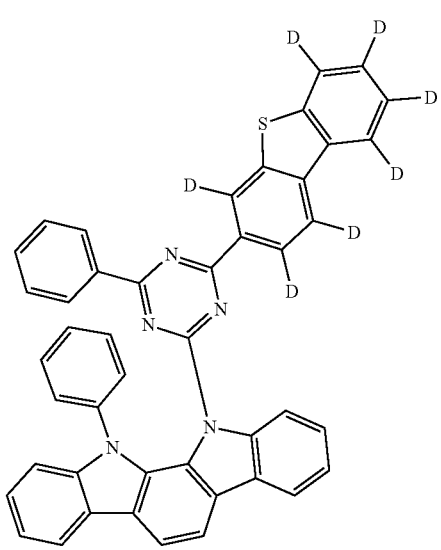
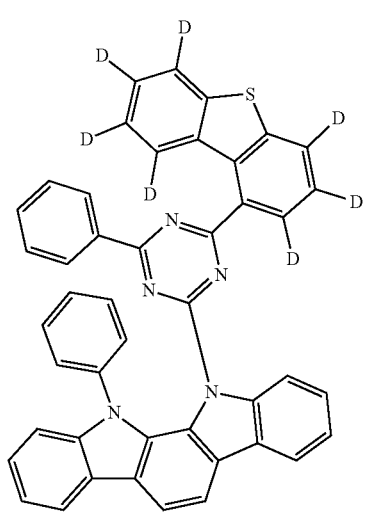
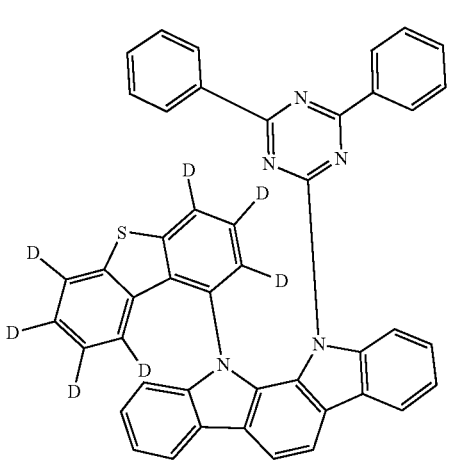

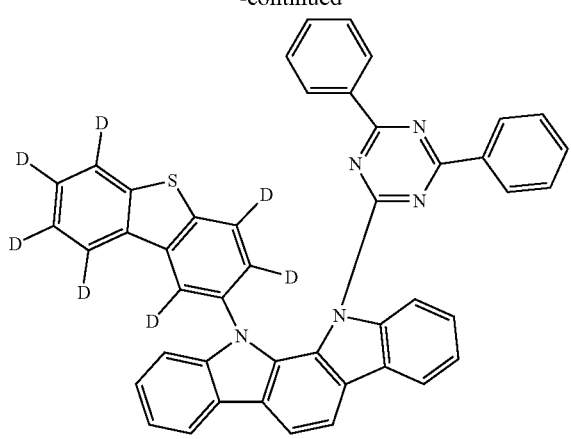
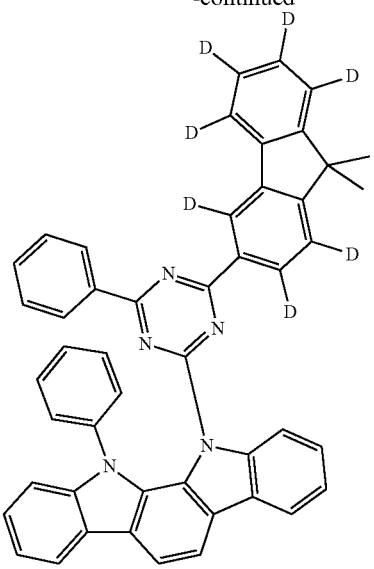
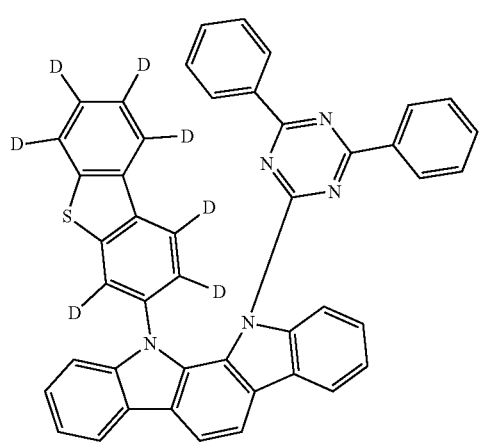
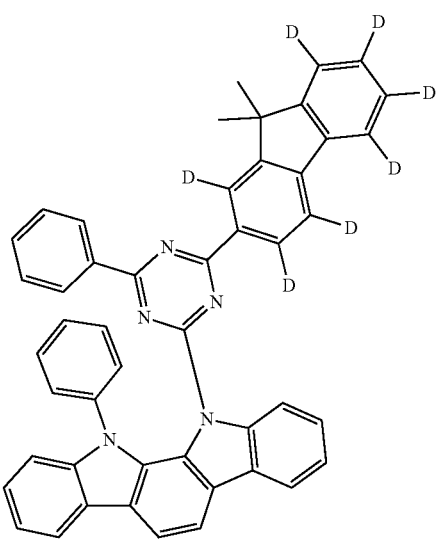
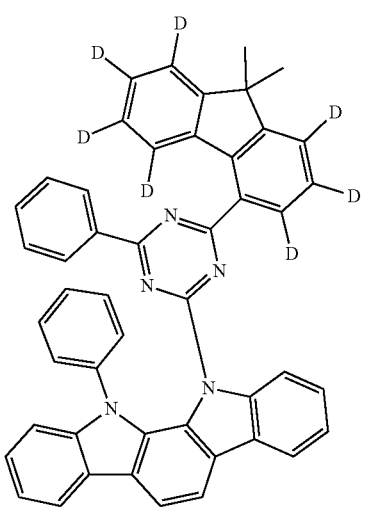
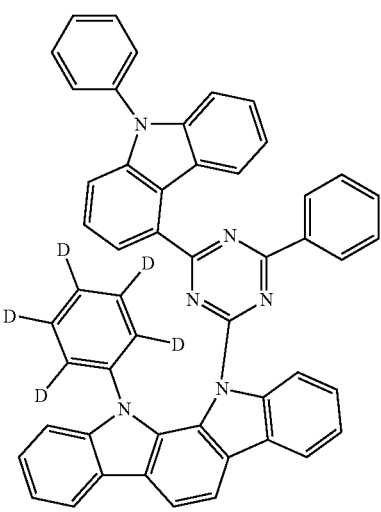

49
-continued
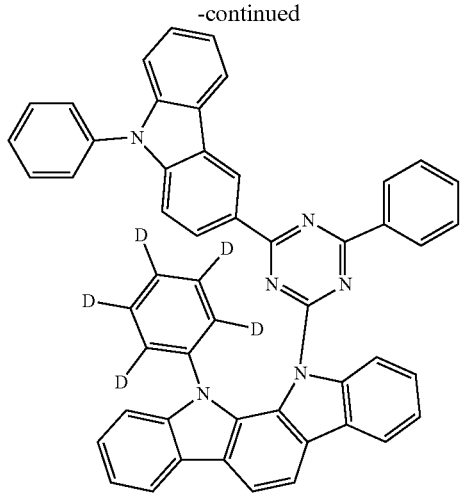
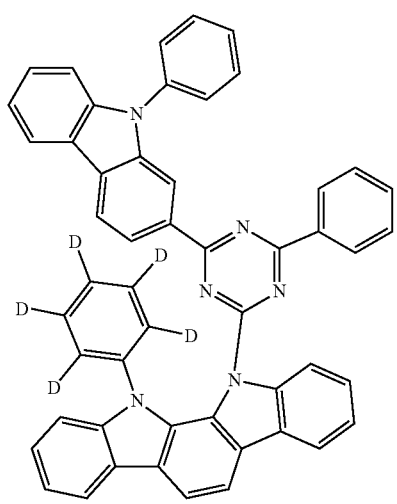
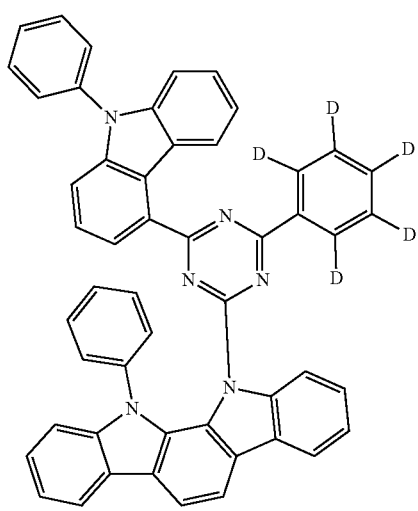
50
-continued
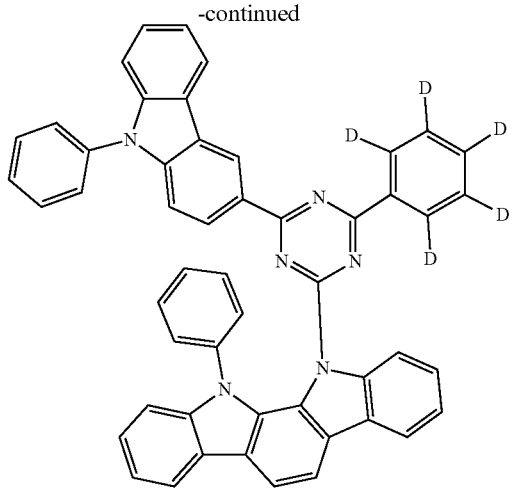
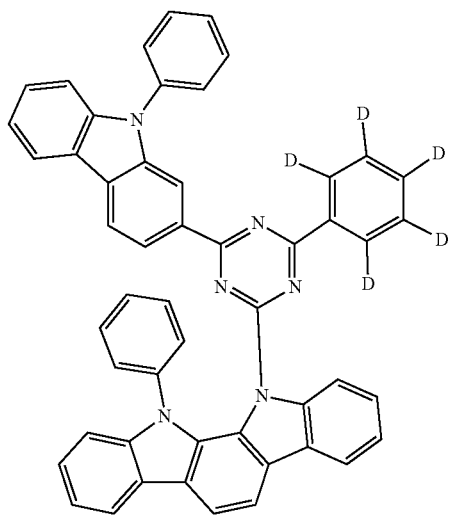
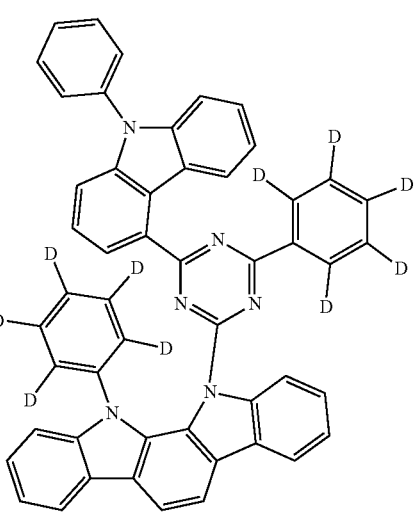

51
-continued
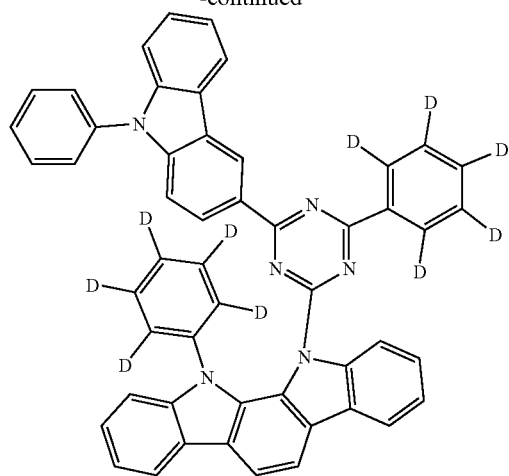
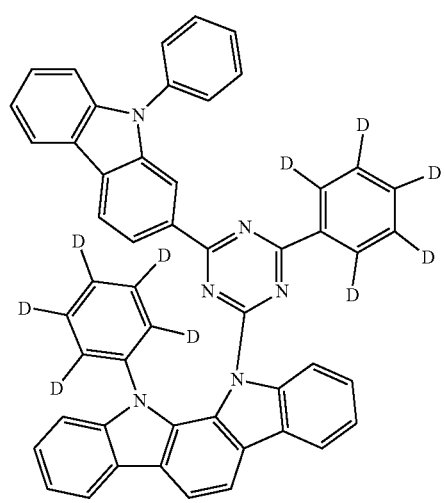
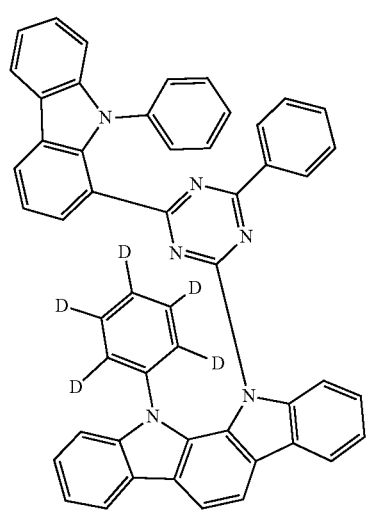
52
-continued
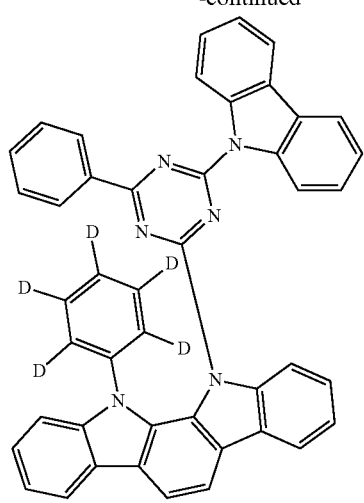
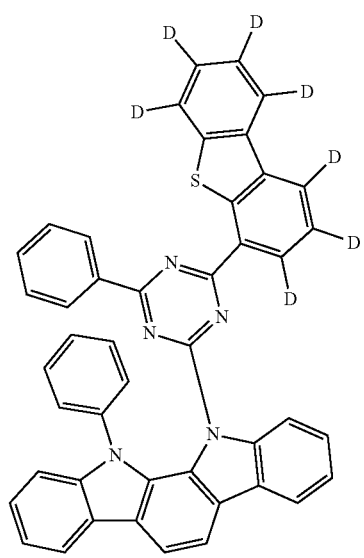
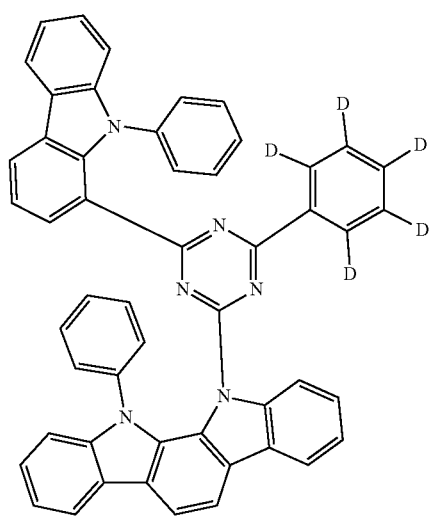

53
-continued
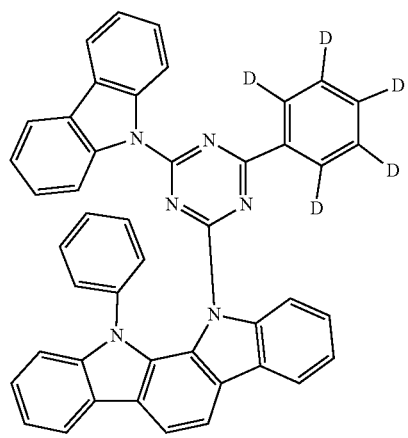
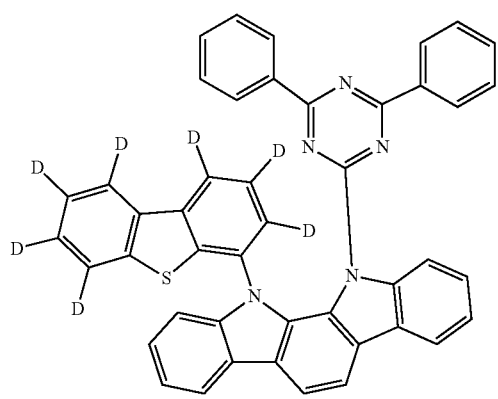
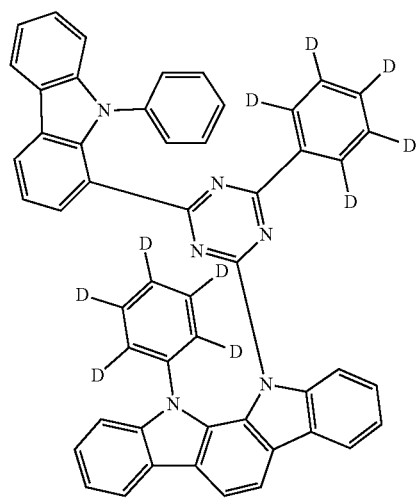
54
-continued
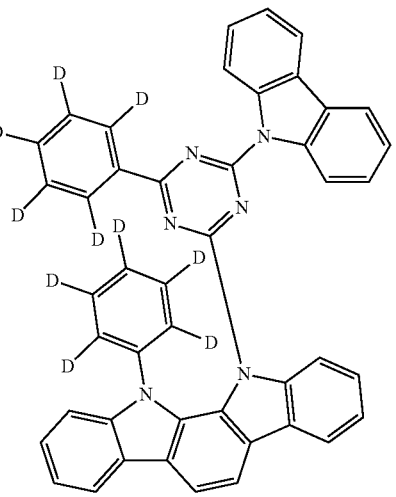
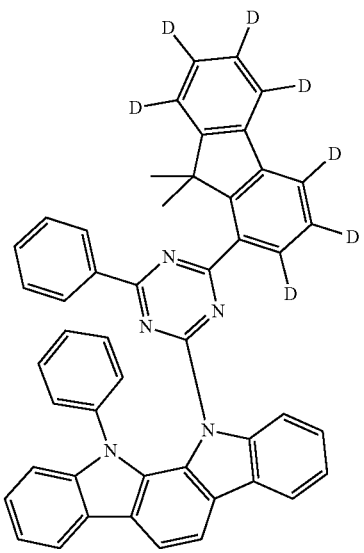
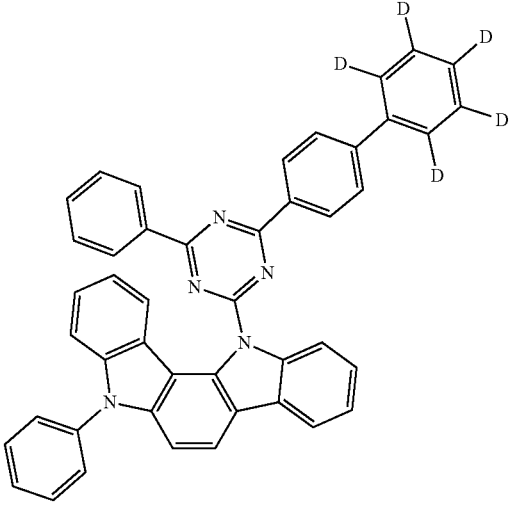

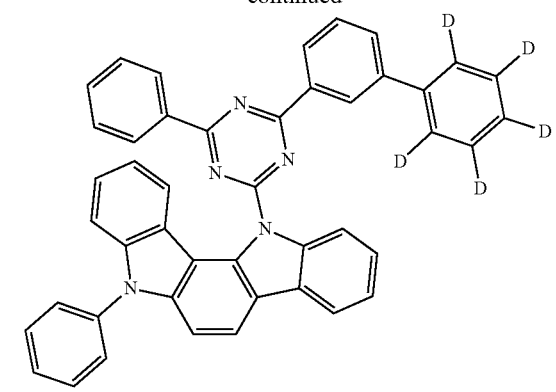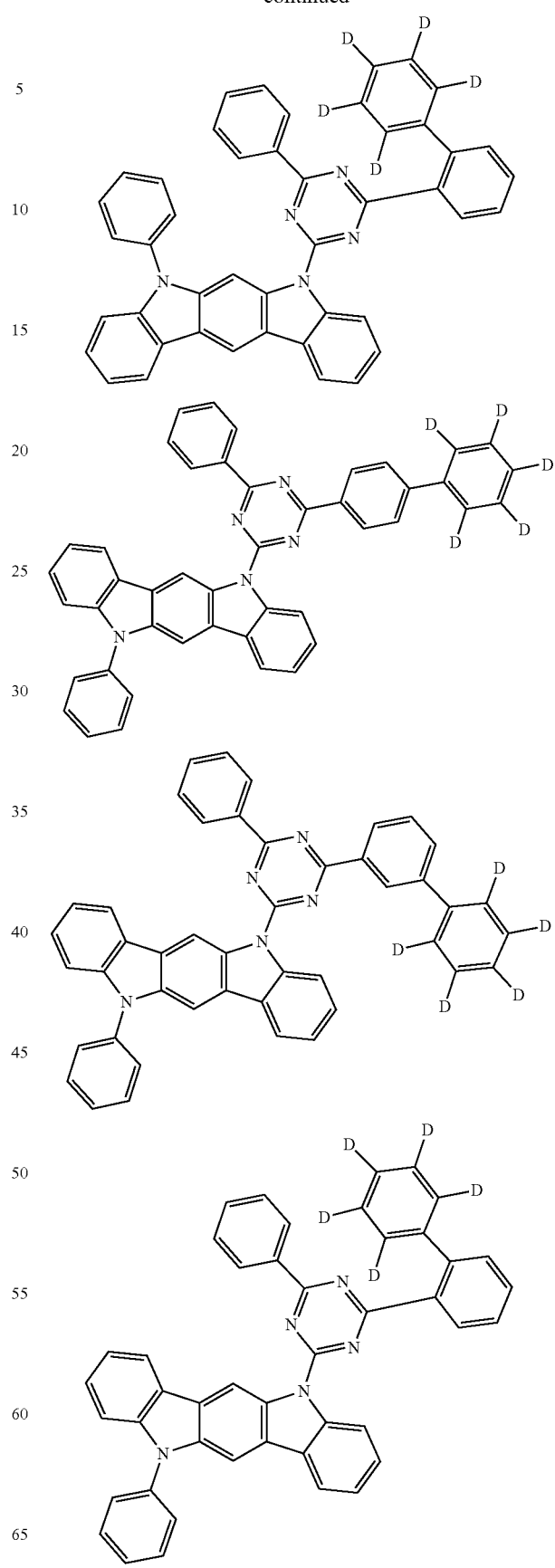

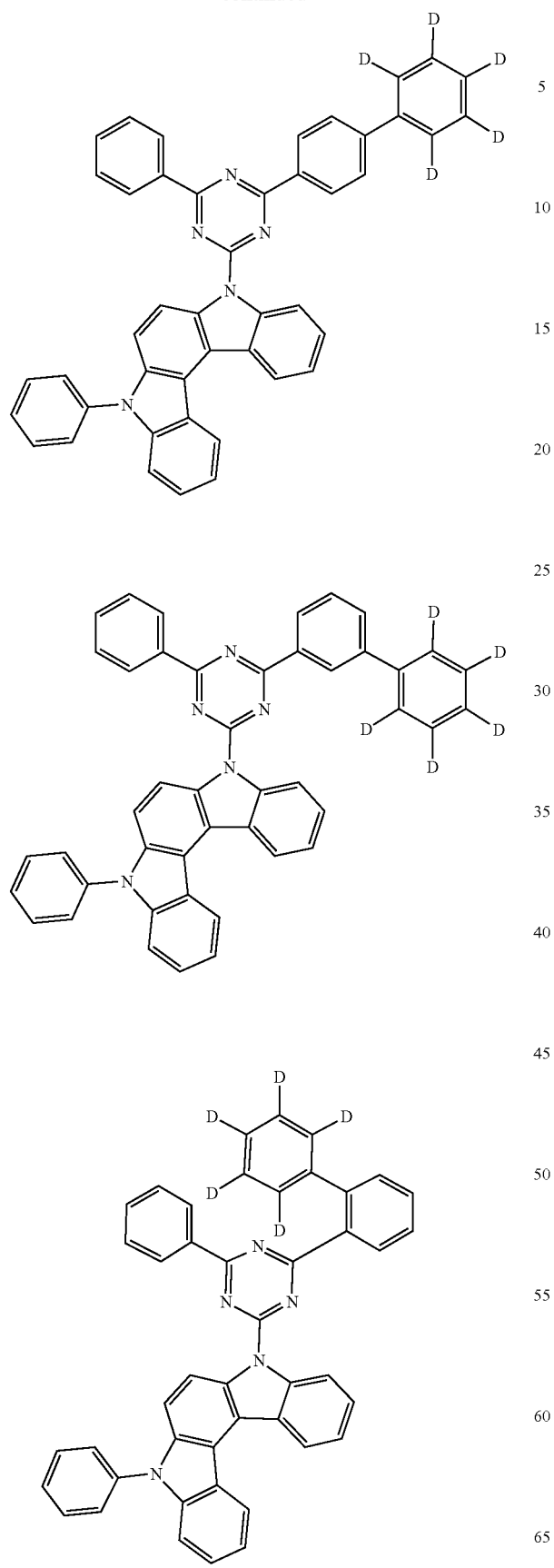
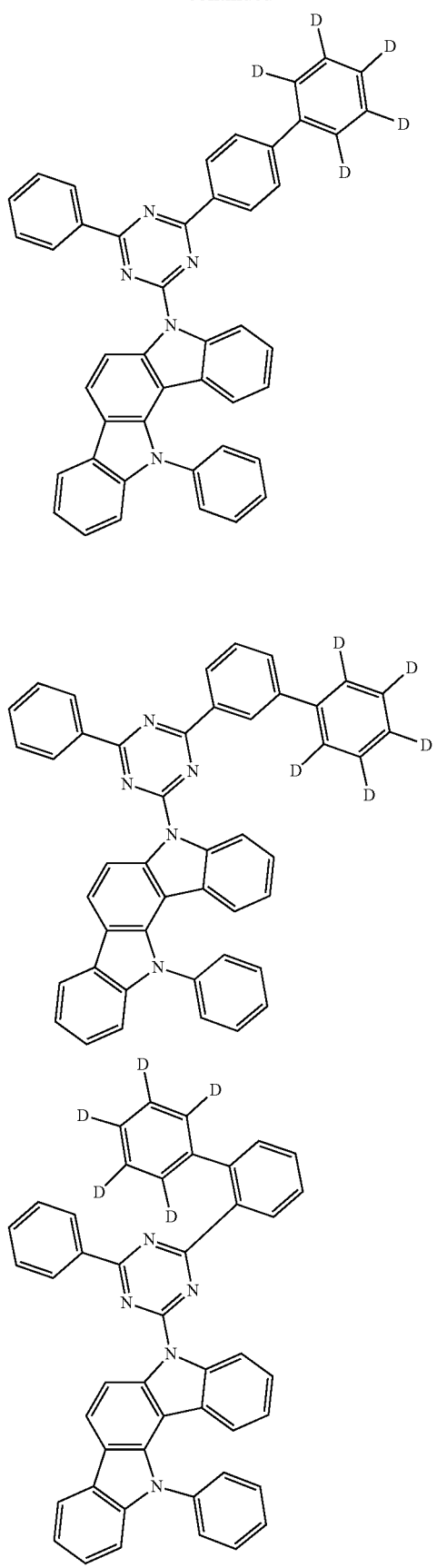

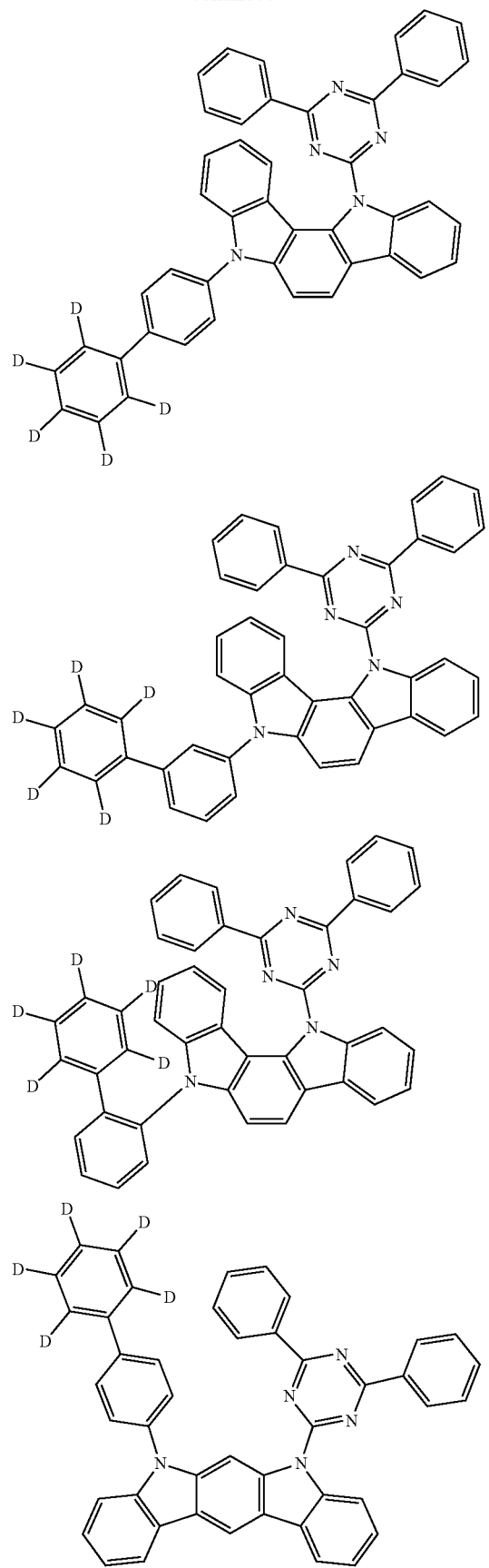
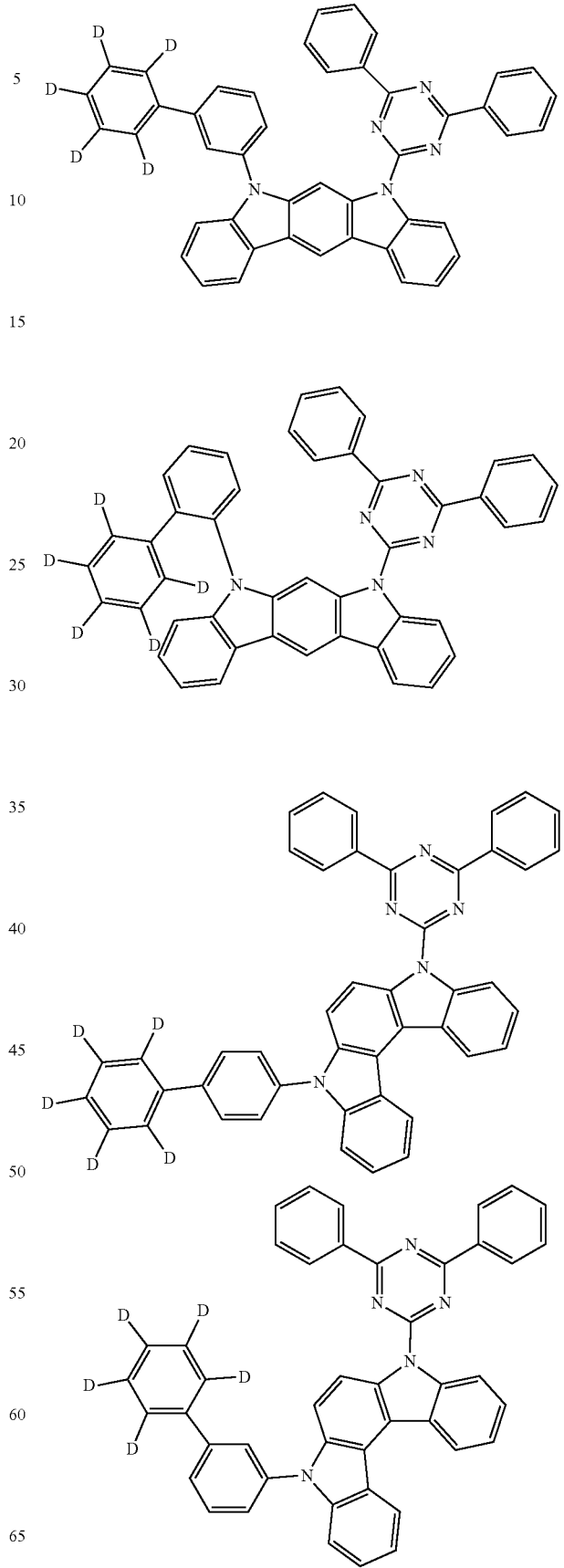

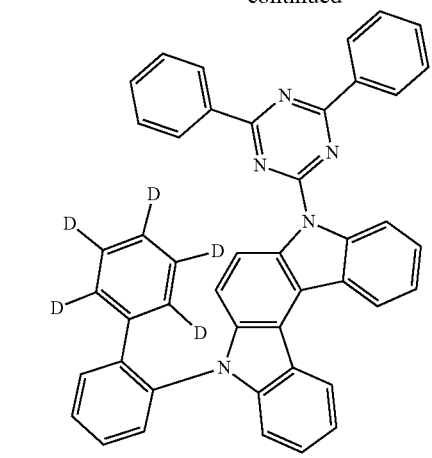
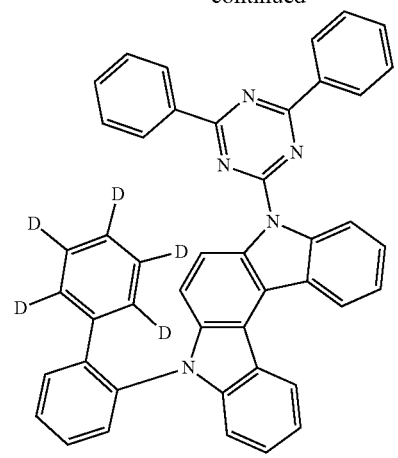
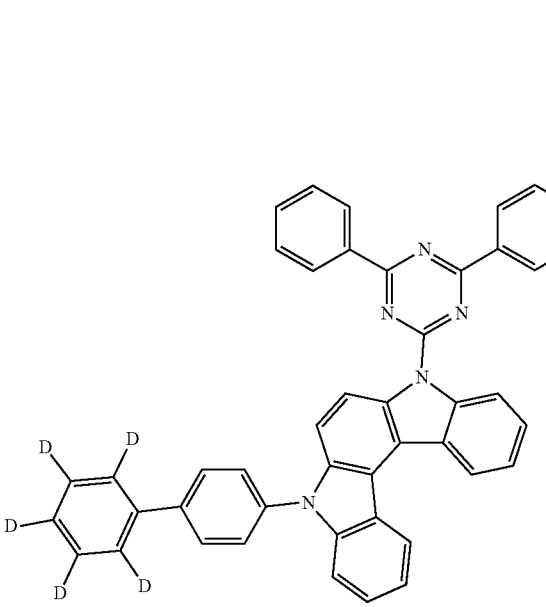
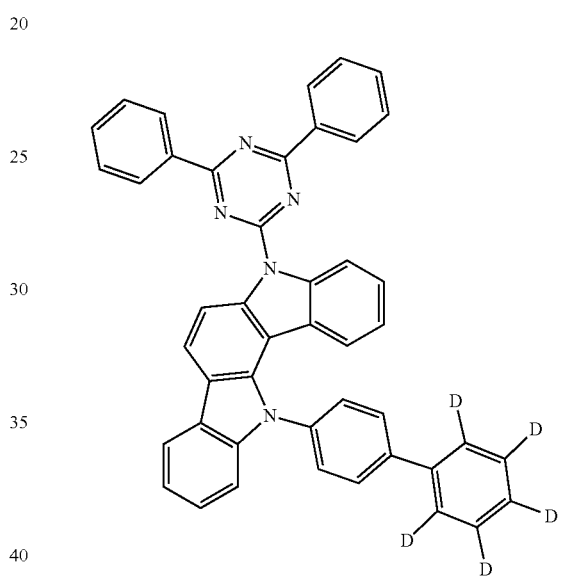
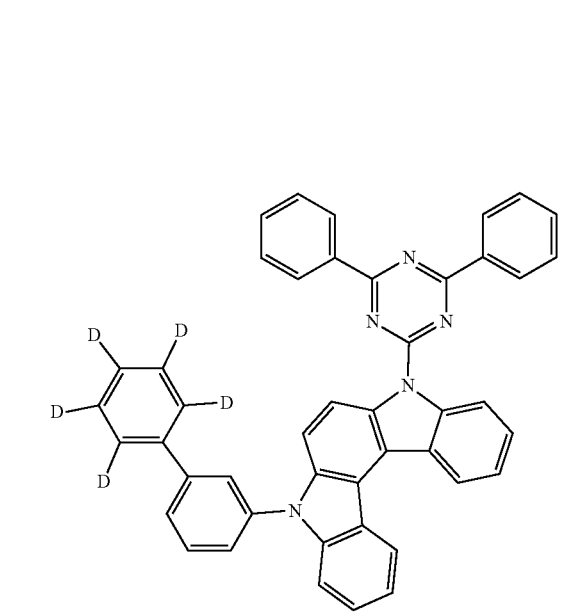
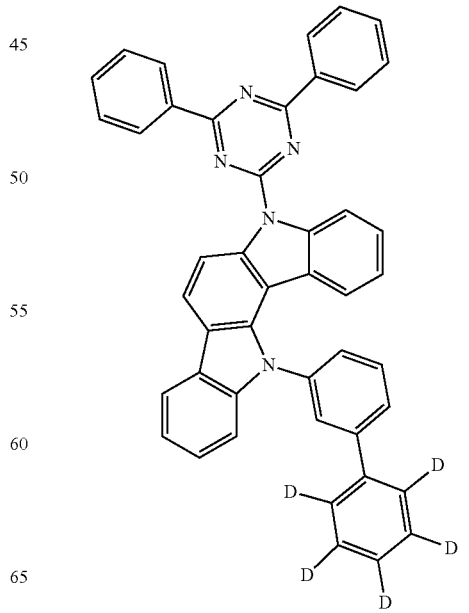

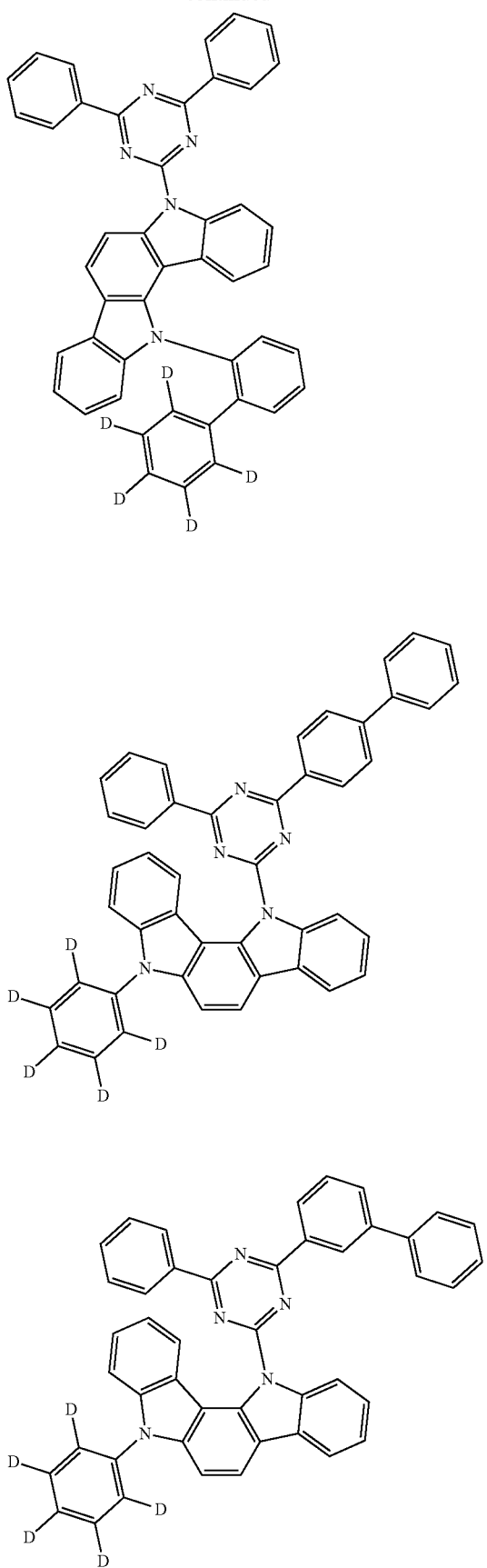
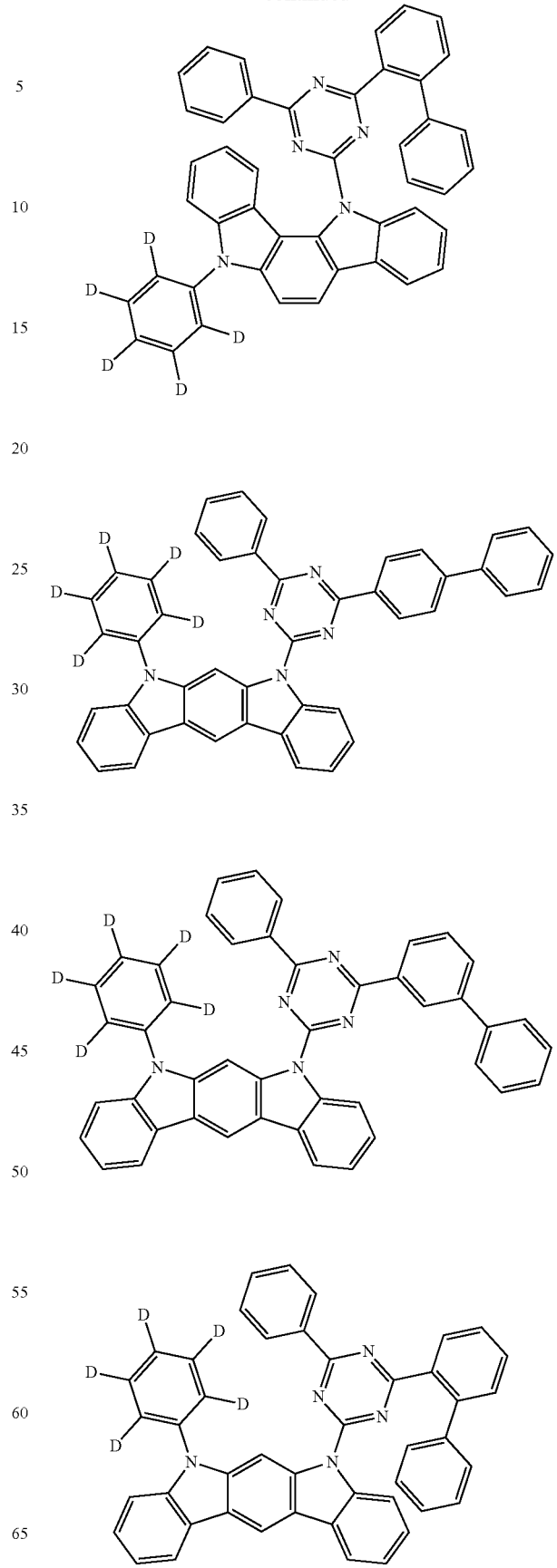

65
-continued
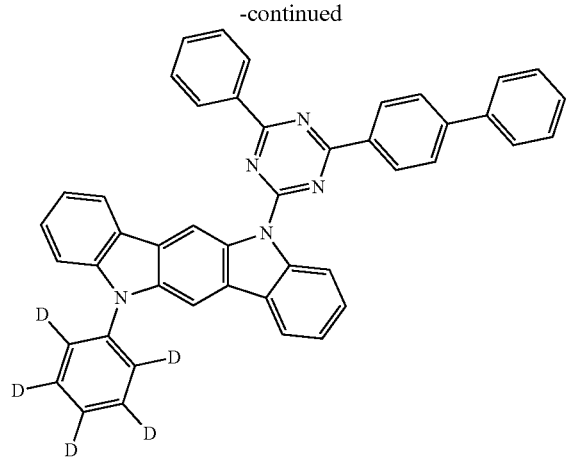
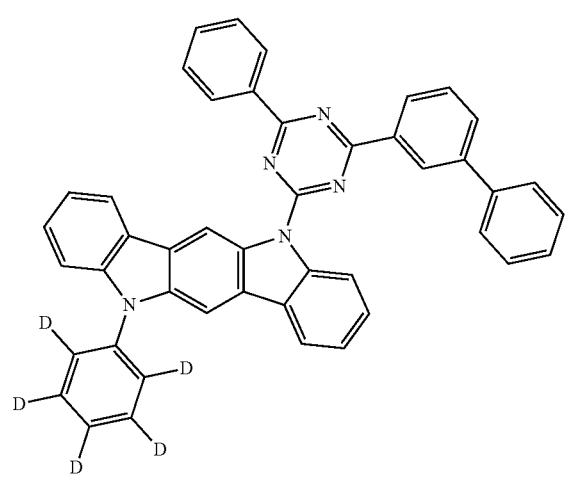
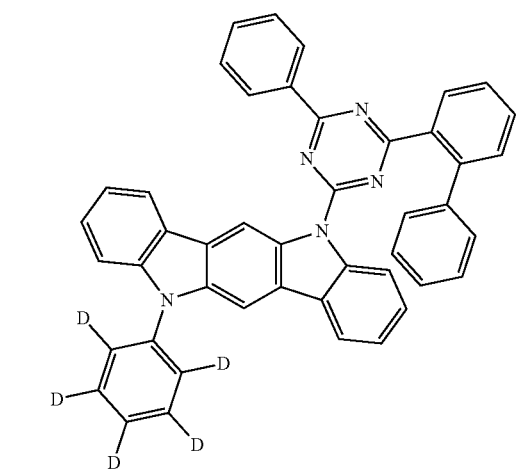
66
-continued
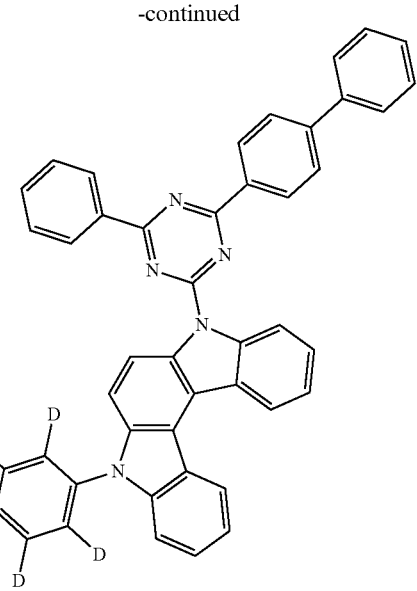
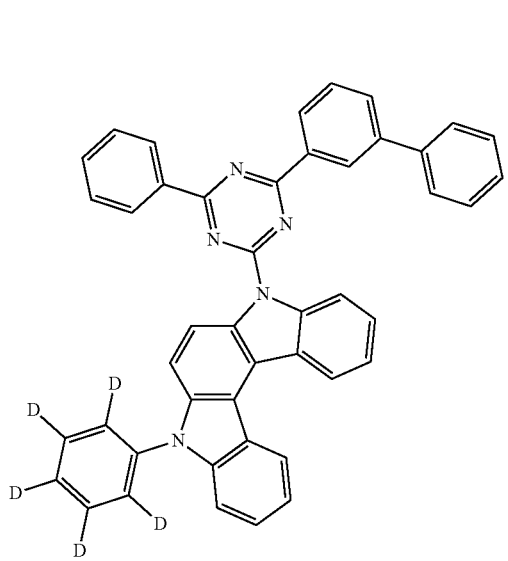
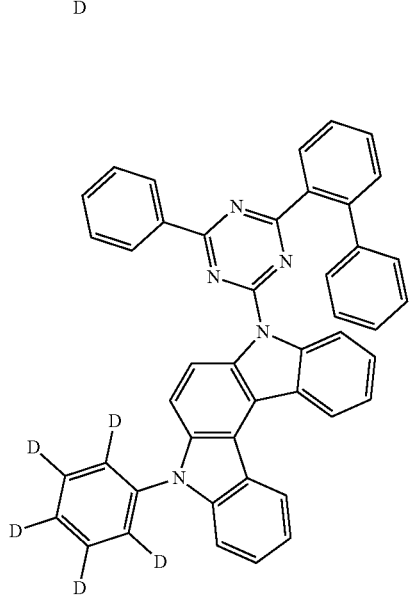

-continued
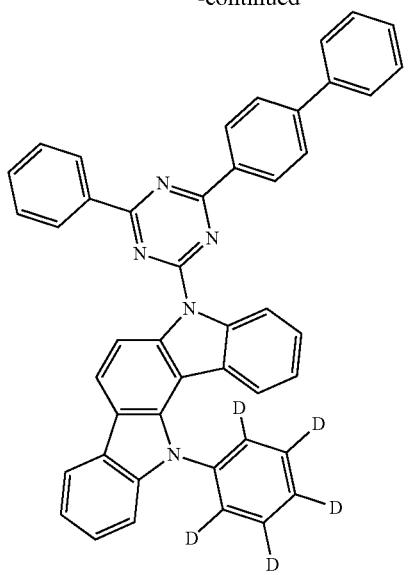
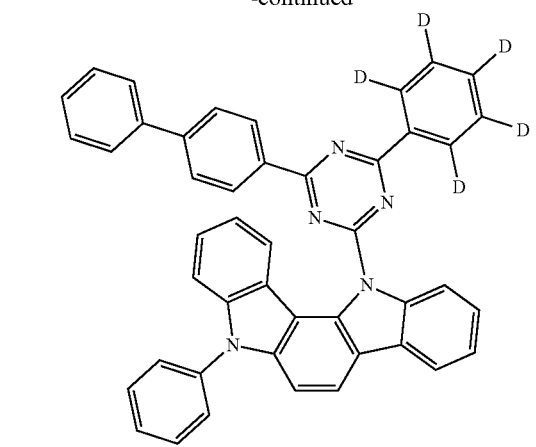
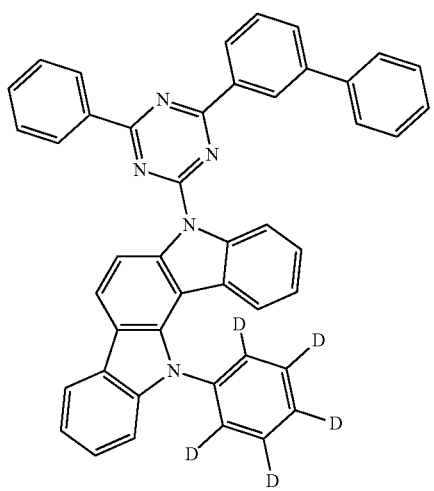
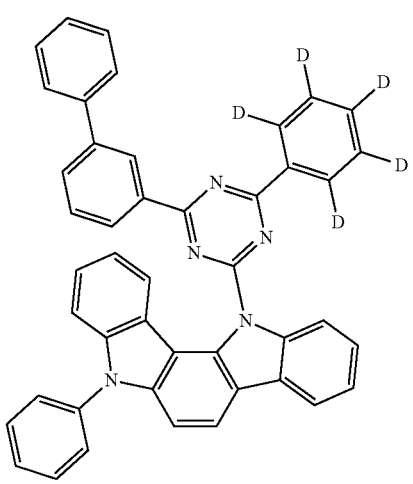
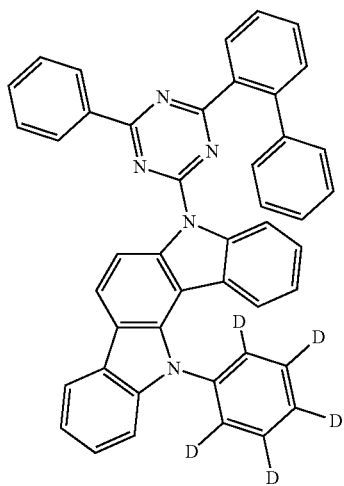
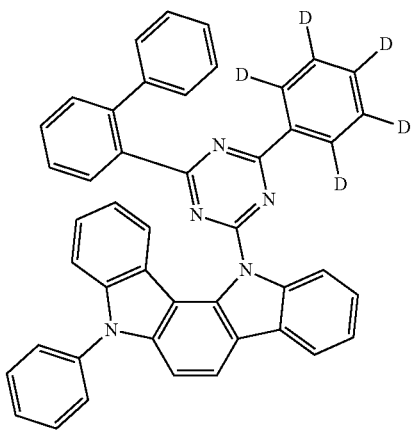

69
-continued
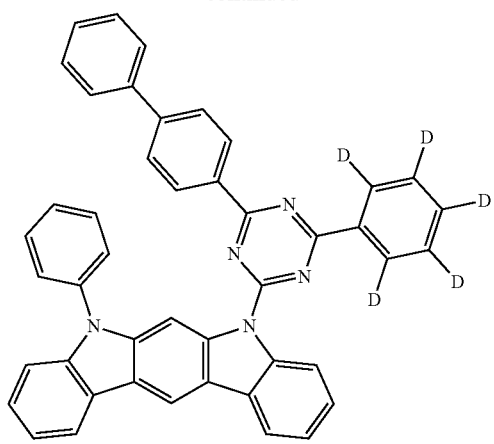
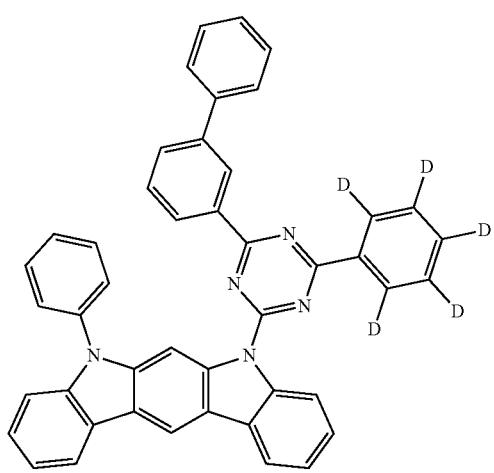
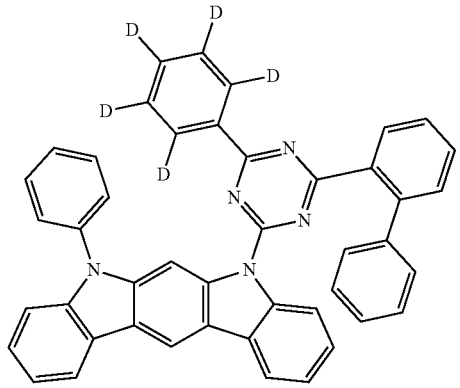
70
-continued
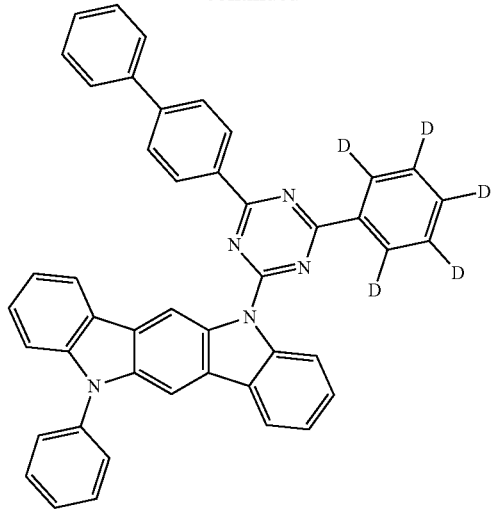
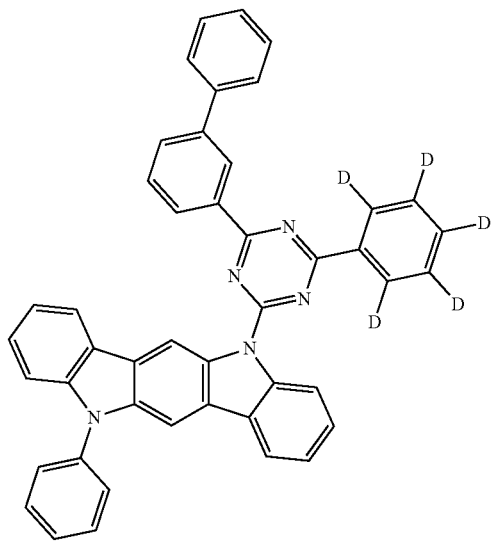
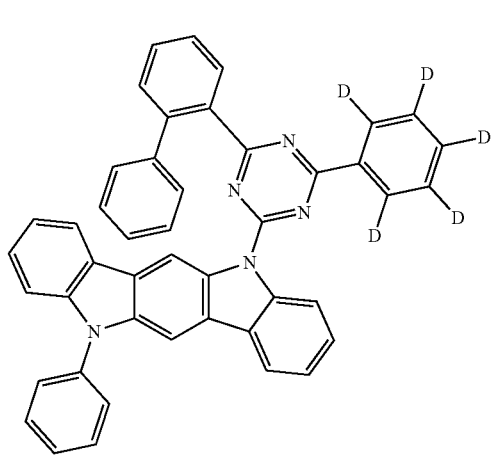

71
-continued
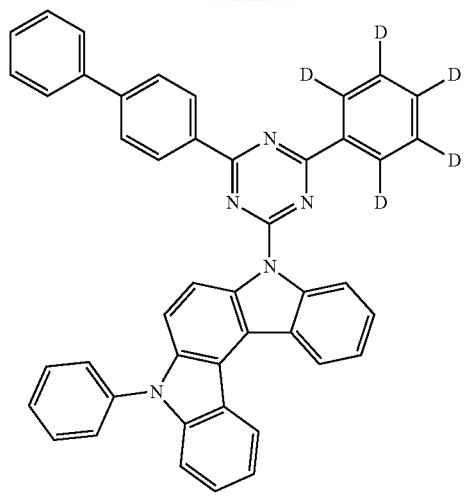
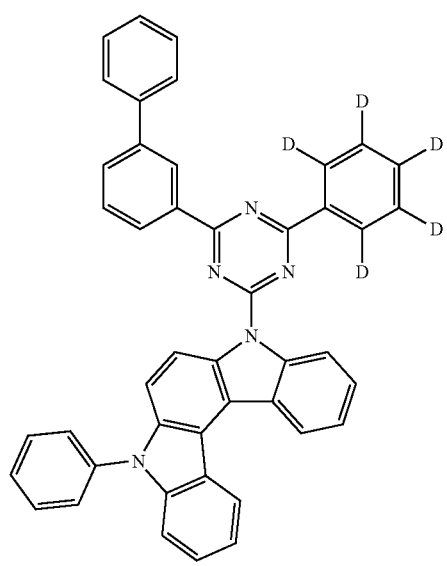
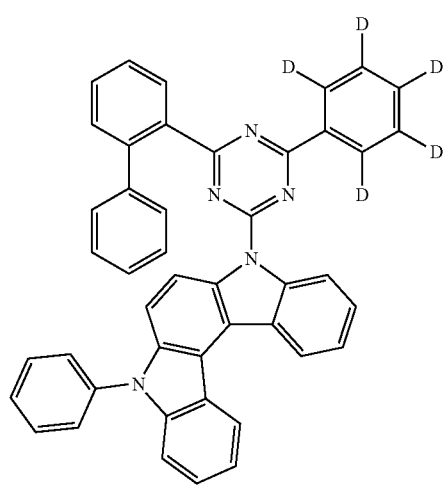
72
-continued
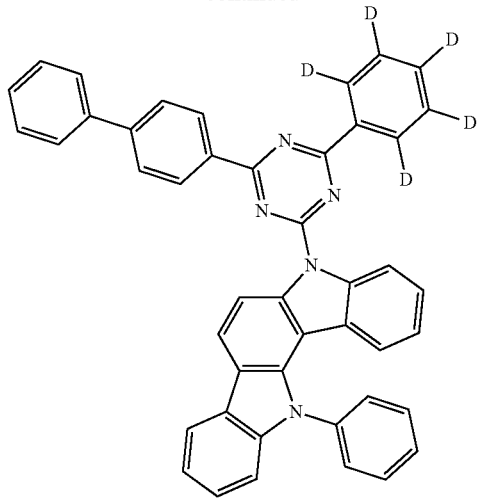
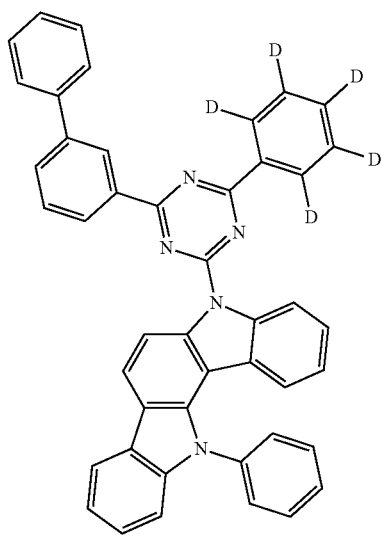
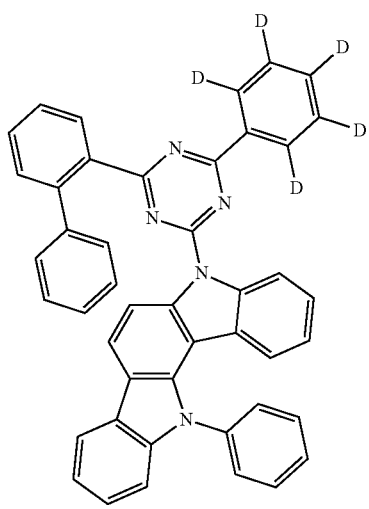

73
-continued
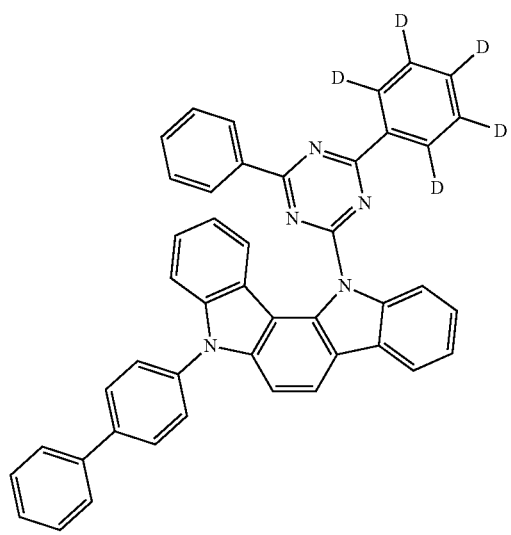
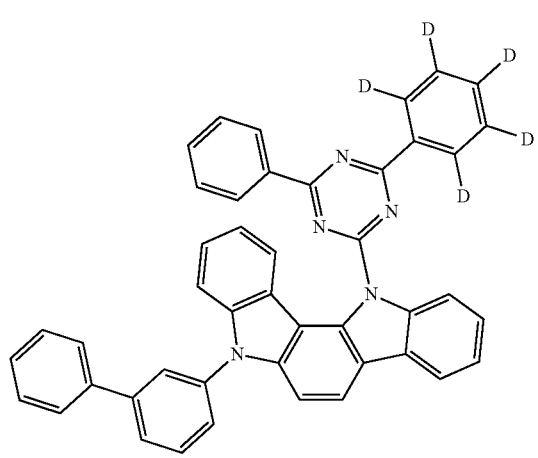
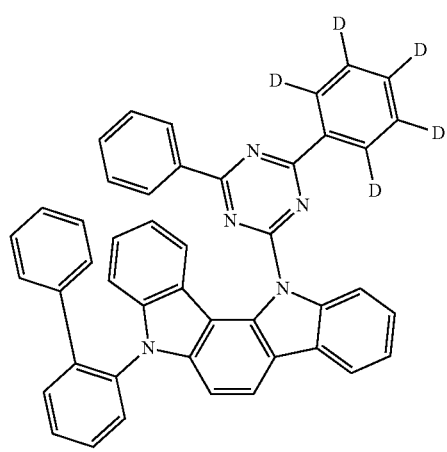
74
-continued
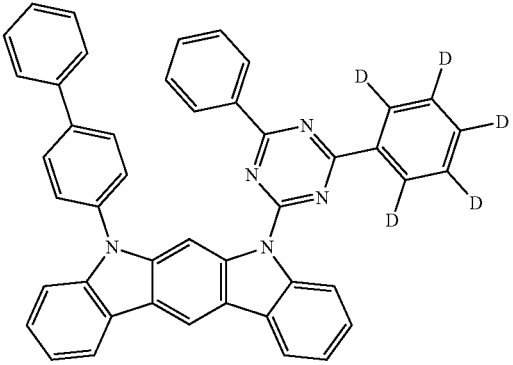
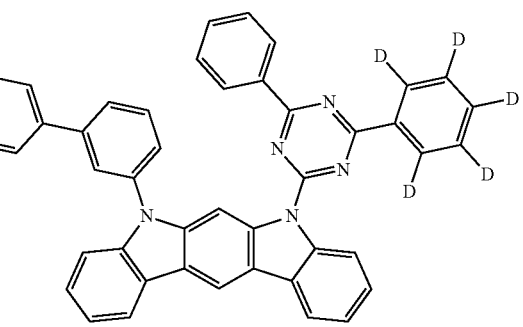
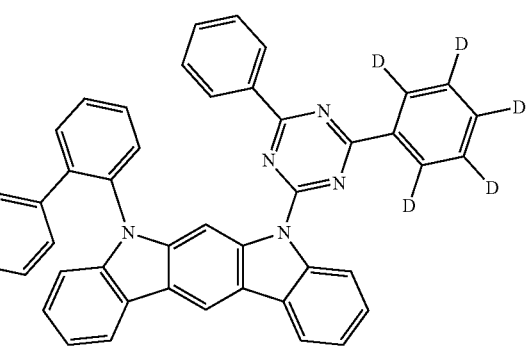
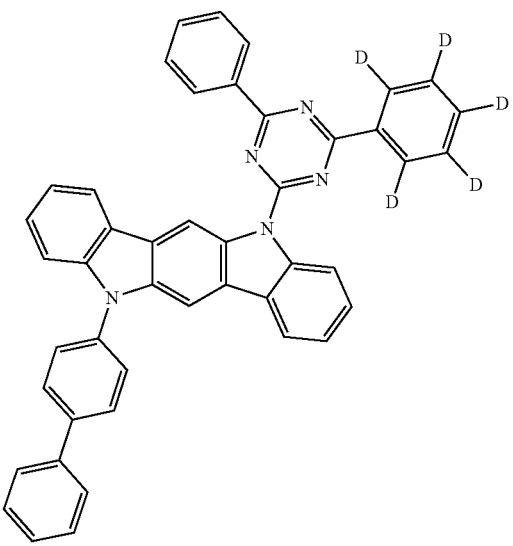

75

76

-continued
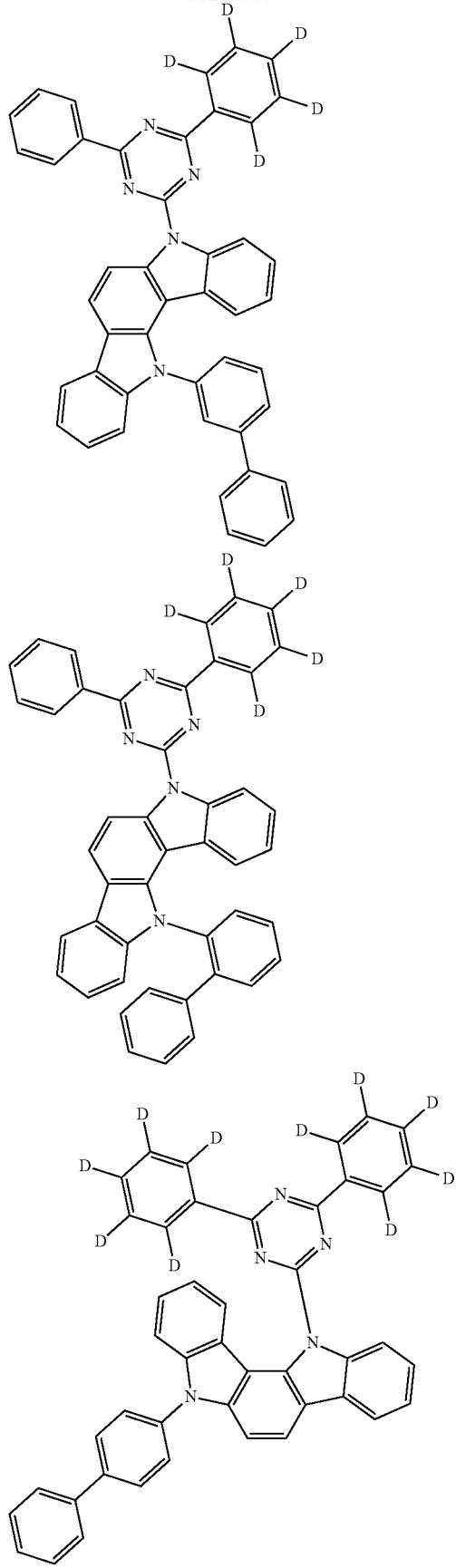
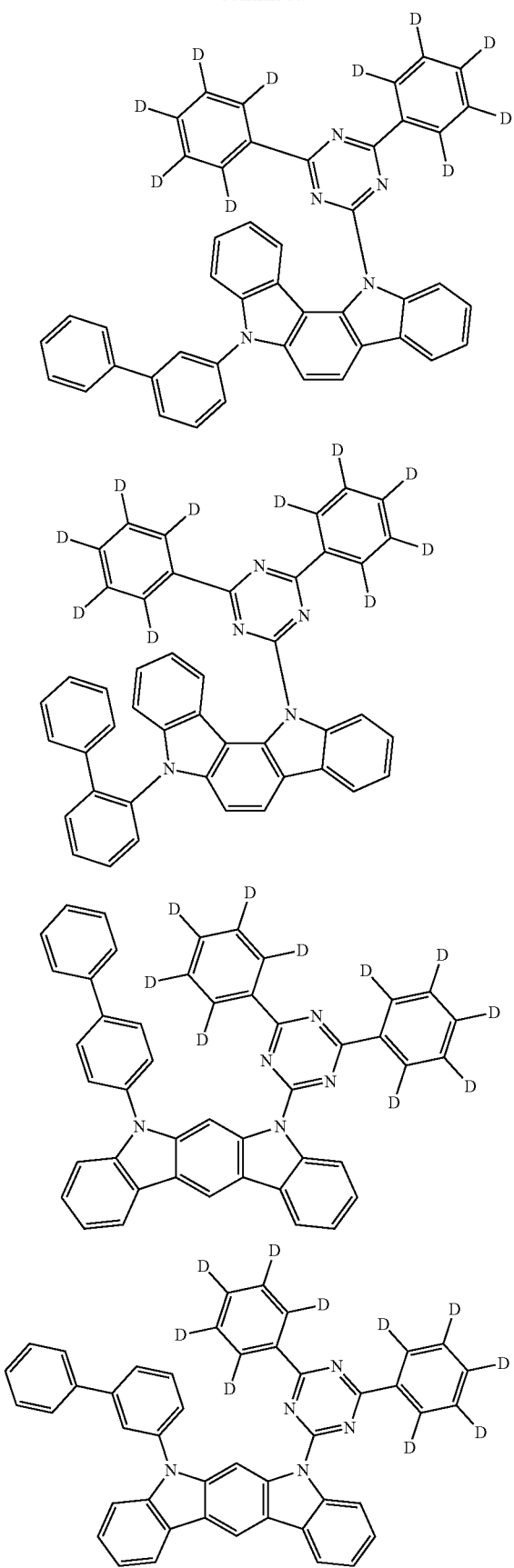

-continued
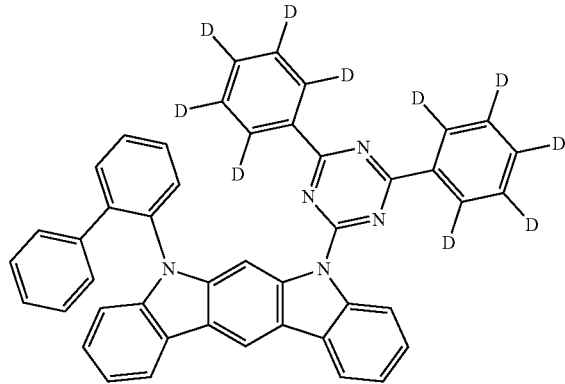
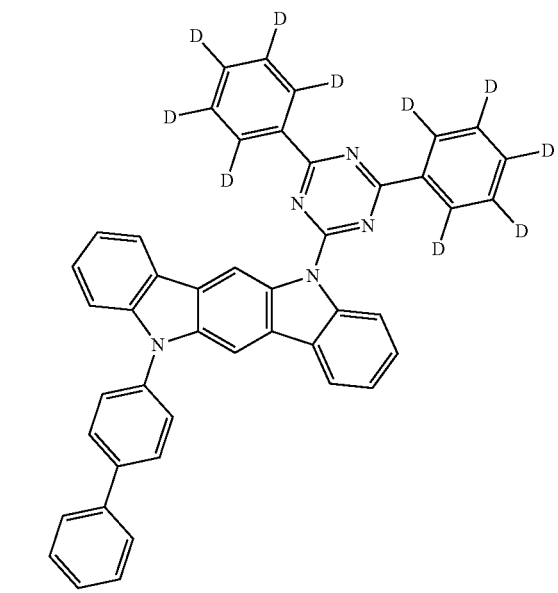
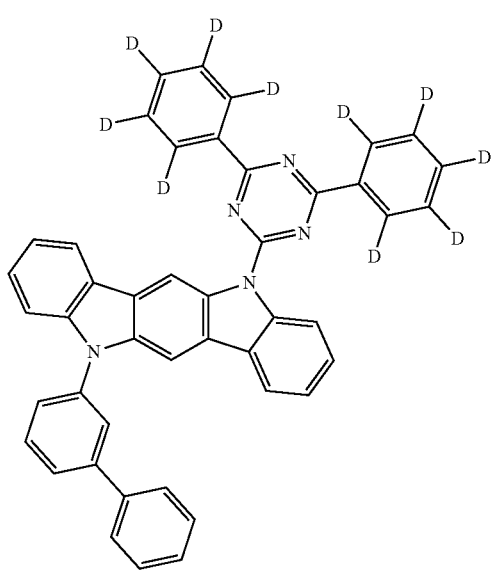
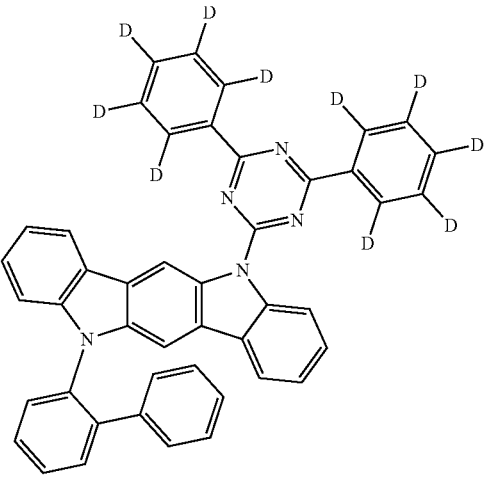
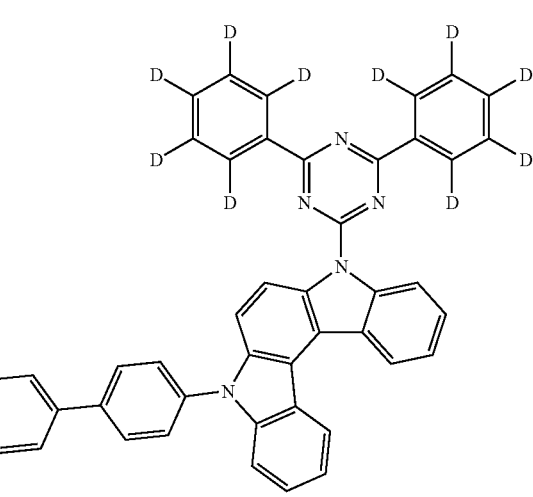
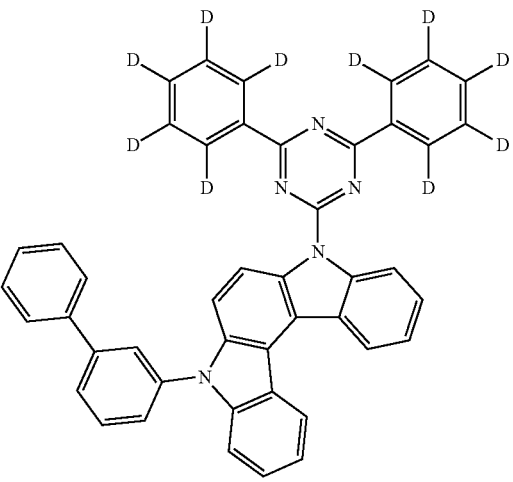

-continued
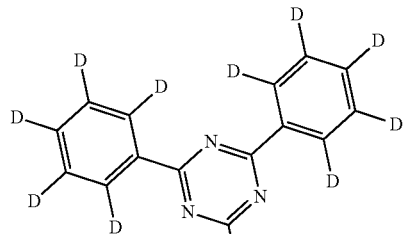
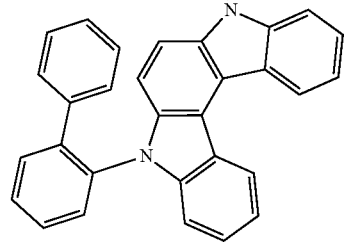
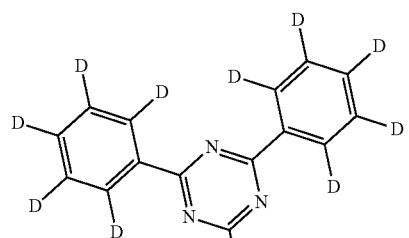
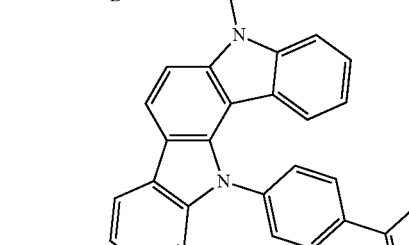
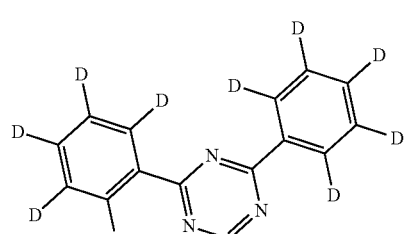
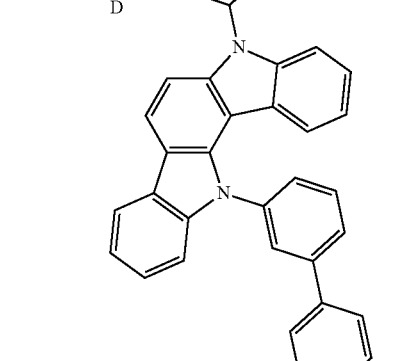
-continued
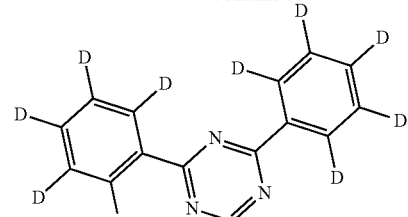
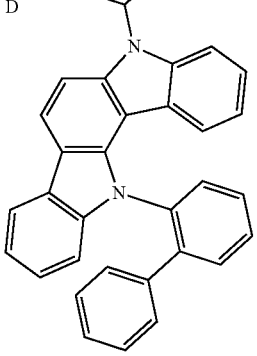
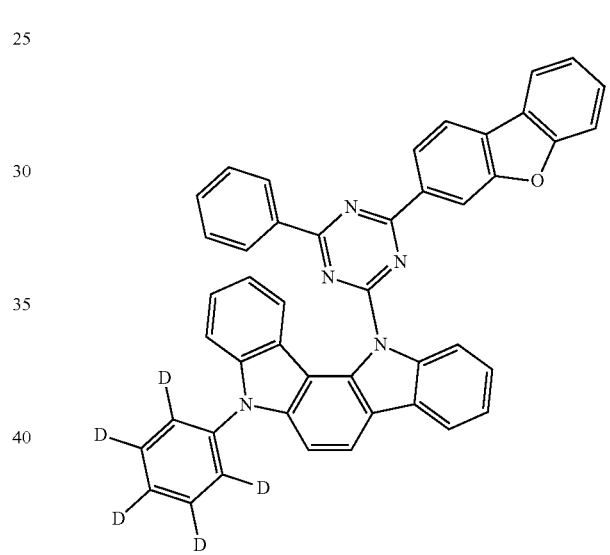
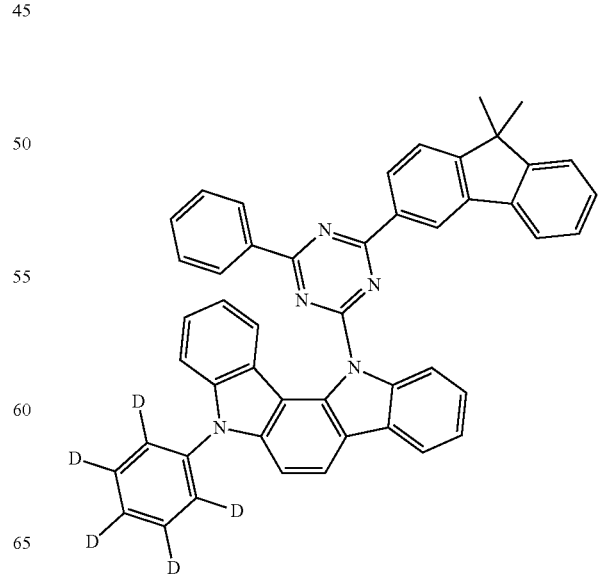

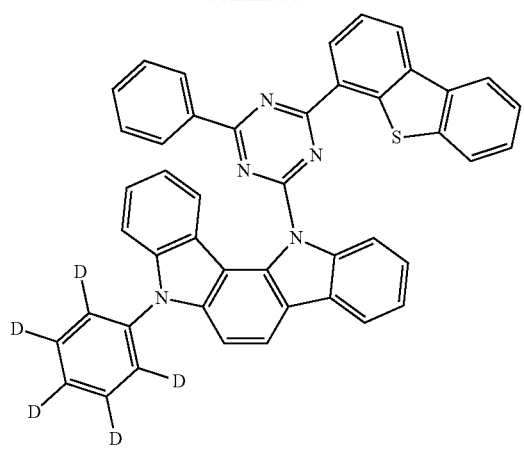
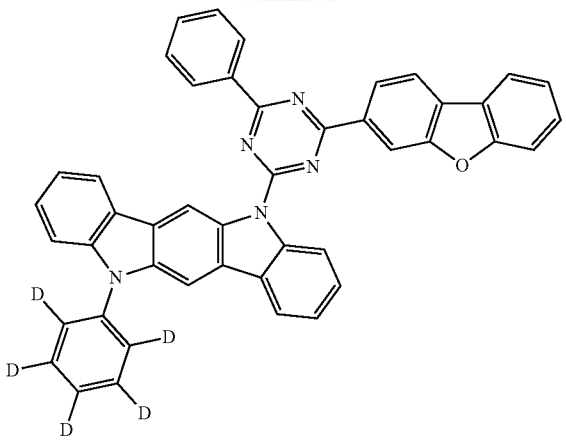
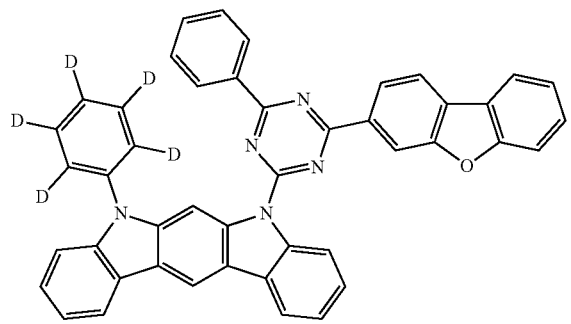
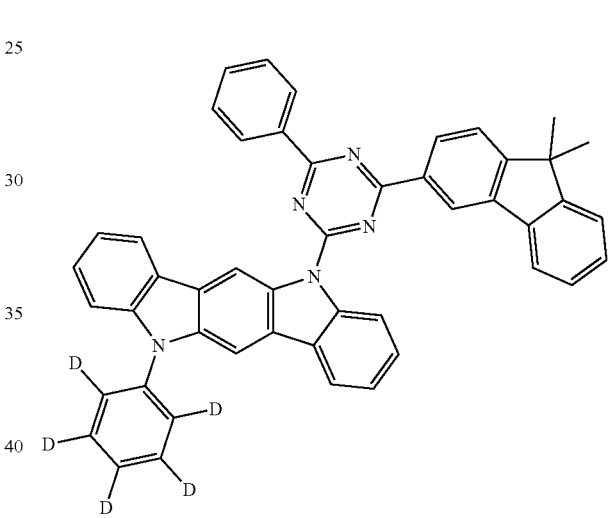
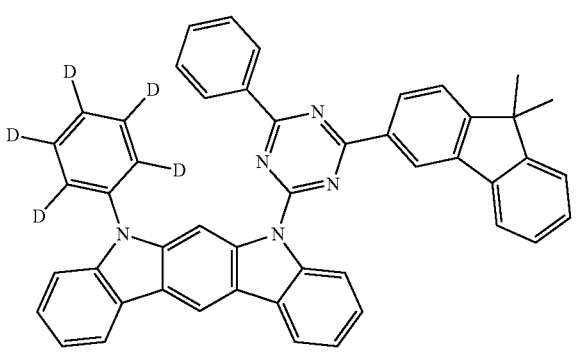
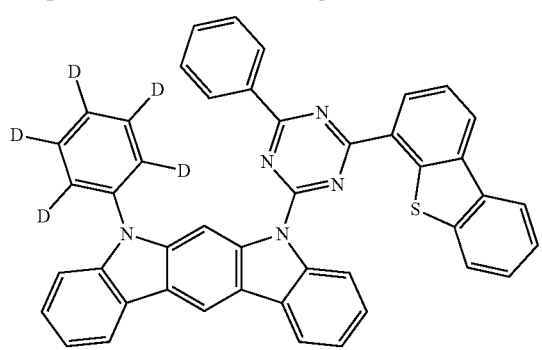
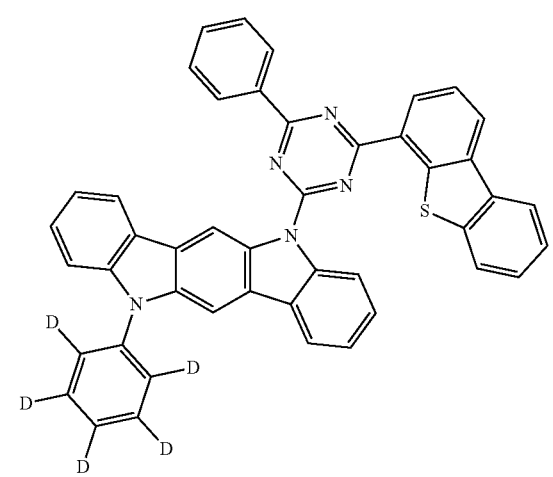

85
-continued
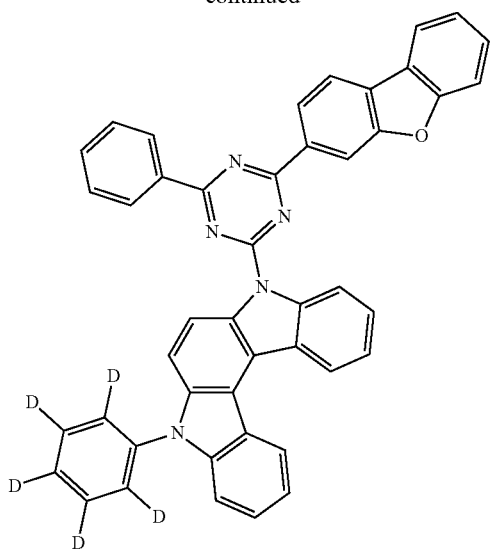
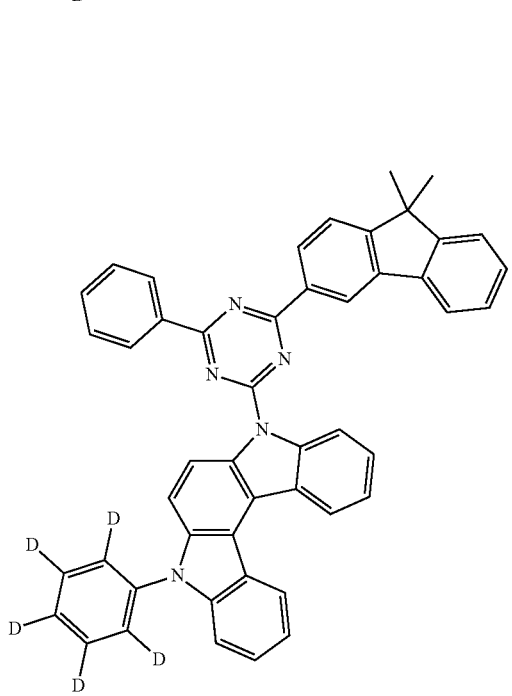
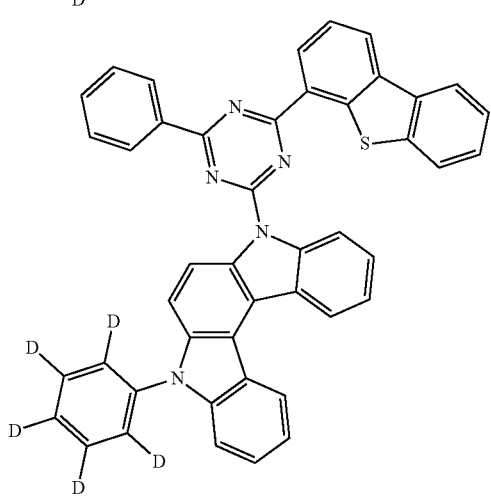
86
-continued
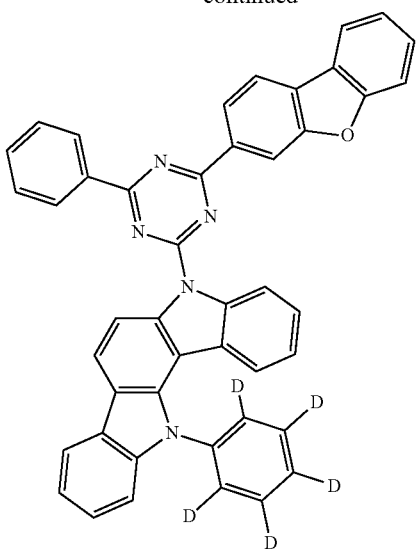
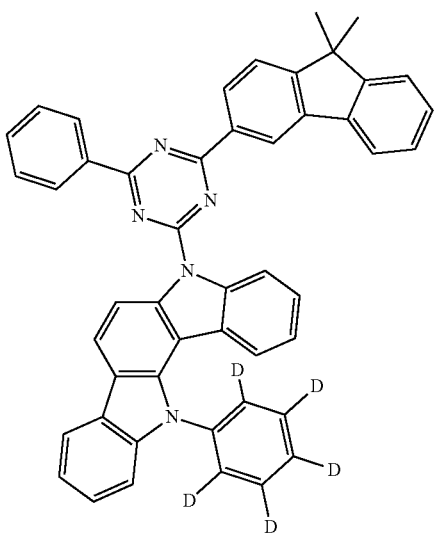
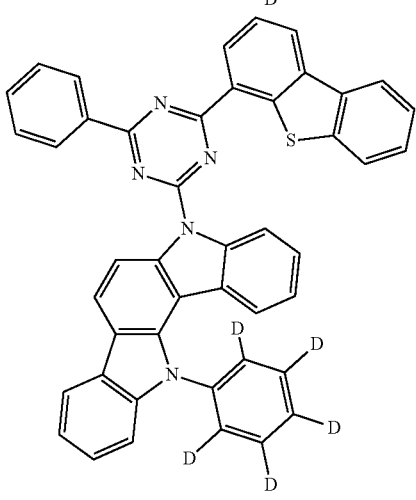

87
-continued
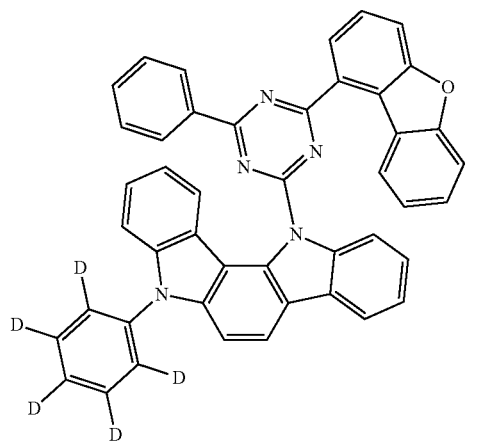
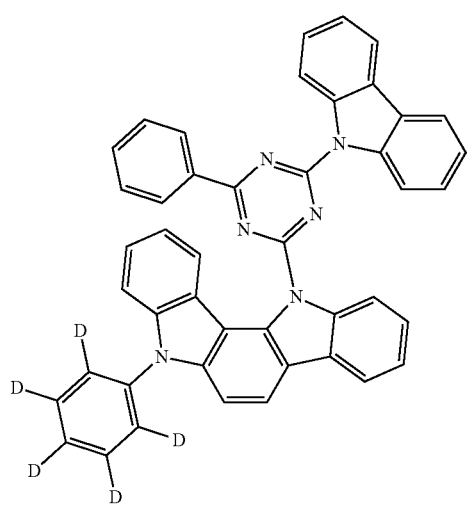
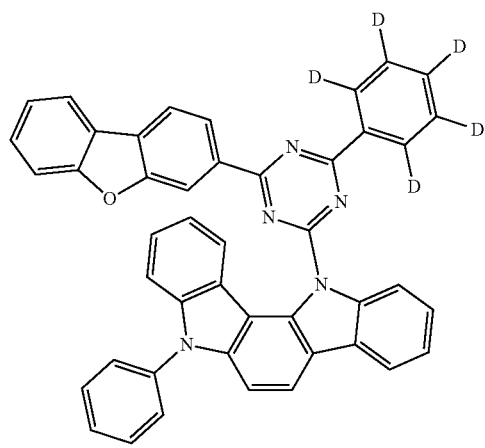
88
-continued
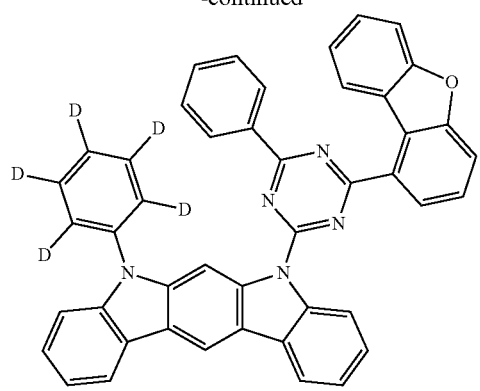
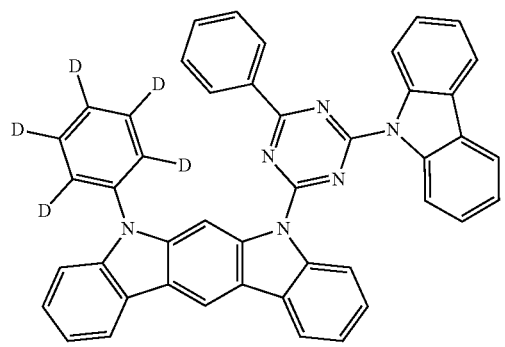
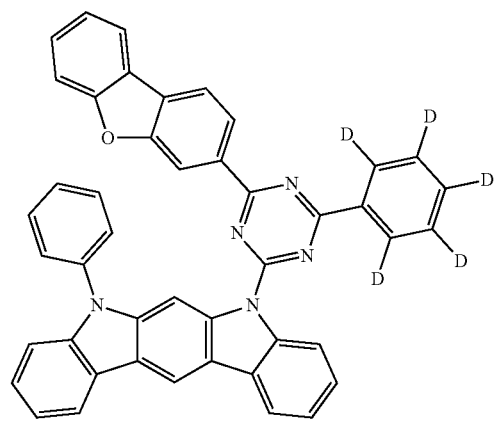
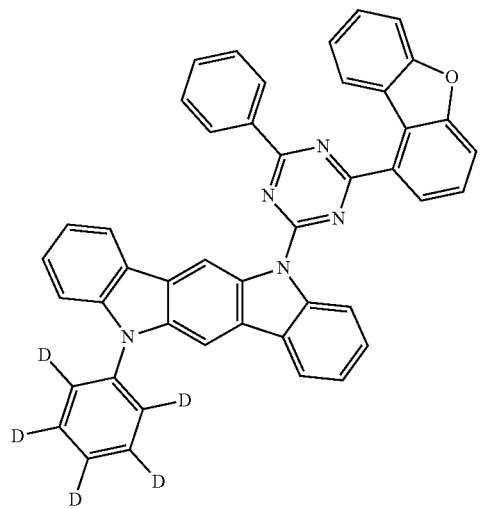

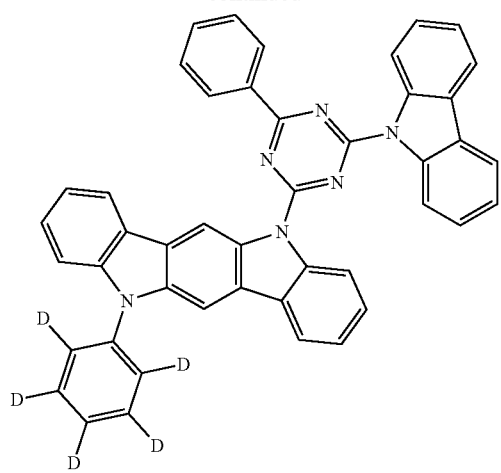
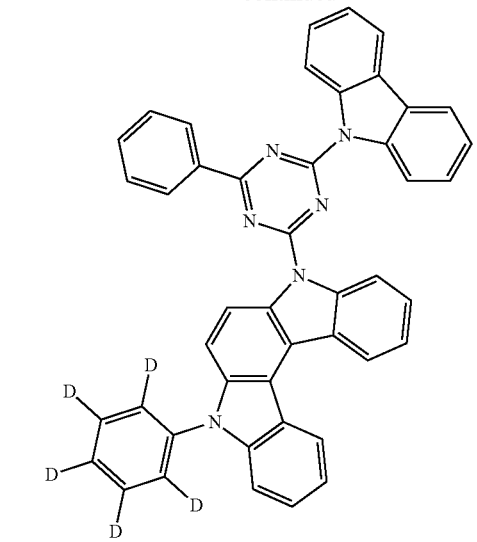
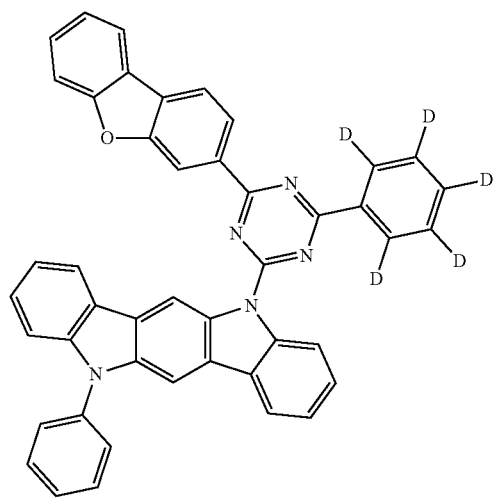
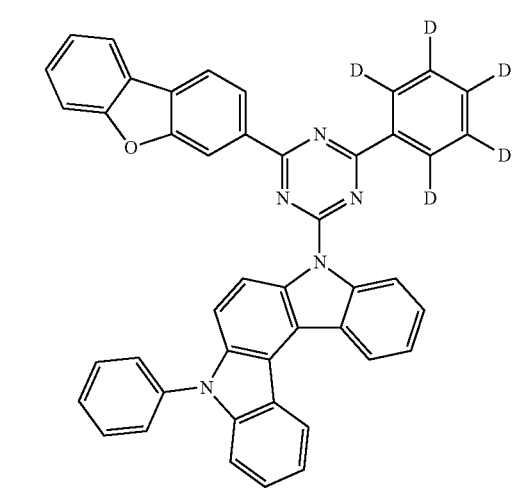
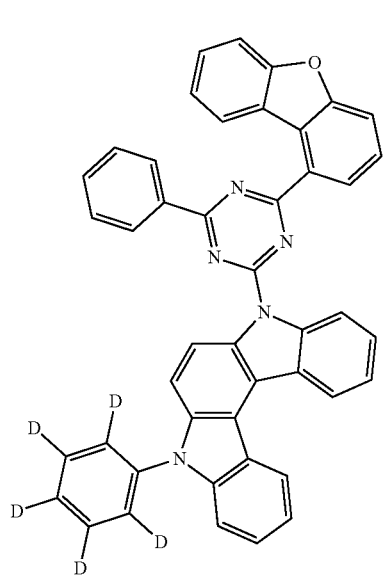
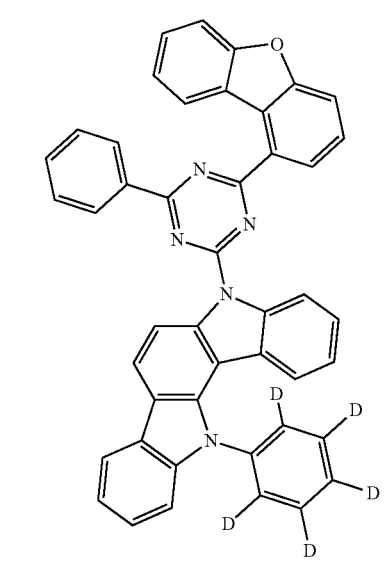

91
-continued
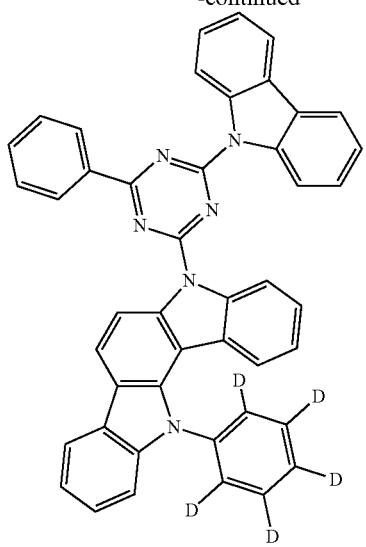
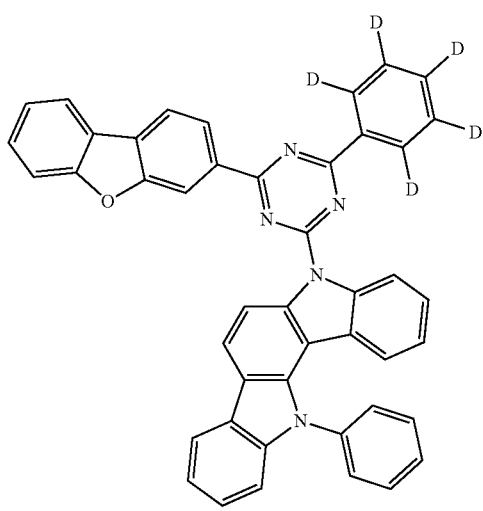
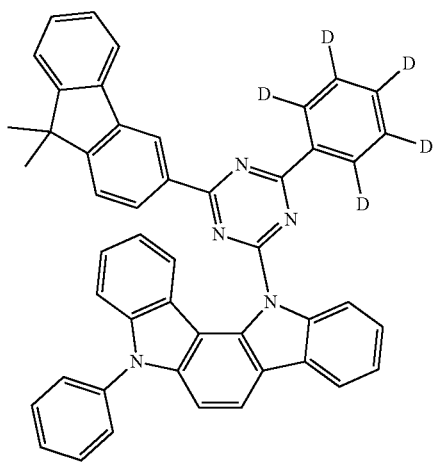
92
-continued
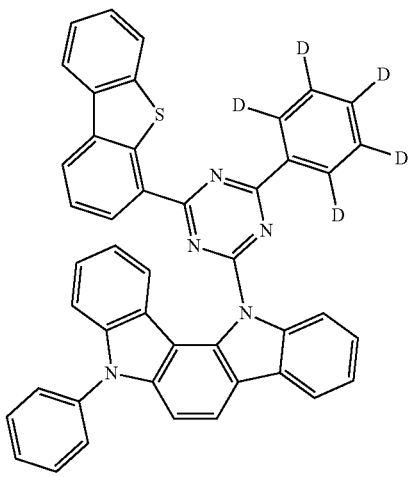
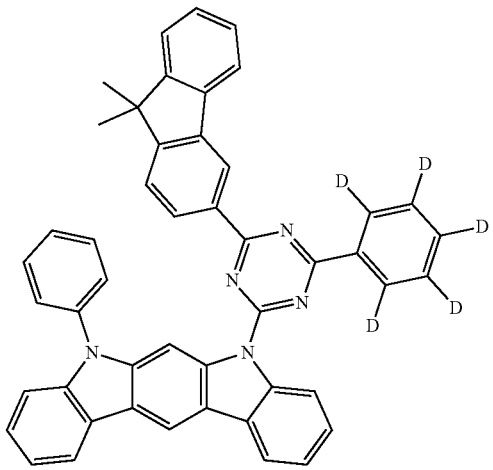

93
-continued
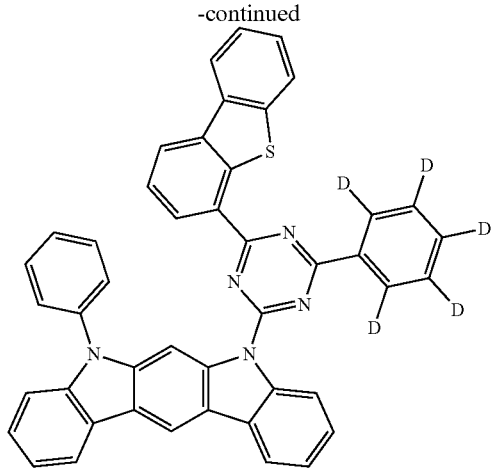
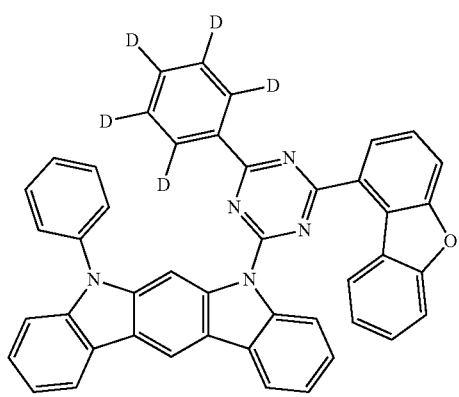
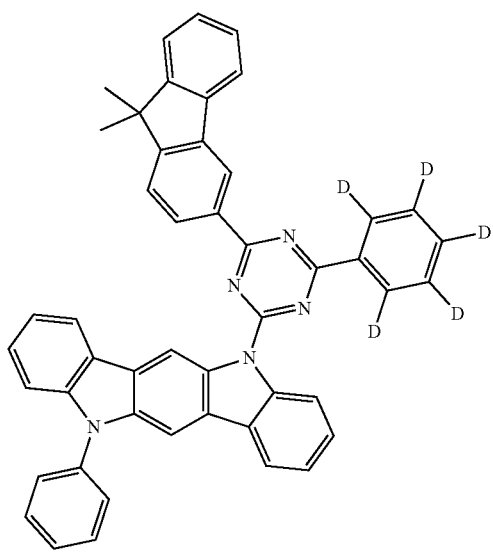
94
-continued
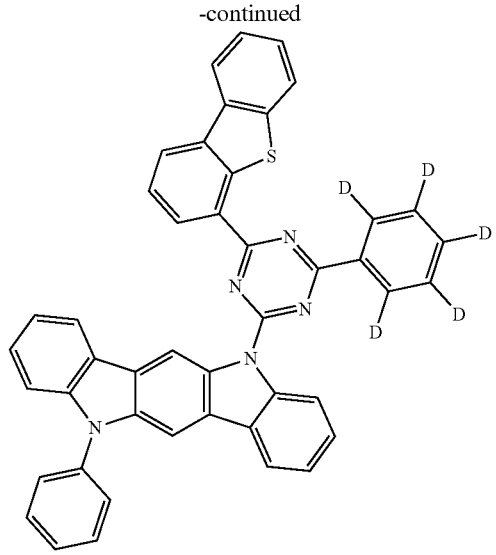
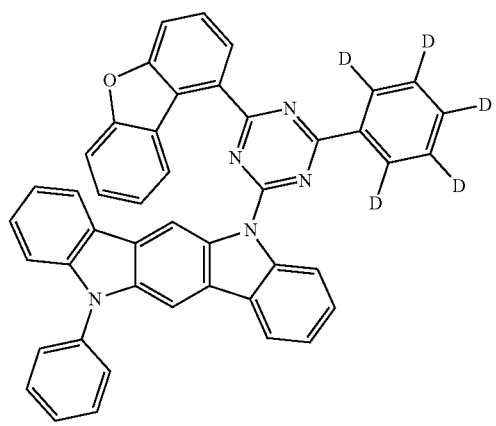
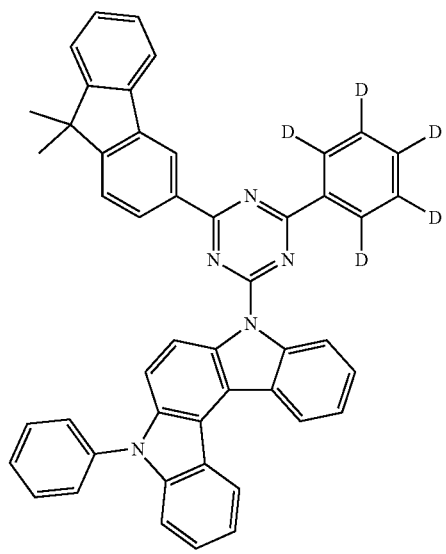

95
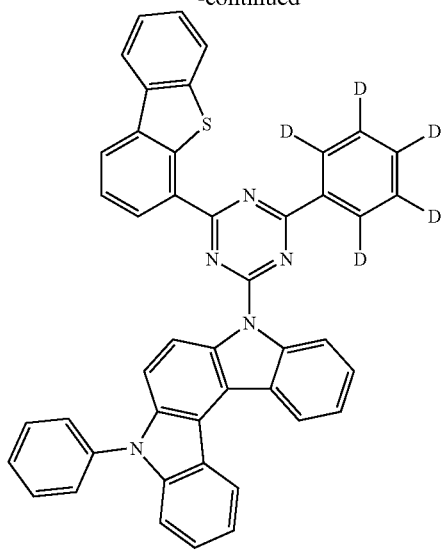
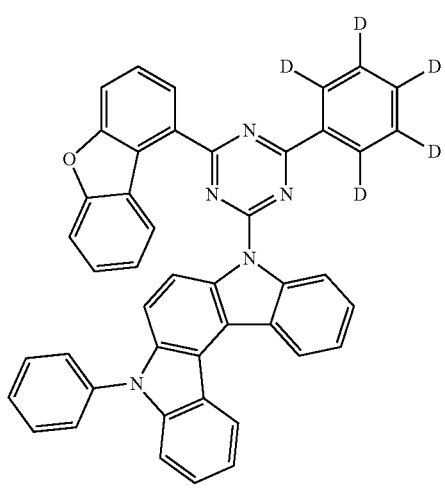
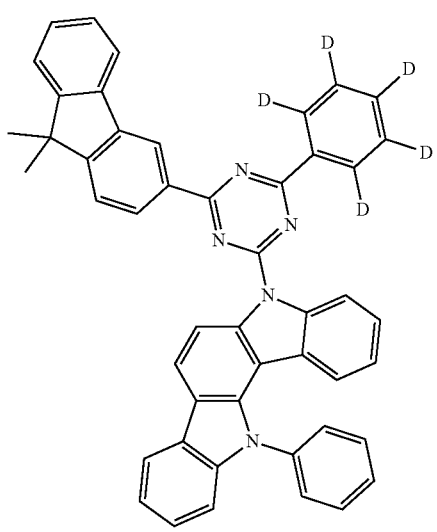
96
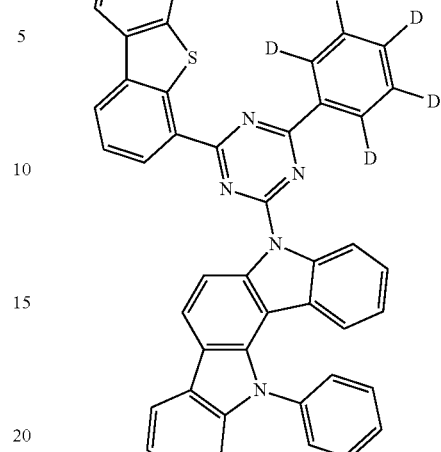
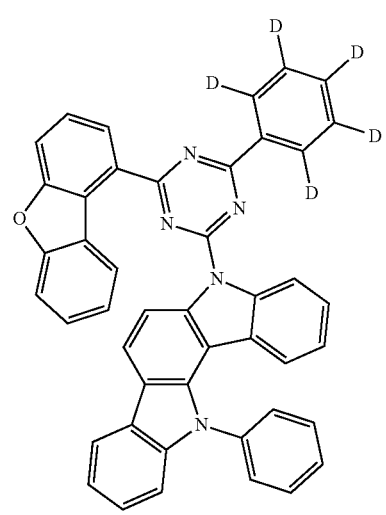
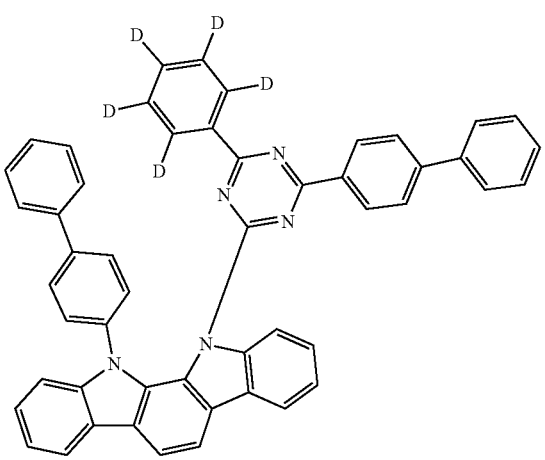

97
-continued
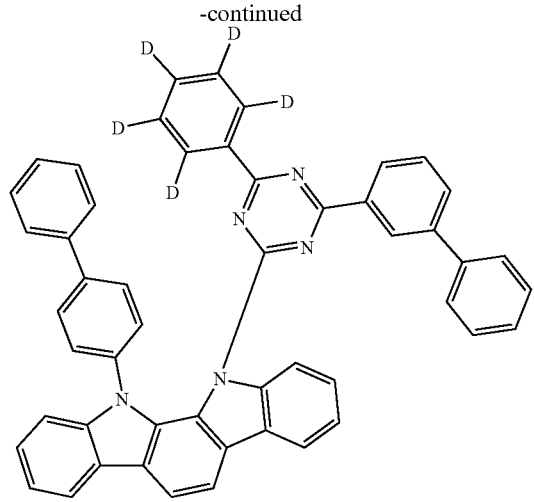
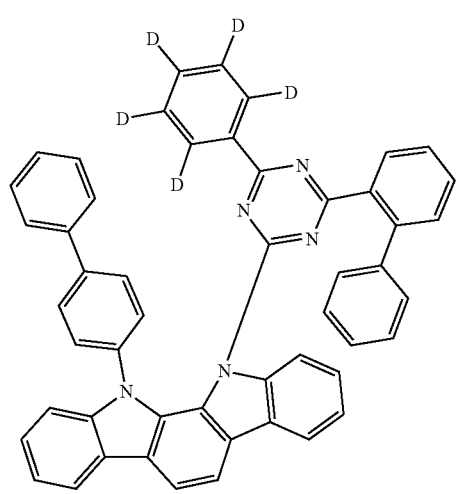
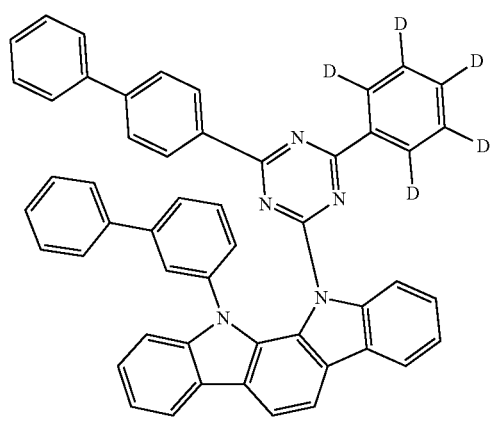
98
-continued
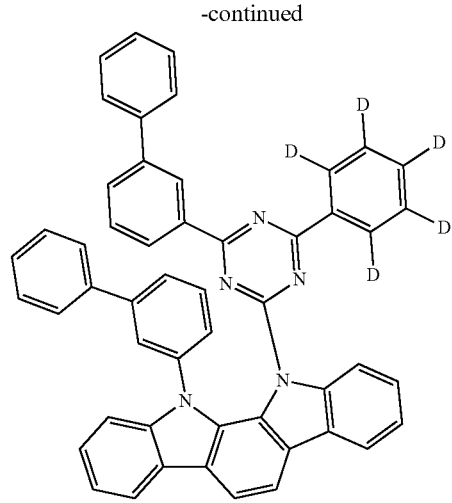
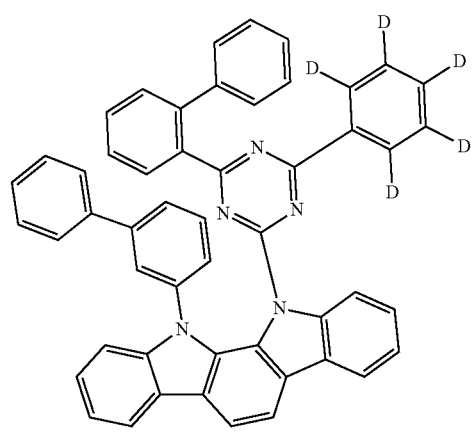
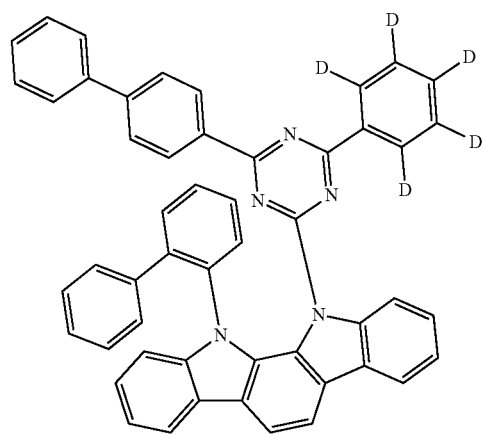

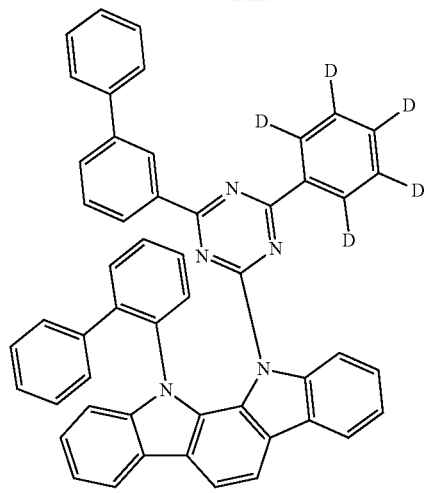
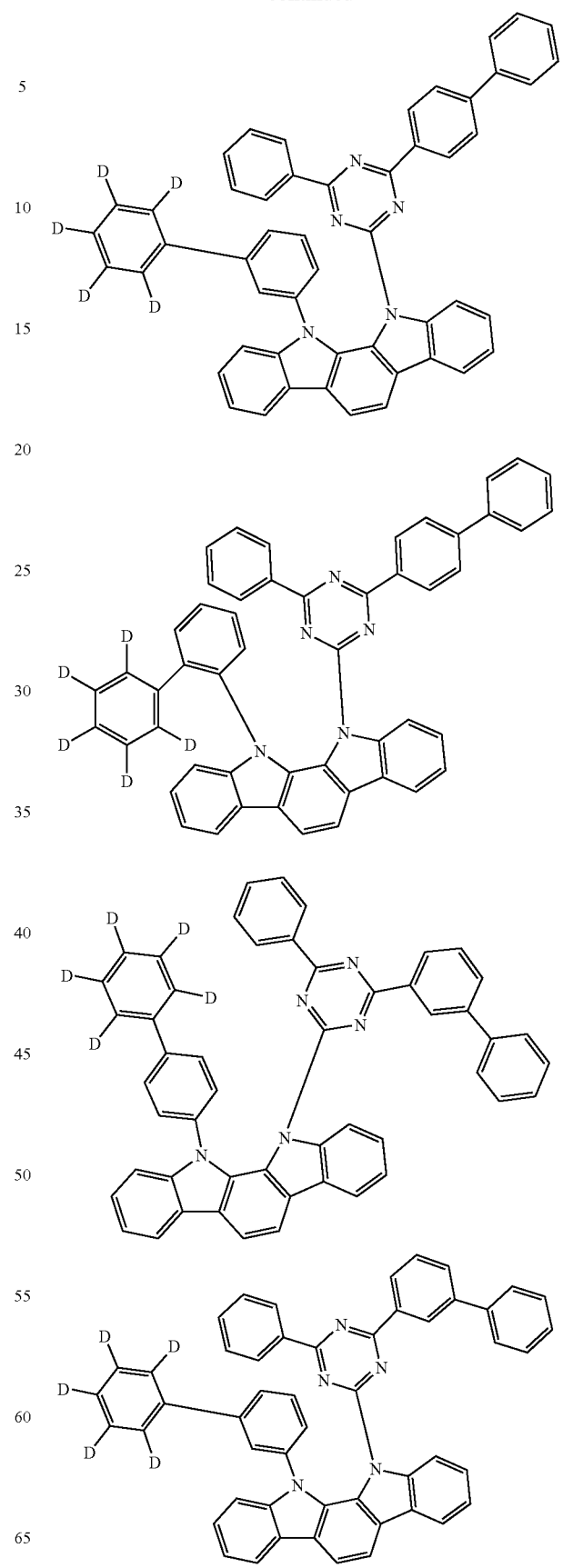

101
-continued
102
-continued
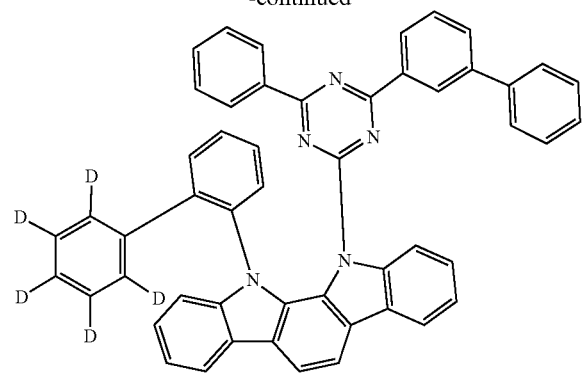
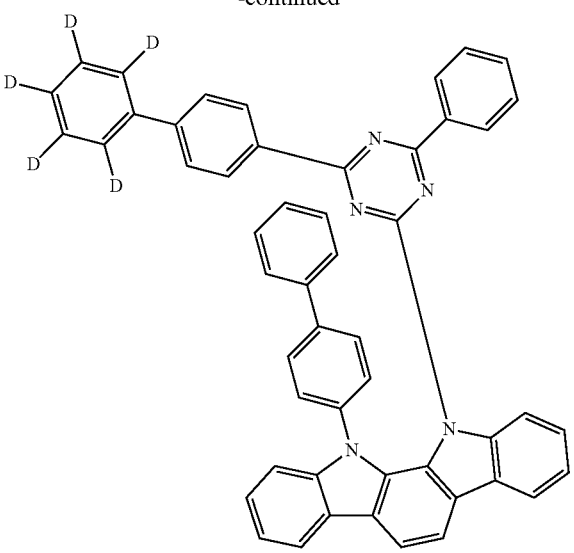
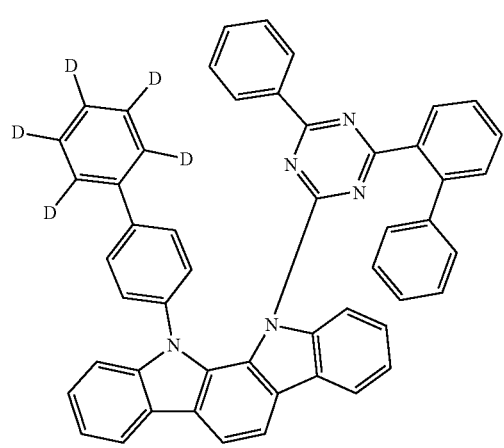
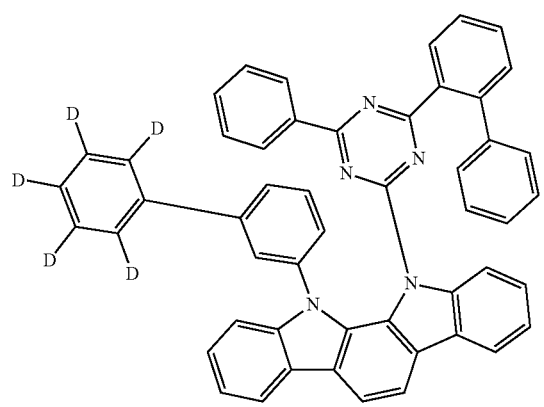
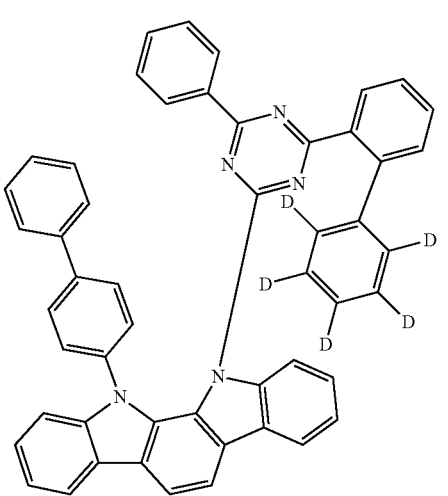
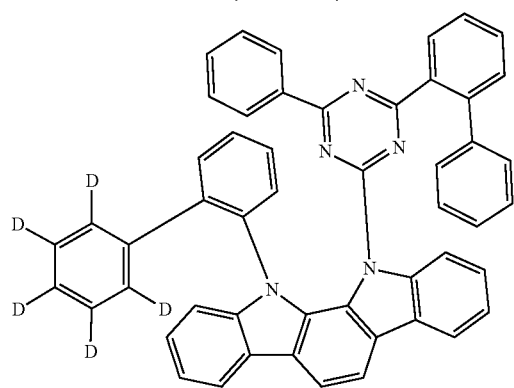

103
-continued
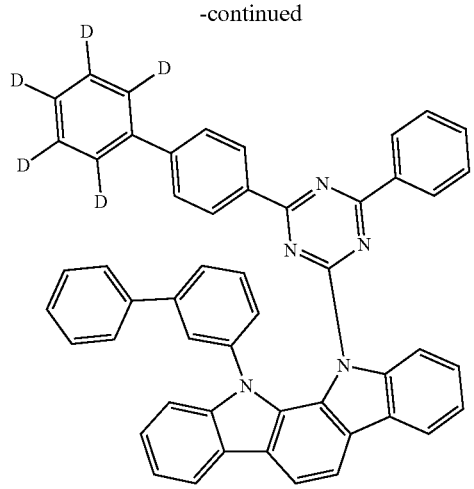
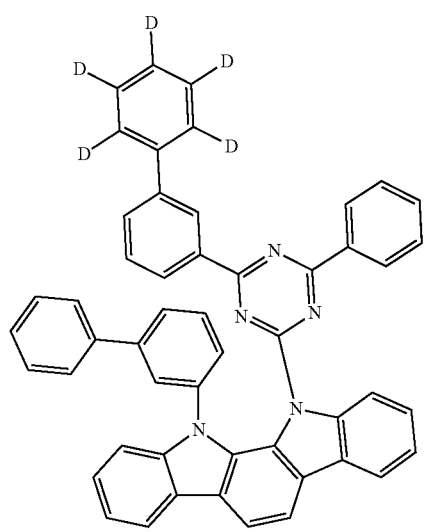
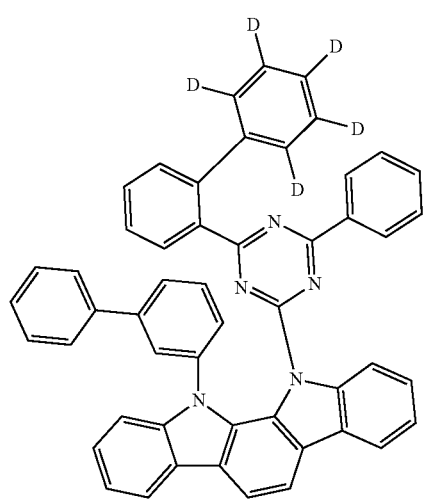
104
-continued
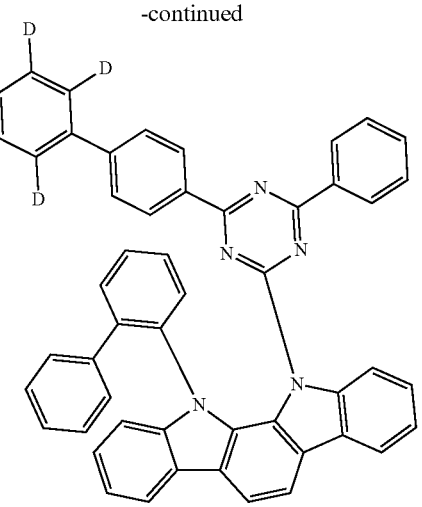
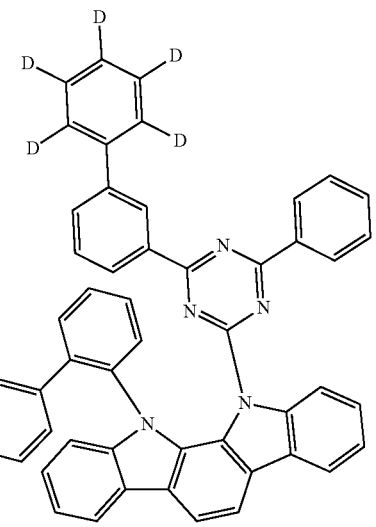
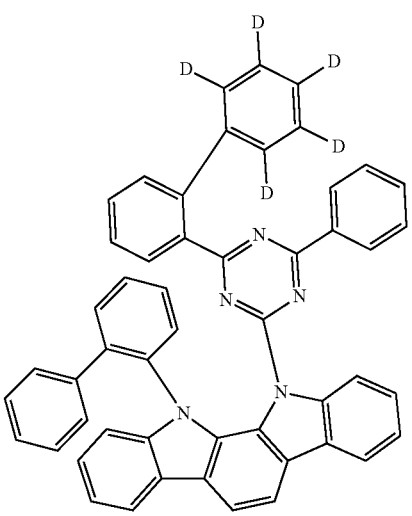

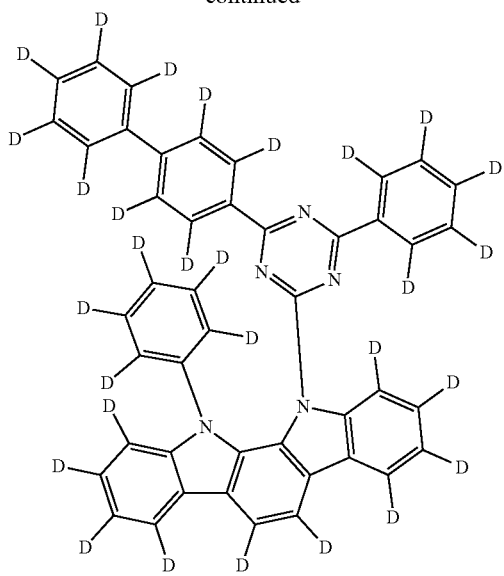
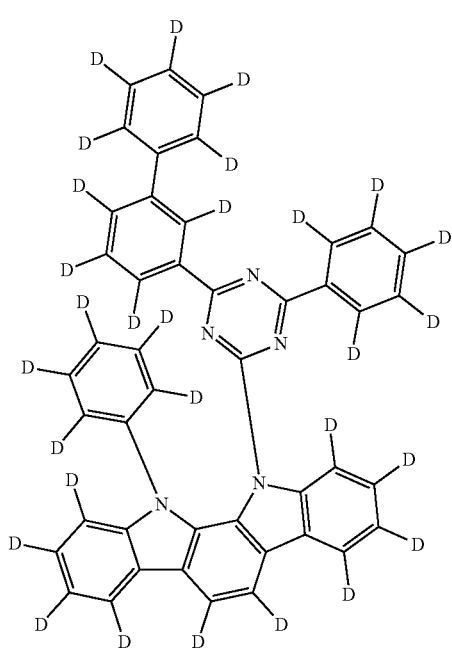
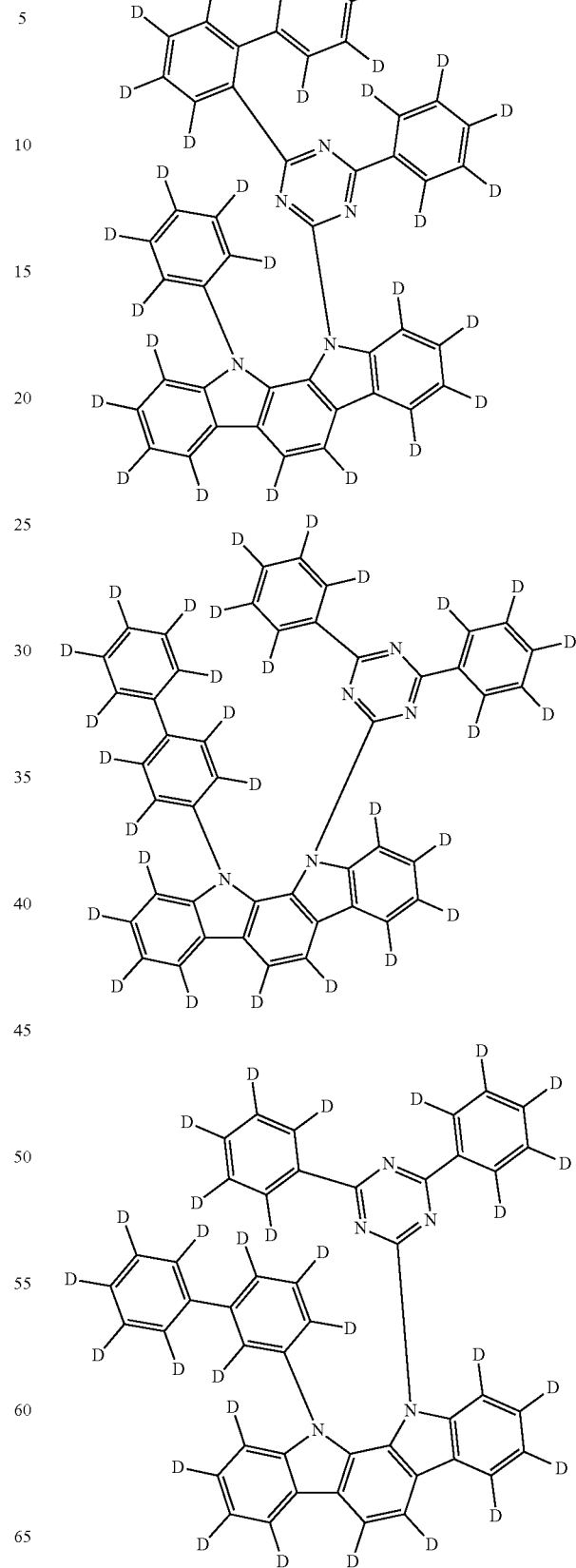

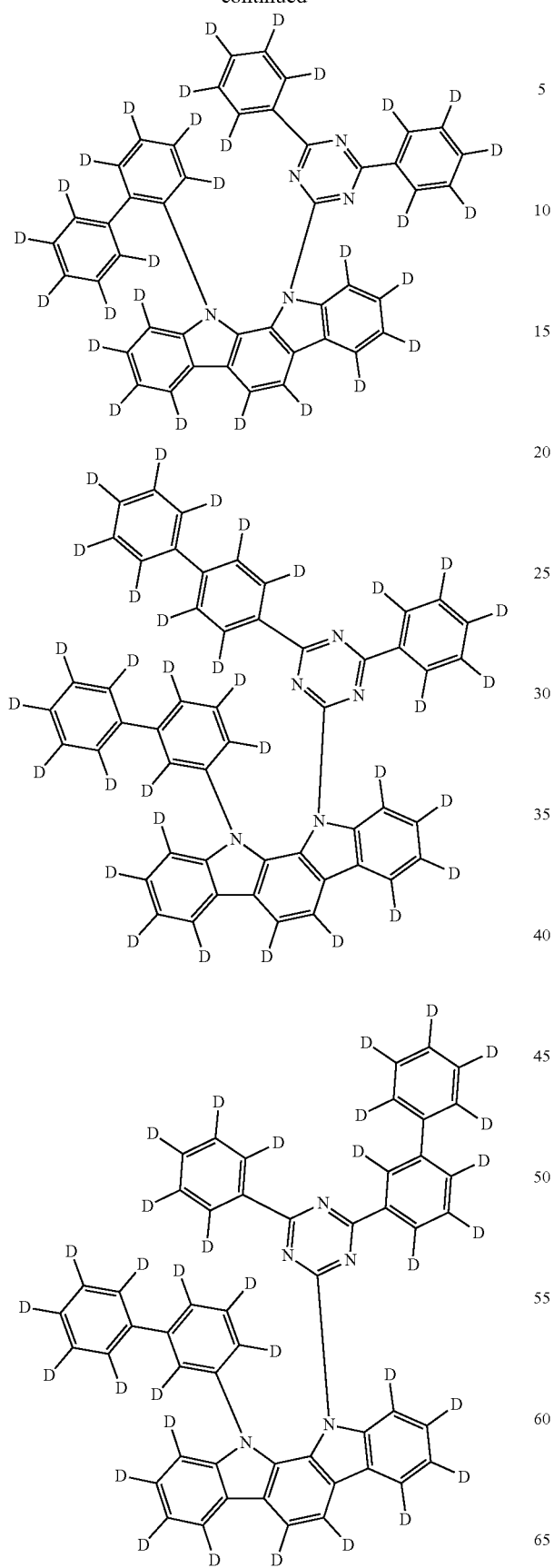
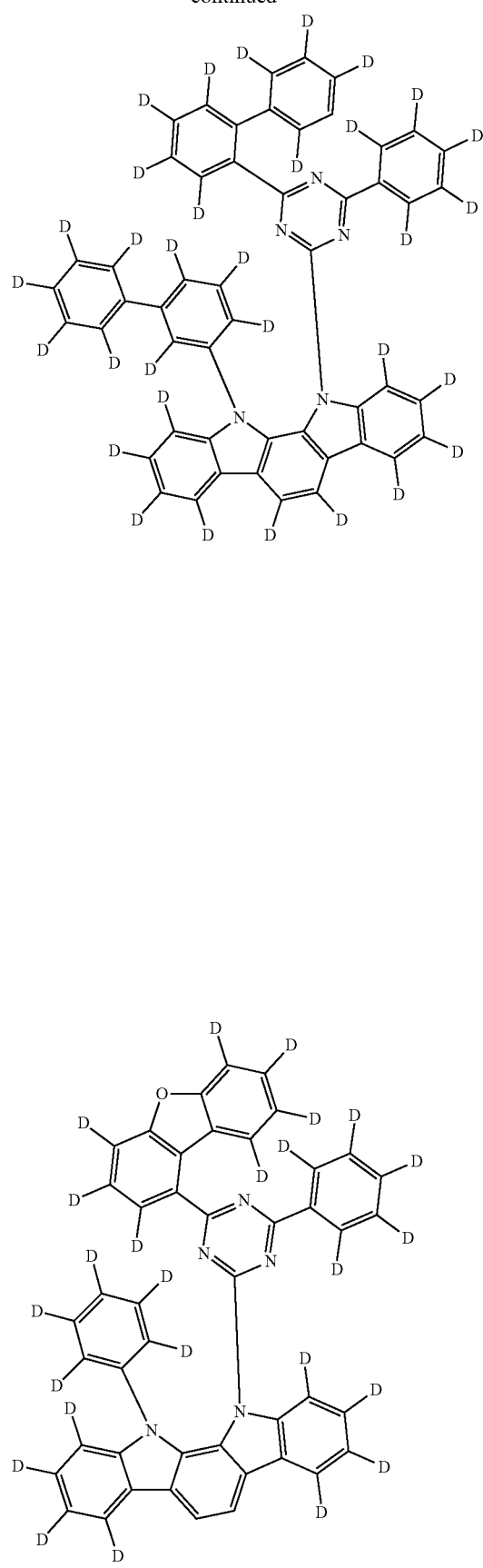

109
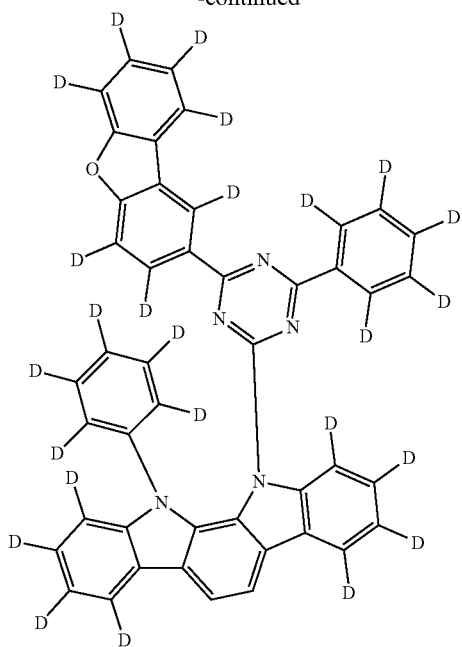
110
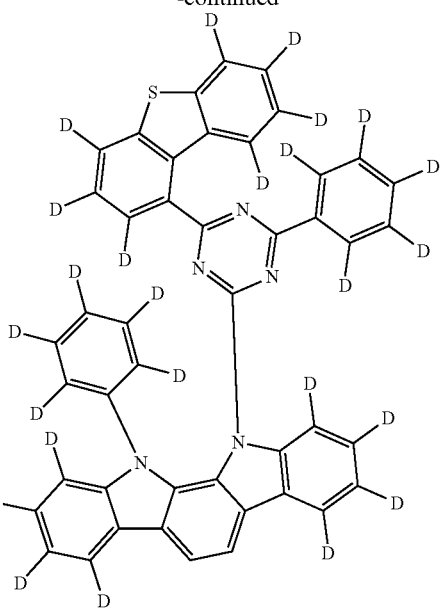
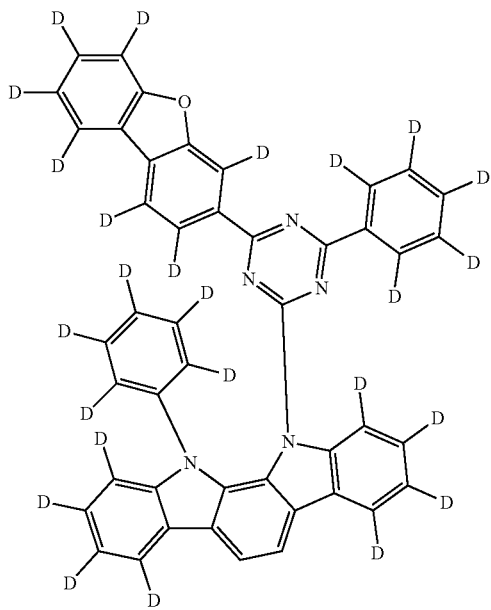
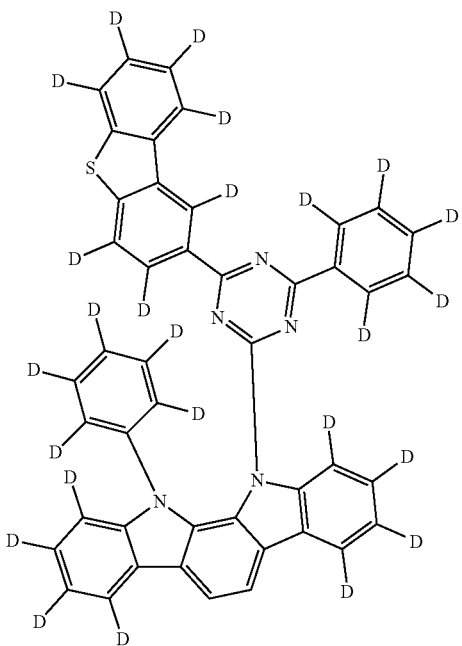

111
-continued
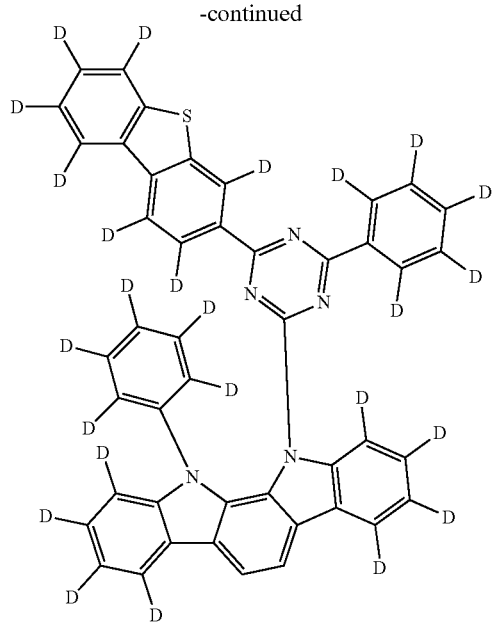
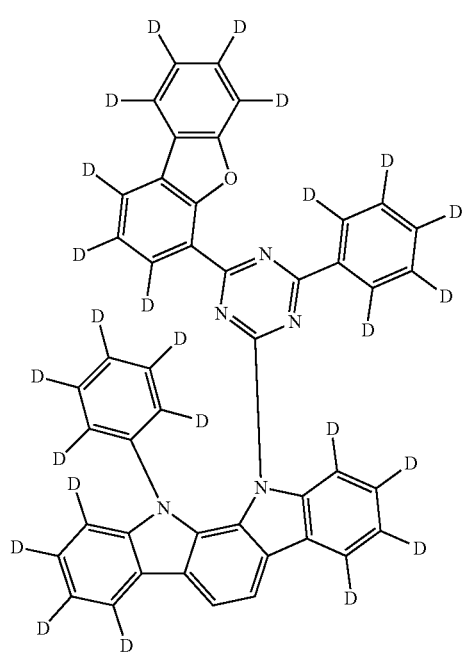
112
-continued
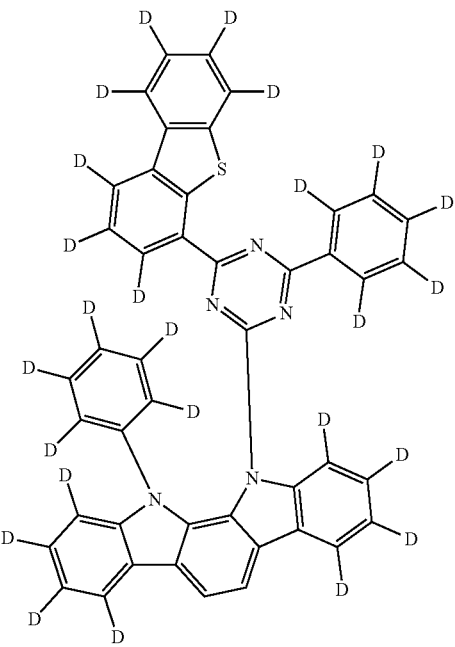
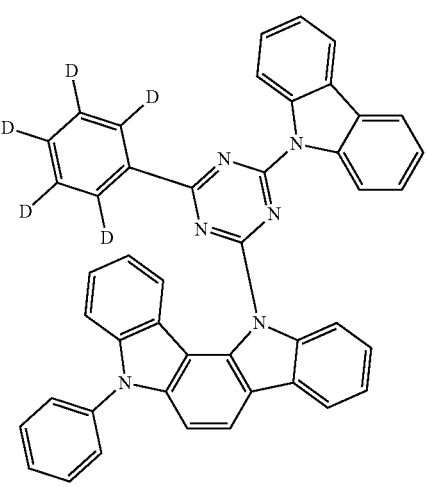
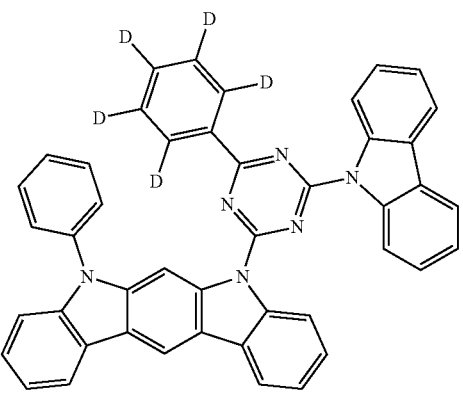

-continued

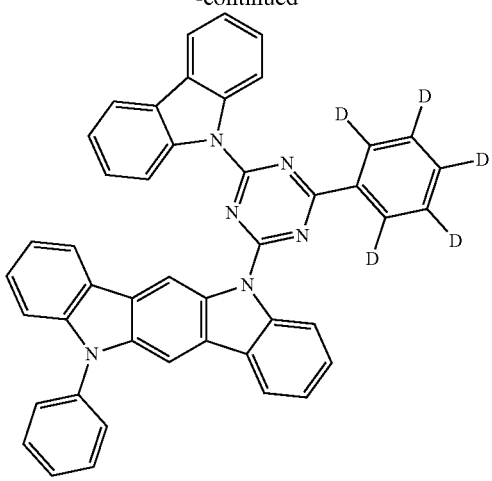

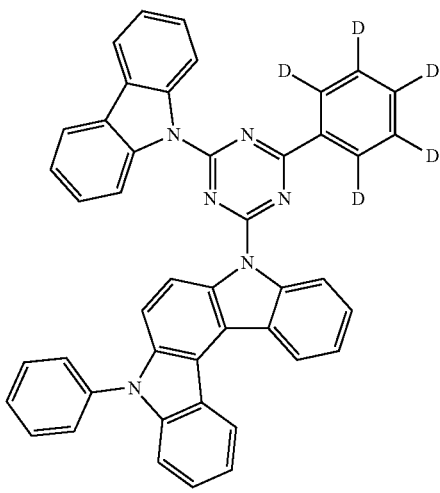

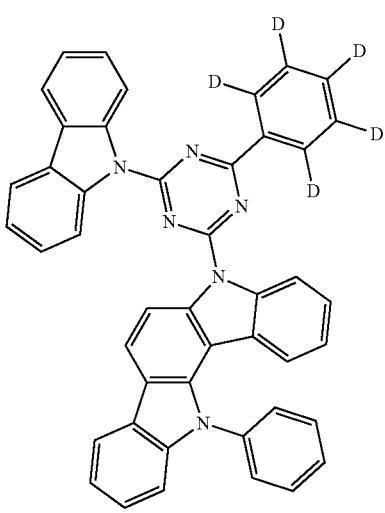

-continued

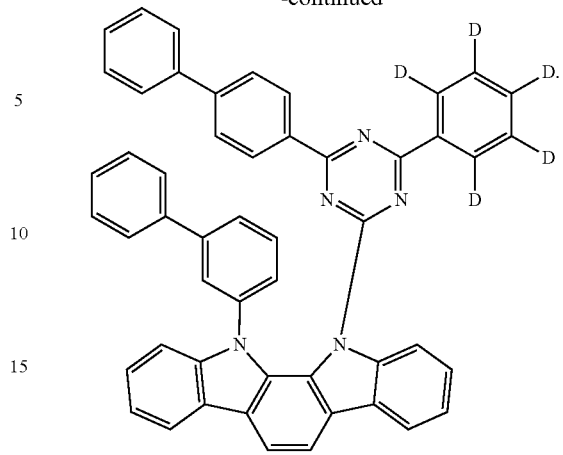

Meanwhile, the present disclosure provides, as an example, a method for preparing the compound represented by Chemical Formula 1 as shown in the following Reaction Scheme 1.

[Reaction Scheme 1]

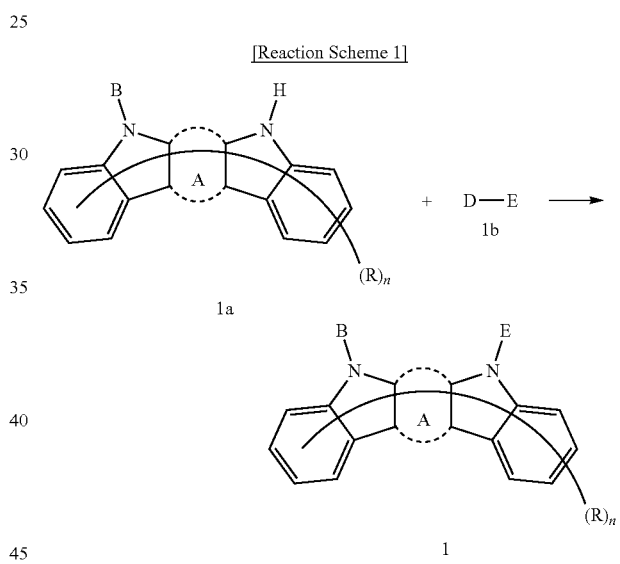

In Reaction Scheme 1, A, R, and n are the same as defined in Chemical Formula 1, B and E are any one selected from the following formula,

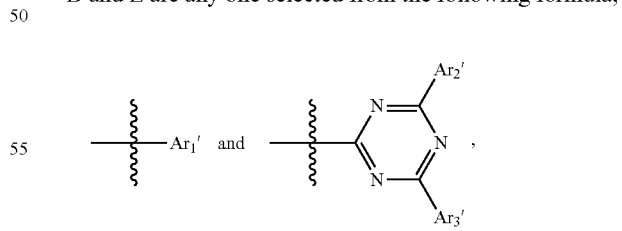

and B and E are not the same one at the same time, at least one of $Ar_1'$, $Ar_2'$ and $Ar_3'$ is a biphenylyl group; a dibenzofuranyl group; a dibenzothiophenyl group; a 9,9-dimethylfluorenyl group; a 9,9-diphenylfluorenyl; a carbazol-9-yl group; a 9-methyl-carbazolyl group; or a 9-phenyl-carbazolyl group, and the rest are a phenyl structure, and $Ar_2'$ and $Ar_3'$ are not a biphenylyl group at the same time, At least one of $Ar_1'$, $Ar_2'$ and $Ar_3'$ is substituted with one or more deuterium, and the rest are unsubstituted, or all of $Ar_1'$, $Ar_2'$ and $Ar_3'$ may be unsubstituted, and D is a halogen group, more preferably bromo or chloro.

As shown in Reaction Scheme 1 above, the compound represented by Chemical Formula 1 is prepared by an amine substitution reaction. However, when all of $Ar_1'$, $Ar_2'$ and $Ar_3'$ are unsubstituted in the compounds 1a and 1b, deuterium substitution reaction of the resulting reactant after amine substitution reaction of the above compounds 1a and 1b is further performed.

Specifically, when at least one of $Ar_1'$, $Ar_2'$ and $Ar_3'$ is substituted with one or more deuterium and the rest are unsubstituted, the compound may be prepared by reacting a compound 1a including a multi-fused ring core structure and a compound 1b including a substituent which will be substituted on the core structure in the presence of a palladium-based catalyst and a base. The reactive group for the amine substitution reaction can be modified as known in the art. The above preparation method may be further embodied in the Preparation Examples described hereinafter.

In the reaction of the compound 1a and the compound 1b, the palladium-based catalyst used may include bis(tri-tert-butylphosphine)palladium(0) (Pd(P-tBu$_3$)$_2$), 1,1'-bis(diphenylphosphino)ferrocene]dichloropalladium(II) (Pd(dppf)Cl$_2$) and the like, and is used in a molar ratio of to 0.01 to 0.1, based on 1 mol of the compound 1a.

Further, the base may include inorganic bases such as potassium carbonate, sodium carbonate, and cesium carbonate; organic bases such as sodium tert-butoxide (NaOtBu), tetraethylammonium hydroxide (Et$_4$NOH), bis(tetraethylammonium) carbonate, or triethylamine; inorganic salts such as cesium fluoride, and the like, and any one or a mixture of two or more thereof may be used. The base may be used in a molar ratio of 1 to 2, more specifically 1.5 to 1.8, based on 1 mol of the compound 1a containing the core structure.

Further, the reaction between the compound 1a and the compound 1b can be carried out in an organic solvent such as benzene, toluene, xylene, mesitylene, 1,4-dioxane, tetrahydrofuran, ethylene glycol dimethyl ether, N,N-dimethylformamide, N,N-dimethylacetamide, N-methyl-2-pyrrolidinone, or dimethyl sulfoxide. Preferably, it may be carried out in tetrahydrofuran or toluene.

In addition, in the compound 1a and the compound 1b, when all of $Ar_1'$, $Ar_2'$ and $Ar_3'$ are unsubstituted, after the amine substitution reaction of the compound 1a and the compound 1b, a deuterium substitution reaction is further performed on the resulting reactant, and thereby, the compound represented by Chemical Formula 1 may be prepared. At this time, the amine substitution reaction of the compound 1a and the compound 1b is as described above.

The deuterium substitution reaction may be carried out by introducing D$_2$O in the presence of a platinum-based catalyst such as PtO$_2$ under the high-temperature and high-pressure conditions of 250 or higher, specifically 250 to 500° C., and 500 to 700 psi.

Meanwhile, the compounds 1a and 1b used in the preparation of the compound represented by Chemical Formula 1 may be prepared according to a conventional method, or may be commercially obtained and used.

As an example, in the case of the compound 1a, it may be prepared by the reaction as shown in the following Reaction Scheme 2.

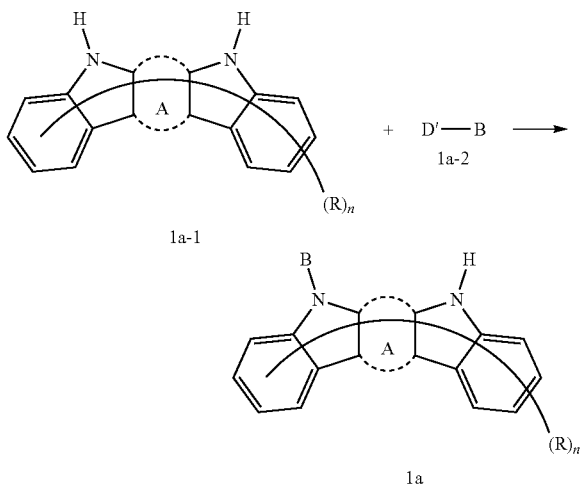

[Reaction Scheme 2]

in Reaction Scheme 2, A, B, R and n are the same as defined in Reaction Scheme 1, D' is a halogen group, more preferably bromo or chloro.

As shown in Reaction Scheme 2, the compound 1a may be prepared by an amine substitution reaction of compound 1a-1 and compound 1a-2 including a substituent for the compound 1a. The amine substitution reaction is the same as described above.

In addition, the present disclosure provides an organic light-emitting device including the compound represented by Chemical Formula 1.

As an example, the present disclosure provides an organic light emitting device comprising: a first electrode; a second electrode that is disposed to face the first electrode; and one or more organic material layers that are disposed between the first electrode and the second electrode, wherein one or more layers of the organic material layers include the compound according to the present disclosure.

In the organic light emitting device according to the present disclosure, the organic material layer comprising the compound is a light emitting layer.

Further, the organic light emitting device according to the present disclosure may be a normal type organic light emitting device in which an anode, one or more organic material layers, and a cathode are sequentially stacked on a substrate. Further, the organic light emitting device according to the present disclosure may be an inverted type organic light emitting device in which a cathode, one or more organic material layers, and an anode are sequentially stacked on a substrate. The organic material layer may include at least one of a hole injection layer, a hole transport layer, a light emitting layer, an electron injection layer, and an electron transport layer. Further, the organic material layer may include an electron injection and transport layer that simultaneously injects and transports electrons, instead of the electron injection layer and the electron transport layer.

For example, the structure of an organic light emitting device according to an embodiment of the present disclosure is illustrated in FIGS. 1 and 2.

FIG. 1 depicts an example of an organic light emitting device comprising a substrate 1, an anode 2, a light emitting layer 3, and a cathode 4. In such a structure, the compound represented by Chemical Formula 1 may be included in the light emitting layer.

FIG. 2 depicts an example of an organic light emitting device comprising a substrate 1, an anode 2, a hole injection layer 5, a hole transport layer 6, a light emitting layer 7, an electron injection and transport layer 8, and a cathode 4. In such a structure, the compound represented by Chemical Formula 1 may be included in the hole injection layer, the hole transport layer, or the light emitting layer. And, in the above structure, an electron blocking layer (not shown) may be further included between the hole transport layer and the light emitting layer, and a hole blocking layer (not shown) between the light emitting layer and the electron injection and transport layer.

The organic light emitting device according to the present disclosure may be manufactured by materials and methods known in the art, except that the light emitting layer includes the compound according to the present disclosure.

For example, the organic light emitting device according to the present disclosure can be manufactured by sequentially stacking an anode, an organic material layer and a cathode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming an organic material layer including at least one of a hole injection layer, a hole transport layer, a light emitting layer, and an electron injection and transport layer thereon, and then depositing a material that can be used as the cathode thereon.

In addition to such a method, the organic light emitting device may be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive compounds such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to an electron injection layer or the electron injection material, and further is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive compound, and the like, but are not limited thereto.

The hole transport layer is a layer that receives holes from a hole injection layer and transports the holes to the light emitting layer. The hole transport layer is suitably a material having large mobility to the holes, which may receive holes from the anode or the hole injection layer and transfer the holes to the light emitting layer. Specific examples thereof include an arylamine-based organic material, a conductive compound, a block copolymer in which a conjugate portion and a non-conjugate portion are present together, and the like, but are not limited thereto.

Meanwhile, the organic light emitting device according to an embodiment may selectively further include an electron blocking layer on the hole transport layer. The electron blocking layer refers to a layer that is formed on the hole transport layer, and is preferably disposed in contact with the light emitting layer to adjust hole mobility, prevent excessive movement of electrons, and increase the probability of hole-electron bonding, thereby serving to improve the efficiency of an organic light emitting device. The electron blocking layer includes an electron blocking material, and an example of such an electron blocking material may be an arylamine-based organic material, but is not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, and fluoranthene compounds. Examples of the heterocycle-containing compound include carbazole derivatives, dibenzofuran derivatives, ladder-type furan compounds, pyrimidine derivatives, and the like, but are not limited thereto.

The dopant material includes an aromatic amine derivative, a styrylamine compound, a boron complex, a fluoranthene compound, a metal complex, or the like. Specifically, the aromatic amine derivative is a fused aromatic ring derivative having a substituted or unsubstituted arylamino group and includes arylamino group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, but the styrylamine compound is not limited thereto. In addition, the metal complex includes iridium complexes, platinum complexes or the like, but is not limited thereto.

Further, the organic light emitting device according to the present disclosure may further include a compound represented by the following Chemical Formula 3 in the light emitting layer:

[Chemical Formula 3]

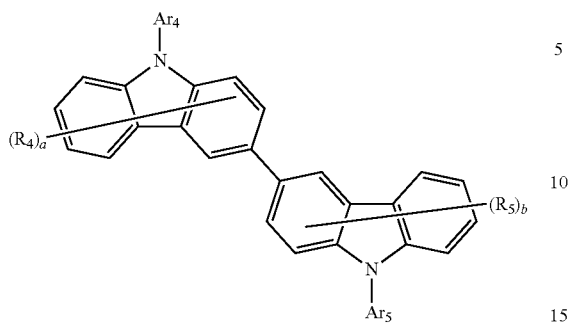

in Chemical Formula 3, $Ar_4$ and $Ar_5$ are each independently a substituted or unsubstituted $C_{6-60}$ aryl group; or a substituted or unsubstituted $C_{2-60}$ heteroaryl group containing any one or more heteroatoms selected from the group consisting of N, O and S, $R_4$ and $R_5$ are each independently hydrogen; deuterium; halogen; cyano; nitro; amino; a substituted or unsubstituted $C_{1-60}$ alkyl group; a substituted or unsubstituted $C_{3-60}$ cycloalkyl group; a substituted or unsubstituted $C_{2-60}$ alkenyl group; a substituted or unsubstituted $C_{6-60}$ aryl group; or a substituted or unsubstituted $C_{2-60}$ heteroaryl group containing any one or more heteroatoms selected from the group consisting of N, O and S, and a and b are each independently an integer of 0 to 7.

Preferably, in Chemical Formula 3, $Ar_4$ and $Ar_5$ are each independently a phenyl group; a biphenylyl group; a terphenylyl group; a naphthyl group; a dibenzofuranyl group; a dibenzothiophenyl group; or a 9,9-dimethylfluorenyl group.

Preferably, in Chemical Formula 3, both $R_4$ and $R_5$ are hydrogen. In this case, a and b are an integer of 0, respectively.

Preferably, the compound represented by Chemical Formula 3 is any one selected from the group consisting of the following:

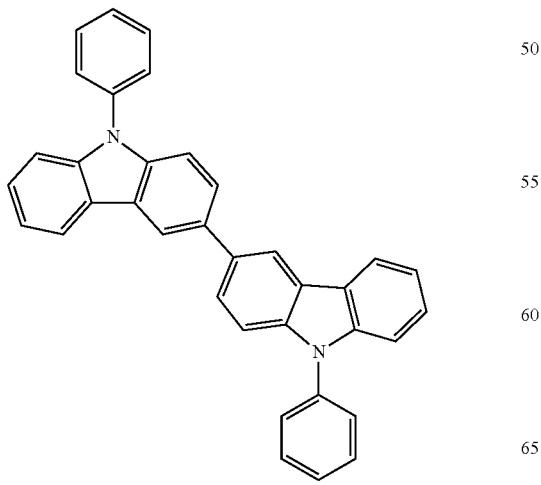

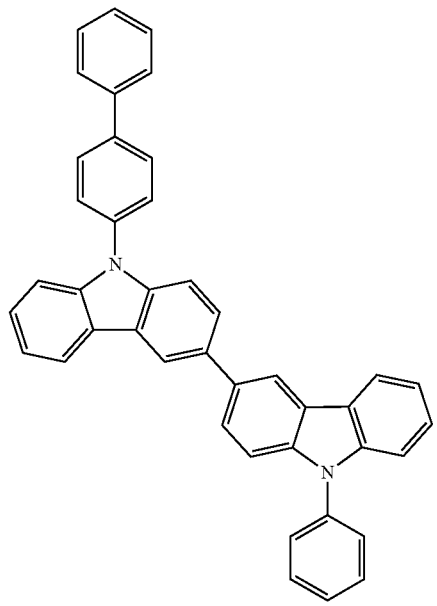

121
-continued
122
-continued
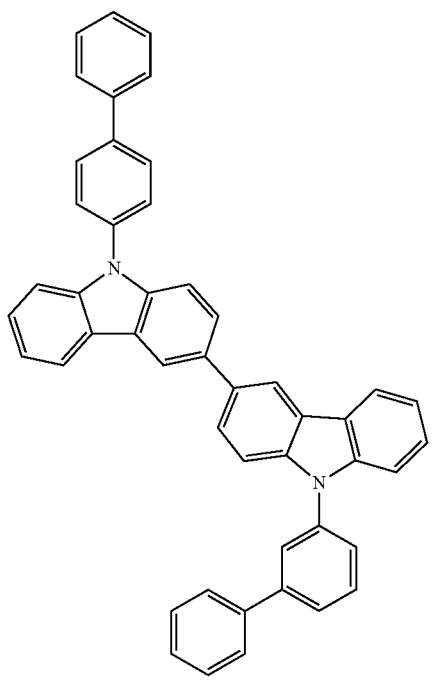
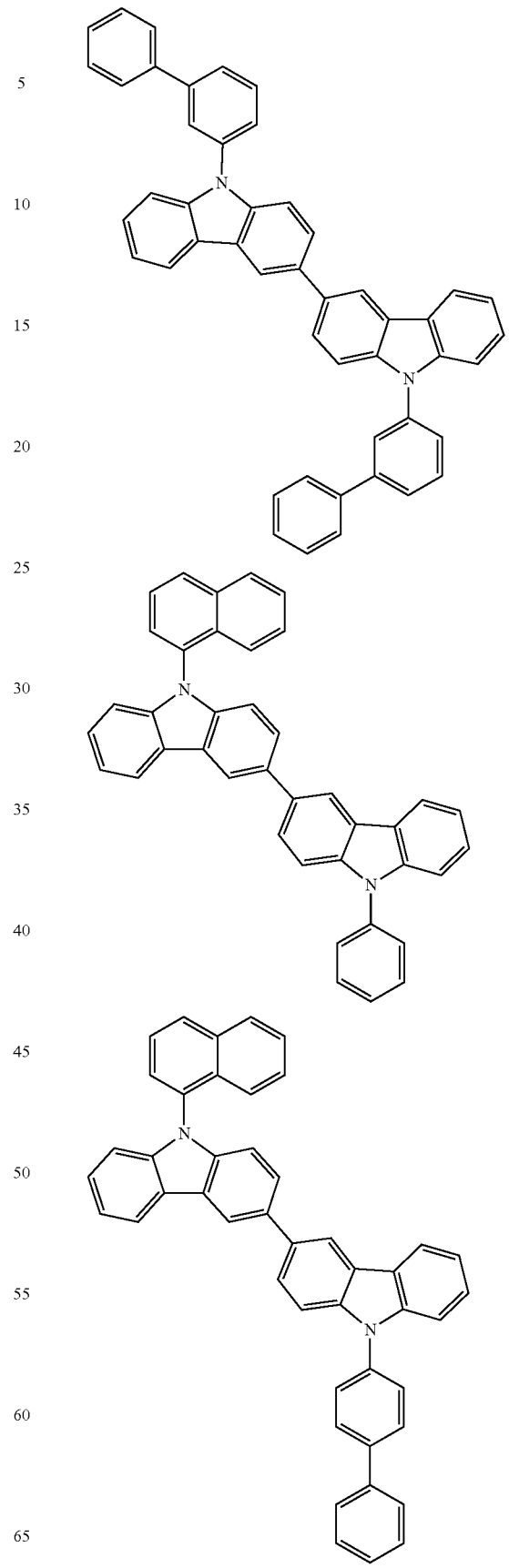

123
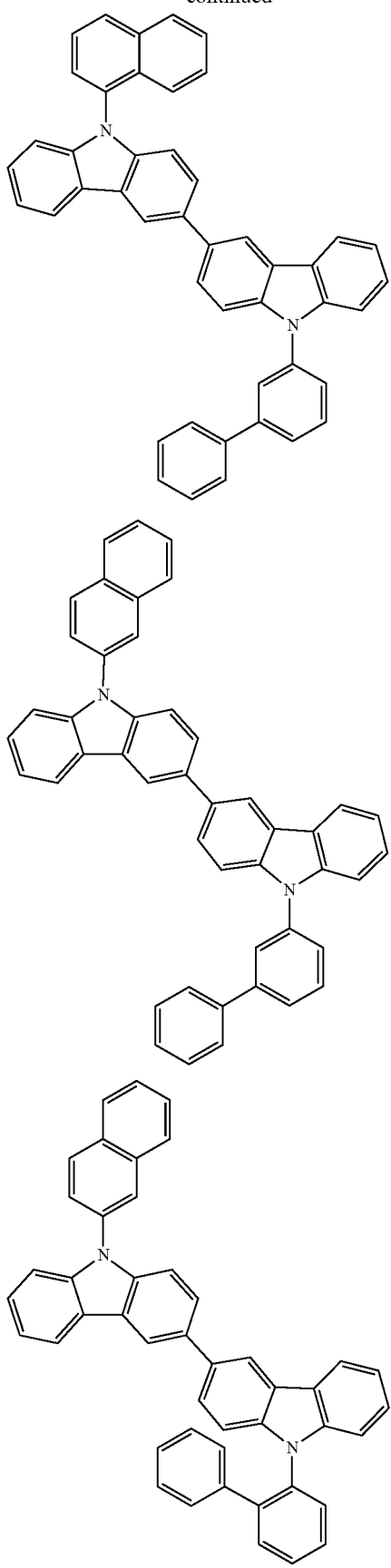
124
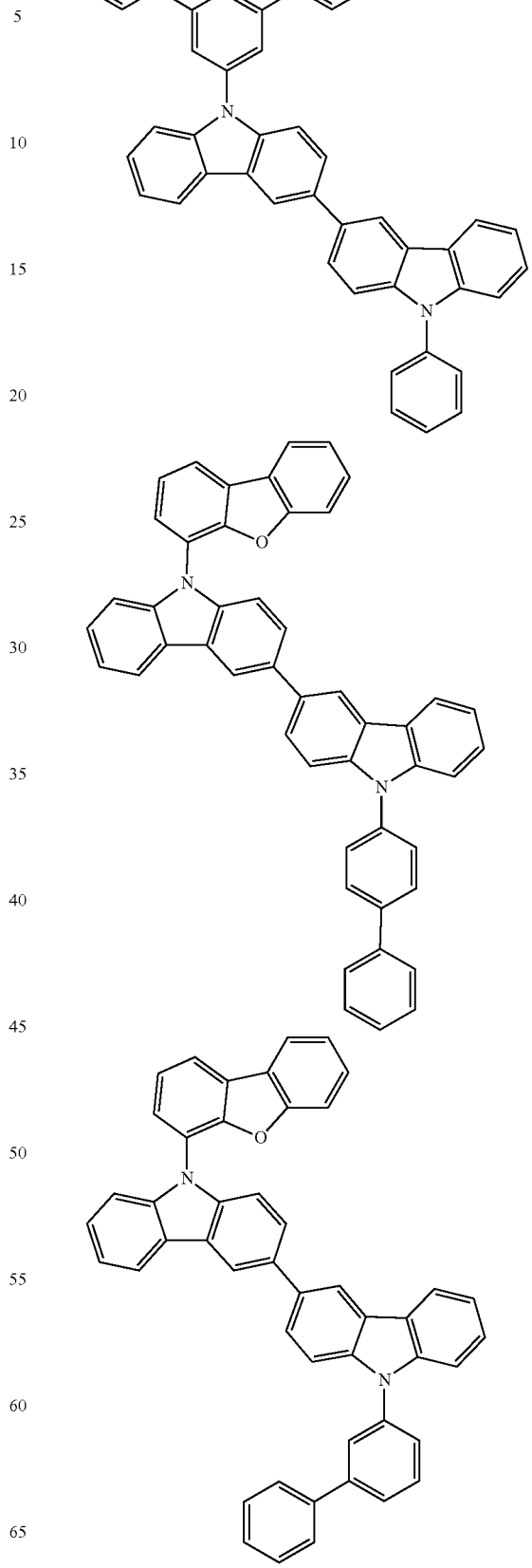

125
-continued
126
-continued
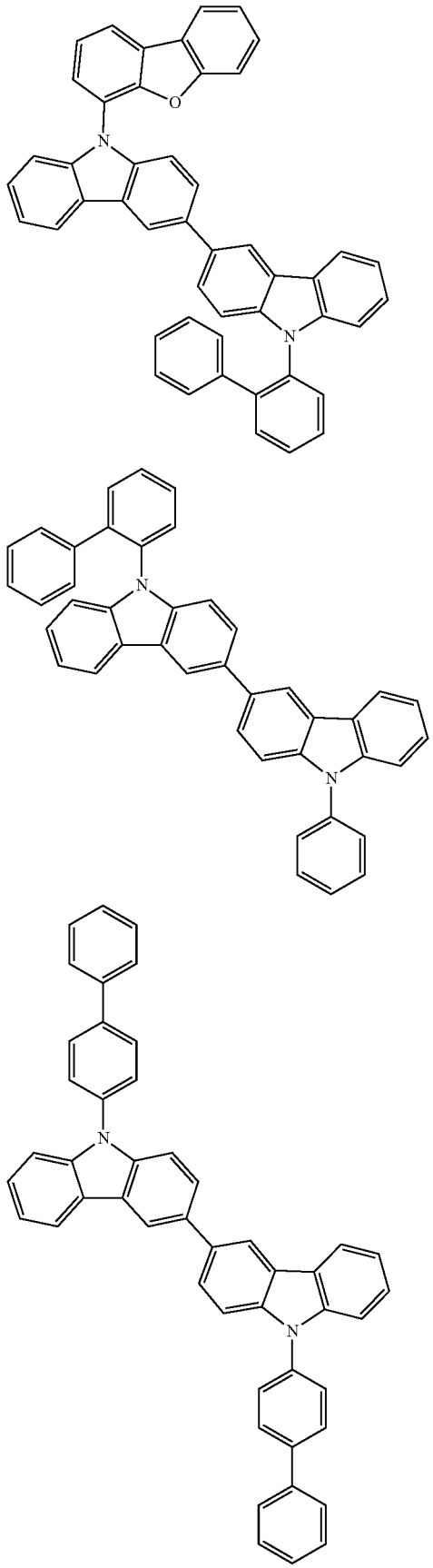
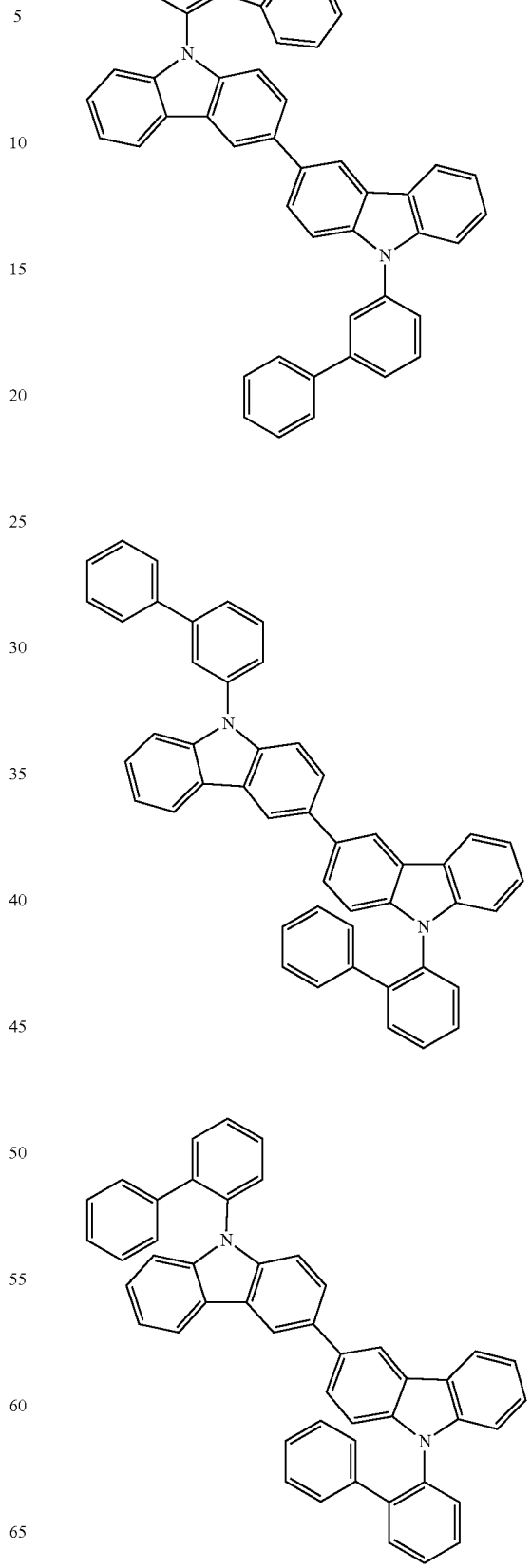

127
-continued
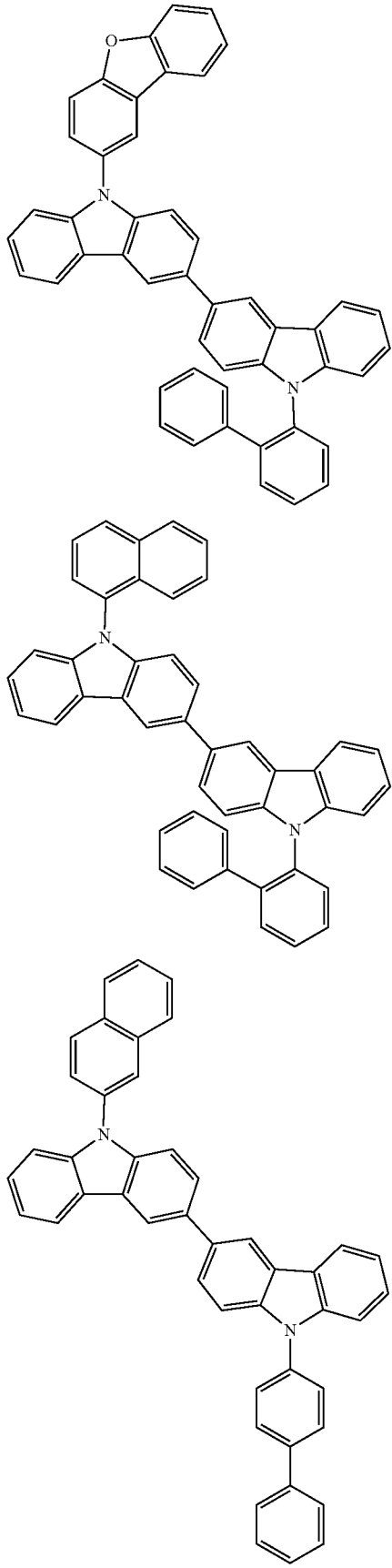
128
-continued
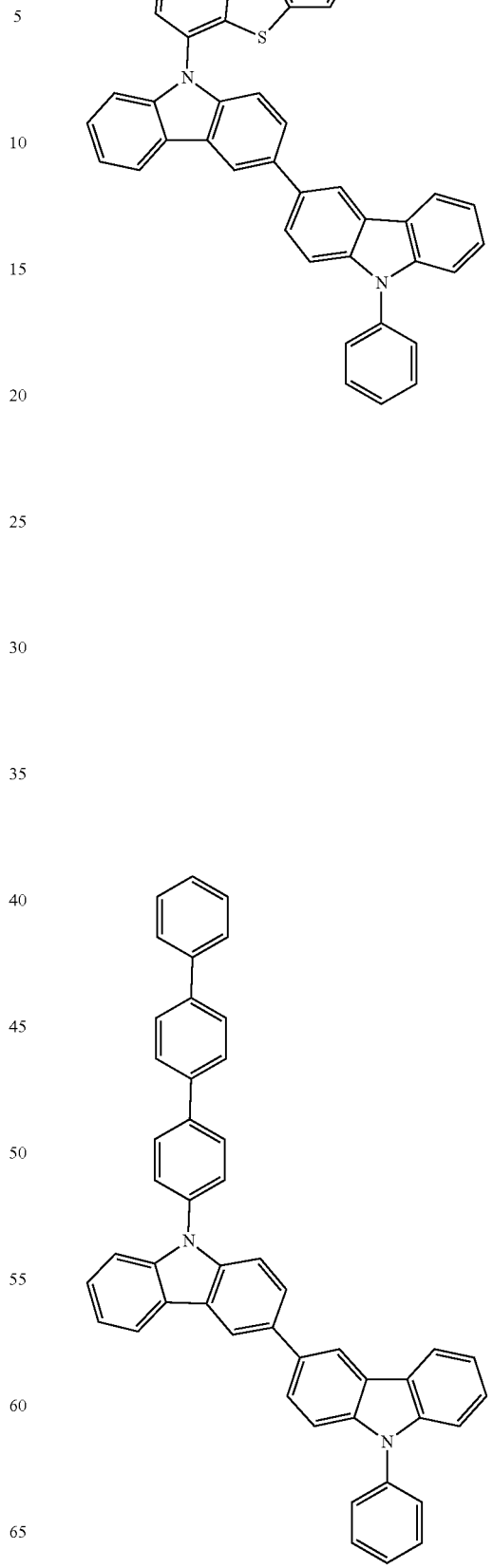

129
-continued
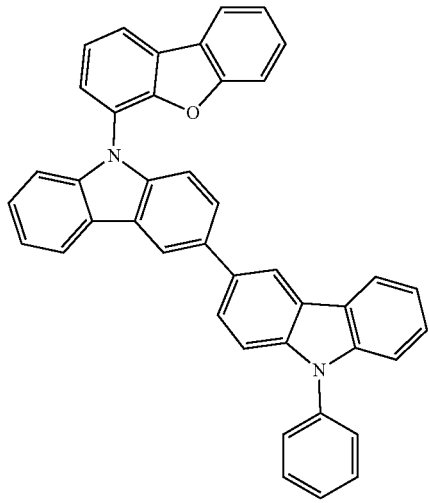
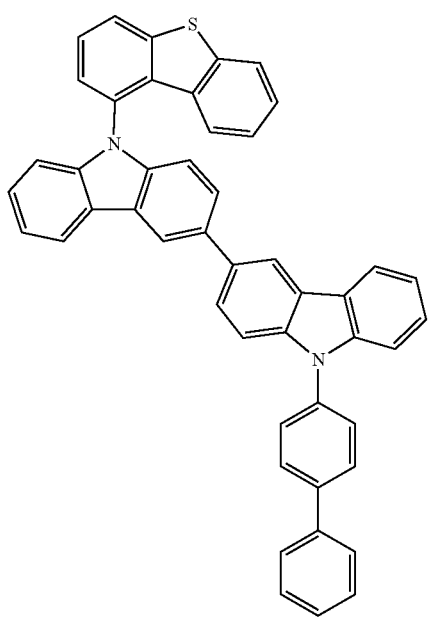
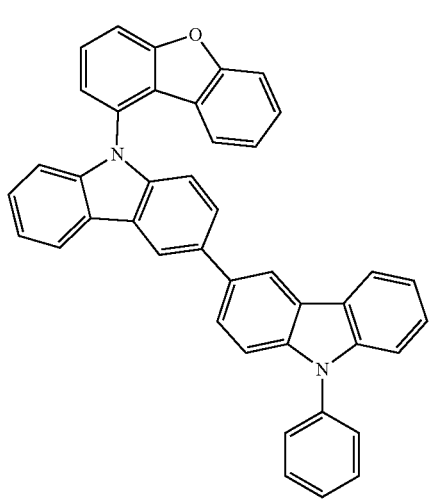
130
-continued
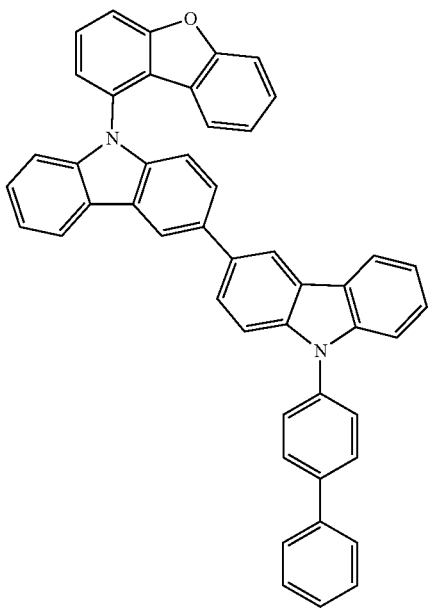
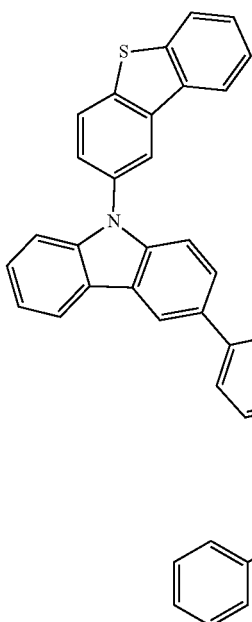
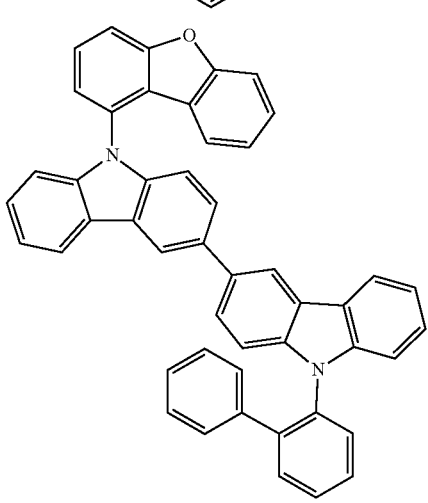

131
-continued
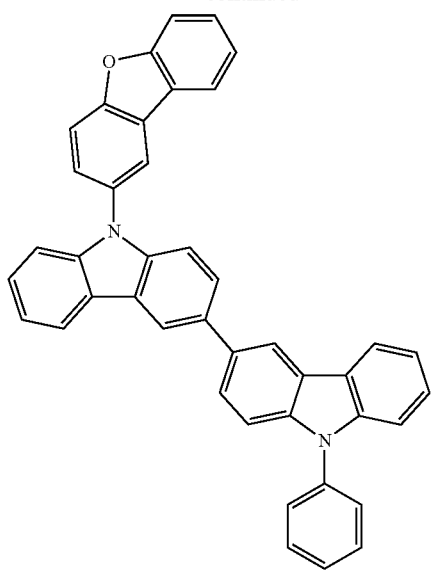
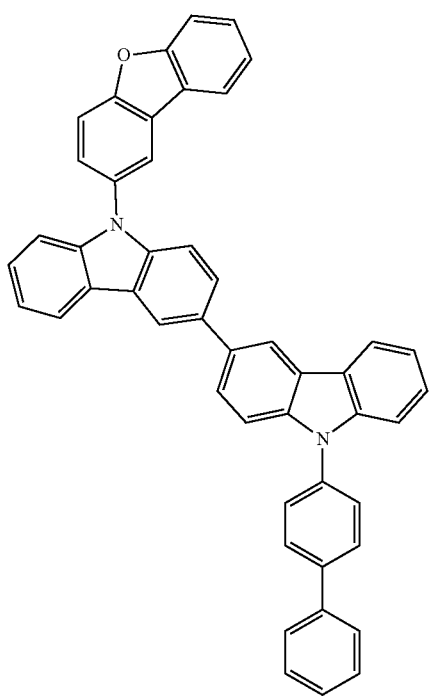
132
-continued
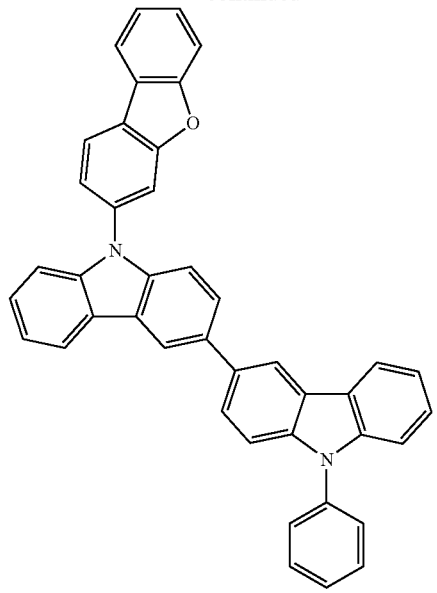
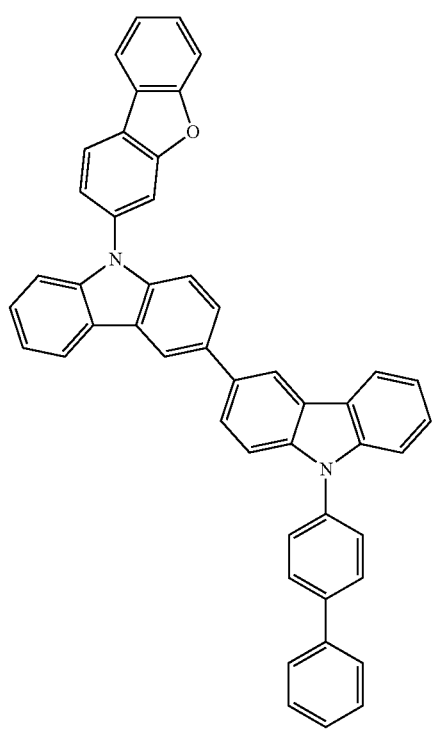

133
-continued
134
-continued
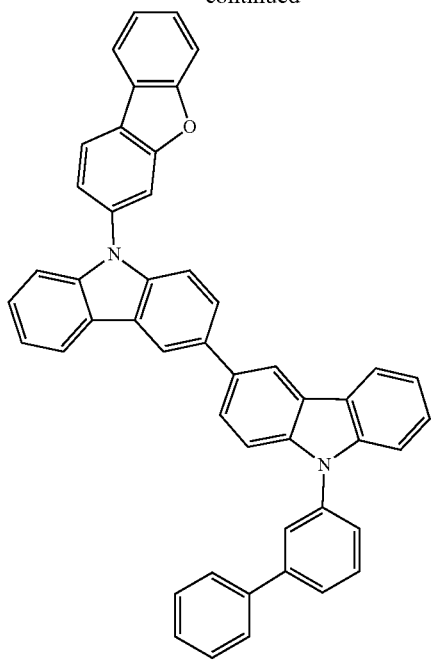
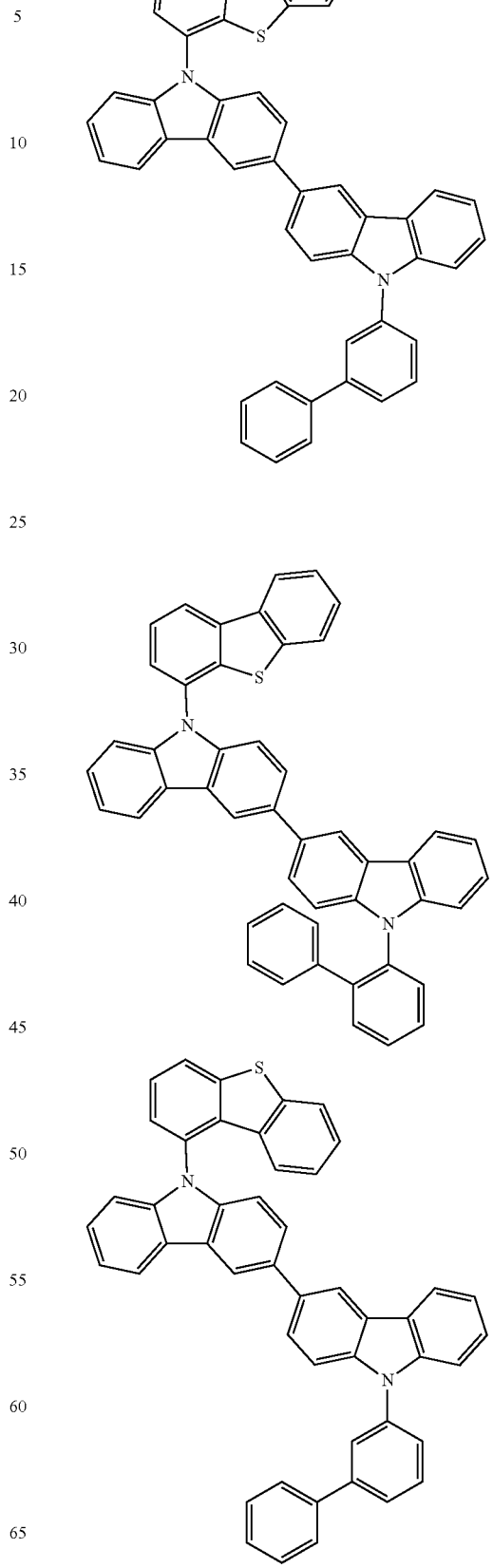

135
-continued
136
-continued
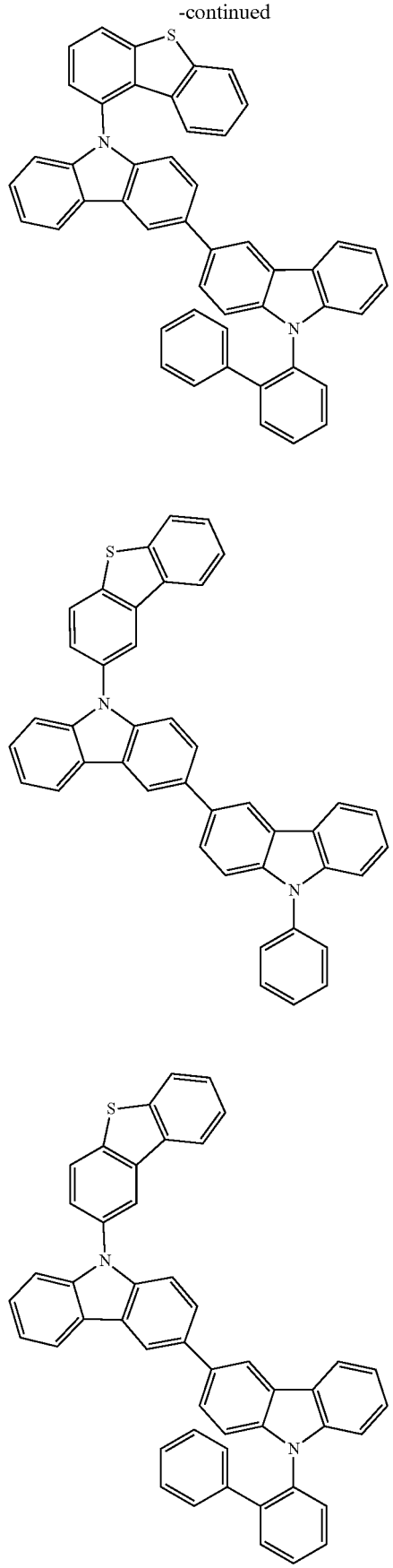
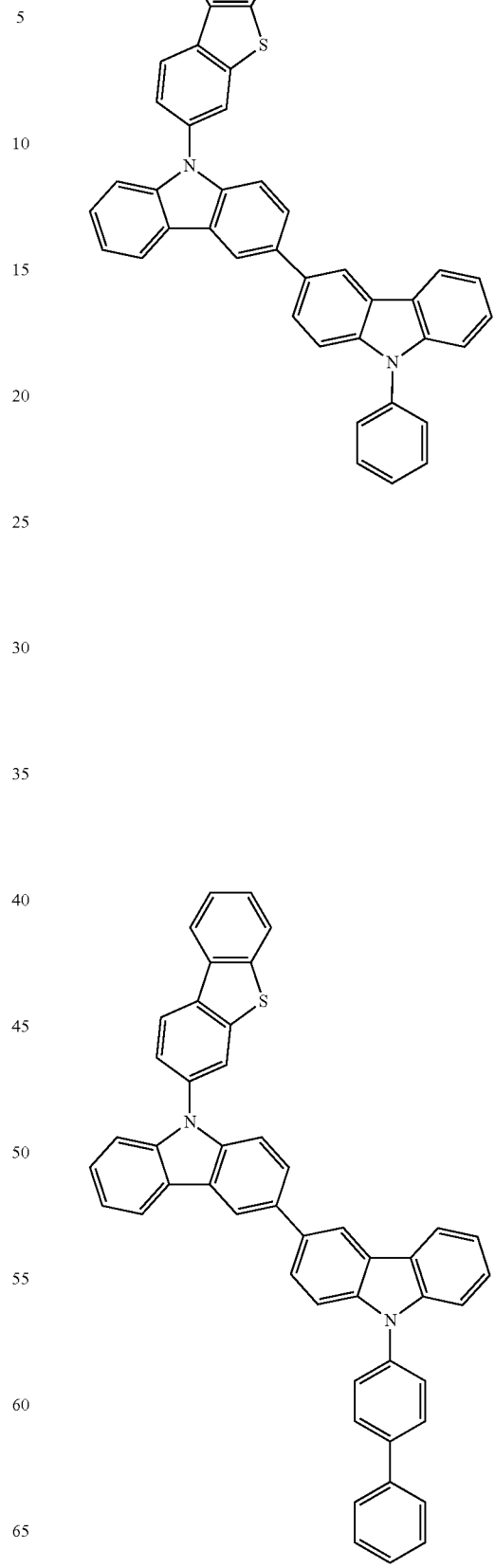

137
-continued
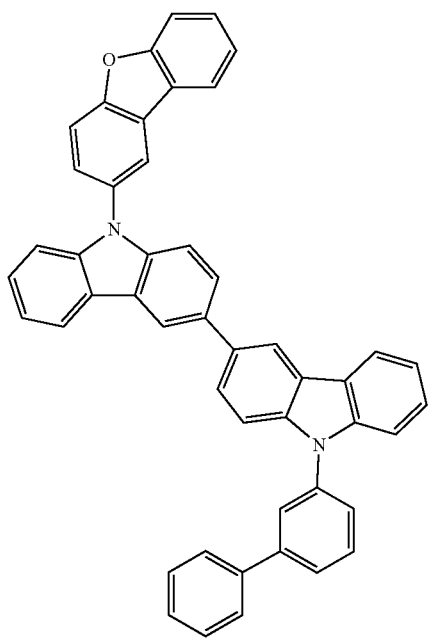
138
-continued
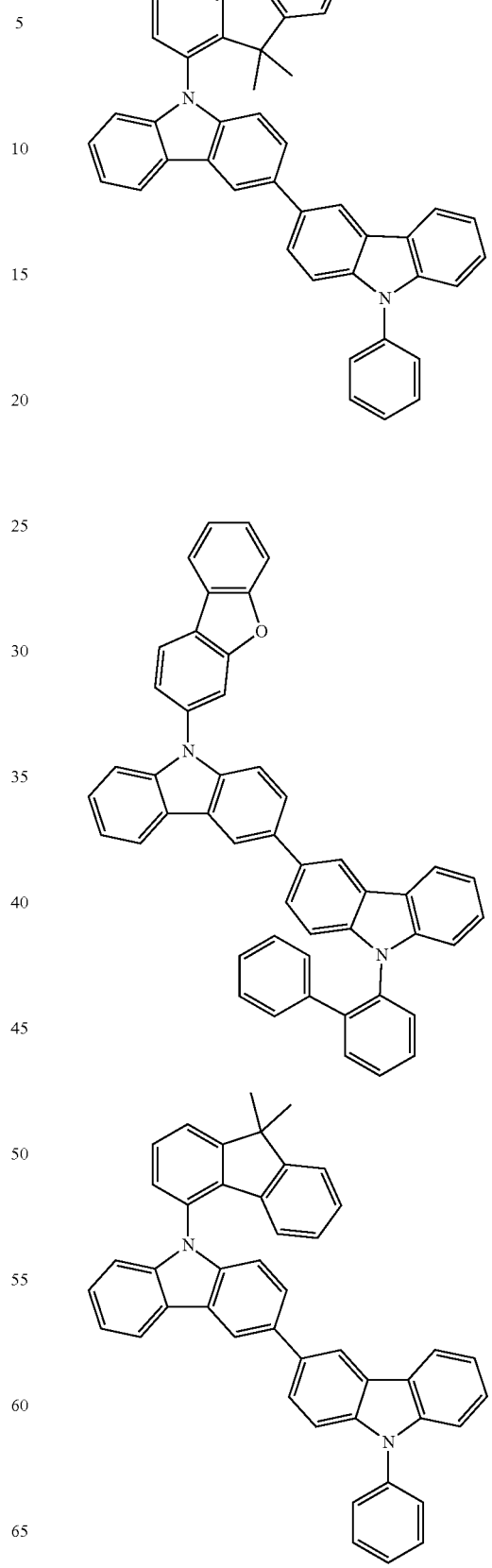

139
-continued
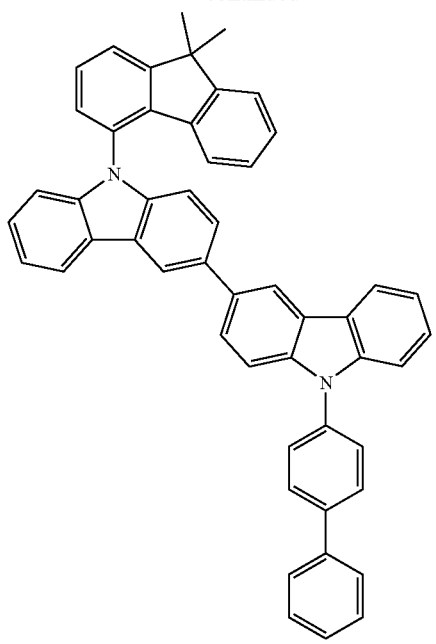
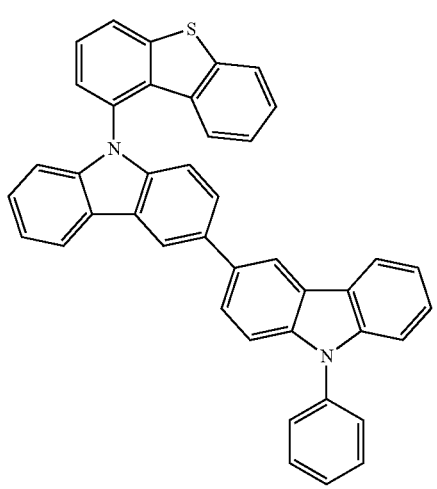
140
-continued
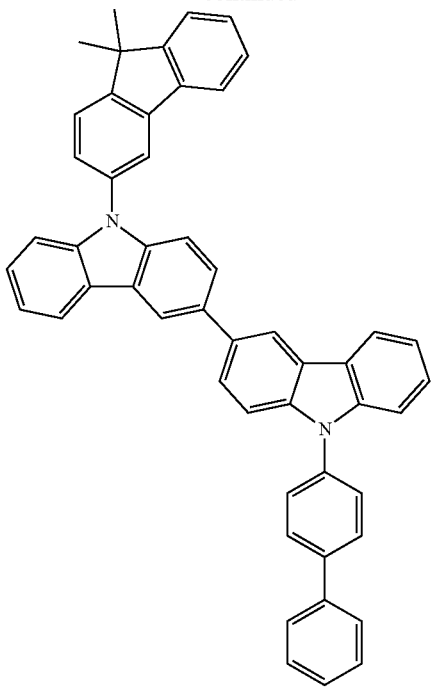
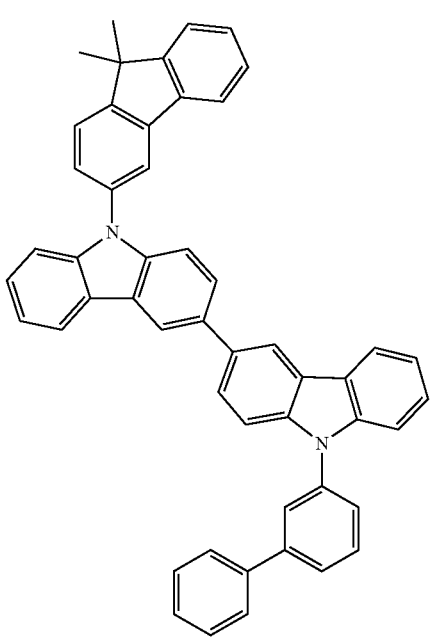

-continued
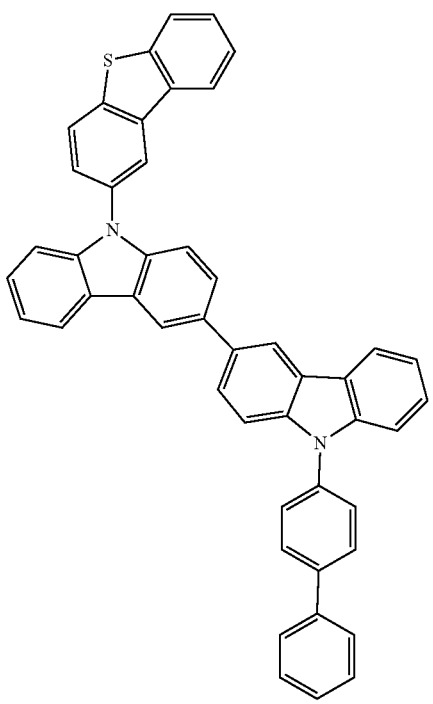
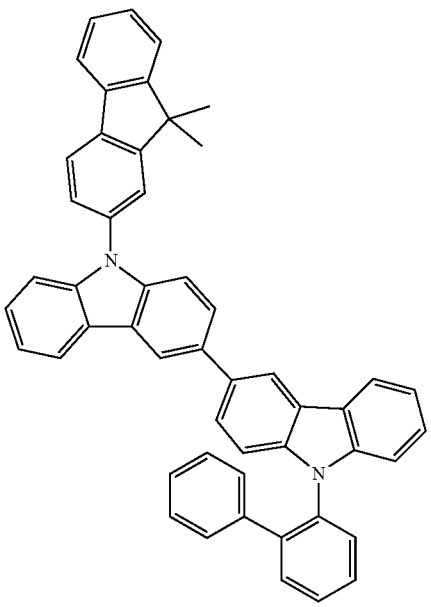
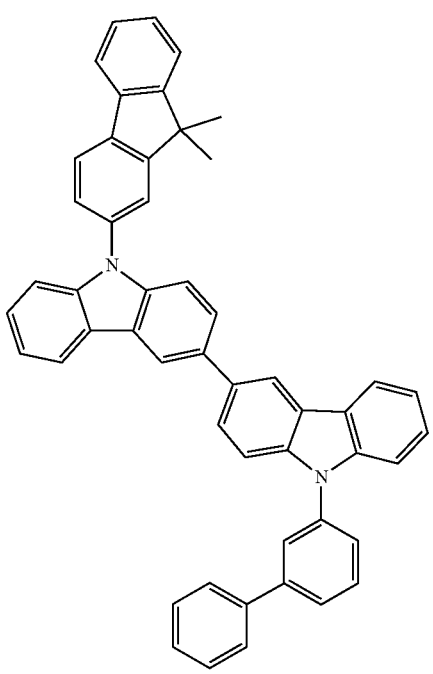
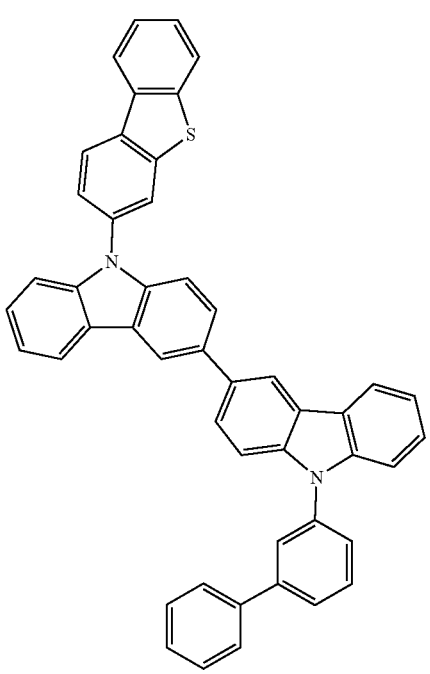

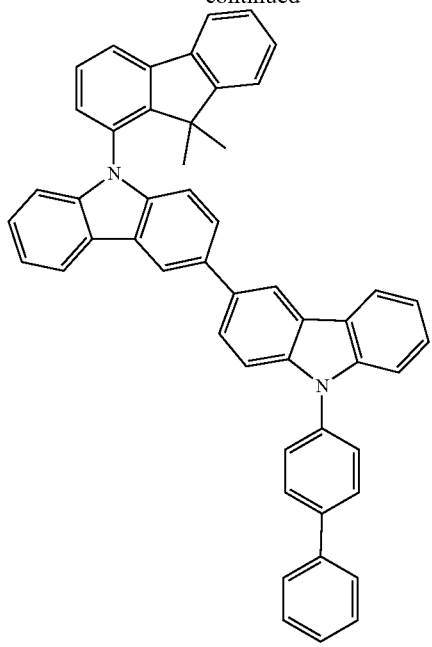
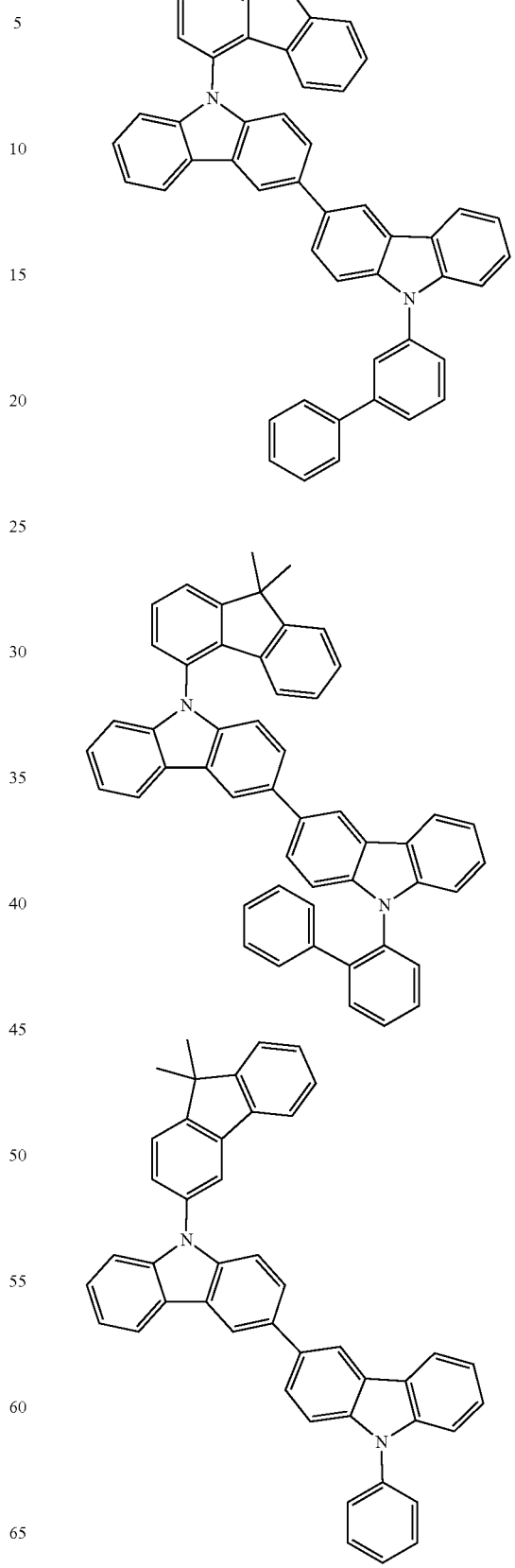
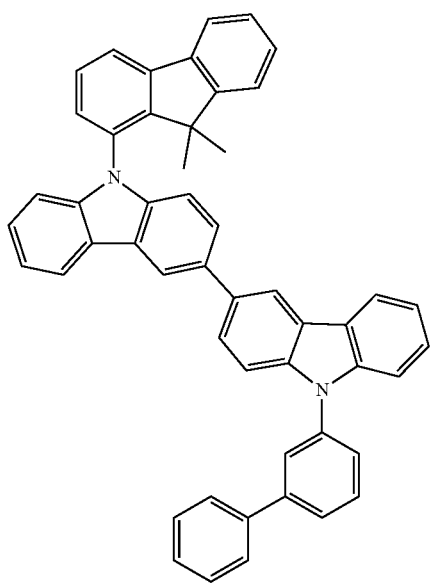

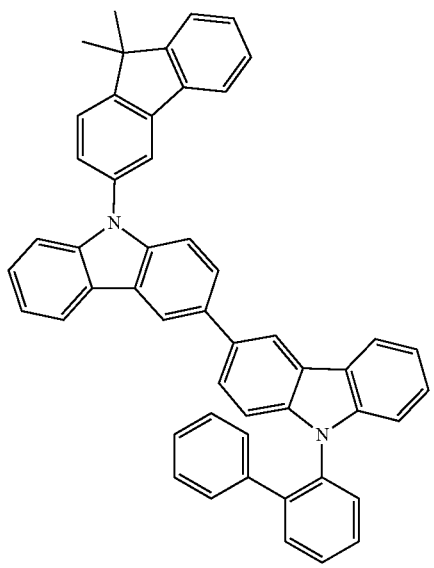

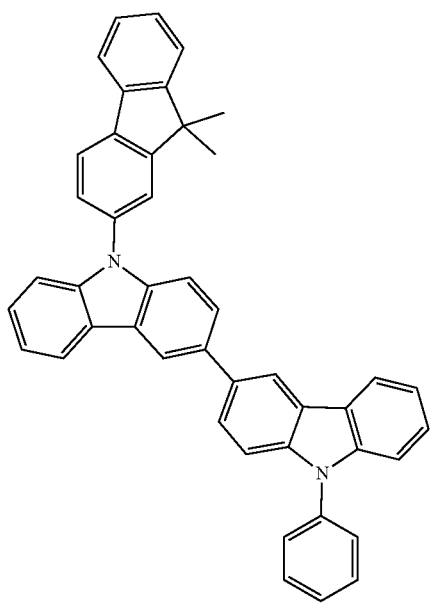

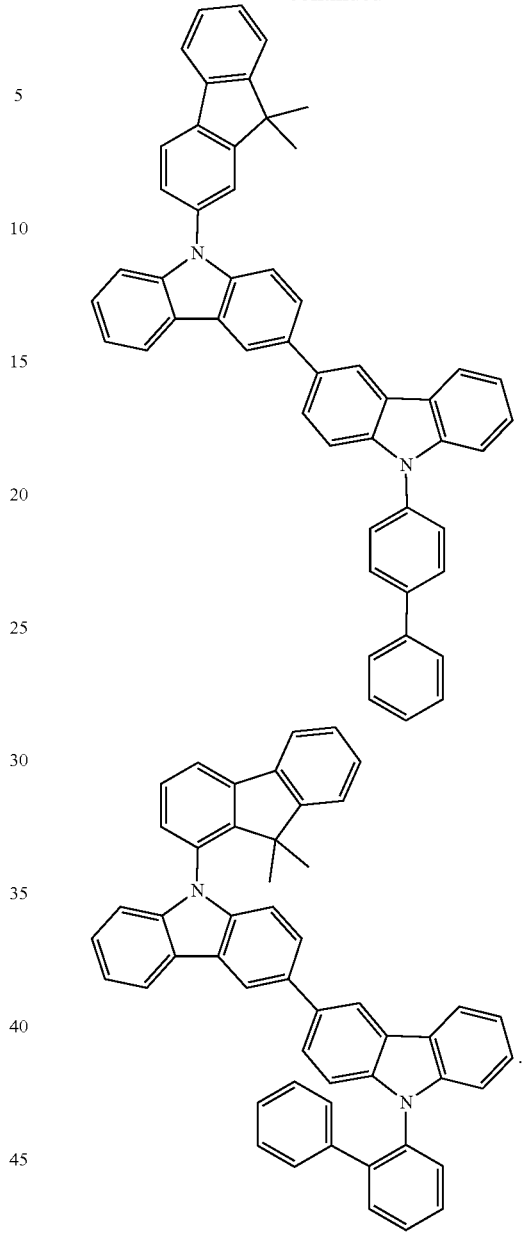

When the light emitting layer further includes the compound represented by Chemical Formula 3, it is included in an amount of 20 to 80 parts by weight based on 100 parts by weight of the compound represented by Chemical Formula 1.

Meanwhile, the organic light emitting device according to the one embodiment may selectively further include a hole blocking layer on the light emitting layer. The hole blocking layer refers to a layer that is formed on the light emitting layer and is preferably disposed in contact with the light emitting layer to adjust electron mobility, prevent excessive movement of hole and increase the probability of hole-electron bonding, thereby serving to improve the efficiency of an organic light emitting device. The hole blocking layer includes a hole blocking material, and examples of such electron blocking materials include a compound into which an electron withdrawing group is introduced, such as triazine derivatives; pyrimidine derivatives; triazole derivatives;

oxadiazole derivatives; phenanthroline derivatives; phosphine oxide derivatives, and the like, but are not limited thereto.

An electron transport layer is formed on the light emitting layer or on the hole blocking layer.

The electron transport layer is a layer which receives electrons from an electron injection layer and transports the electrons to a light emitting layer, and an electron transport material is suitably a material which may receive electrons well from a cathode and transfer the electrons to a light emitting layer, and has a large mobility for electrons. Specific examples of the electron transport material include: an Al complex of 8-hydroxyquinoline; a complex including Alq₃; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure may be a front side emission type, a back side emission type, or a double side emission type according to the used material.

In addition, the compound according to the present disclosure may be included in an organic solar cell or an organic transistor in addition to an organic light emitting device.

The preparation of the compound represented by Chemical Formula 1 according to the present disclosure and the organic light emitting device containing the same will be described in detail in the following examples. However, these examples are presented for illustrative purposes only, and are not intended to limit the scope of the present disclosure.

SYNTHESIS EXAMPLES

Synthesis Example 1: Synthesis of Compound 1

Step 1) Synthesis of Intermediate A

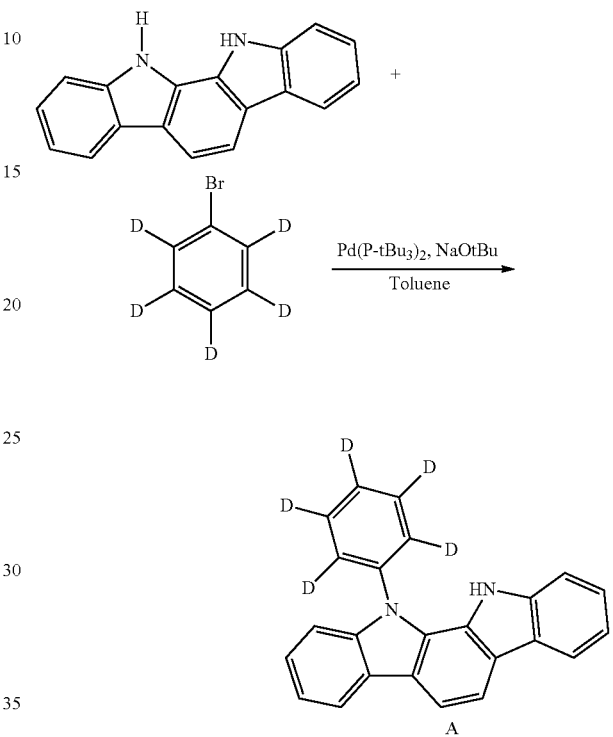

11,12-dihydroindolo[2,3-a]carbazole (15.0 g, 58.5 mmol), 1-bromobenzene-2,3,4,5,6-d5 (10.4 g, 64.4 mmol), bis(tri-tert-butylphosphine)palladium(0) (0.6 g, 1.2 mmol), sodium tert-butoxide (8.4 g, 87.8 mmol) and toluene (500 ml) were placed in a three-necked flask, and the mixture was stirred under reflux for 8 hours in an argon atmosphere. When the reaction was completed, the reaction mixture was cooled to room temperature, to which H₂O was added, and the reaction solution was transferred to a separatory funnel and extracted. The extract was dried over MgSO₄, concentrated, and the sample was purified by silica gel column chromatography to give 13.2 g of Intermediate A. (yield: 67%, MS[M+H]⁺=337)

Step 2) Synthesis of Compound 1

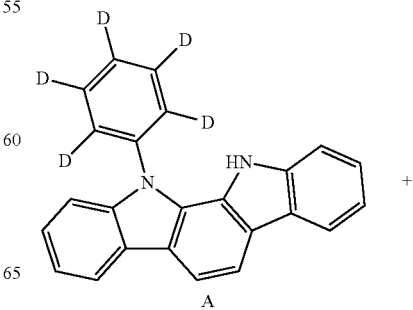

-continued

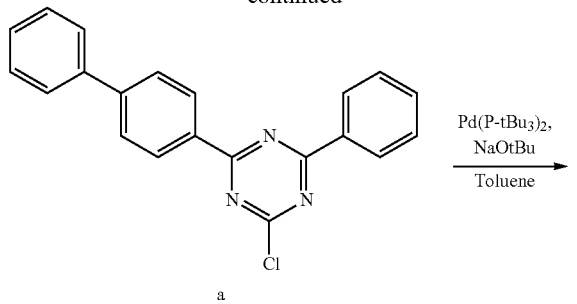

a

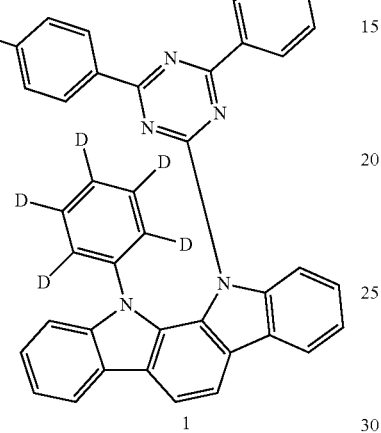

1

Intermediate A (13.0 g, 38.5 mmol), Intermediate a (14.6 g, 42.4 mmol), bis(tri-tert-butylphosphine)palladium(0) (0.4 g, 0.8 mmol), sodium tert-butoxide (5.6 g, 57.8 mmol), and 400 ml of toluene were placed in a three-necked flask, and the mixture was stirred under reflux for 8 hours in an argon atmosphere. When the reaction was completed, the reaction mixture was cooled to room temperature, to which H$_2$O was added, and the reaction solution was transferred to a separatory funnel and extracted. The extract was dried over MgSO$_4$, concentrated, and the sample was purified by silica gel column chromatography and then subjected to sublimation purification to give 7.9 g of Compound 1. (yield: 32%, MS[M+H]$^+$=644)

Synthesis Example 2: Synthesis of Compound 2

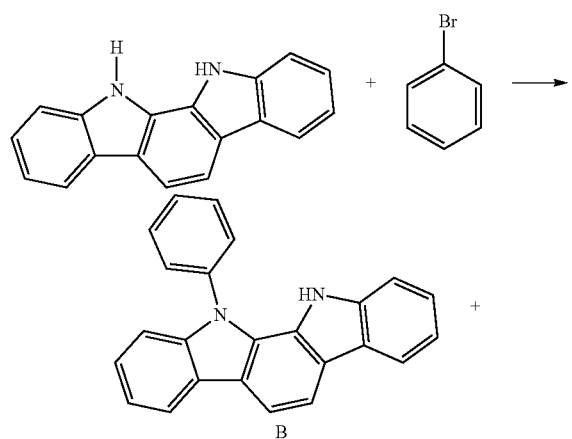

-continued

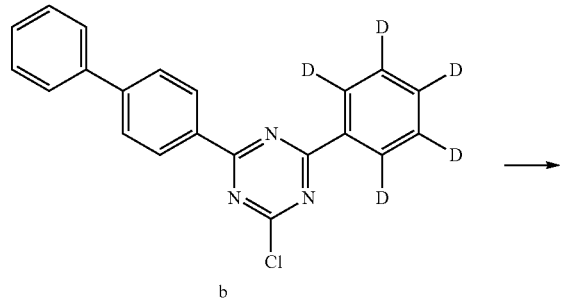

b

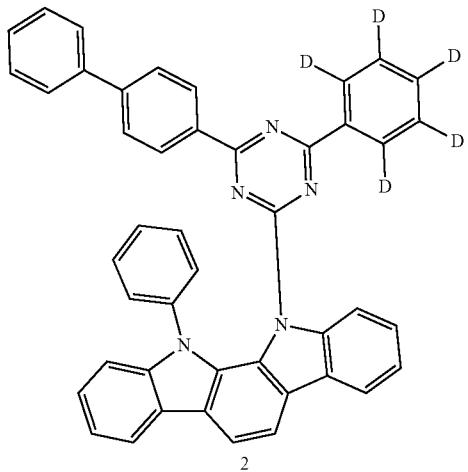

2

Compound 2 was prepared by performing the same method as the method for preparing Compound 1, except that in step 1 of Synthesis Example 1, 1-bromobenzene-2,3,4,5,6-d5 was changed to bromobenzene to prepare Intermediate B, and in step 2 of Synthesis Example 1, Intermediate B prepared above was used instead of Intermediate A, and Intermediate a was changed to Intermediate b. (MS[M+H]$^+$=644)

Synthesis Example 3: Synthesis of Compound 3

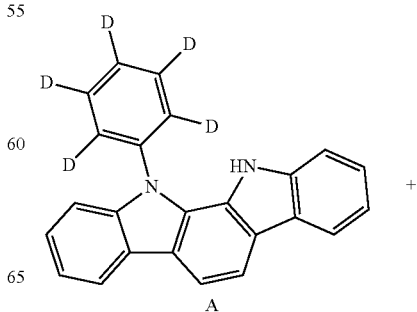

-continued

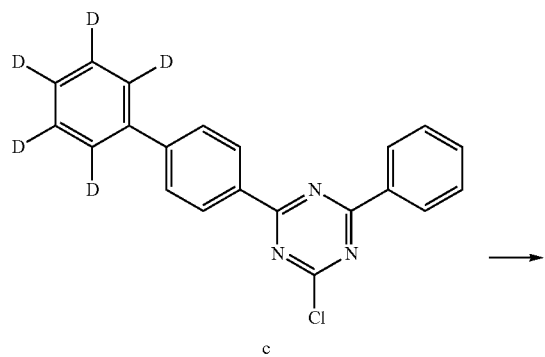

c

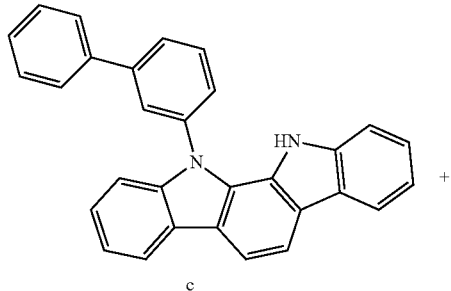

c

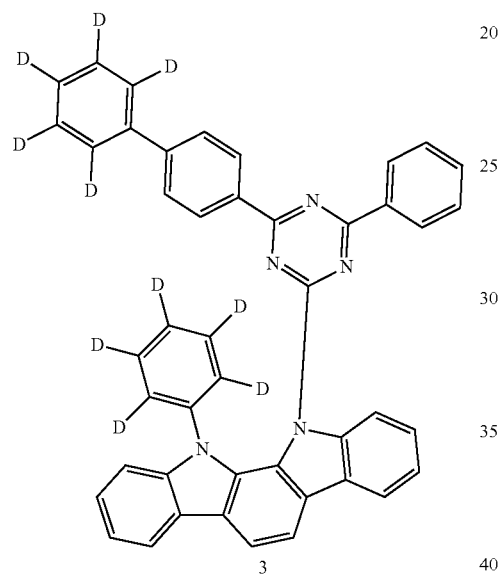

3

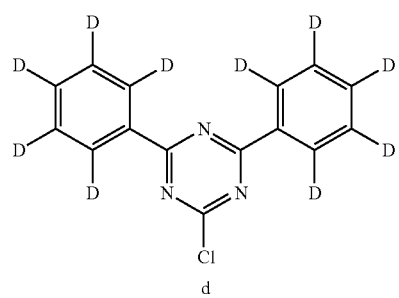

d

Compound 3 was prepared by performing the same method as the method for preparing Compound 1, except that in step 2 of Synthesis Example 1, Intermediate a was changed to Intermediate c. (MS[M+H]$^+$=649)

Synthesis Example 4: Synthesis of Compound 4

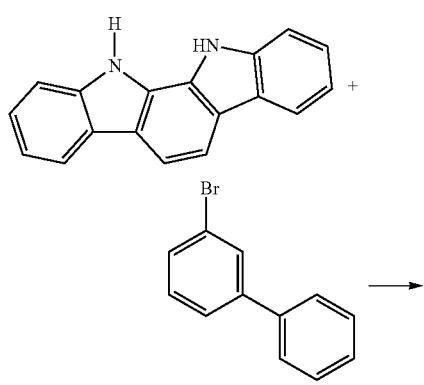

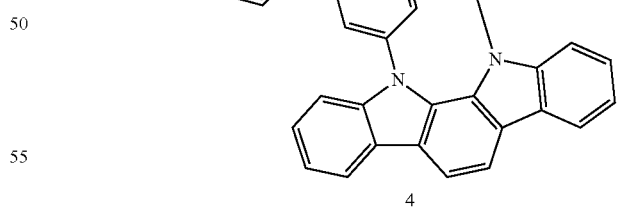

4

Compound 4 was prepared by performing the same method as the method for preparing Compound 1, except that in step 1 of Synthesis Example 1, 1-bromobenzene-2,3,4,5,6-d5 was changed to bromo-1,1'-biphenyl to prepare Intermediate C, and in step 2 of Synthesis Example 1, Intermediate C prepared above was used instead of intermediate A, and Intermediate a was changed to Intermediate d. (MS[M+H]$^+$=649)

Synthesis Example 5: Synthesis of Compound 5

Step 1) Synthesis of Compound 5-1

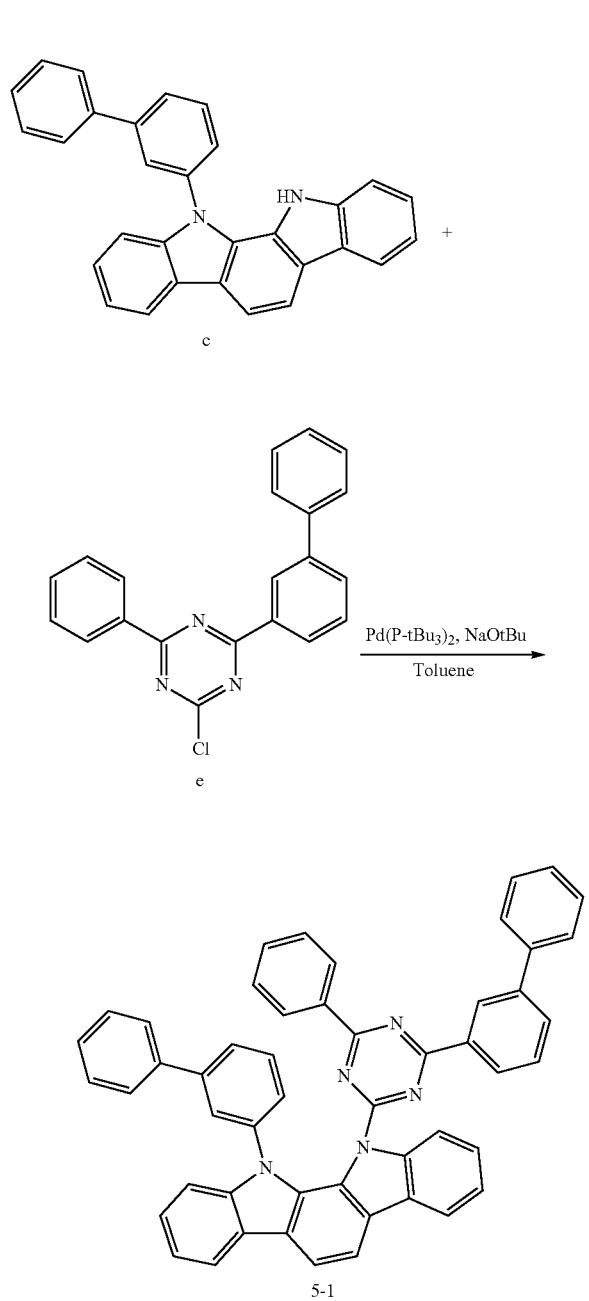

Step 2) Synthesis of Compound 5

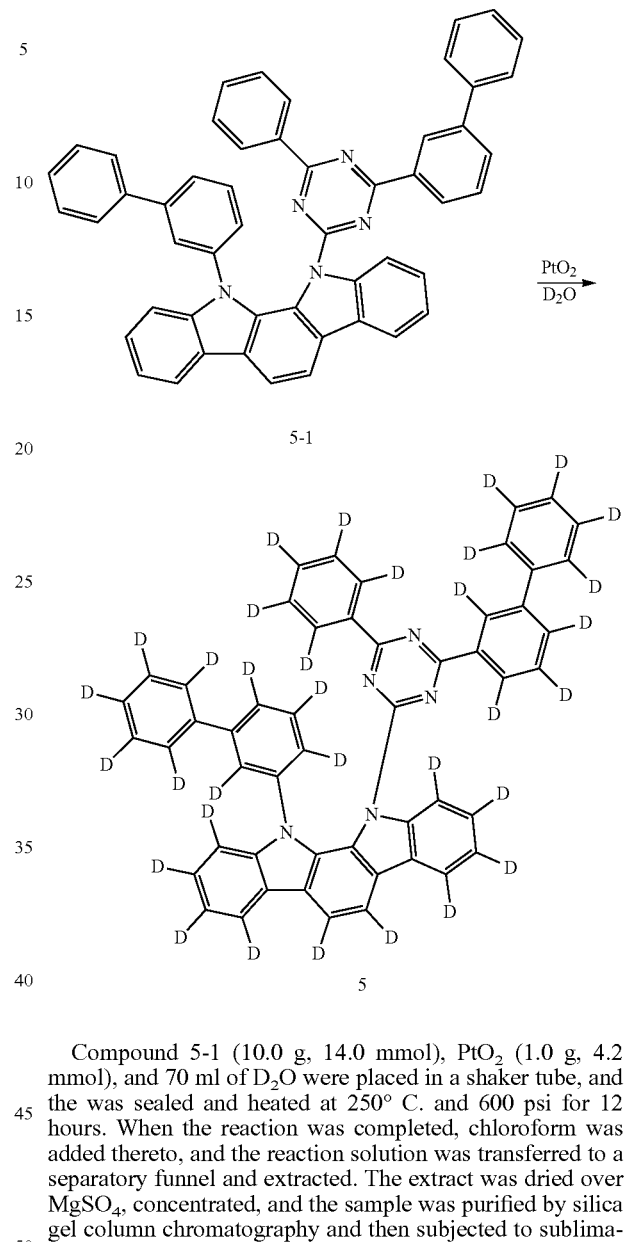

Intermediate C (15.0 g, 36.7 mmol), Intermediate e (13.9 g, 40.4 mmol), bis(tri-tert-butylphosphine)palladium(0) (0.4 g, 0.7 mmol), sodium tert-butoxide (5.3 g, 55.1 mmol) and toluene 400 ml were placed in a three-necked flask, and the mixture was stirred under reflux for 8 hours in an argon atmosphere. When the reaction was completed, the reaction mixture was cooled to room temperature, to which H$_2$O was added, and the reaction solution was transferred to a separatory funnel and extracted. The extract was dried over MgSO$_4$, concentrated, and the sample was purified by silica gel column chromatography to give 17.1 g of Compound 5-1. (yield: 65%, MS[M+H]$^+$=715)

Compound 5-1 (10.0 g, 14.0 mmol), PtO$_2$ (1.0 g, 4.2 mmol), and 70 ml of D$_2$O were placed in a shaker tube, and the was sealed and heated at 250° C. and 600 psi for 12 hours. When the reaction was completed, chloroform was added thereto, and the reaction solution was transferred to a separatory funnel and extracted. The extract was dried over MgSO$_4$, concentrated, and the sample was purified by silica gel column chromatography and then subjected to sublimation purification to give 4.4 g of Compound 5. (yield: 42%, deuterium substitution rate: 82%, MS[M+H]$^+$=749)

Synthesis Example 6: Synthesis of Compound 6

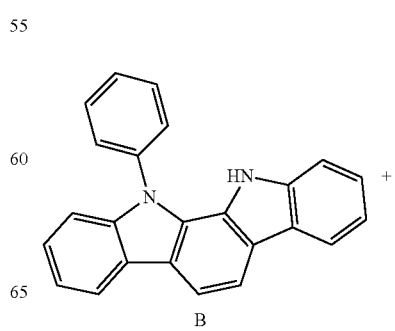

-continued

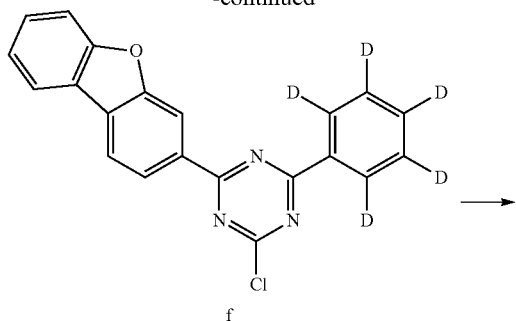
f

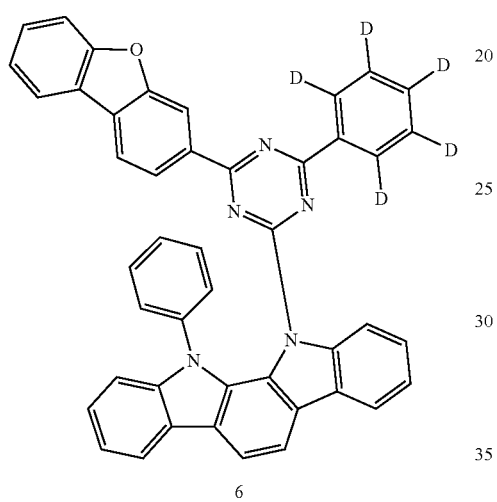
6

Compound 6 was prepared by performing the same method as the method for preparing Compound 1, except that in step 2 of Synthesis Example 1, Intermediate A was changed to Intermediate B and Intermediate a was changed to Intermediate f. (MS[M+H]⁺=658)

Synthesis Example 7: Synthesis of Compound 7

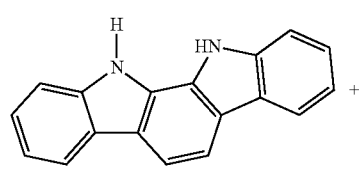

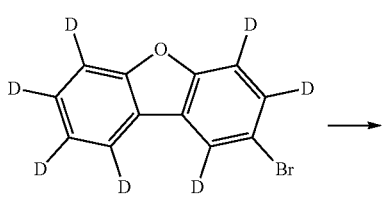

-continued

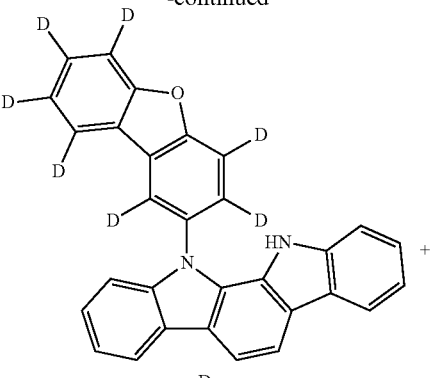

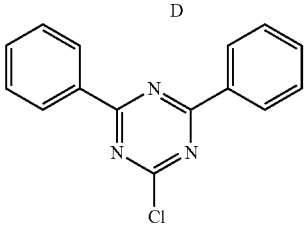
g

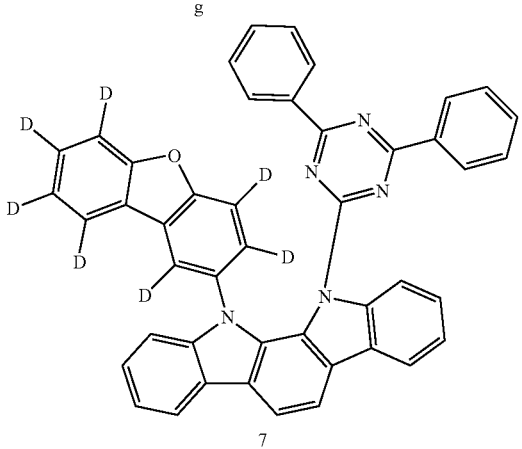
7

Compound 7 was prepared by performing the same method as the method for preparing Compound 1, except that in step 1 of Synthesis Example 1, 1-bromobenzene-2,3,4,5,6-d5 was changed to 2-bromodibenzo[b,d]furan-1,3,4,6,7,8,9-d7 to prepare Intermediate D, and in step 2 of Synthesis Example 1, Intermediate D prepared above was used instead of Intermediate A, and Intermediate a was changed to Intermediate g. (MS[M+H]⁺=660)

Synthesis Example 8: Synthesis of Compound 8

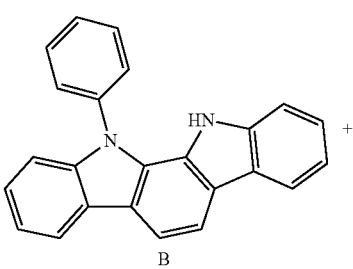
B

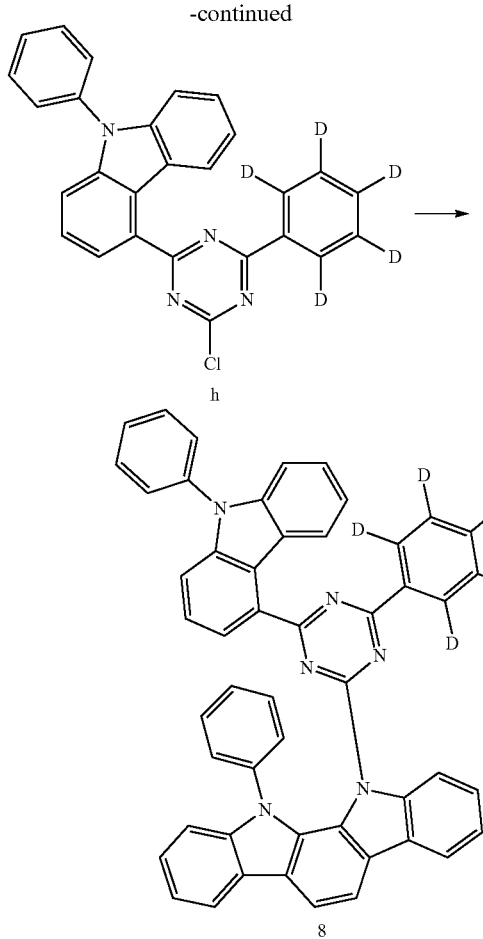

8

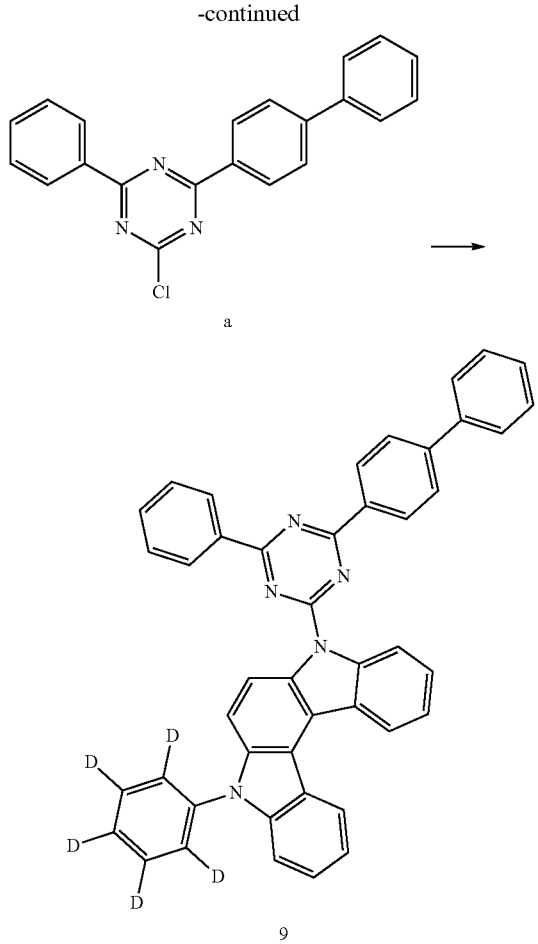

9

Compound 8 was prepared by performing the same method as the method for preparing Compound 1, except that in step 2 of Synthesis Example 1, Intermediate A was changed to Intermediate B and Intermediate a was changed to Intermediate h. (MS[M+H]$^+$=733)

Synthesis Example 9: Synthesis of Compound 9

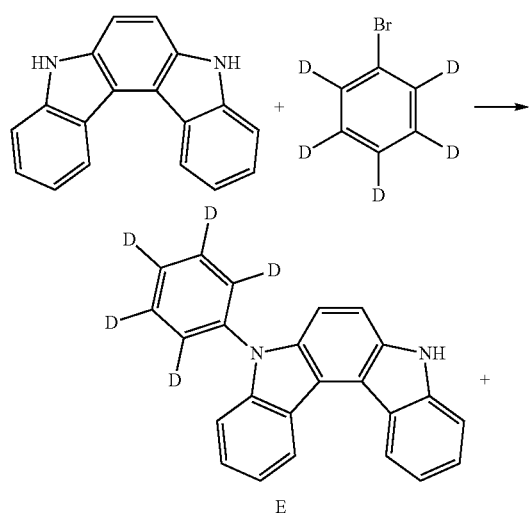

E

Compound 9 was prepared by performing the same method as the method for preparing Compound 1, except that in step 1 of Synthesis Example 1, 11,12-dihydroindolo[2,3-a]carbazole was changed to 5,8-dihydroindolo[2,3-c]carbazole. (MS[M+H]$^+$=644)

Synthesis Example 10: Synthesis of Compound 10

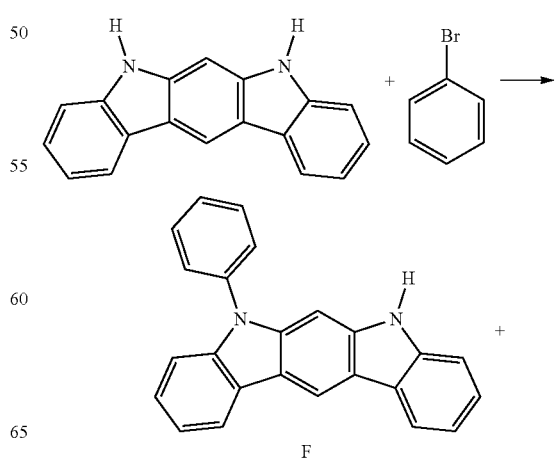

F

-continued

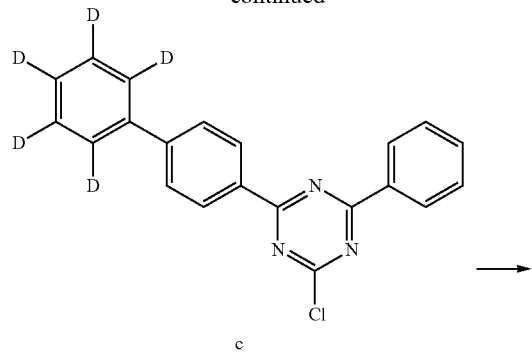
c

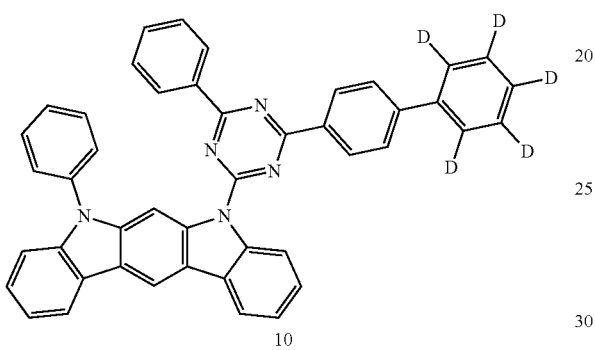
10

Compound 10 was prepared by performing the same method as the method for preparing Compound 1, except that in step 1 of Synthesis Example 1, 11,12-dihydroindolo[2,3-a]carbazole was changed to 5,7-dihydroindolo[2,3-b]carbazole, and 1-bromobenzene-2,3,4,5,6-d5 was changed to bromobenzene to prepare Intermediate F, and in step 2 of Synthesis Example 1, Intermediate F prepared above was used instead of Intermediate A, and Intermediate a was changed to Intermediate c. (MS[M+H]$^+$=644)

Synthesis Example 11: Synthesis of Compound 11

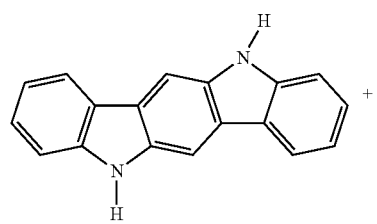
+

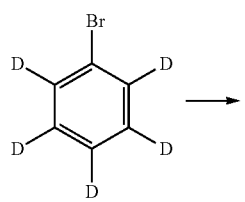

-continued

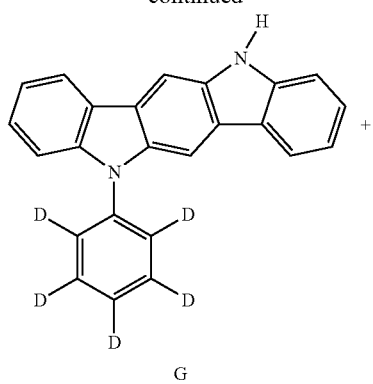
G

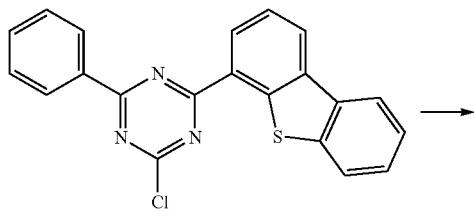
i

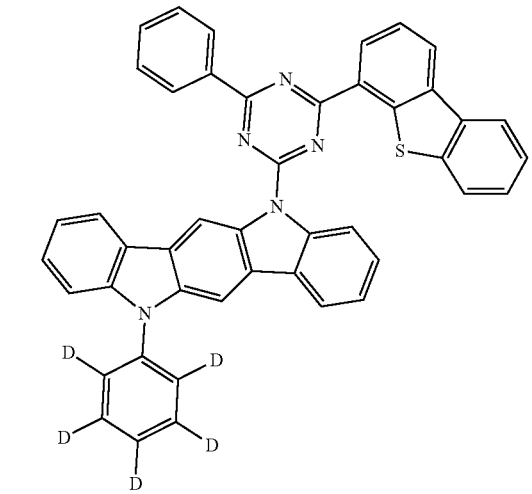
11

Compound 11 was prepared by performing the same method as the method for preparing Compound 1, except that in step 1 of Synthesis Example 1, 11,12-dihydroindolo[2,3-a]carbazole was changed to 5,11-dihydroindolo[3,2-b]carbazole to prepare Intermediate G, and in step 2 of Synthesis Example 1, Intermediate G prepared above was used instead of Intermediate A, and Intermediate a was changed to Intermediate i. (MS[M+H]$^+$=674)

Synthesis Example 12: Synthesis of Compound 12

Step 1) Synthesis of Intermediate H

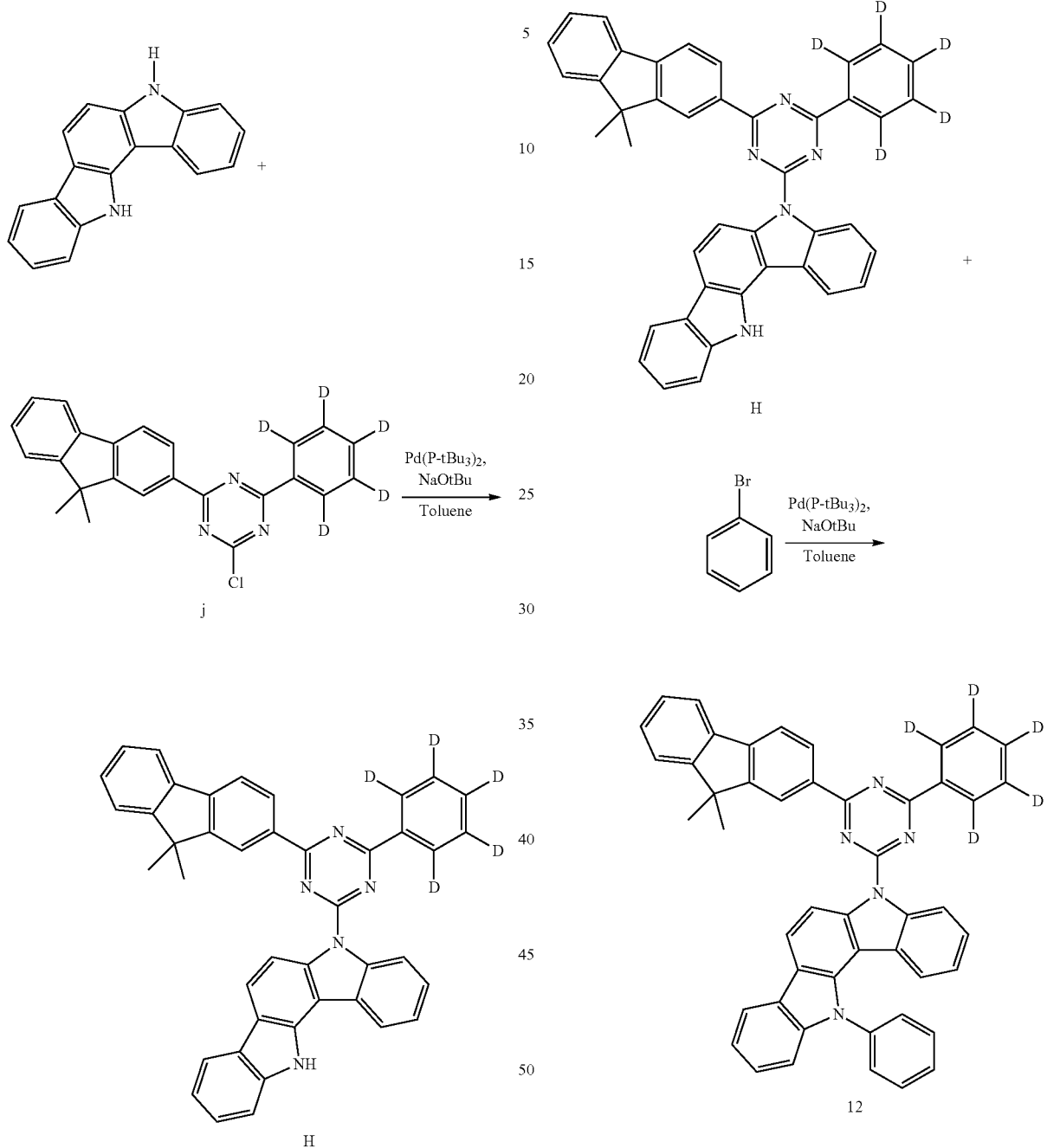

Step 2) Synthesis of Compound 12

5,12-dihydroindolo[3,2-a]carbazole (10.0 g, 39.0 mmol), Intermediate j (16.7 g, 42.9 mmol), bis(tri-tert-butylphosphine) palladium(0) (0.4 g, 0.8 mmol), sodium tert-butoxide (5.6 g, 58.5 mmol), and toluene (400 m) were placed in a three-necked flask, and the mixture was stirred under reflux for 8 hours in an argon atmosphere. When the reaction was completed, the reaction mixture was cooled to room temperature, to which H₂O was added, and the reaction solution was transferred to a separatory funnel and extracted. The extract was dried over MgSO₄, concentrated, and the sample was purified by silica gel column chromatography to give 16.9 g of Intermediate H. (yield: 71%, MS[M+H]⁺=608)

Intermediate H (15.0 g, 24.6 mmol), bromobenzene (4.3 g, 27.1 mmol), bis(tri-tert-butylphosphine)palladium(0) (0.3 g, 0.5 mmol), sodium tert-butoxide (3.6 g, 37.0 mmol) and 250 ml of xylene were placed in a three-necked flask, and the mixture was stirred under reflux for 8 hours in an argon atmosphere. When the reaction was completed, the reaction mixture was cooled to room temperature, to which H₂O was added, and the reaction solution was transferred to a separatory funnel and extracted. The extract was dried over MgSO₄, concentrated, and the sample was purified by silica gel column chromatography and then subjected to sublimation purification to give 5.4 g of Compound 12. (yield: 32%, MS[M+H]⁺=684)

Synthesis Example 13: Synthesis of Compound 13

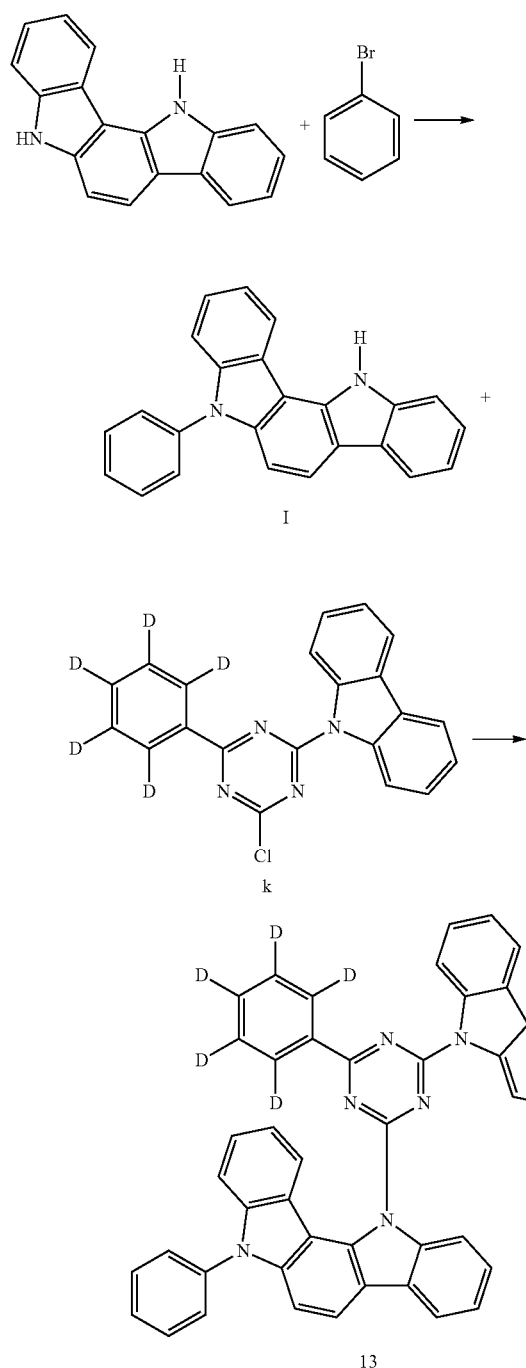

Compound 13 was prepared by performing the same method as the method for preparing Compound 1, except that in step 1 of Synthesis Example 1, 11,12-dihydroindolo[2,3-a]carbazole was changed to 5,12-dihydroindolo[3,2-a]carbazole, and 1-bromobenzene-2,3,4,5,6-d5 was changed to bromobenzene to prepare Intermediate I, and in step 2 of Synthesis Example 1, Intermediate I prepared above was used instead of Intermediate A, and Intermediate a was changed to Intermediate k. (MS[M+H]$^+$=657)

Synthesis Example 14: Synthesis of Compound 14

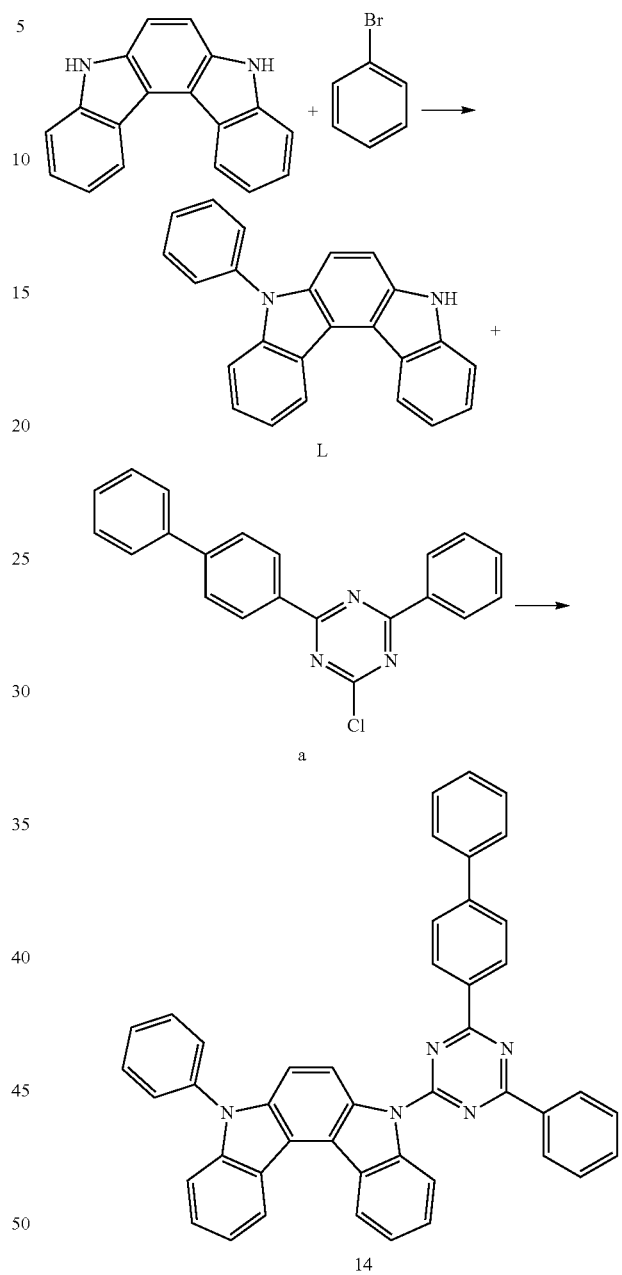

Compound 14 was prepared by performing the same method as the method for preparing Compound 1, except that in step 1 of Synthesis Example 1, 11,12-dihydroindolo[2,3-a]carbazole was changed to 5,8-dihydroindolo[2,3-c]carbazole, and 1-bromobenzene-2,3,4,5,6-d5 was changed to bromobenzene to prepare Intermediate L, and in step 2 of Synthesis Example 1, Intermediate L prepared above was used instead of Intermediate A. (MS[M+H]$^+$=639)

EXAMPLES AND COMPARATIVE EXAMPLES

Example 1

A glass substrate on which ITO (indium tin oxide) was coated as a thin film to a thickness of 1400 Å was put into distilled water in which a detergent was dissolved, and ultrasonically cleaned. At this time, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone and methanol, dried, and then transferred to a plasma cleaner. In addition, the substrate was cleaned for 5 minutes using oxygen plasma and then transferred to a vacuum depositor.

On the transparent ITO electrode thus prepared, the following HT-A and 5 wt. % of PD were thermally vacuum deposited to a thickness of 100 Å to form a hole injection layer, and then only the HT-A material was deposited to a thickness of 1150 Å to form a hole transport layer. The following HT-B was thermally vacuum deposited thereon to a thickness of 450 Å as an electron blocking layer. Then, vacuum deposition was performed to a thickness of 400 Å by using Compound 1 as a host of the light emitting layer, and 15 wt. % of GD of the host as a dopant. Then, the following compound ET-A was vacuum-deposited to a thickness of 50 Å as a hole blocking layer. Then, the following compound ET-B and Liq were thermally vacuum-deposited in a ratio of 2:1 to a thickness of 250 Å as an electron injection and transport layer, and LiF and magnesium were then vacuum deposited in a ratio of 1:1 to a thickness of 30 Å. Magnesium and silver were deposited in a ratio of 1:4 to a thickness of 160 Å on the electron injection and transport layer to form a cathode, thereby completing the manufacture of an organic light emitting device.

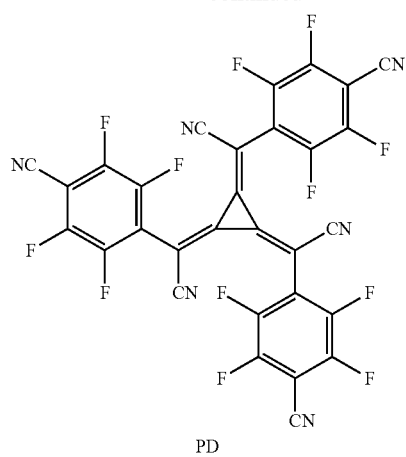

PD

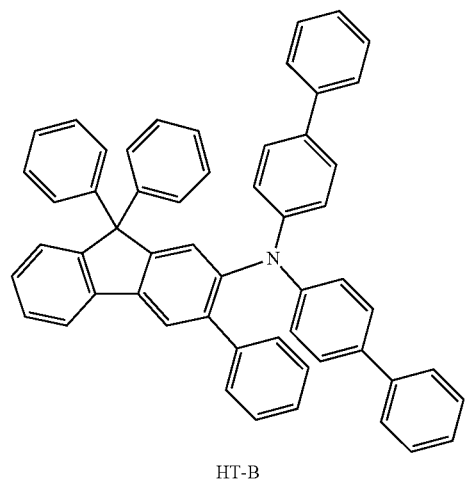

HT-B

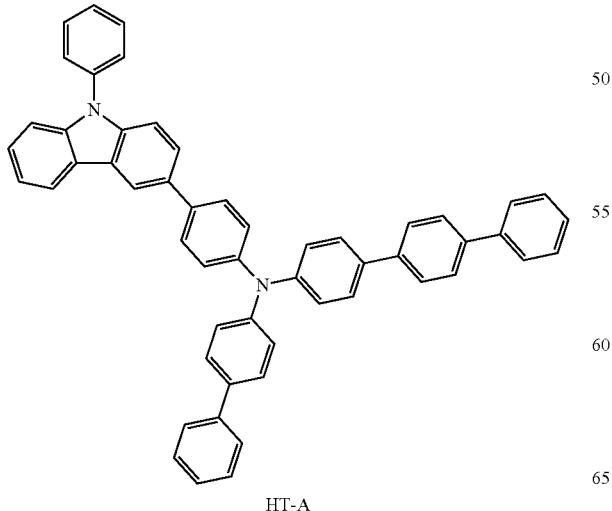

HT-A

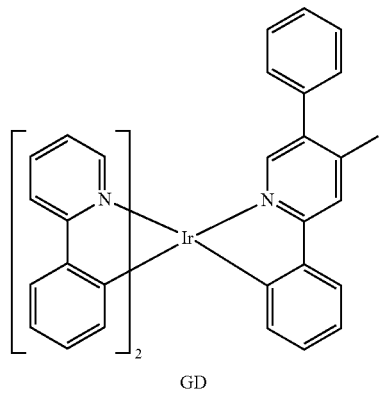

GD

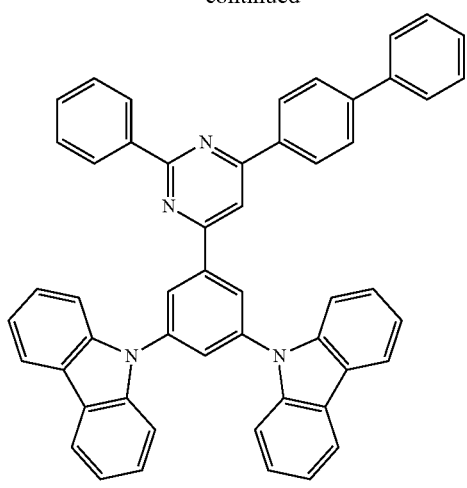
ET-A

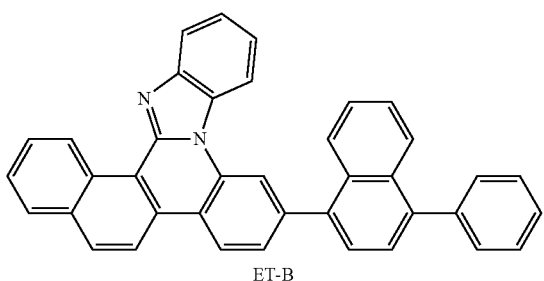
ET-B

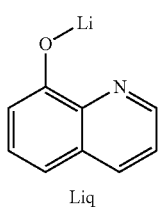
Liq

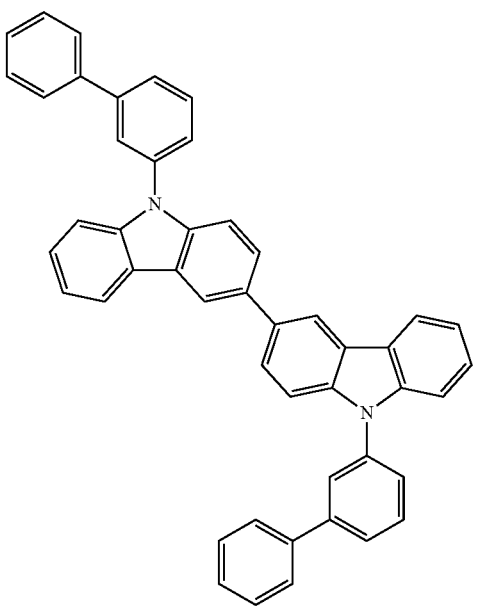
PGH-1

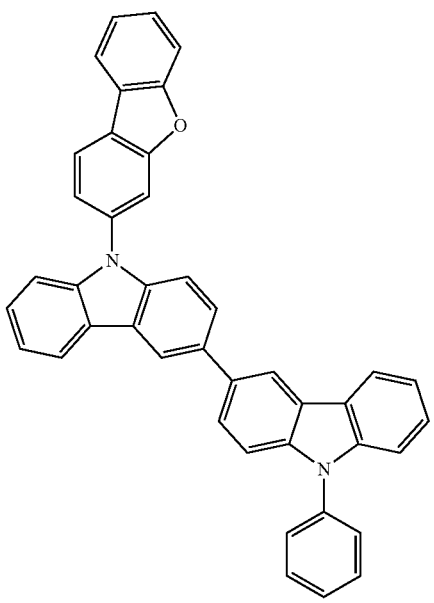
PGH-2

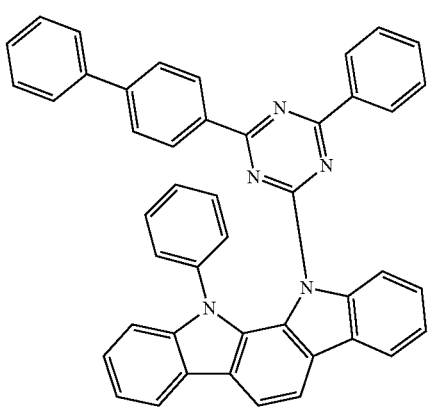
GH-A

Examples 2 to 21, and Comparative Examples 1 to 12

The organic light emitting devices of Examples 2 to 21 and Comparative Examples 1 to 12 were respectively manufactured in the same manner as in Example 1, except that the host material was changed as shown in Table 1 below. In this case, when a mixture of two kinds of compounds was used as the host, the parenthesis means the weight ratio between the host compounds.

GH-B
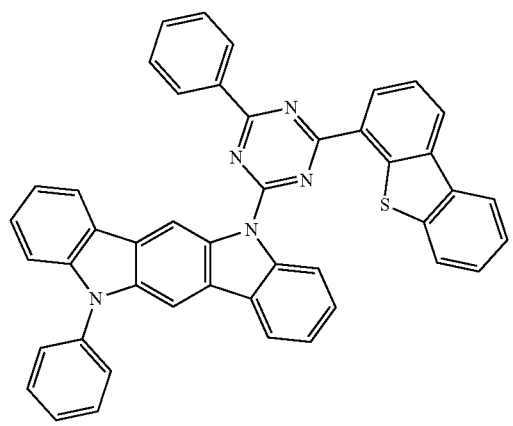
GH-C
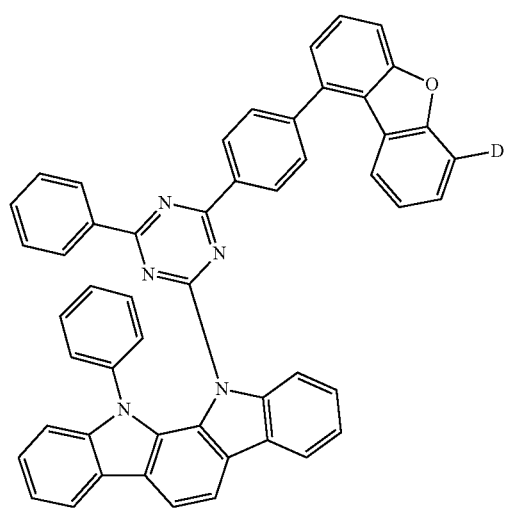
GH-D
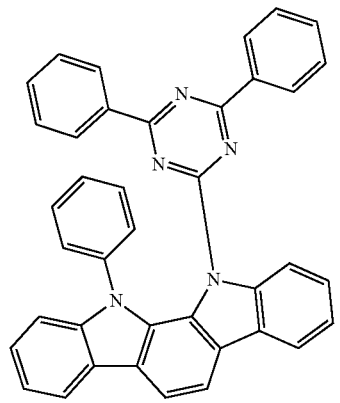
GH-E
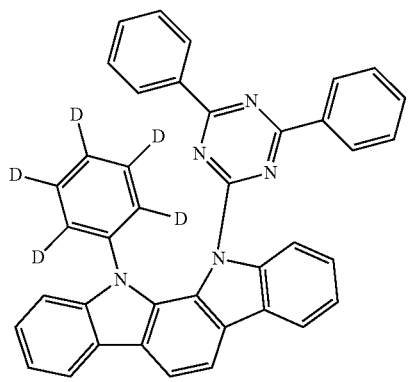
GH-F
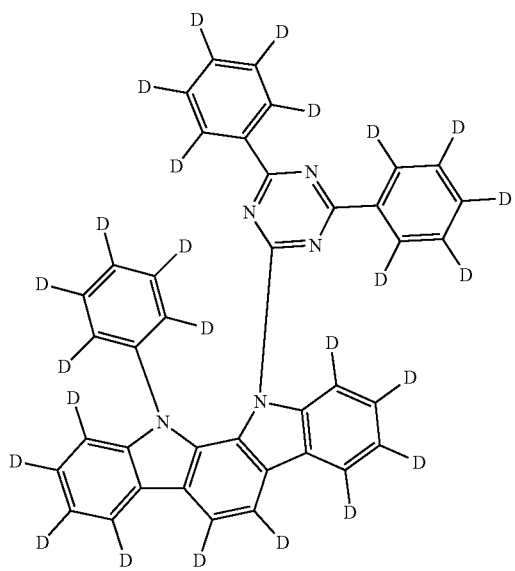
GH-G
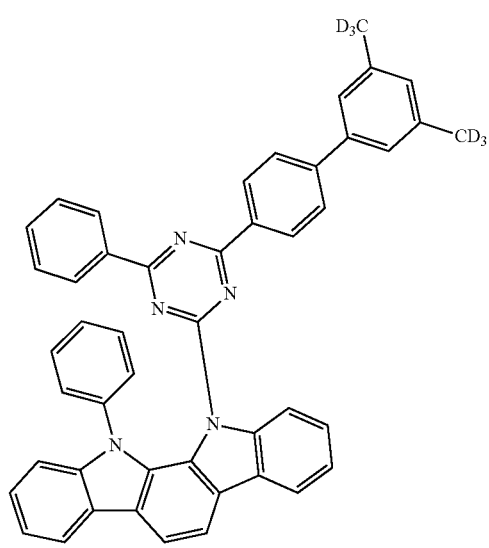

GH-H

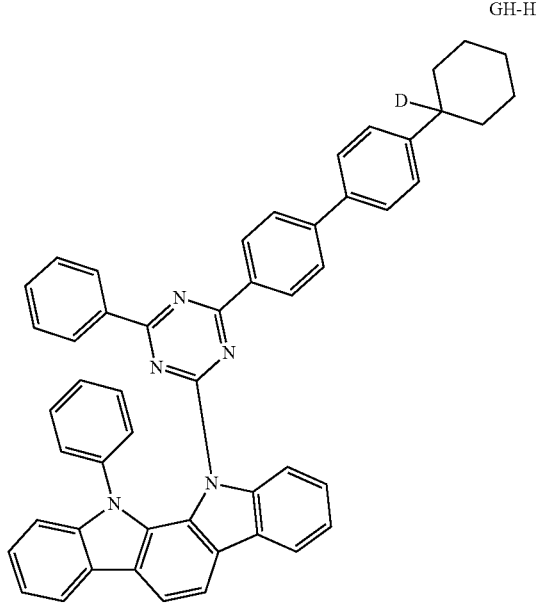

GH-I

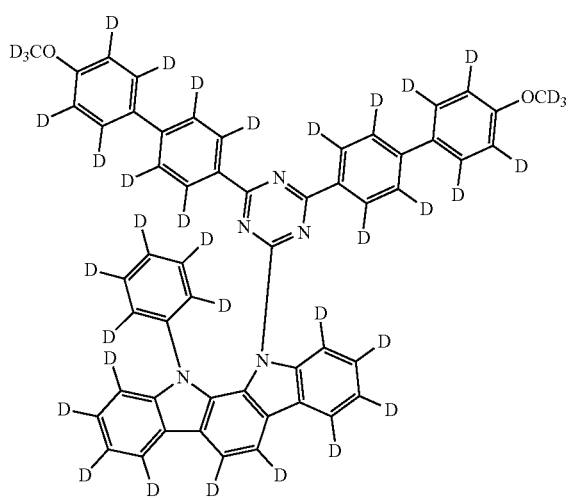

Test Example: Evaluation of Device Characteristics

The organic light emitting devices manufactured in Examples 1 to 21 and Comparative Examples 1 to 12 were heat-treated in an oven at 100° C. for 30 minutes and then taken out, and a current was applied to measure voltage, efficiency and lifetime (T95), and the results are shown in Table 1 below. At this time, the voltage and efficiency were measured by applying a current density of 10 mA/cm², and T95 means the time required for the luminance to be reduced to 95% of the initial luminance at the current density of 20 mA/cm².

TABLE 1

| | | @ 10 mA/cm² | | @ 20 mA/cm² |
|---|---|---|---|---|
| | Host material | Voltage (V) | Efficiency (cd/A) | Lifetime (T95, hr) |
| Example 1 | Compound 1 | 4.71 | 54.1 | 91 |
| Example 2 | Compound 2 | 4.71 | 54.1 | 93 |
| Example 3 | Compound 3 | 4.71 | 54.2 | 98 |
| Example 4 | Compound 4 | 4.73 | 55.2 | 93 |
| Example 5 | Compound 5 | 4.76 | 56.8 | 98 |
| Example 6 | Compound 6 | 4.67 | 52.7 | 84 |
| Example 7 | Compound 7 | 4.61 | 51.2 | 85 |
| Example 8 | Compound 8 | 4.68 | 52.1 | 88 |
| Example 9 | Compound 9 | 4.87 | 53.7 | 93 |
| Example 10 | Compound 10 | 4.81 | 53.2 | 94 |
| Example 11 | Compound 11 | 4.75 | 50.8 | 85 |
| Example 12 | Compound 12 | 4.77 | 53.7 | 86 |
| Example 13 | Compound 13 | 4.70 | 50.2 | 80 |
| Example 14 | PGH-1:Compound 1 (60:40) | 4.38 | 60.5 | 120 |
| Example 15 | PGH-1:Compound 3 (60:40) | 4.38 | 60.4 | 123 |
| Example 16 | PGH-1:Compound 5 (60:40) | 4.40 | 62.1 | 128 |
| Example 17 | PGH-1:Compound 8 (60:40) | 4.28 | 55.2 | 114 |
| Example 18 | PGH-1:Compound 10 (60:40) | 4.48 | 67.3 | 125 |
| Example 19 | PGH-2:Compound 3 (60:40) | 4.28 | 61.1 | 120 |
| Example 20 | PGH-2:Compound 4 (60:40) | 4.25 | 62.0 | 125 |
| Example 21 | PGH-2:Compound 11 (60:40) | 4.37 | 57.1 | 121 |
| Comparative Example 1 | GH-A | 4.71 | 54.2 | 60 |
| Comparative Example 2 | GH-B | 4.75 | 50.8 | 55 |
| Comparative Example 3 | GH-C | 5.21 | 45.0 | 58 |
| Comparative Example 4 | GH-D | 6.51 | 31.2 | 30 |
| Comparative Example 5 | GH-E | 6.49 | 32.0 | 34 |
| Comparative Example 6 | GH-F | 6.51 | 31.3 | 36 |
| Comparative Example 7 | GH-G | 7.01 | 28.2 | 13 |
| Comparative Example 8 | GH-H | 6.99 | 21.0 | 9 |
| Comparative Example 9 | GH-I | 7.50 | 24.2 | 8 |
| Comparative Example 10 | PGH-1:GH-A (60:40) | 4.38 | 57.5 | 81 |
| Comparative Example 11 | PGH-2:GH-B (60:40) | 4.37 | 55.1 | 70 |
| Comparative Example 12 | Compound 14 | 4.87 | 53.6 | 62 |

As can be seen from the comparison of the compound GH-A of Comparative Example 1 and the compounds 1 to 3 of Examples 1 to 3, the organic light emitting devices including the compounds of Examples 1 to 3 exhibited excellent long lifetime characteristics due to substitution of deuterium. This can be seen from the comparison between the compound GH-B of Comparative Example 2 and the compound 11 of Example 11. Meanwhile, in the GH-C compound of Comparative Example 3 including one deuterium, the effect due to deuterium was insignificant, and the efficiency was reduced due to a phenyl ring between dibenzofuran and triazine. The compounds of Comparative Examples 4 to 6 have a small molecular weight and a low glass transition temperature, so that deformation in the device appeared during the heat treatment process and the device characteristics were deteriorated. In the compounds GH-G and GH-H of Comparative Examples 7 and 8 in which deuterium is substituted at a position other than an aromatic ring, there is no effect of long lifetime due to deuterium, and the device characteristics were degraded due to the alkyl substituent which does not contribute to the movement of electrons. In the compound GH-I of Comparative Example 9 in which deuterium is present in the aromatic ring, an alkoxy group that does not contribute to the movement of electrons induced a decrease in device characteristics, and even the deuterium substituted in the alkoxy group did not offset for this decrease.

As can be seen from the results of Examples 14 to 21, when the compound of Chemical Formula 1 is used in combination with the compound of Chemical Formula 3, the effects of low voltage, high efficiency and long lifetime characteristics was found to be greater. As can be seen in Comparative Example 10 and Comparative Example 11, in the case of GH-A and GH-B, the device characteristics are improved when used in combination with Chemical Formula 3. It can be seen that when the compound of Chemical Formula 1 is mixed with Chemical Formula 3, the stability of the exciplex is greatly improved, resulting in a greater range of lifetime.

As a result, when the compound of Chemical Formula 1 is used as a light emitting layer of an organic light emitting device, a device having low voltage, high efficiency, and long lifetime can be obtained.

DESCRIPTION OF REFERENCE NUMERALS

| | |
|---|---|
| 1: substrate | 2: anode |
| 3: light emitting layer | 4: cathode |
| 5: hole injection layer | 6: hole transport layer |
| 7: light emitting layer | 8: electron injection and transport layer |

The invention claimed is:
1. A compound represented by Chemical Formula 1:

[Chemical Formula 1]

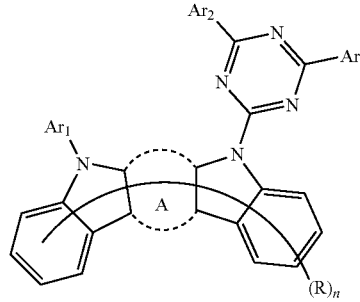

wherein, in Chemical Formula 1,
A is a benzene ring fused with two adjacent pentagonal rings,
at least one of $Ar_1$, $Ar_2$ and $Ar_3$ is a biphenylyl group; a dibenzofuranyl group; a dibenzothiophenyl group; a 9,9-dimethylfluorenyl group; a 9,9-diphenylfluorenyl group; a carbazol-9-yl group; a 9-methyl-carbazolyl group; or a 9-phenyl-carbazolyl group, and the rest are a phenyl group, and $Ar_2$ and $Ar_3$ are not a biphenylyl group at the same time, at least one of $Ar_1$, $Ar_2$ and $Ar_3$ is substituted with one or more deuterium, and the rest are unsubstituted, R is hydrogen; deuterium; halogen; cyano; a substituted or unsubstituted $C_{1-60}$ alkyl group; a substituted or unsubstituted $C_{1-60}$ alkoxy group; a substituted or unsubstituted $C_{2-60}$ alkenyl group; a substituted or unsubstituted $C_{2-60}$ alkynyl group; a substituted or unsubstituted $C_{3-60}$ cycloalkyl group; a substituted or unsubstituted $C_{6-60}$ aryl group; a substituted or unsubstituted $C_{2-60}$ heteroaryl group containing any one or more heteroatoms selected from the group consisting of N, O, and S; a substituted or unsubstituted tri ($C_{1-60}$ alkyl) silyl group; or a substituted or unsubstituted tri ($C_{6-60}$ aryl) silyl group, and n is an integer of 0 to 10.

2. The compound of claim 1, wherein the compound is represented by any one of the following Chemical Formulas 1-1 to 1-6:

[Chemical Formula 1-1]

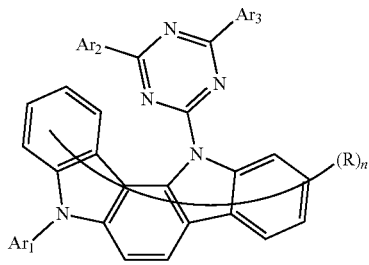

[Chemical Formula 1-2]

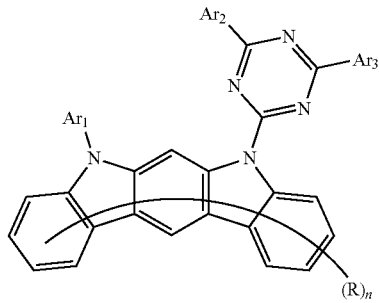

[Chemical Formula 1-3]

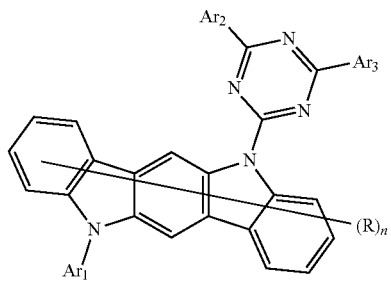

-continued

[Chemical Formula 1-4]

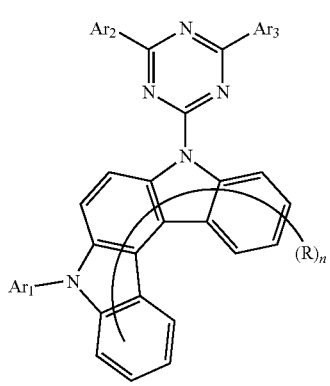

[Chemical Formula 1-5]

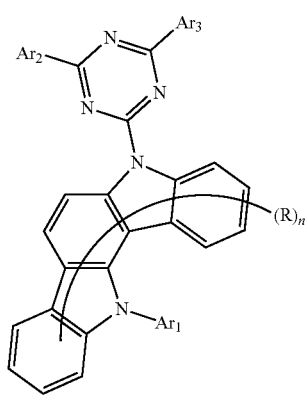

[Chemical Formula 1-6]

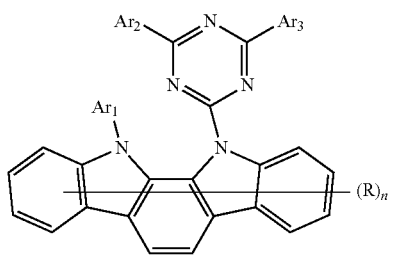

wherein, in Chemical Formulas 1-1 to 1-6, $Ar_1$, $Ar_2$, $Ar_3$, R and n are the same as defined in claim 1.

3. The compound of claim 1, wherein $Ar_1$, $Ar_2$ or $Ar_3$ is any one selected from the group consisting of the following Chemical Formulas 2-1 to 2-4:

[Chemical Formula 2-1]

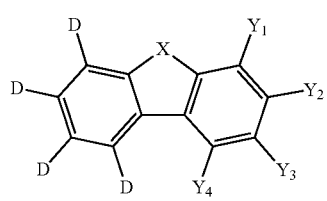

-continued

[Chemical Formula 2-2]

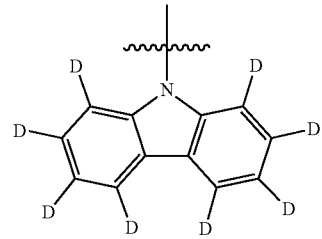

[Chemical Formula 2-3]

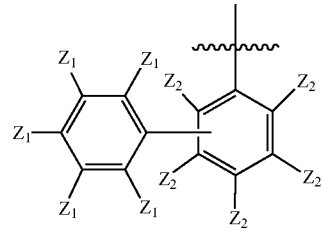

[Chemical Formula 2-4]

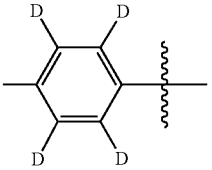

wherein, in Chemical Formulas 2-1 to 2-4,
X is O; S; —$NR_1$; or —$CR_2R_3$,
$R_1$, $R_2$ and $R_3$ are each independently a methyl group; or a phenyl group,
one of $Y_1$, $Y_2$, $Y_3$ and $Y_4$ is a single bond linked to a carbon atom in the triazinyl group or a nitrogen atom in the indolocarbazole group, and the rest are deuterium,
all $Z_1$ are hydrogen or all $Z_1$ are deuterium, all $Z_2$ are hydrogen or all $Z_2$ are deuterium, and all $Z_1$ and all $Z_2$ are not simultaneously hydrogen.

4. The compound of claim 1, wherein $Ar_1$, $Ar_2$ or $Ar_3$ is any one selected from the group consisting of the following formulas:

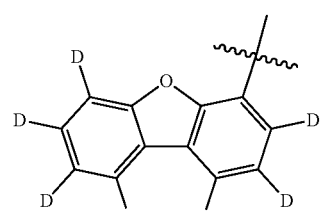

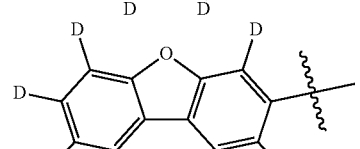

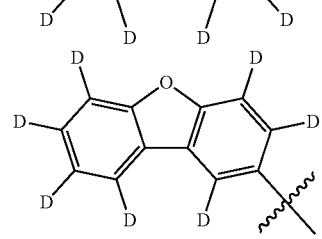

177
-continued
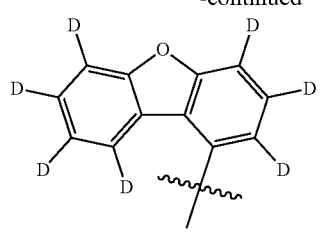
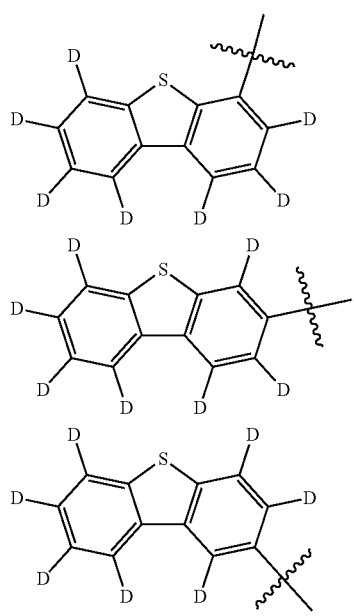
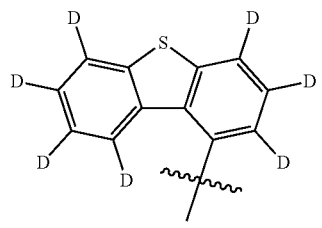
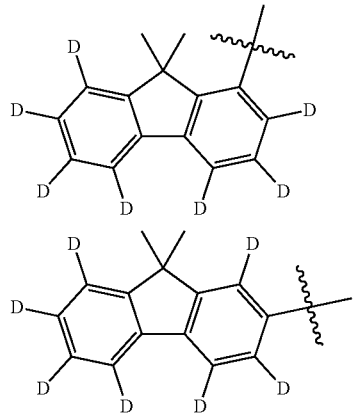
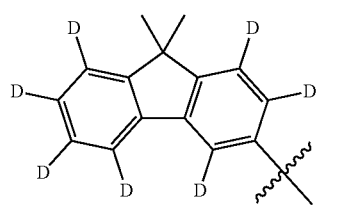
178
-continued
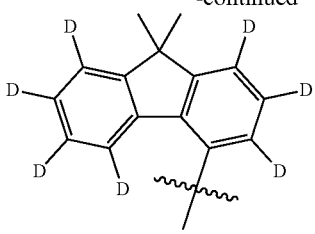
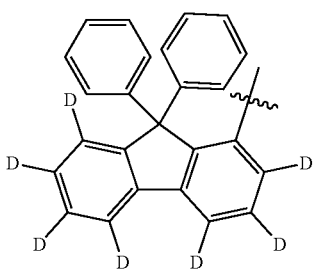
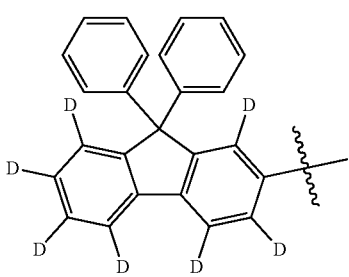
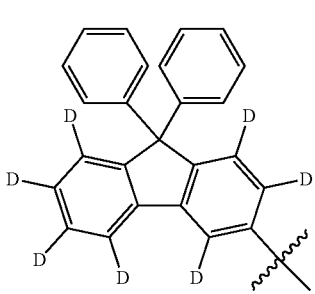
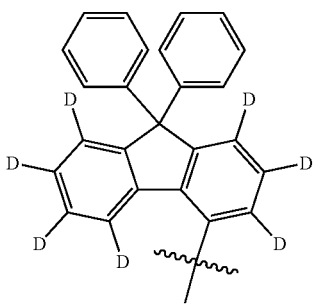
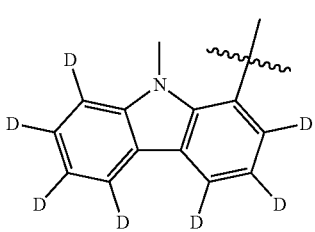

179
-continued
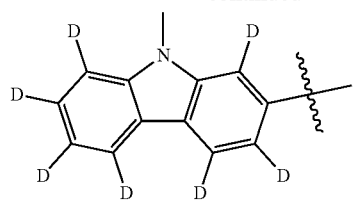
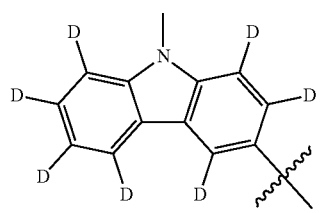
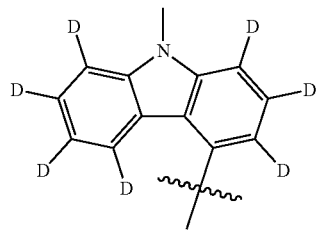
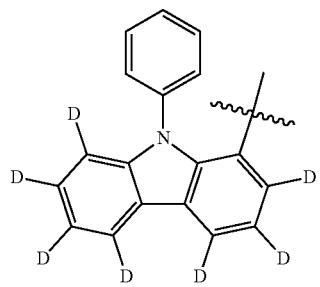
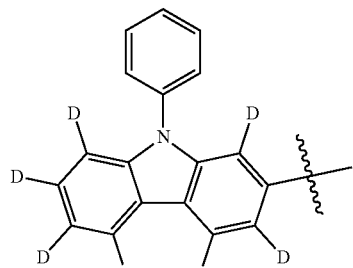
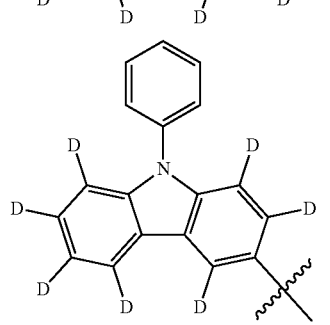
180
-continued
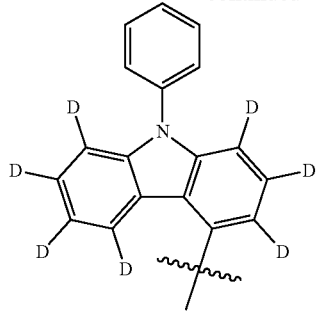
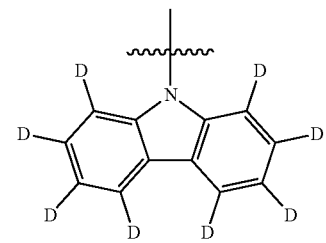
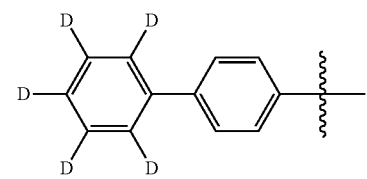
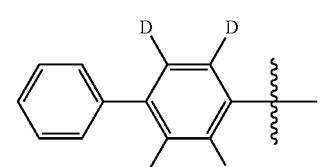
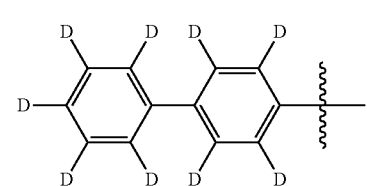
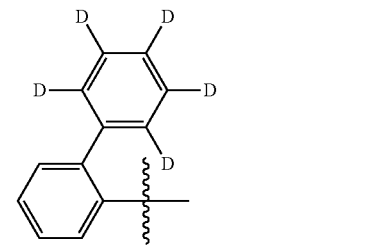
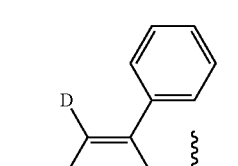
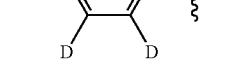

-continued

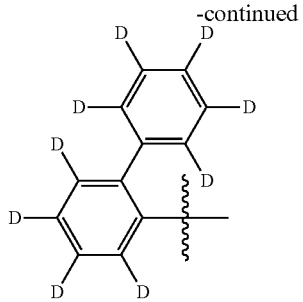

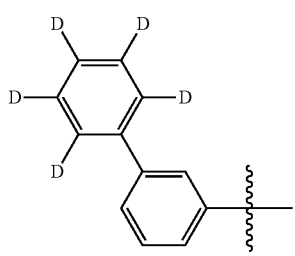

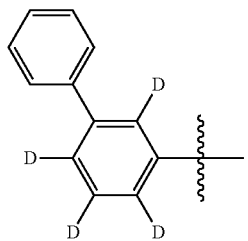

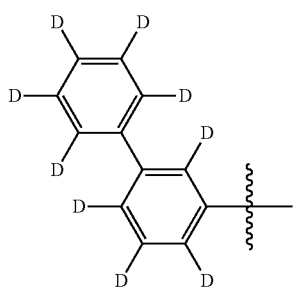

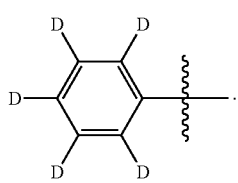

5. The compound of claim 1, wherein one of $Ar_1$, $Ar_2$ and $Ar_3$ is a biphenylyl group, and the rest are a phenyl group, and
at least one of $Ar_1$, $Ar_2$ and $Ar_3$ is substituted with one or more deuterium, and the rest are unsubstituted.

6. The compound of claim 1, wherein one of $Ar_1$, $Ar_2$ and $Ar_3$ is represented by Chemical Formula 2-3, and the rest are an unsubstituted phenyl group:

[Chemical Formula 2-2]

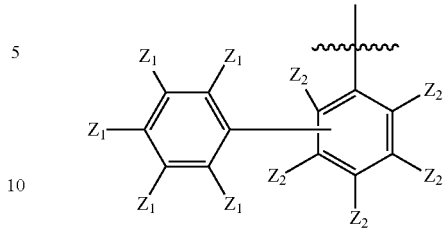

wherein, in Chemical Formula 2-3,
all $Z_1$ are deuterium and all $Z_2$ are hydrogen.

7. The compound of claim 1, wherein one of $Ar_1$, $Ar_2$ and $Ar_3$ is an unsubstituted biphenylyl group, the rest are a phenyl group, and at least one of the rest is represented by Chemical Formula 2-4.

[Chemical Formula 2-3]

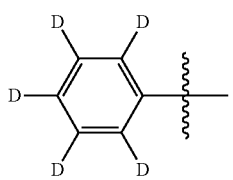

8. The compound of claim 1, wherein $Ar_1$ has a biphenylyl group,
one of $Ar_2$ and $Ar_3$ is a biphenylyl group, and the other is a phenyl group, and
at least one of $Ar_1$, $Ar_2$ and $Ar_3$ is substituted with one or more deuterium, and the rest are unsubstituted.

9. The compound of claim 1, wherein $Ar_1$, $Ar_2$ and $Ar_3$ is an unsubstituted dibenzofuranyl group; an unsubstituted dibenzothiophenyl group; an unsubstituted 9,9-dimethylfluorenyl group; an unsubstituted carbazol-9-yl group; or an unsubstituted 9-phenyl-carbazolyl group, and the rest are a phenyl group, and at least one of the rest is substituted with deuterium.

10. The compound of claim 1, wherein one of $Ar_1$, $Ar_2$ and $Ar_3$ is a dibenzofuranyl group substituted with deuterium; a dibenzothiophenyl group substituted with deuterium; or a 9,9-dimethylfluorenyl group substituted with deuterium, and the rest are an unsubstituted phenyl group.

11. The compound of claim 1, wherein all R are hydrogen, or all R are deuterium.

12. The compound of claim 1, wherein the compound represented by Chemical Formula 1 is any one selected from the group consisting of the following compounds:

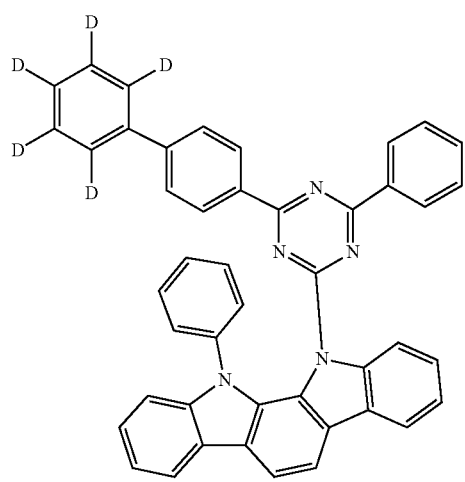
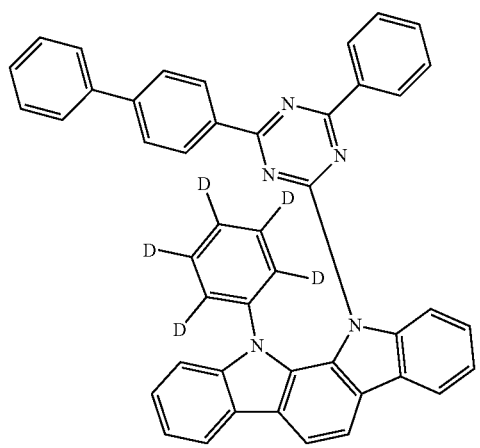
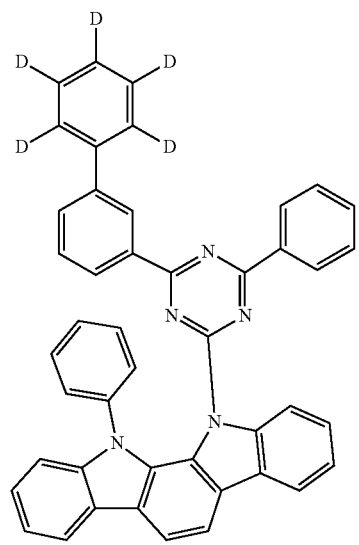
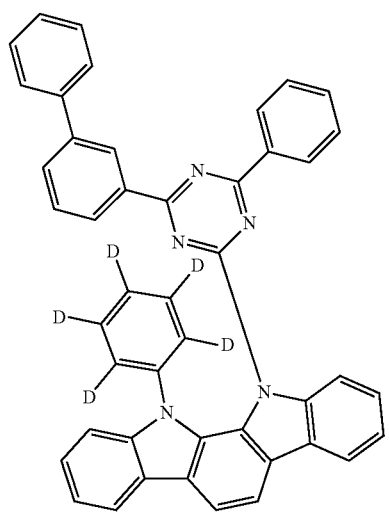
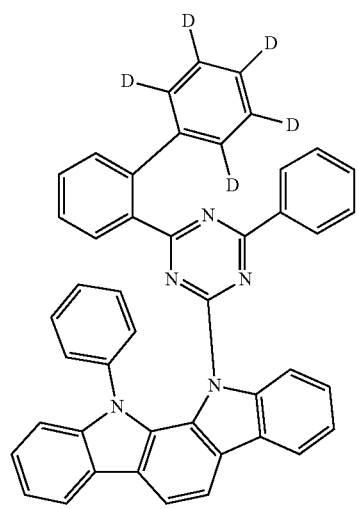
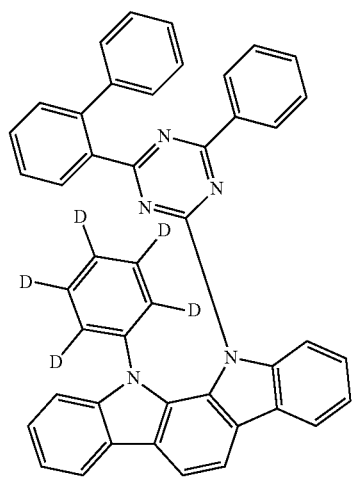

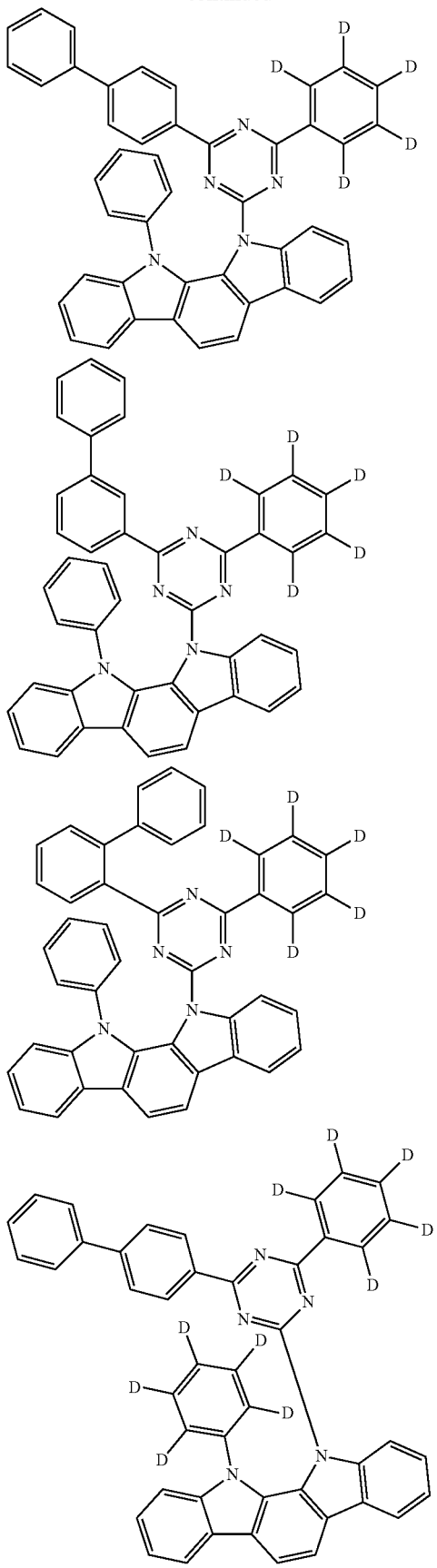
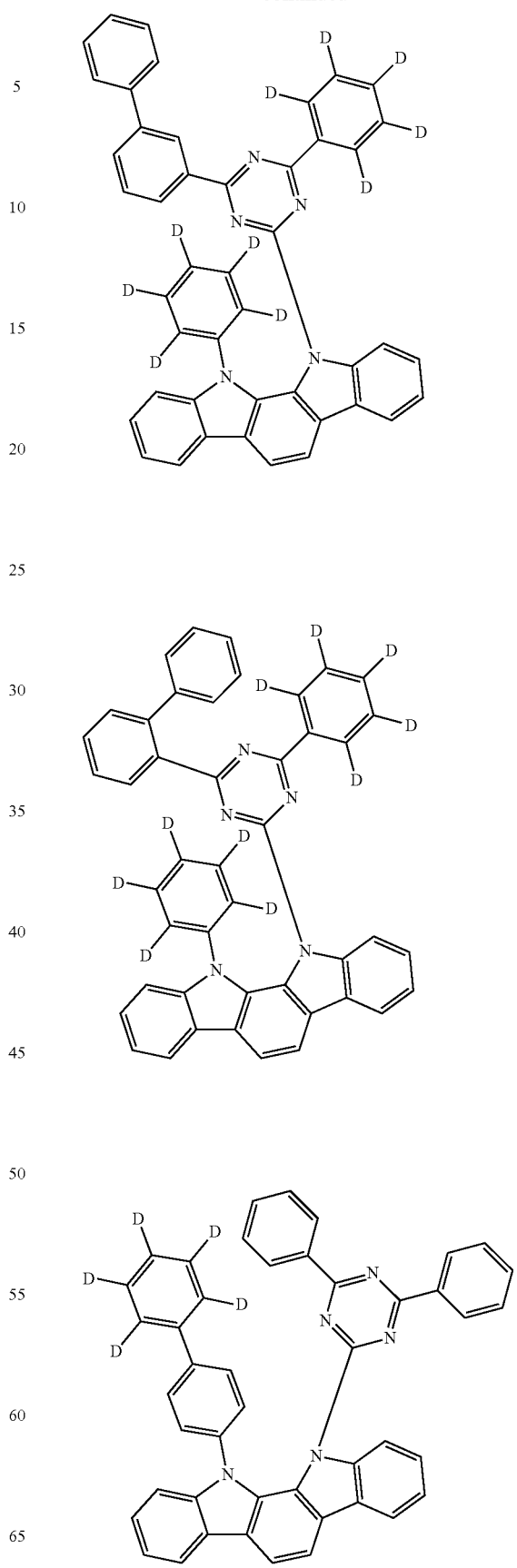

187
-continued
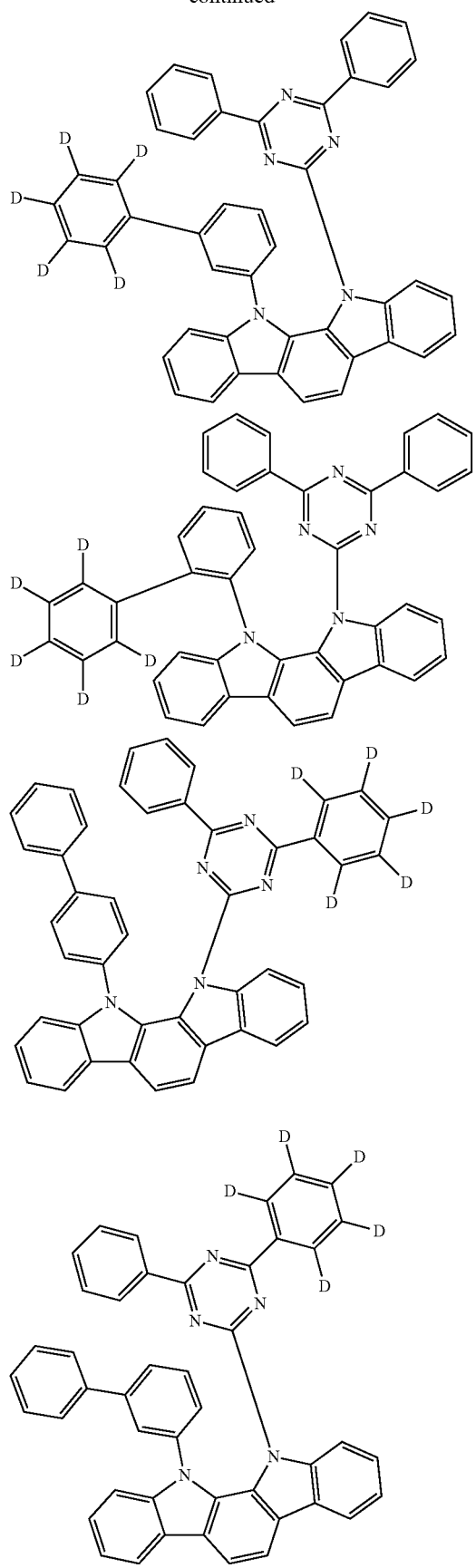
188
-continued
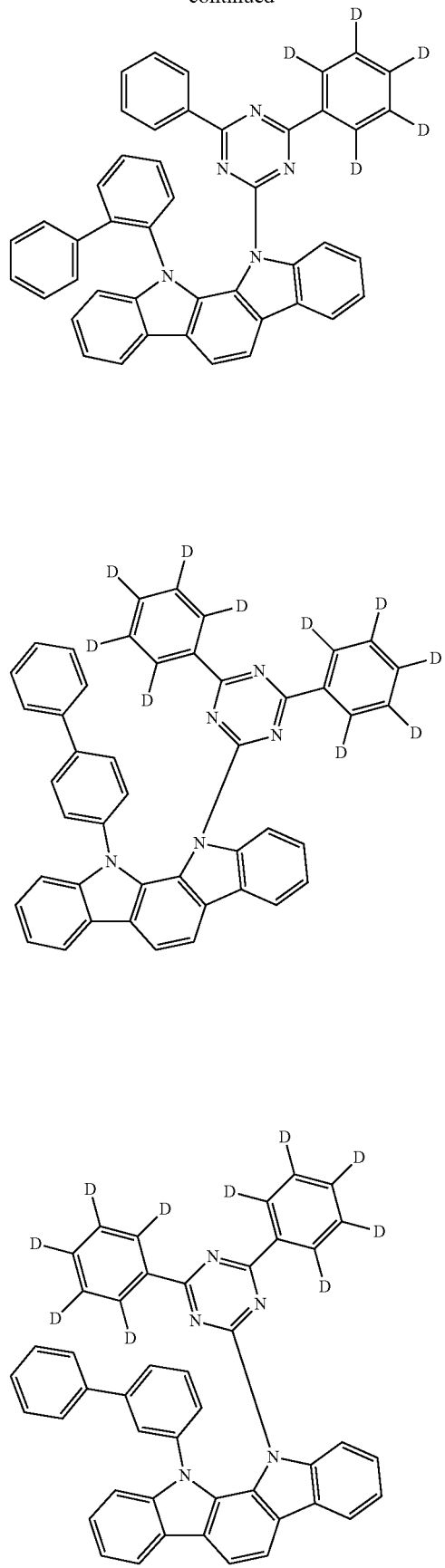

189
-continued
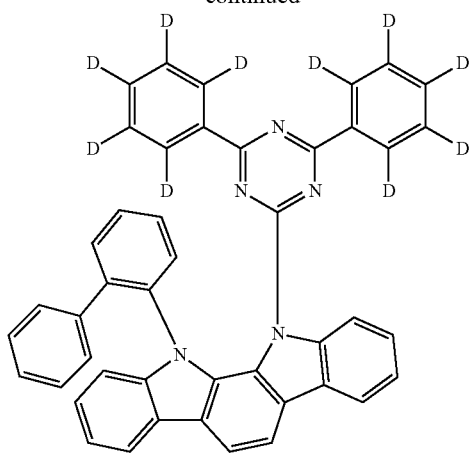
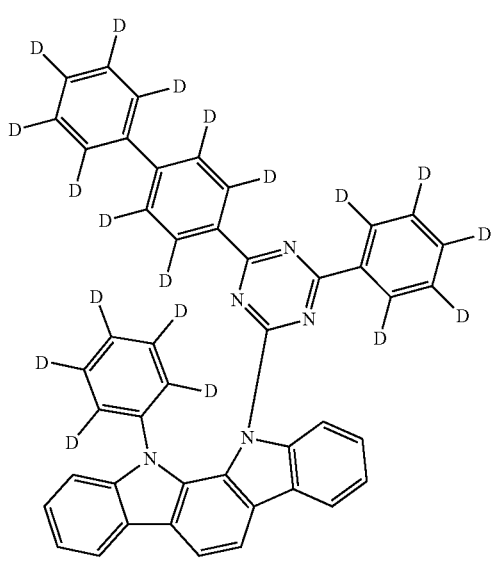
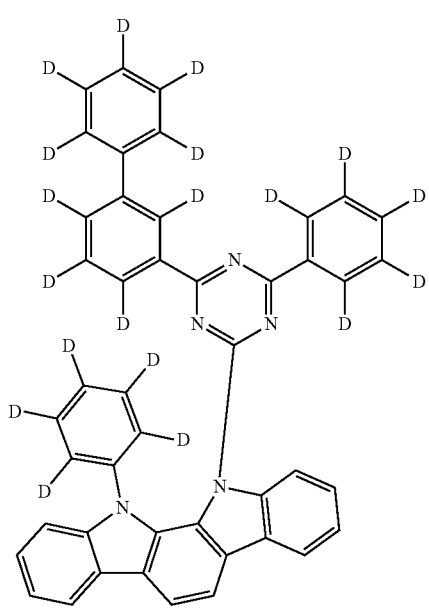
190
-continued
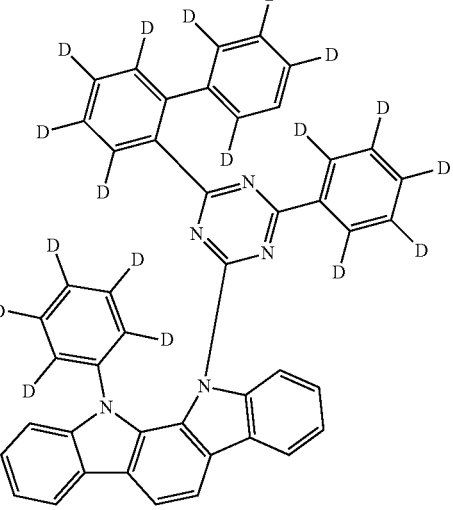
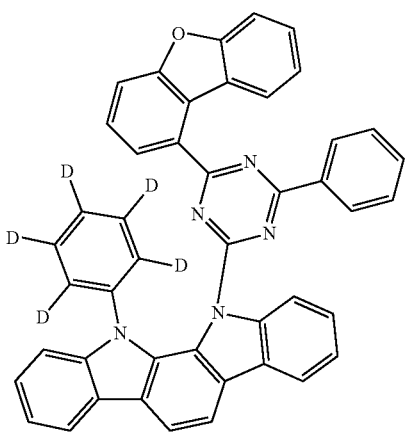
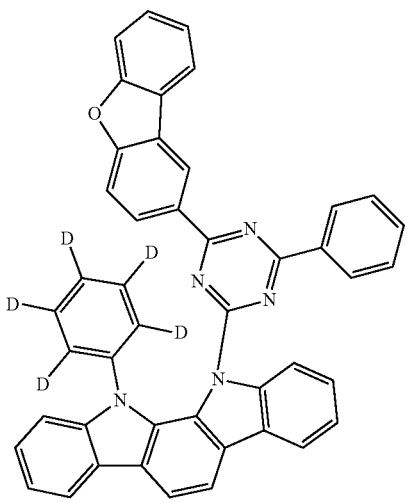

191
-continued
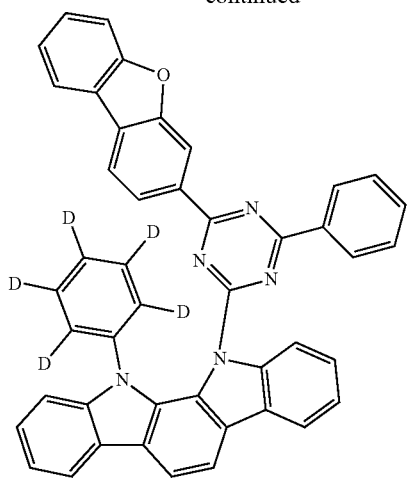
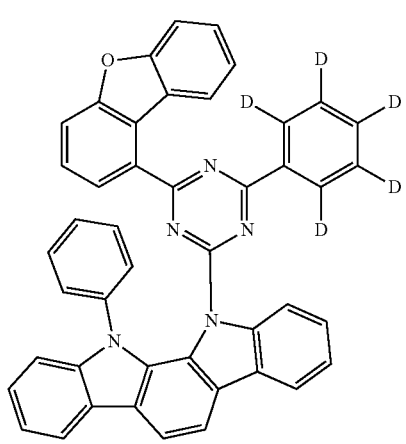
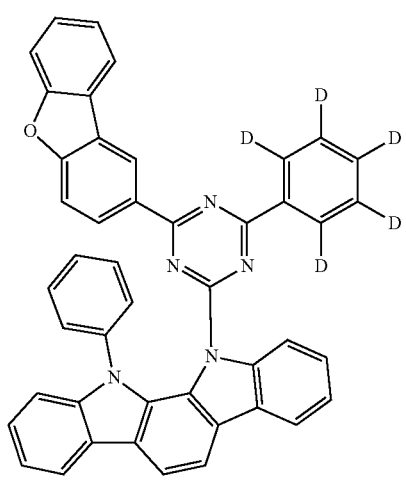
192
-continued
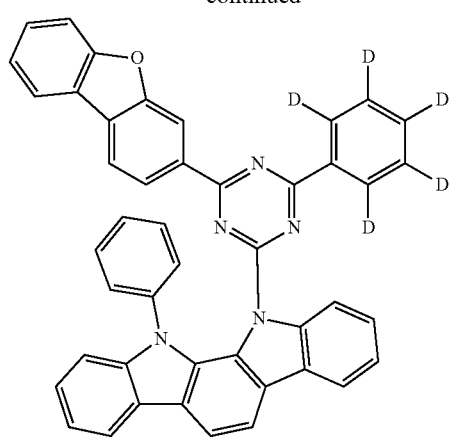
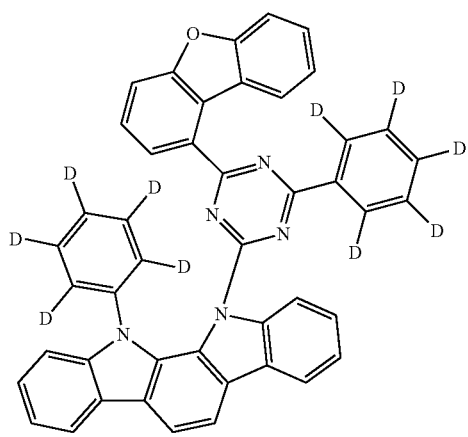
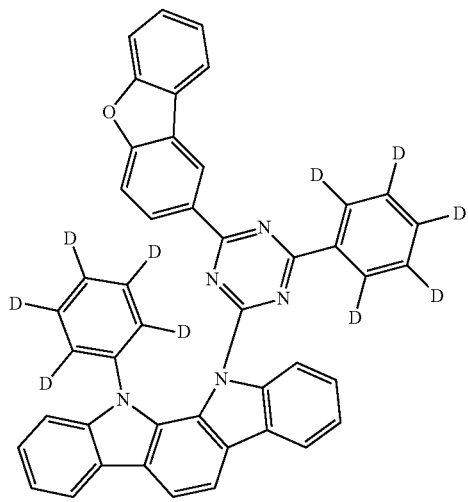

193
-continued
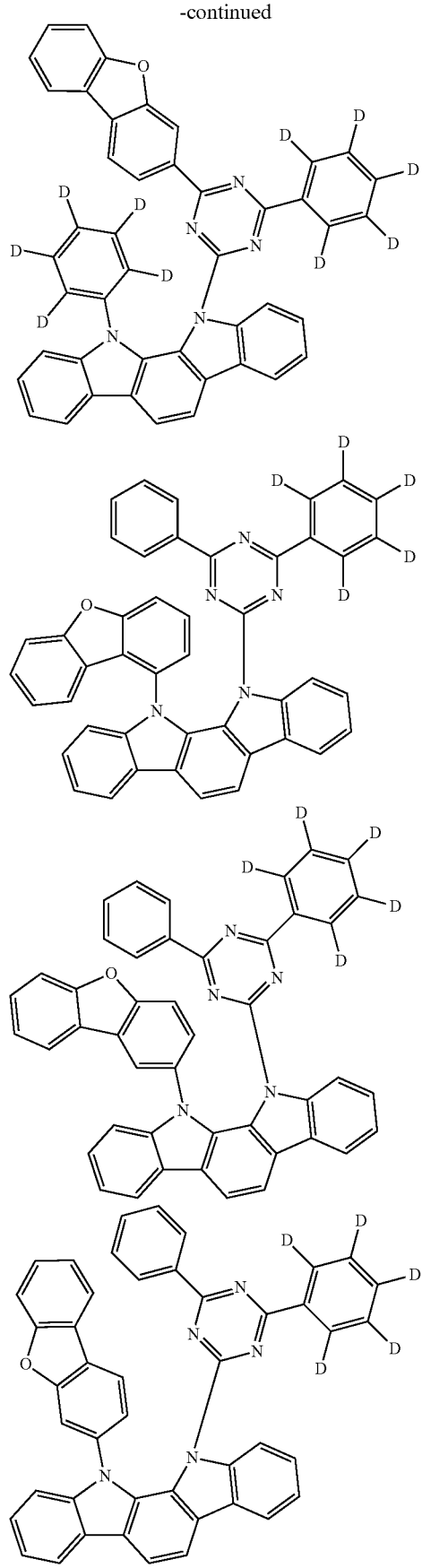
194
-continued
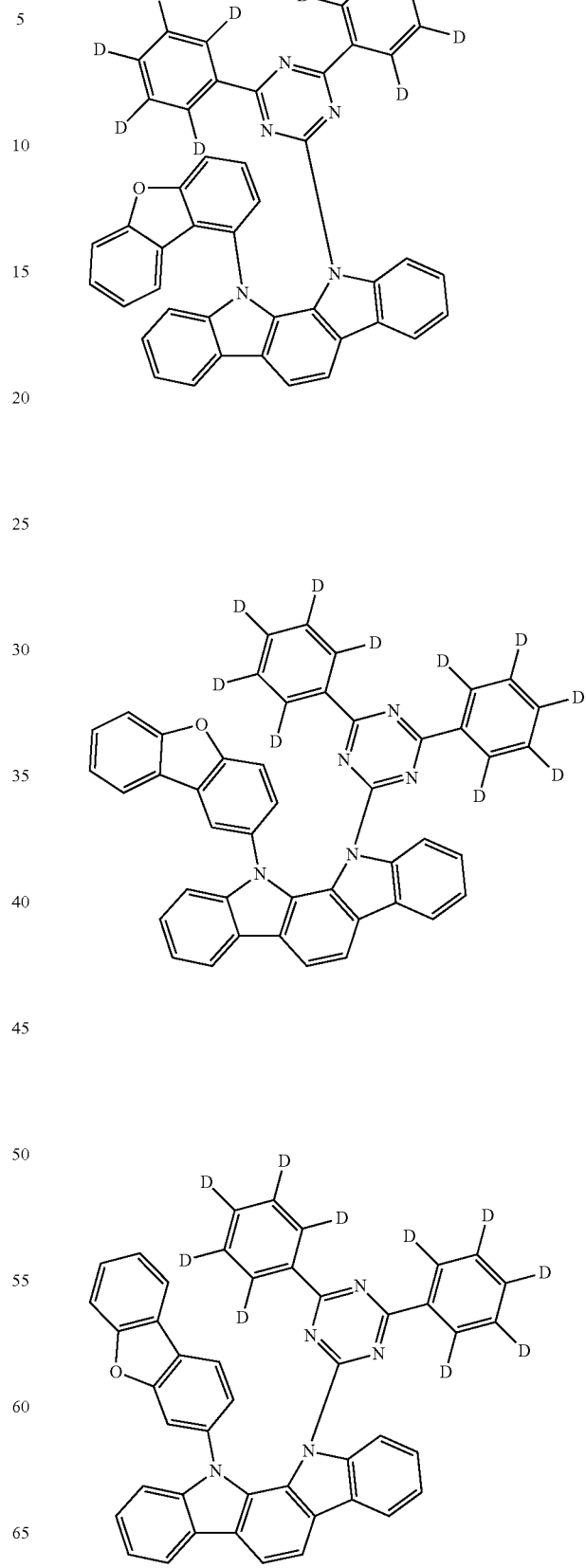

195
-continued
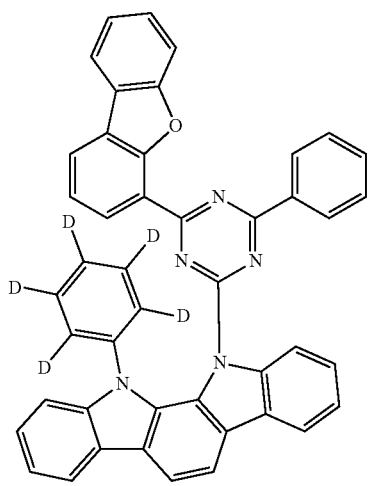
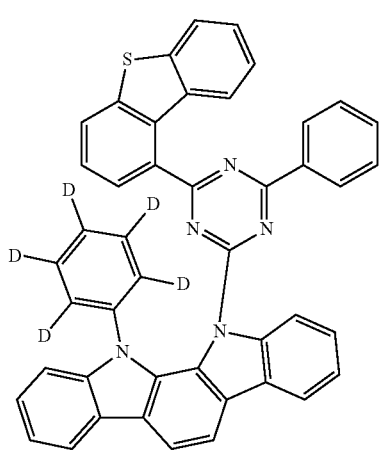
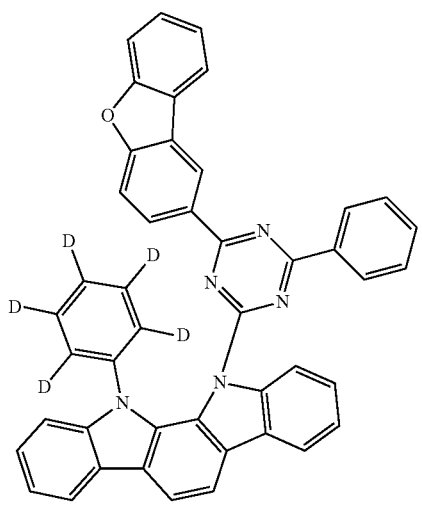
196
-continued
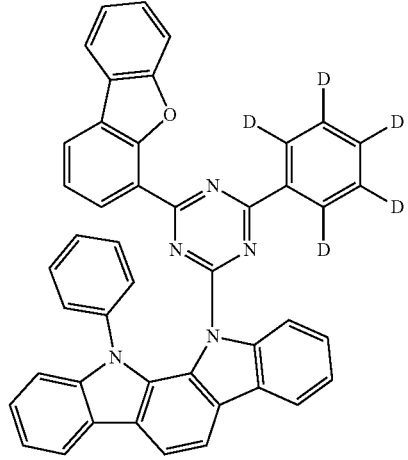
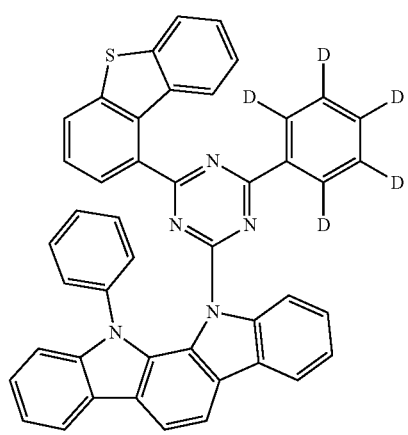
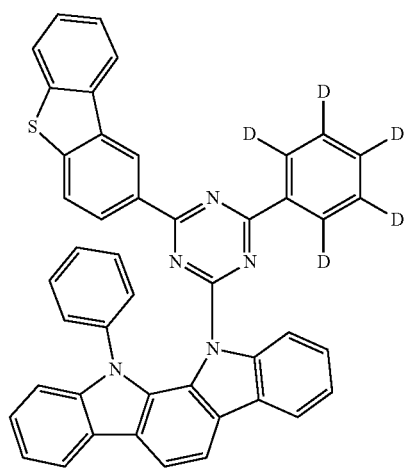

197
-continued
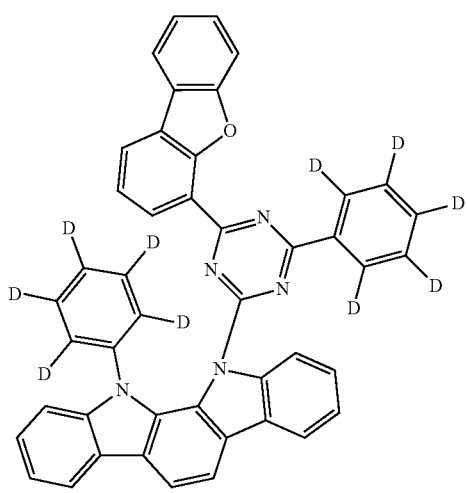
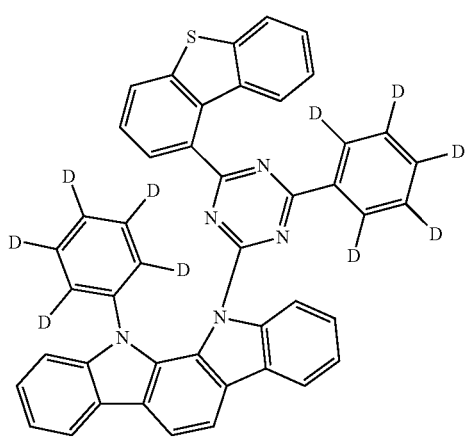
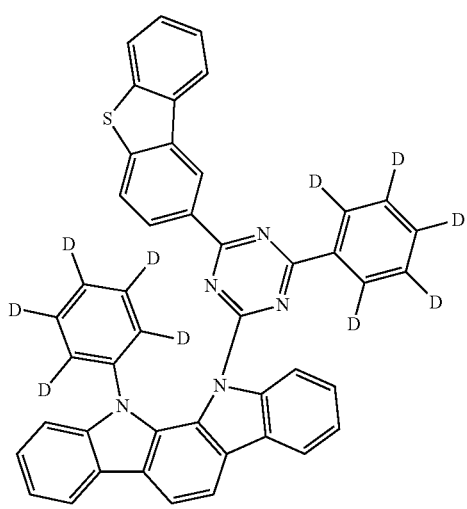
198
-continued
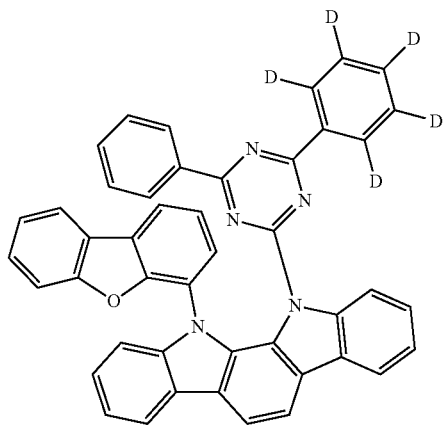
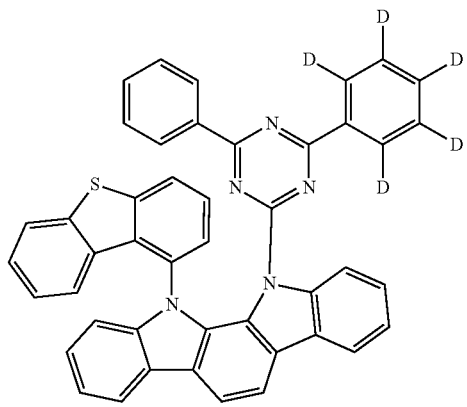
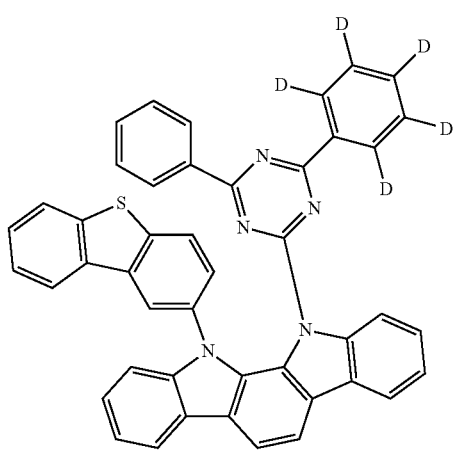

199
-continued
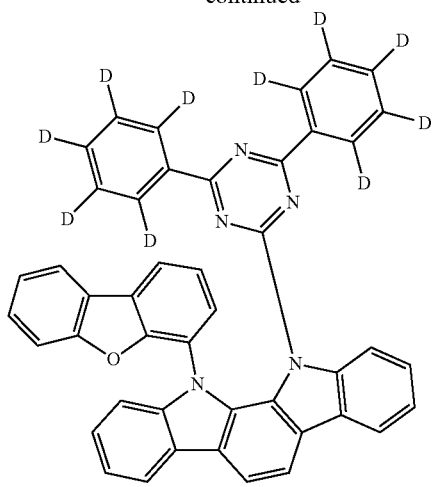
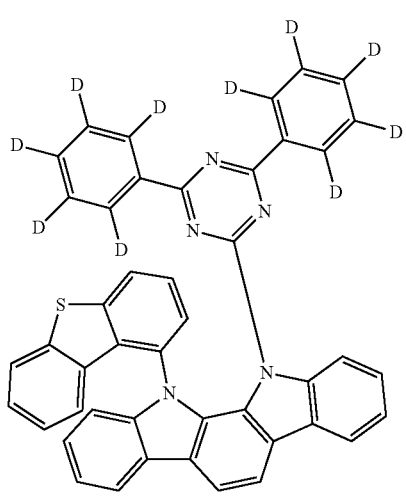
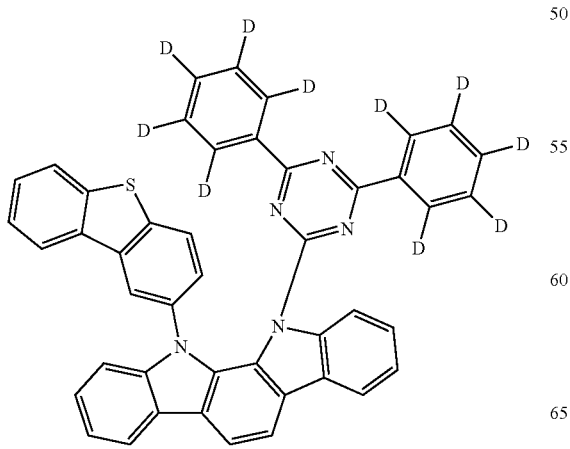
200
-continued
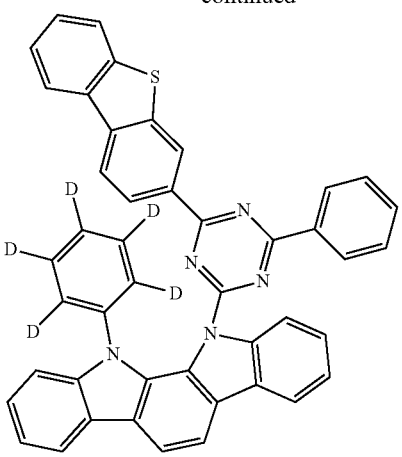
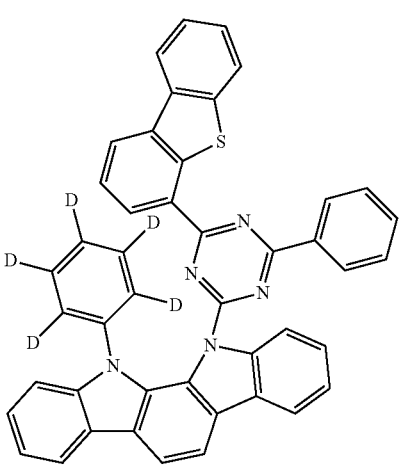
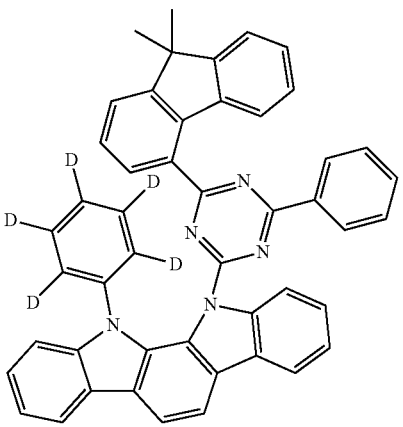

201
-continued
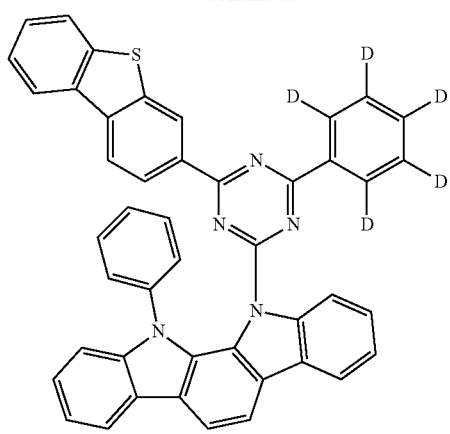
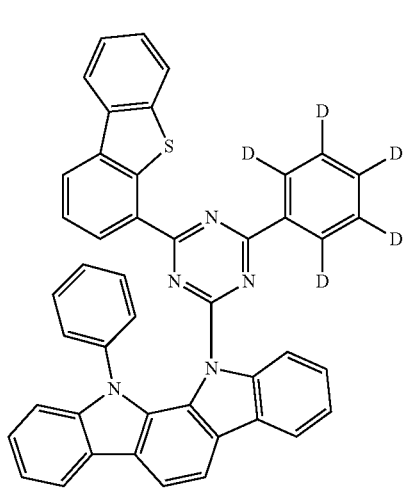
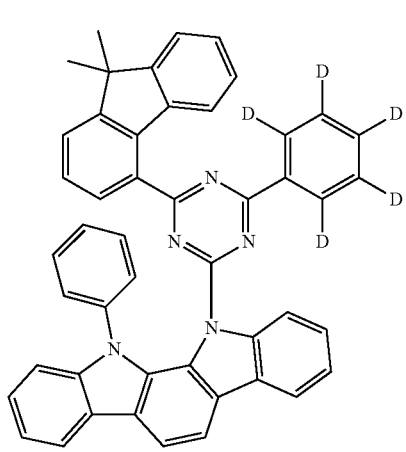
202
-continued
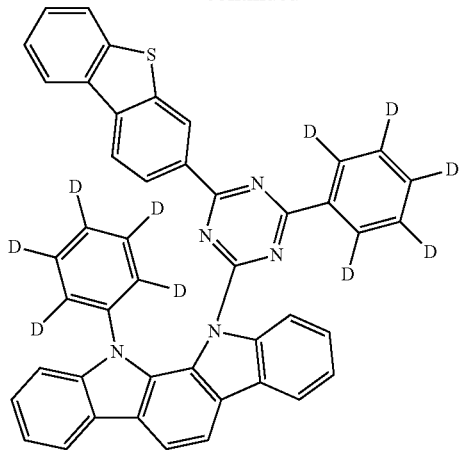
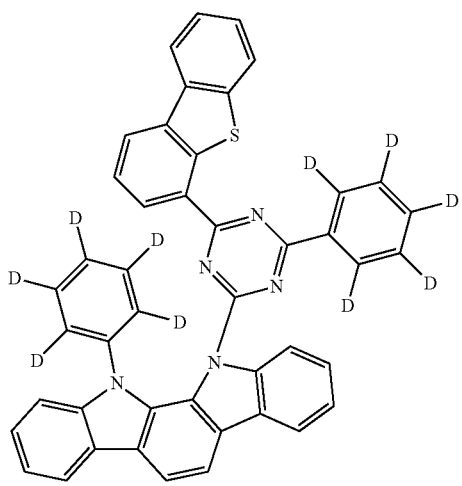
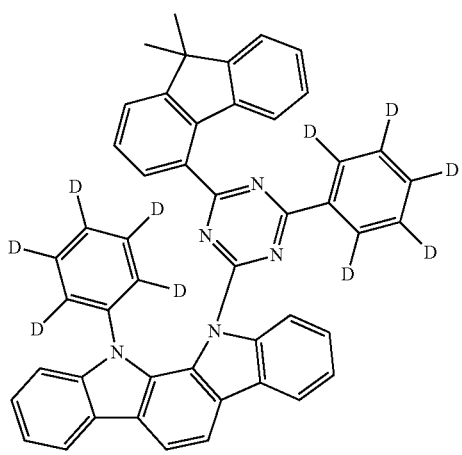

203
-continued
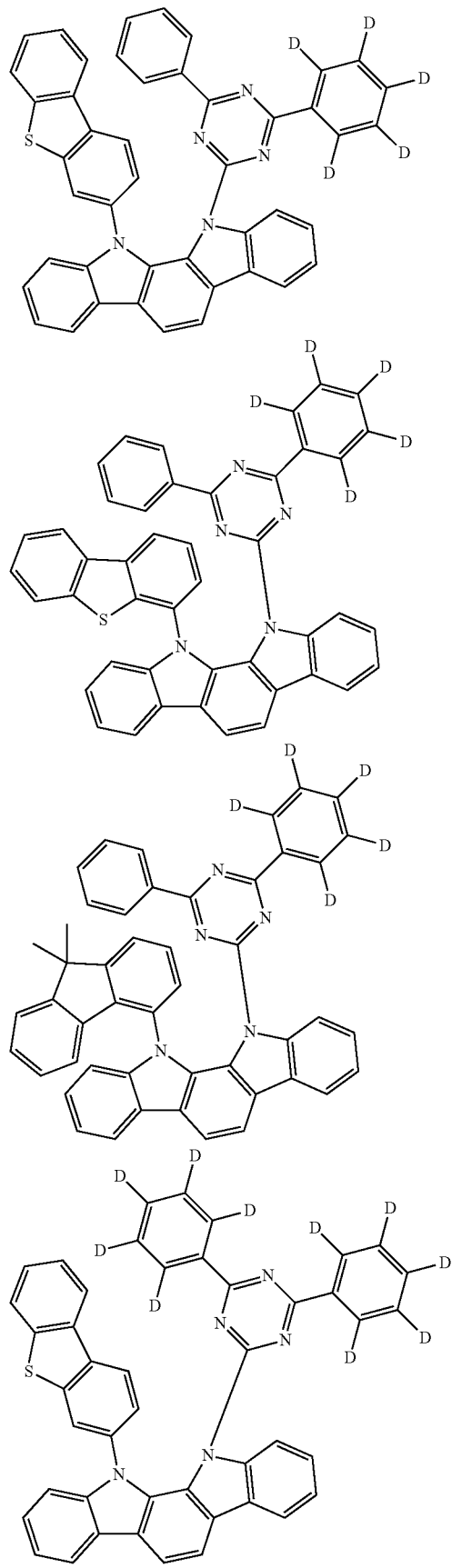
204
-continued
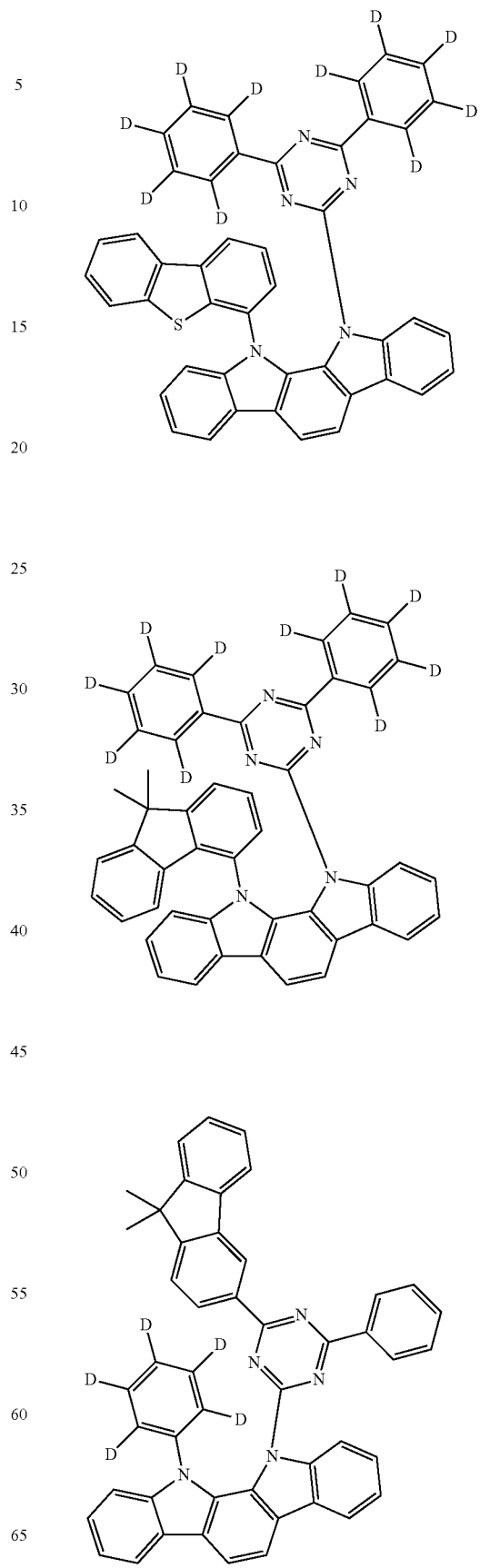

205
-continued
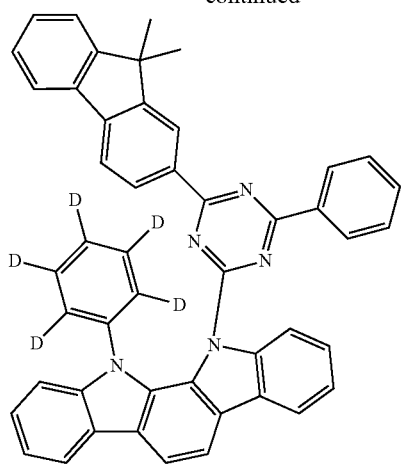
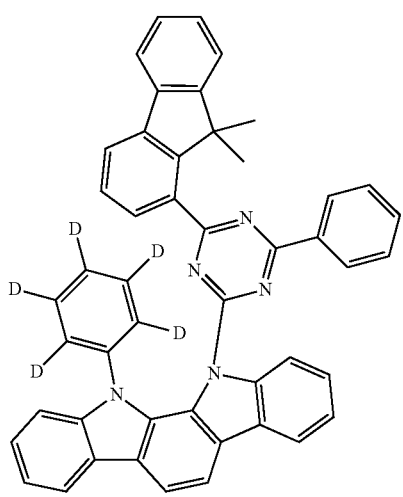
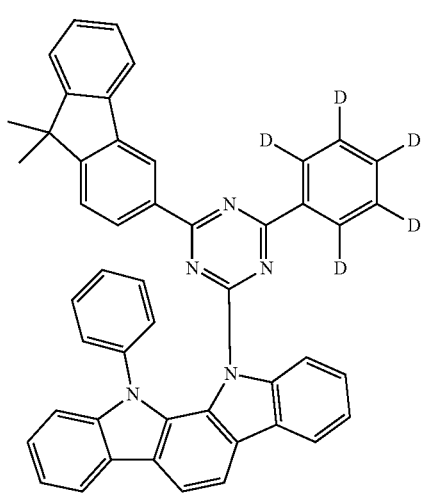
206
-continued
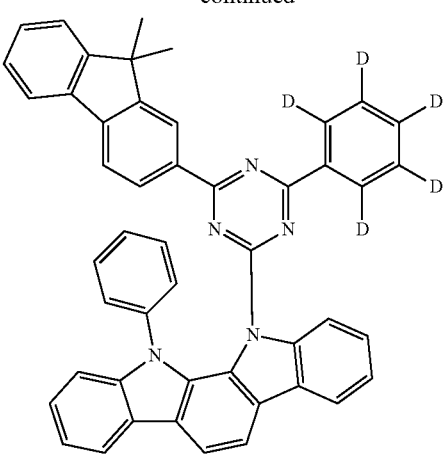
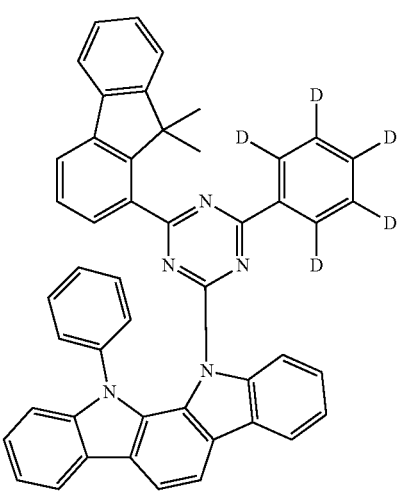
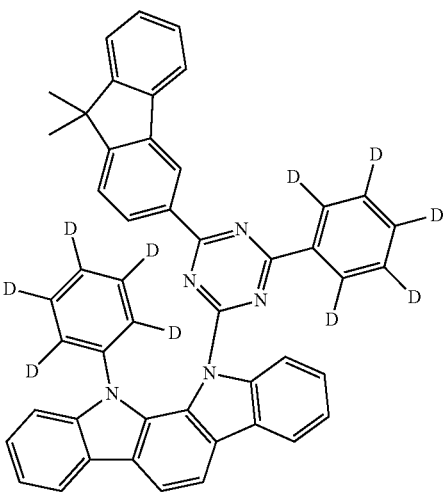

207
-continued
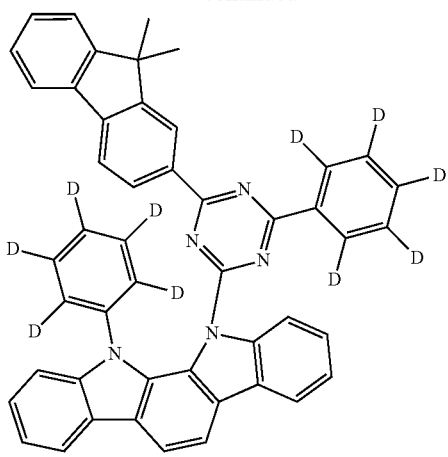
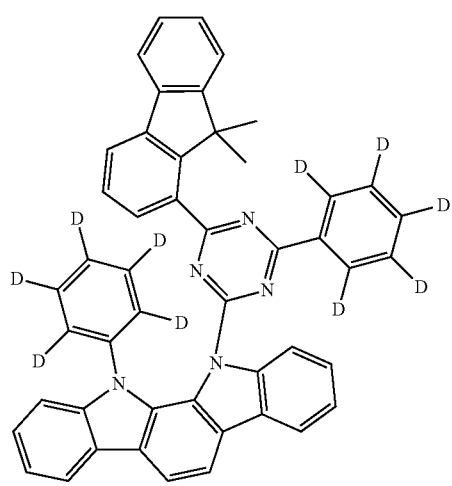
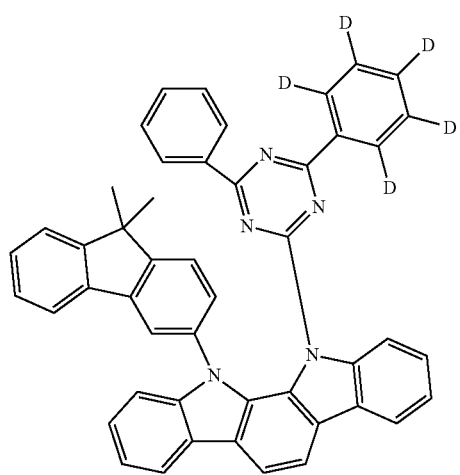
208
-continued
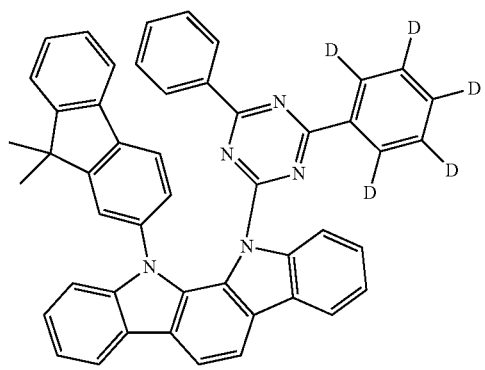
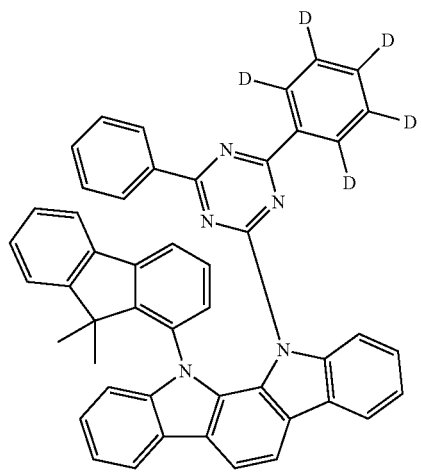
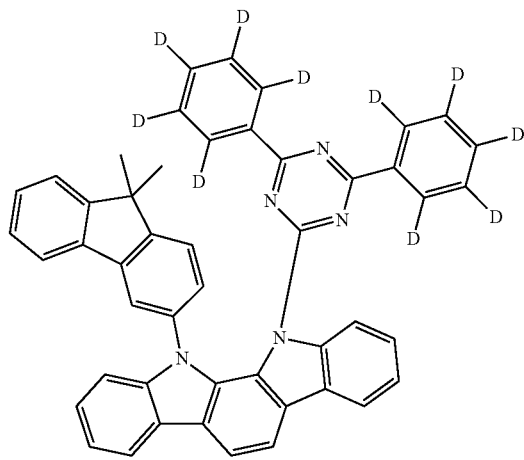

209
-continued
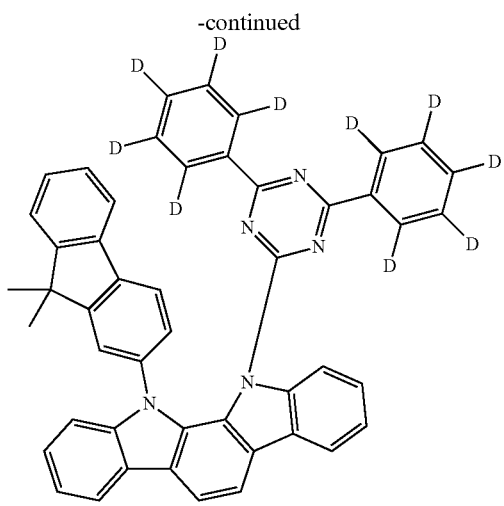
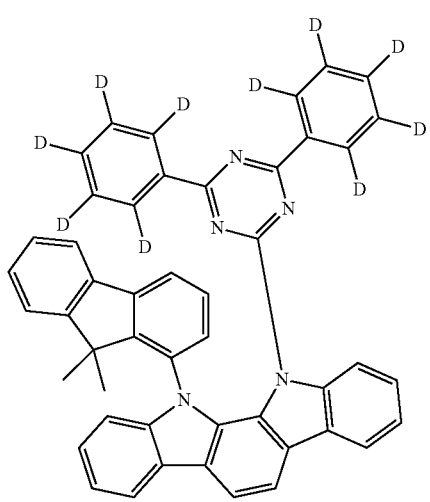
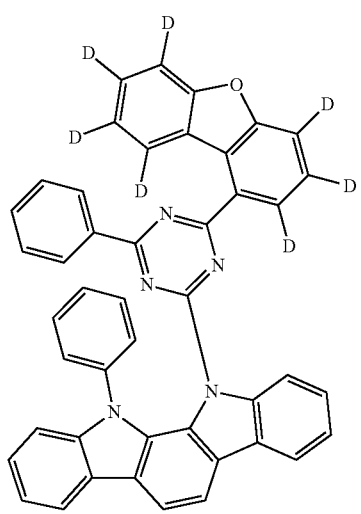
210
-continued
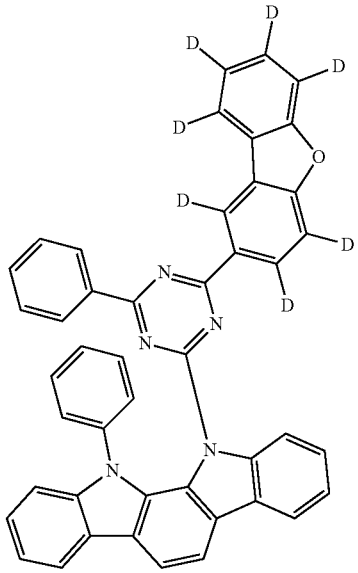
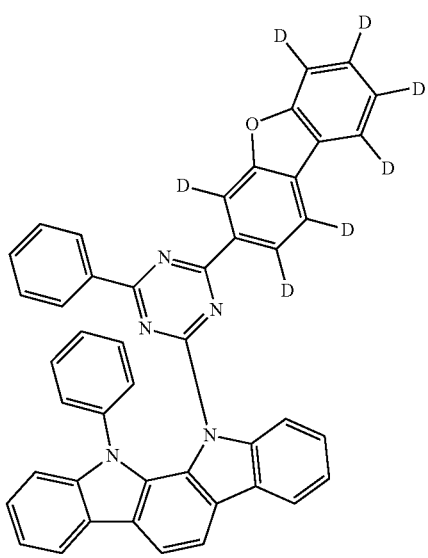
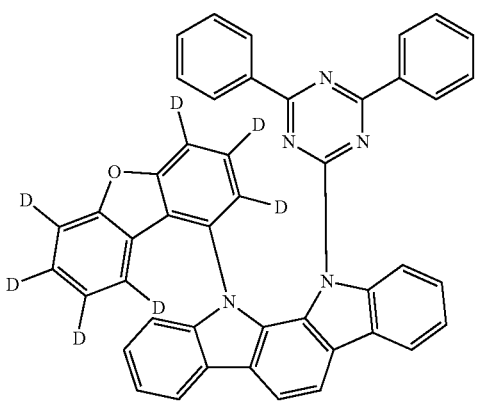

211
-continued
212
-continued
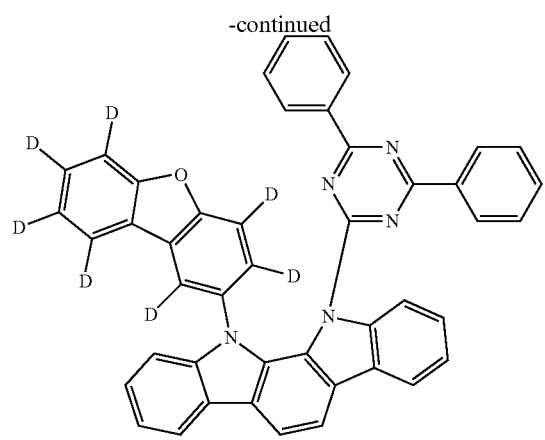
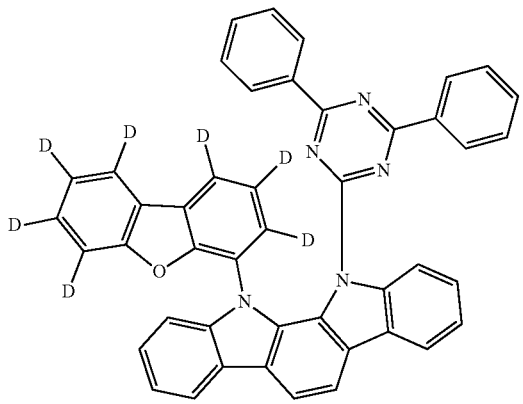
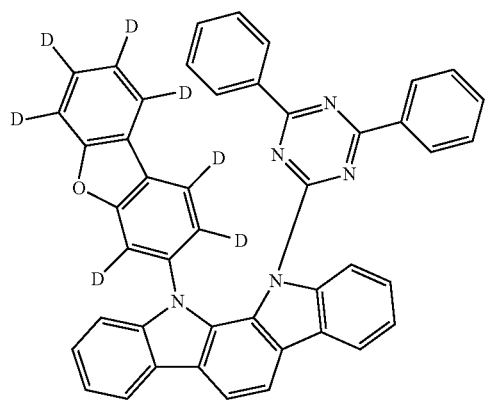
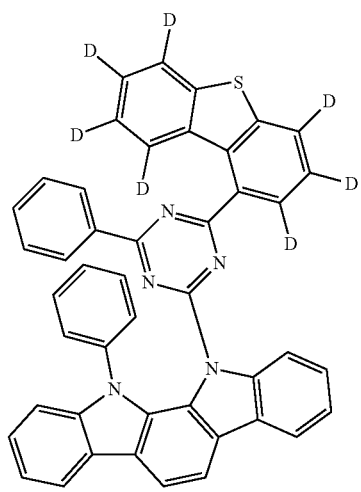
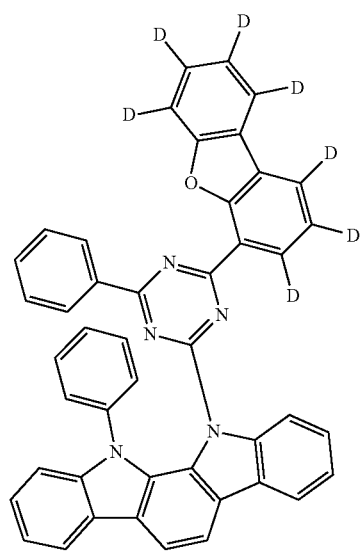
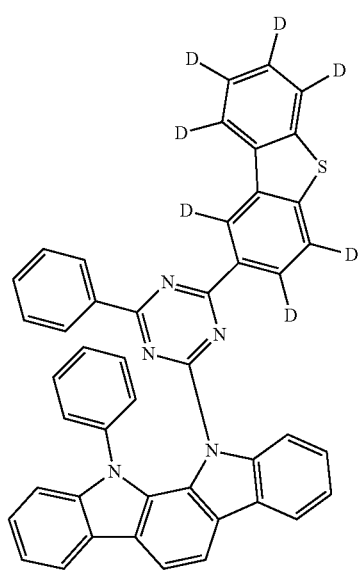

213
-continued
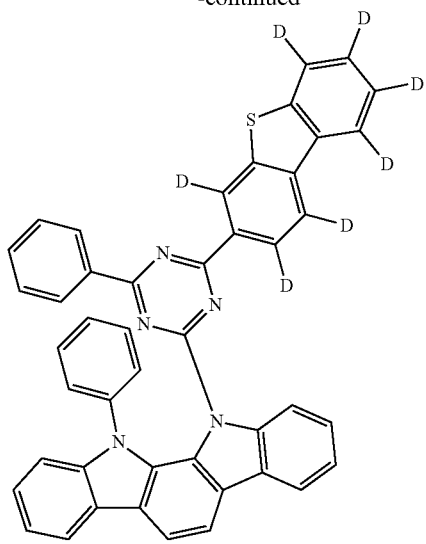
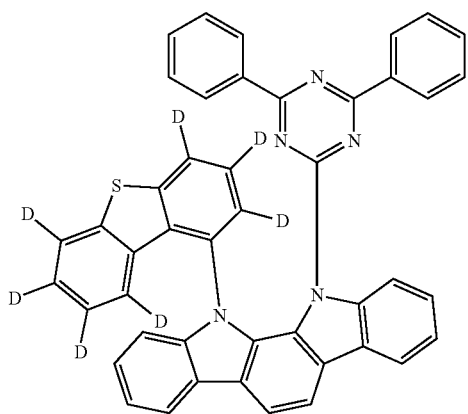
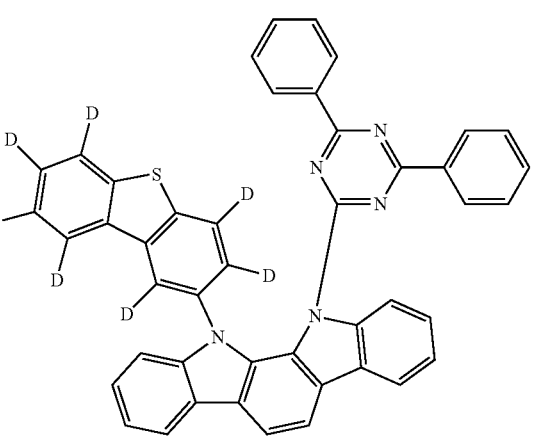
214
-continued
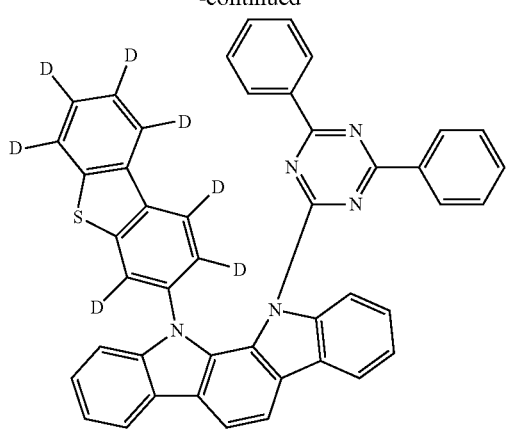
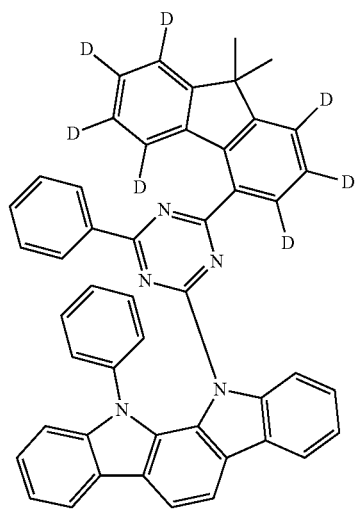
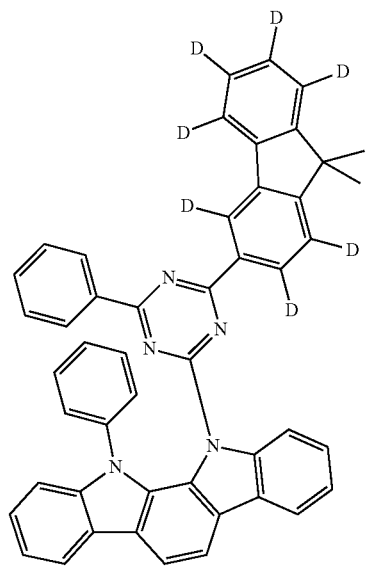

-continued
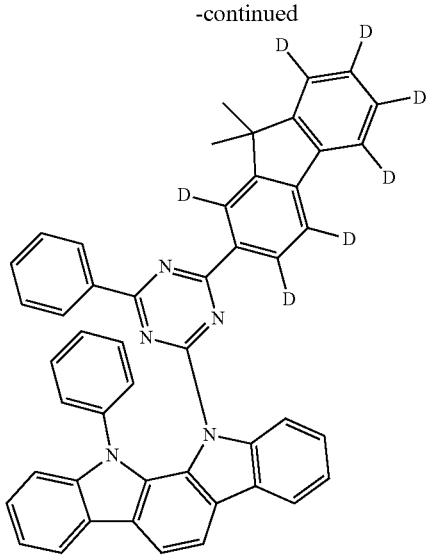
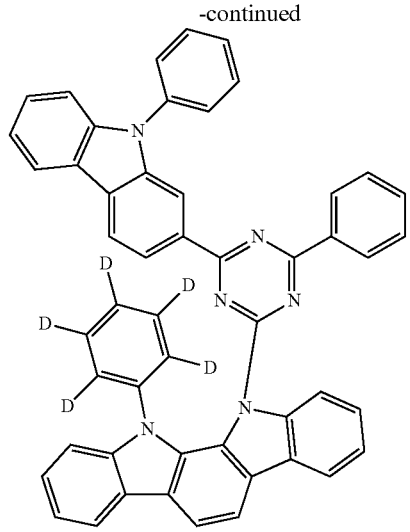
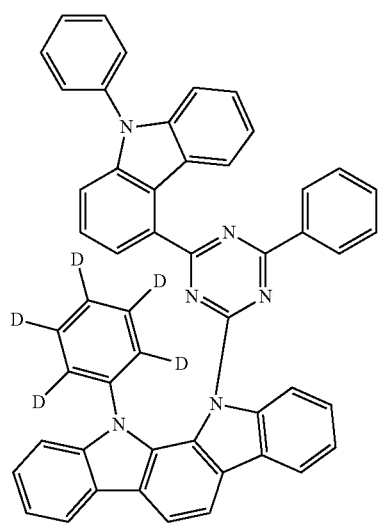
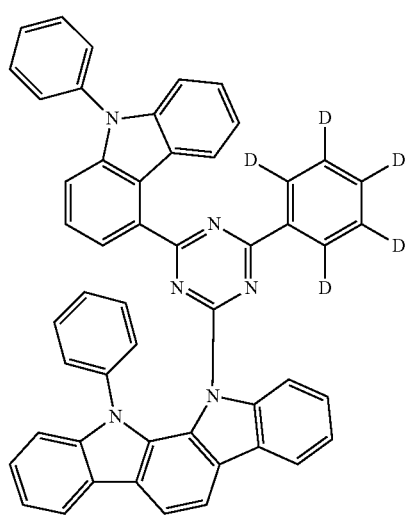
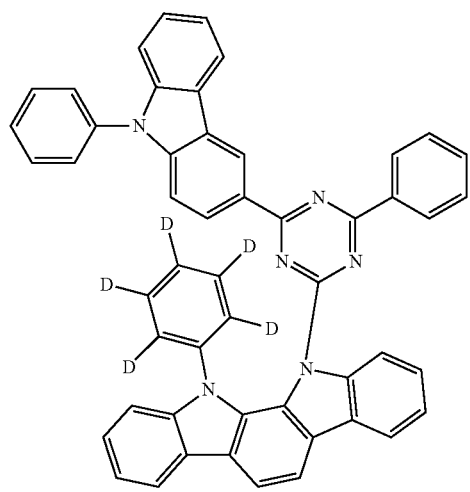
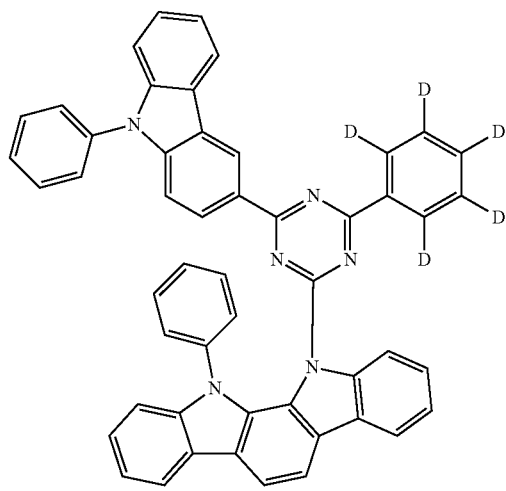

217
-continued
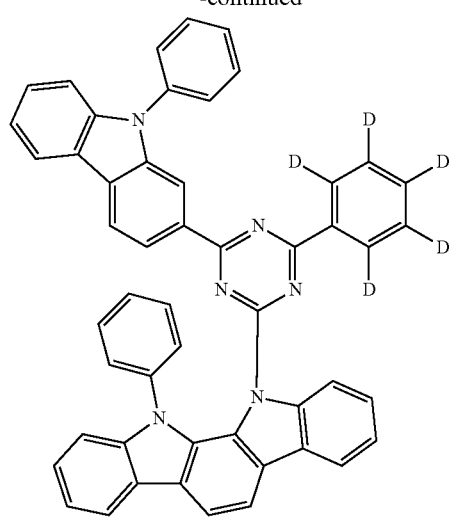
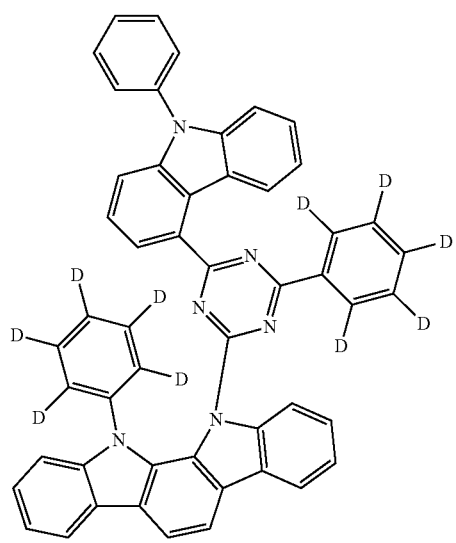
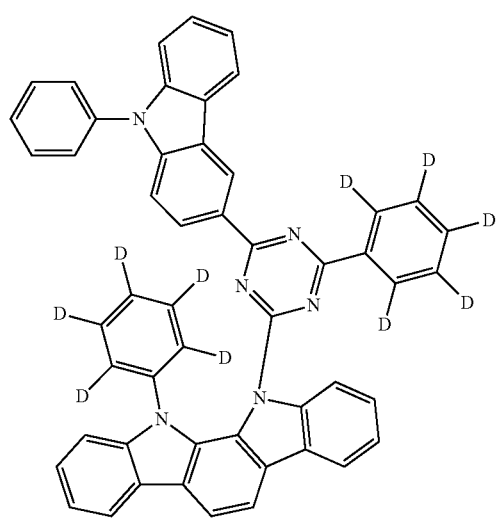
218
-continued
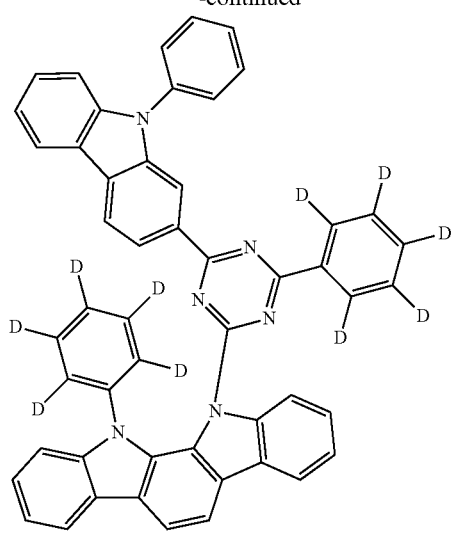
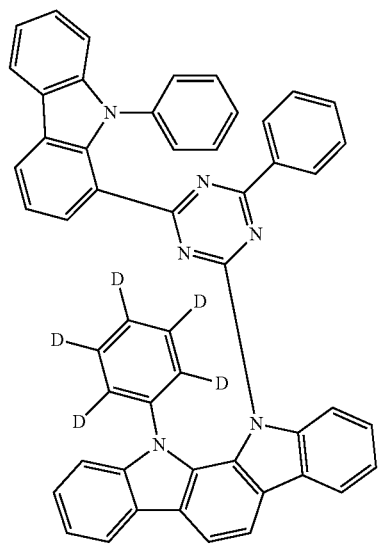
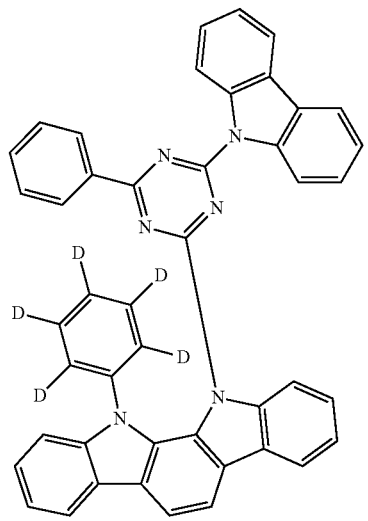

219
-continued
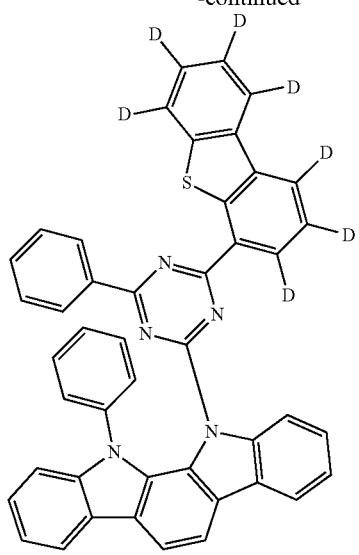
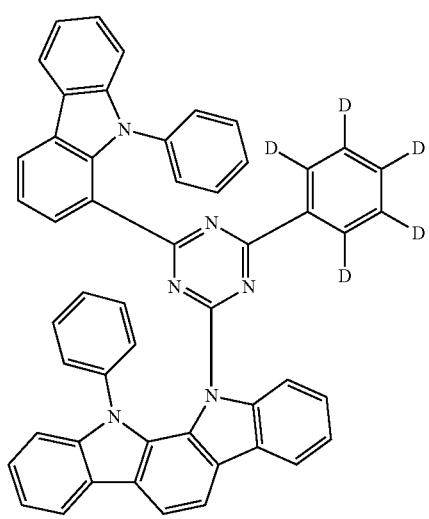
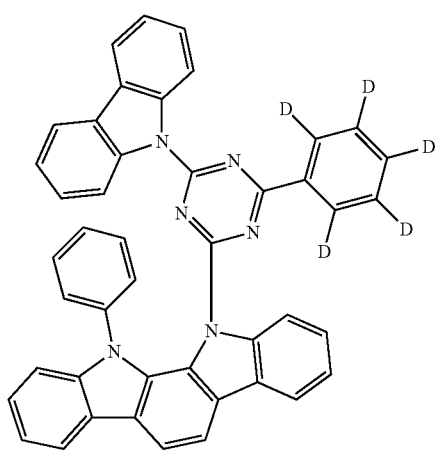
220
-continued
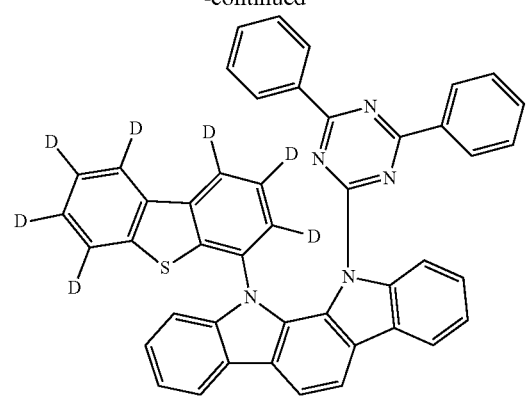
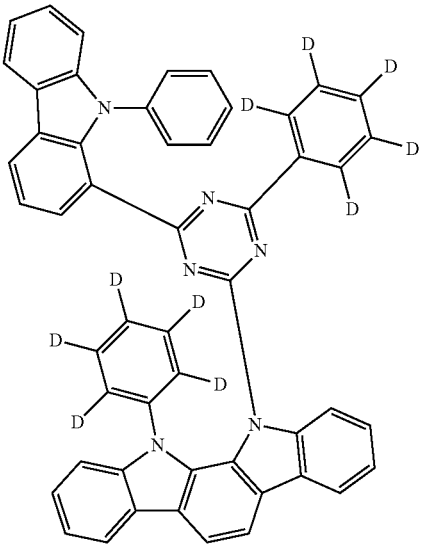
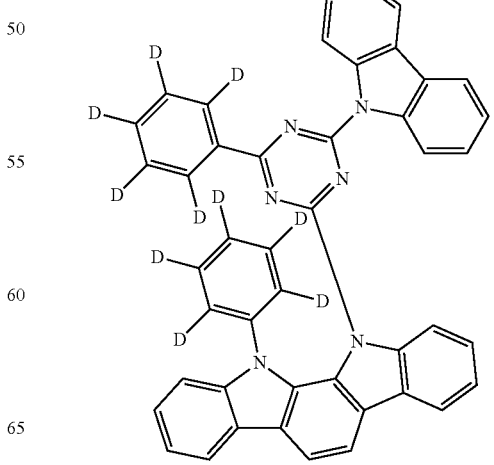

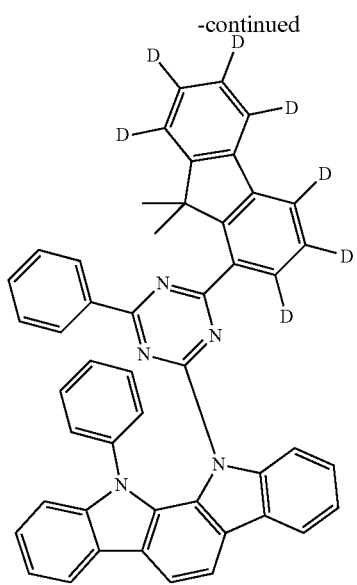
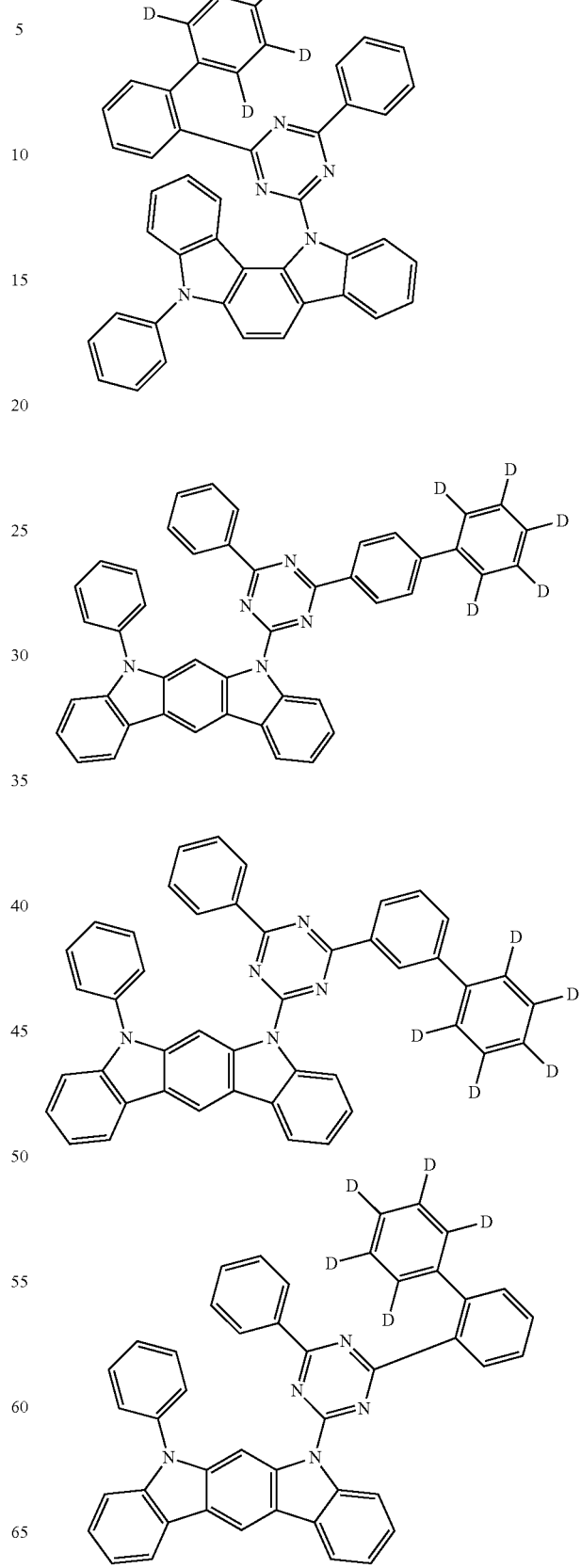

223
-continued
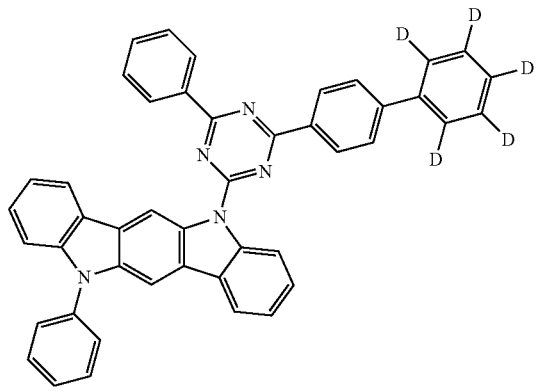
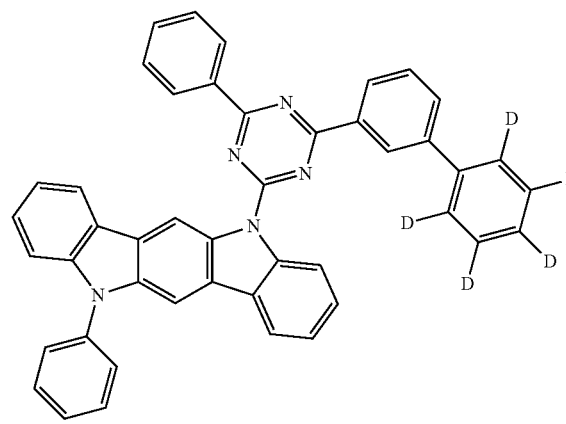
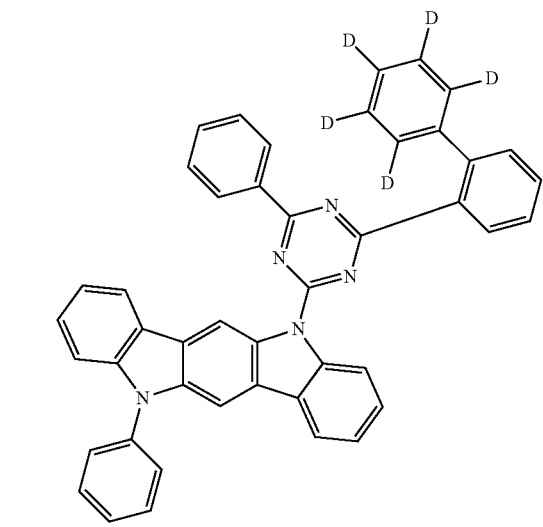
224
-continued
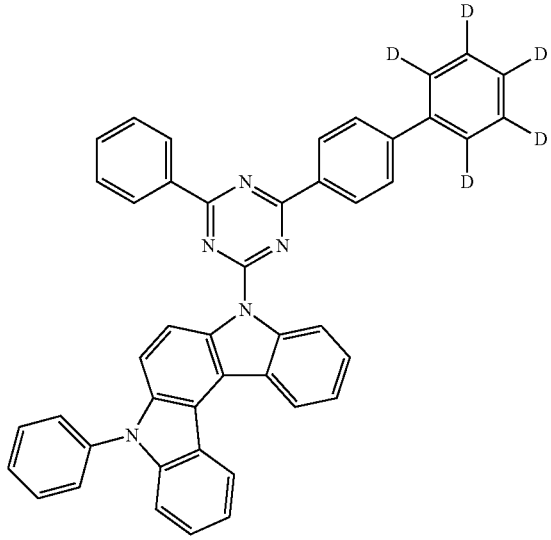
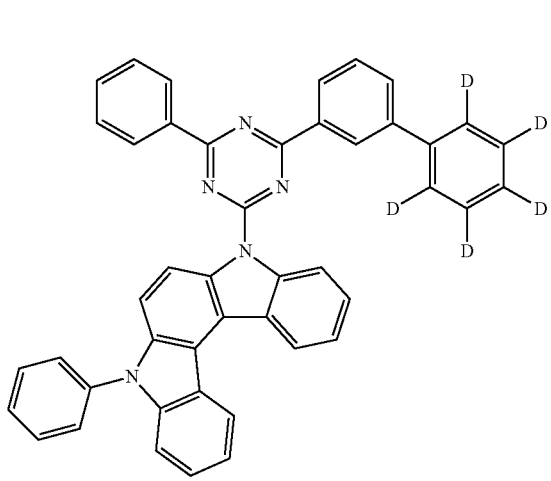
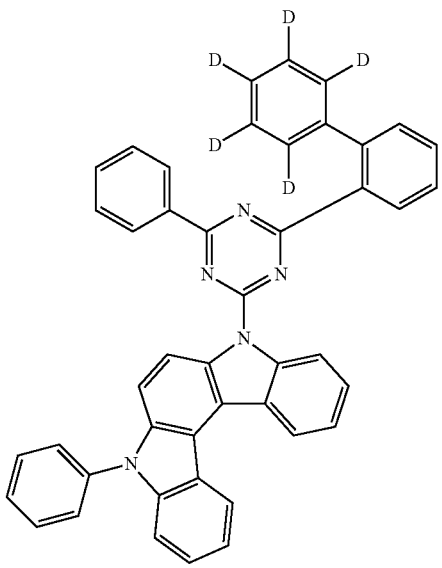

225
-continued
226
-continued
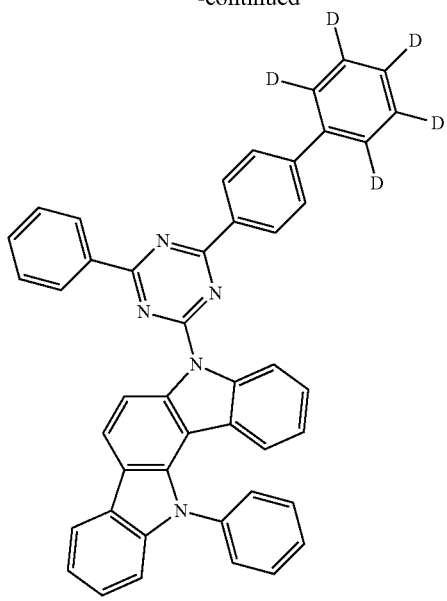
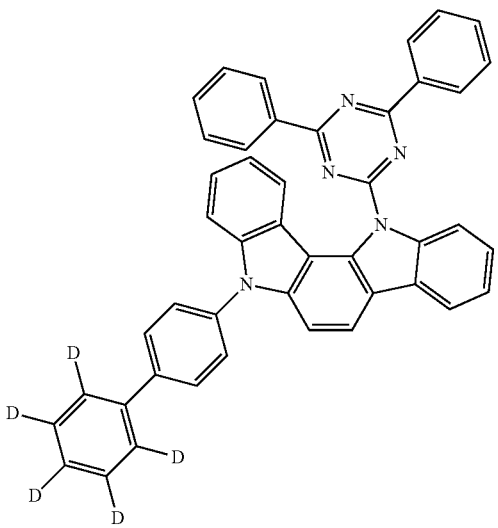

227
-continued
228
-continued
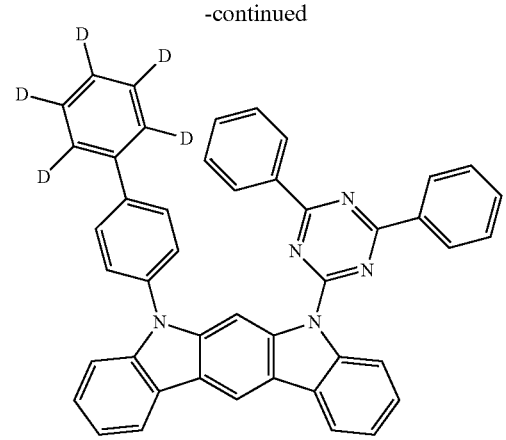
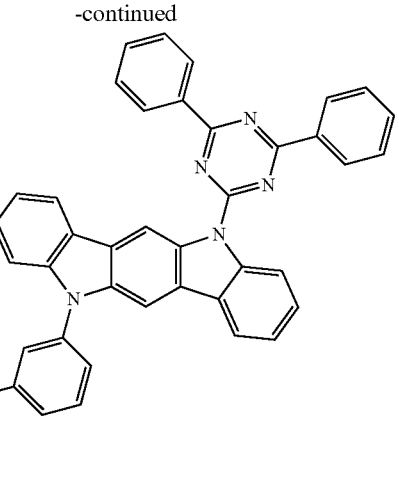
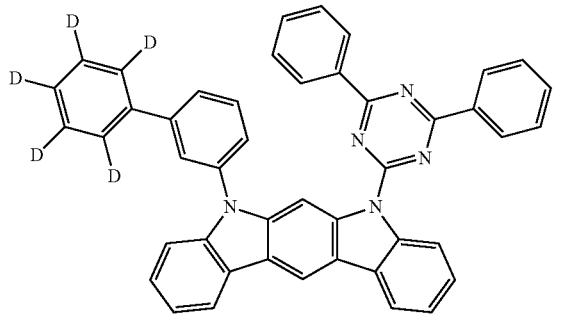
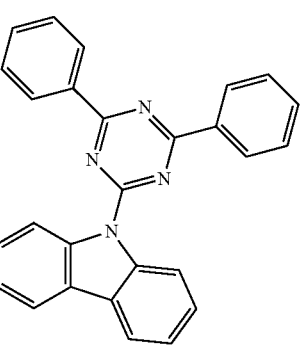
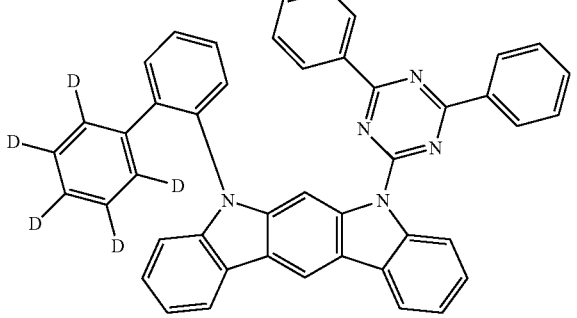
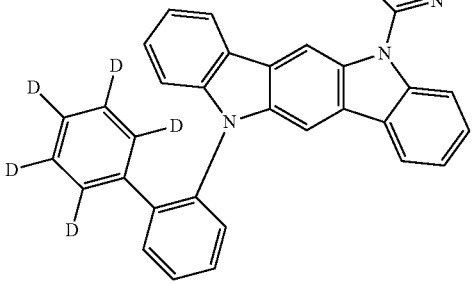
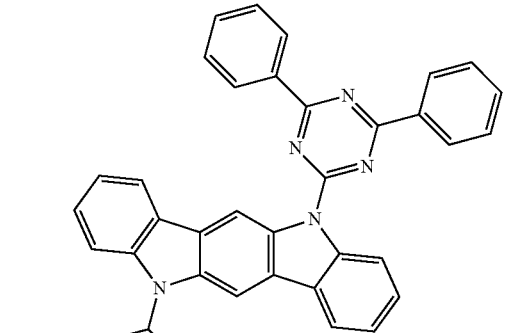
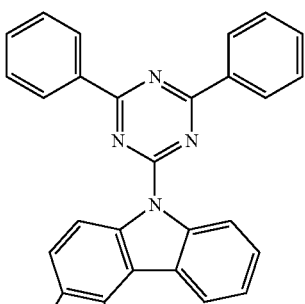
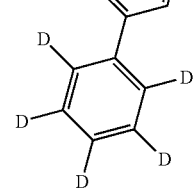
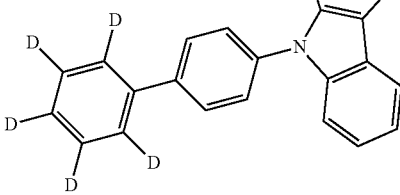

229
-continued
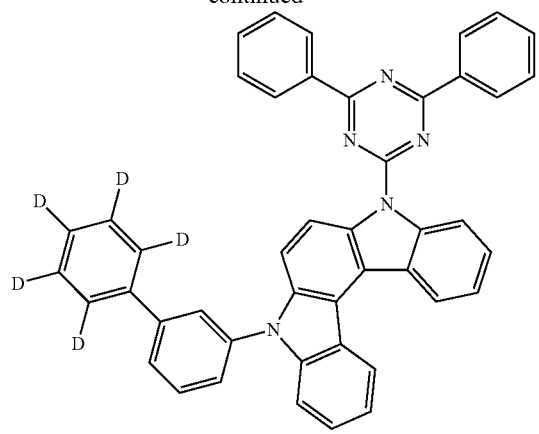
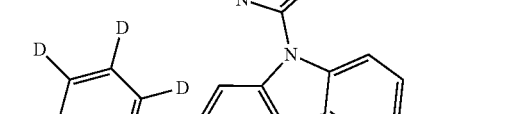
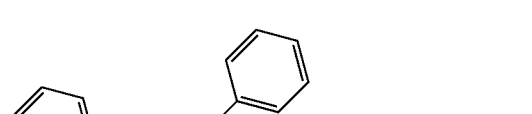
230
-continued
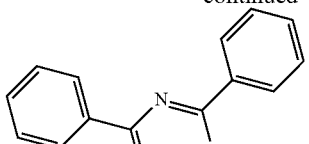
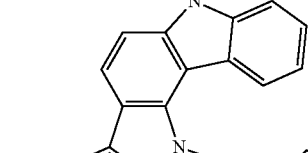

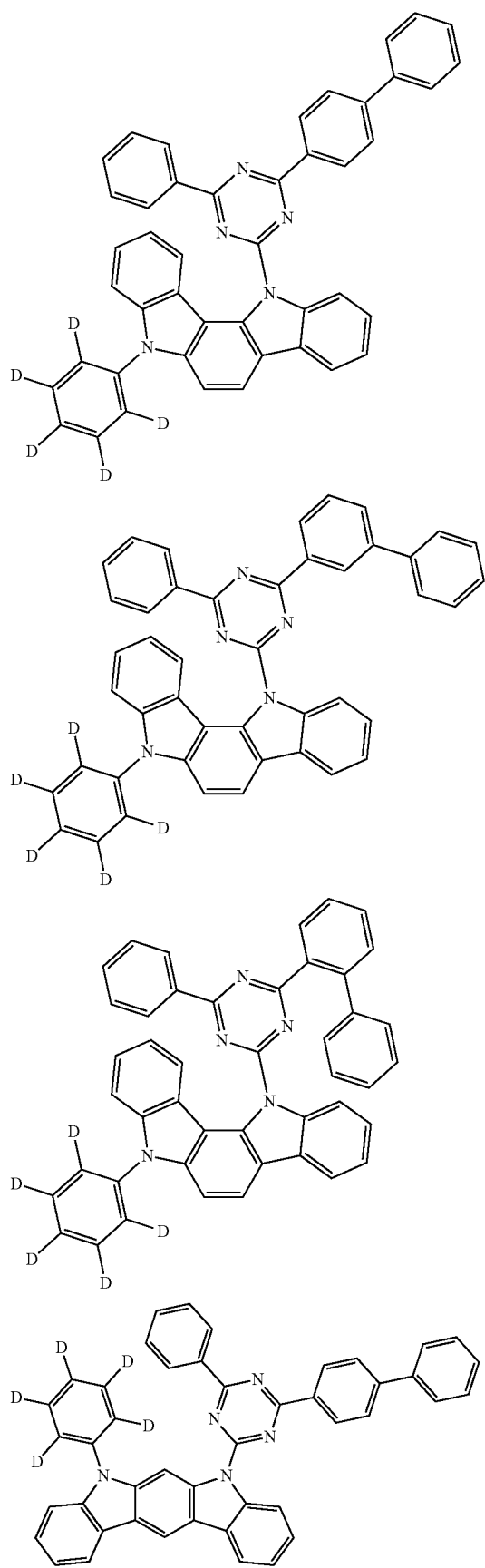
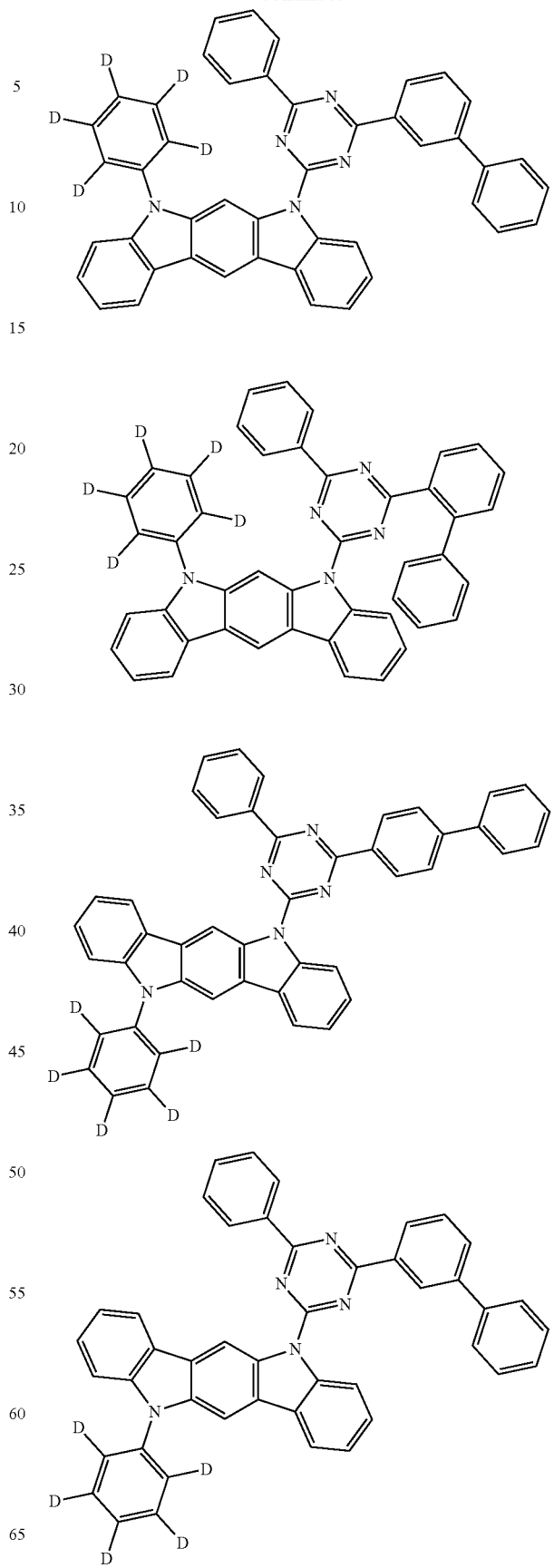

233
-continued
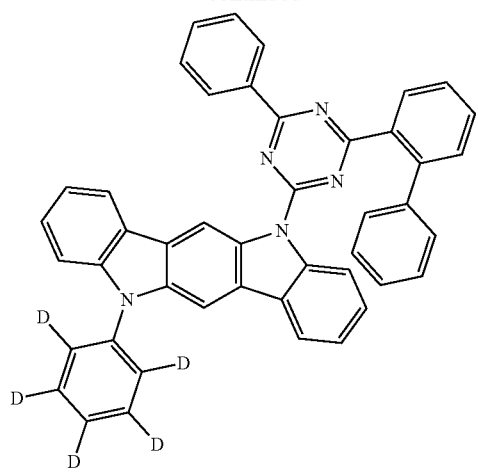
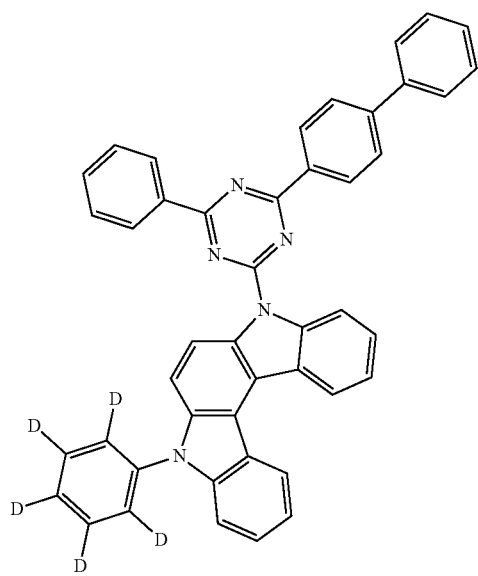
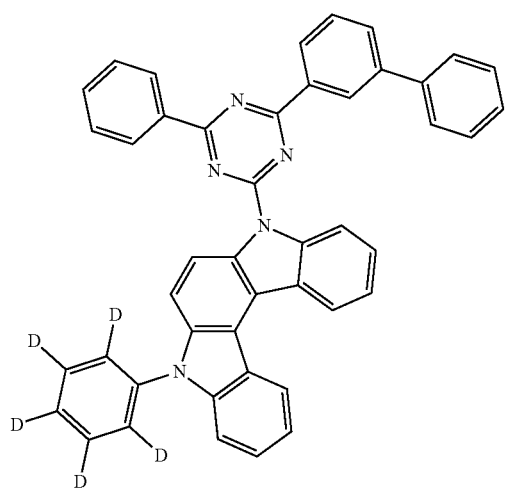
234
-continued
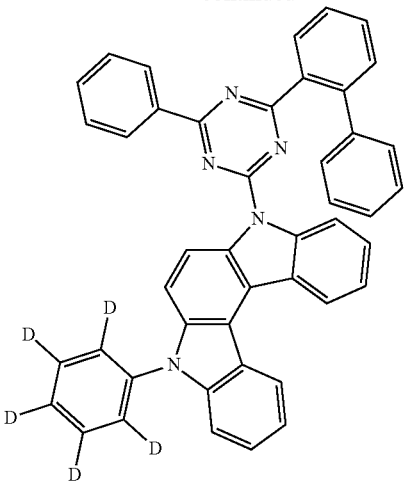
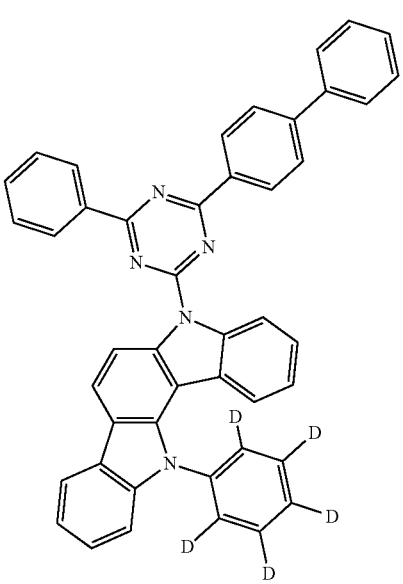
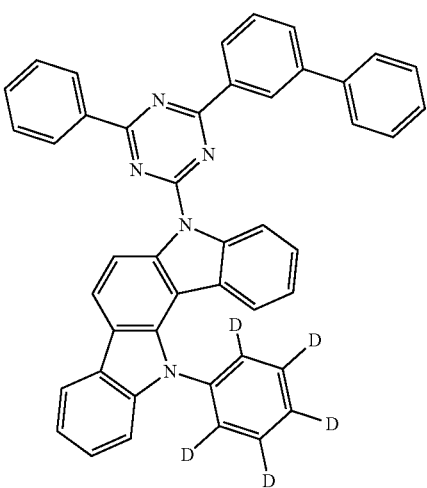

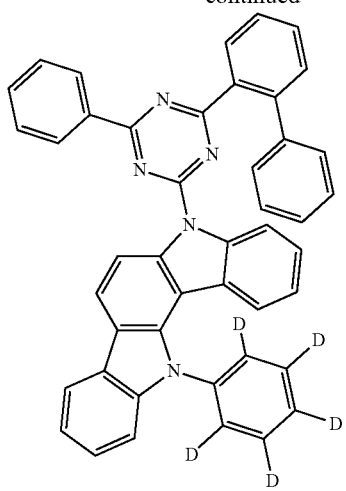
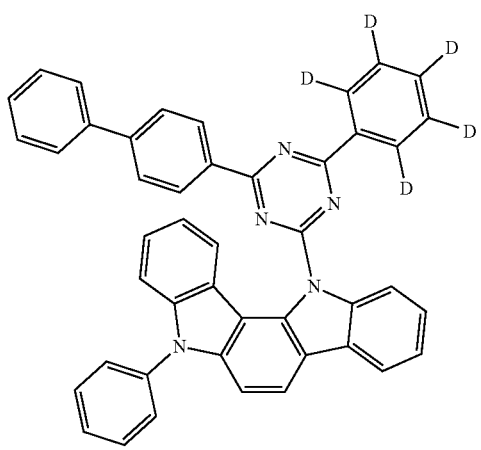
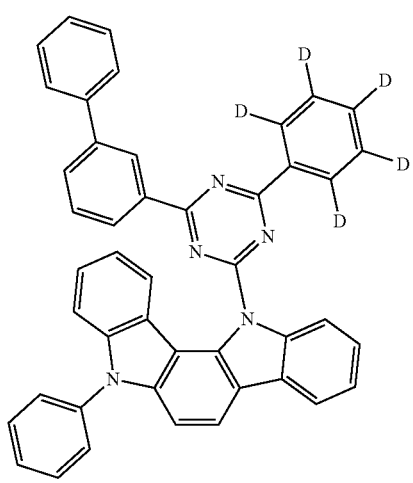
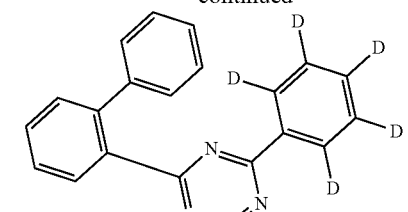
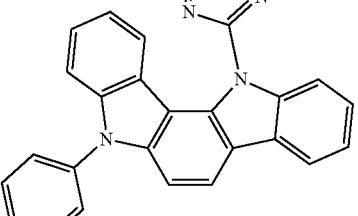
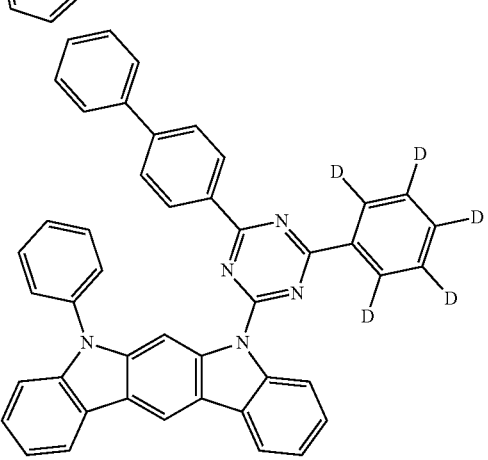
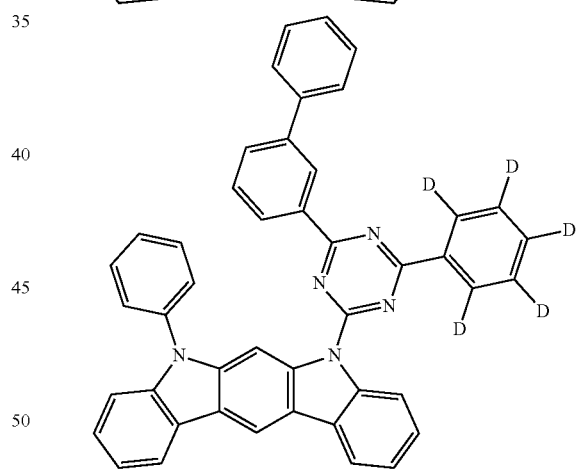
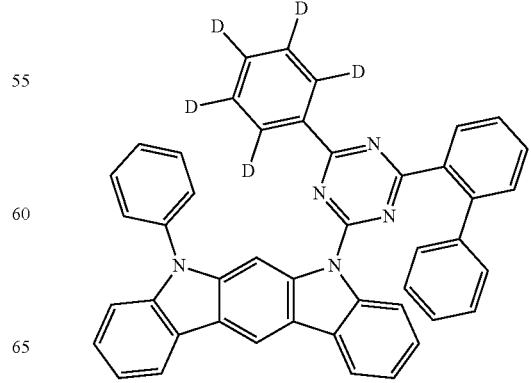

237
-continued
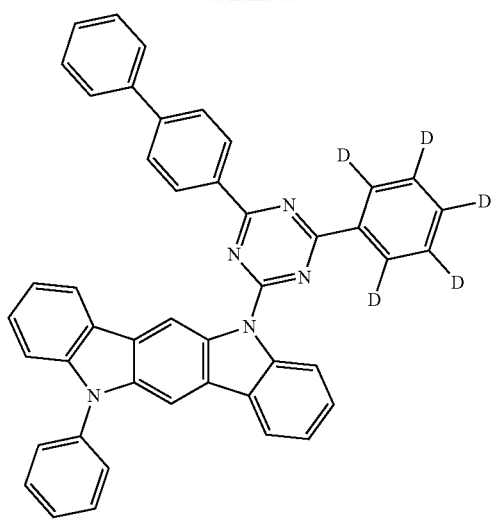
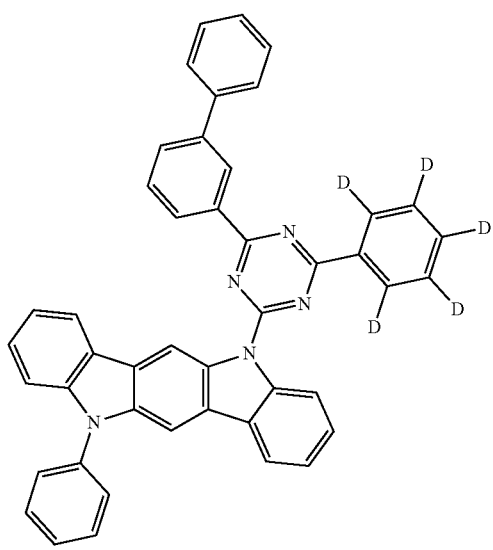
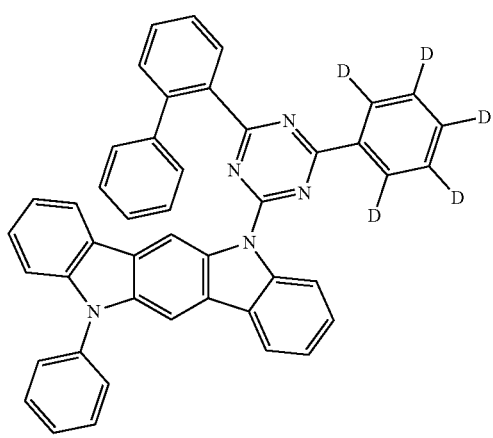
238
-continued
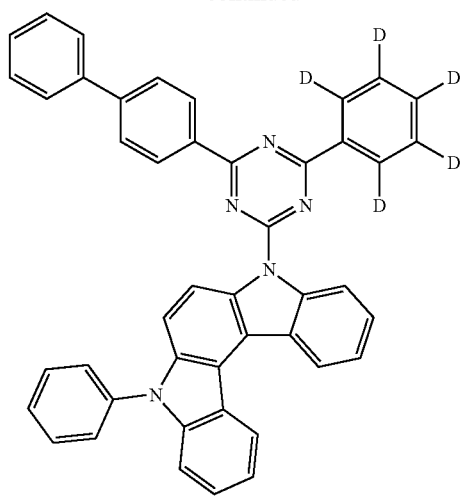
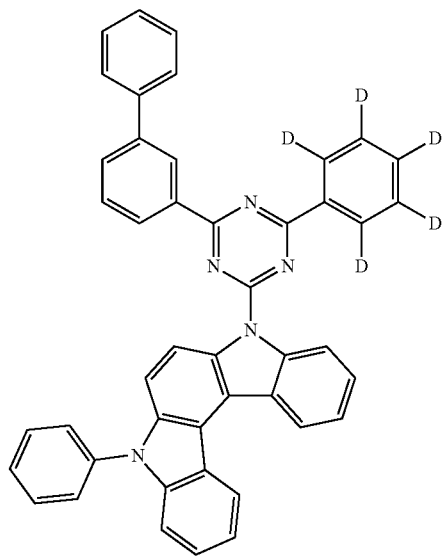
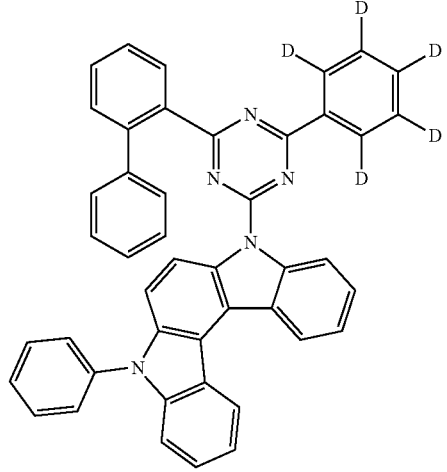

239
-continued
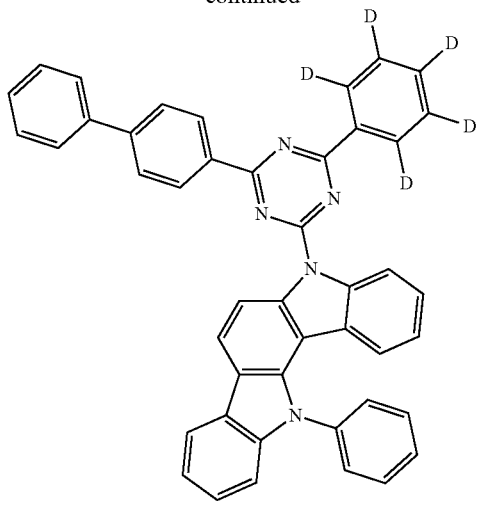
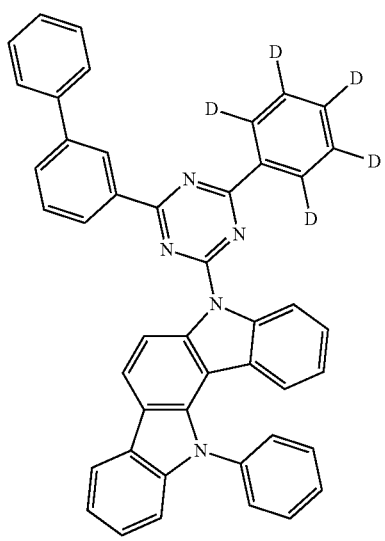
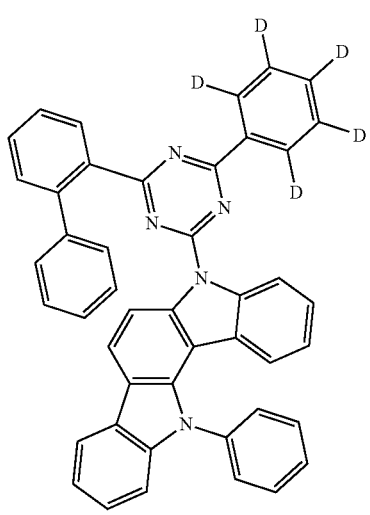
240
-continued
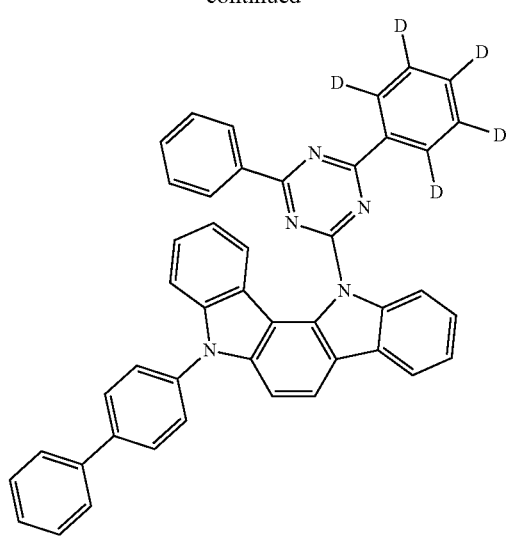
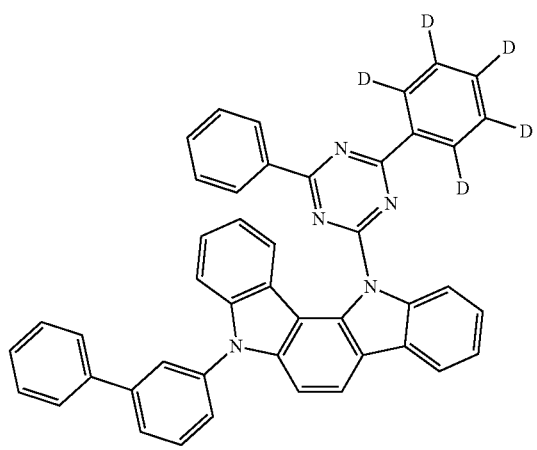
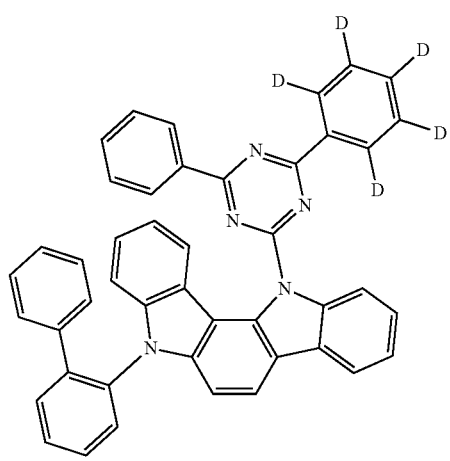

241
-continued
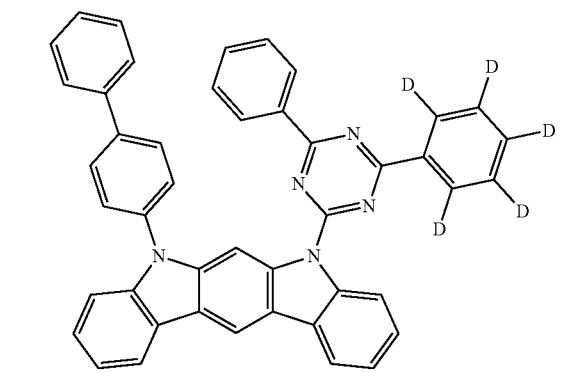
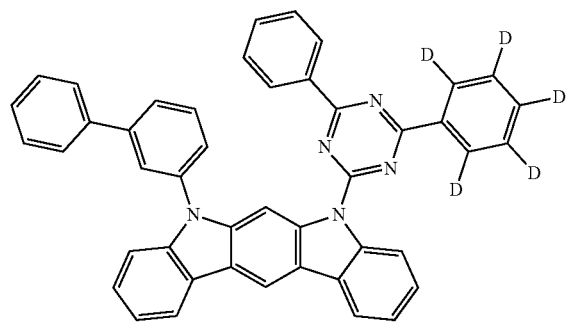
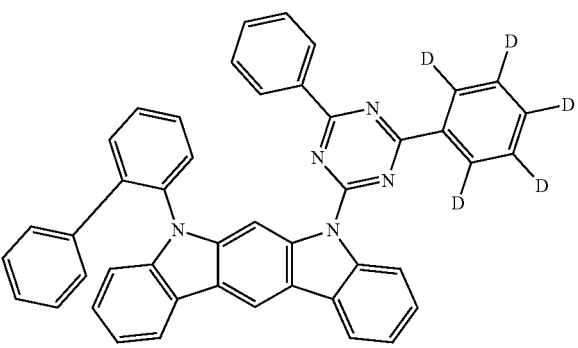
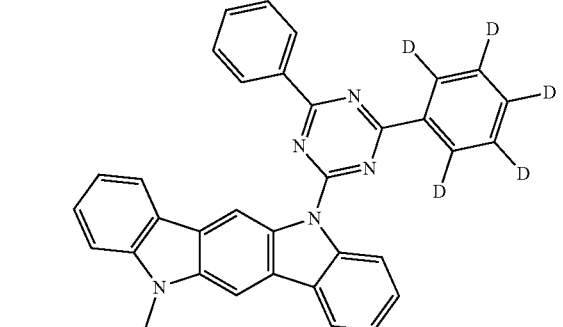
242
-continued
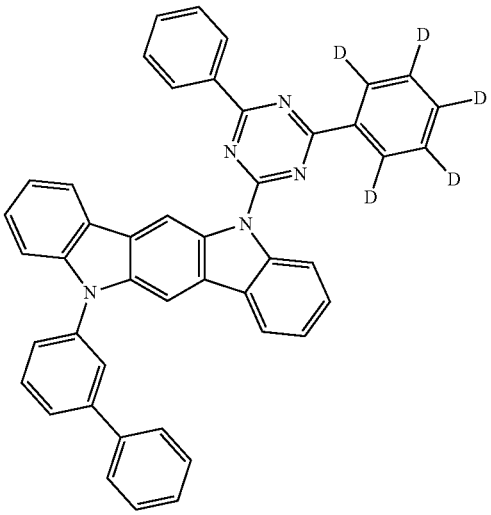
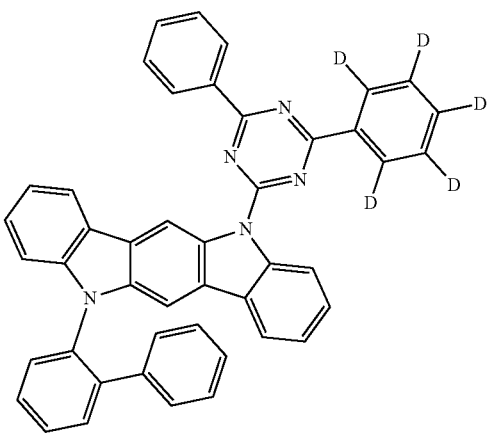
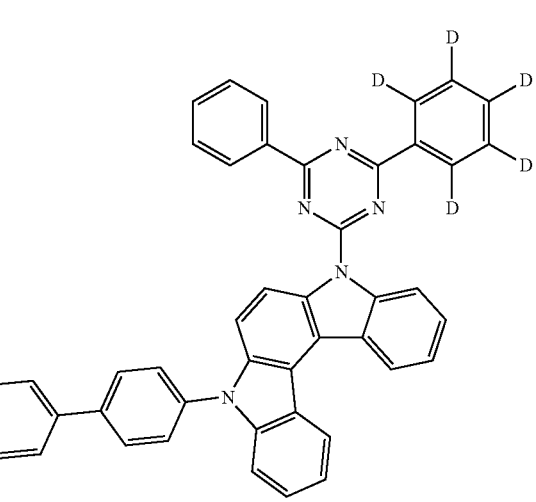

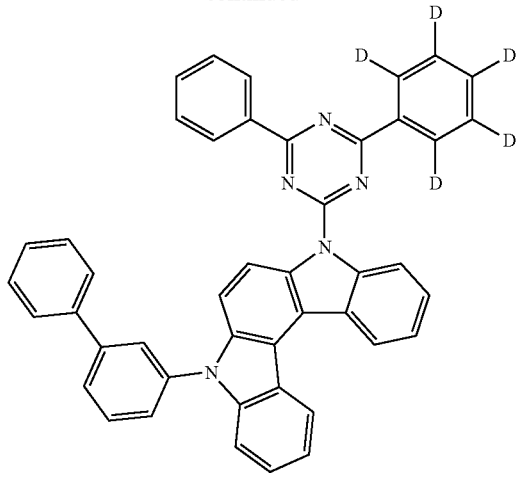
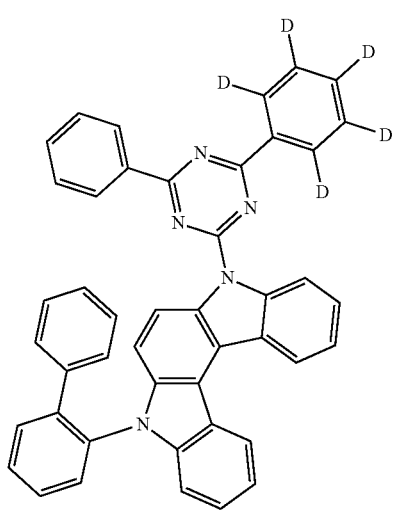
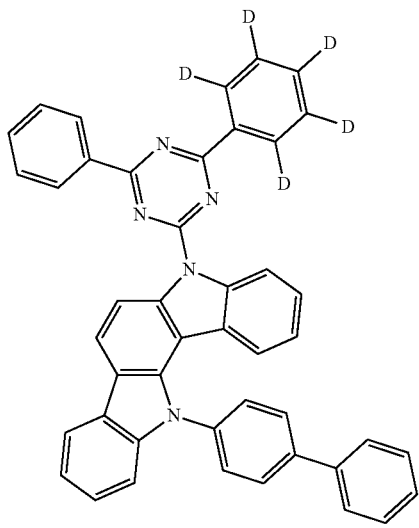
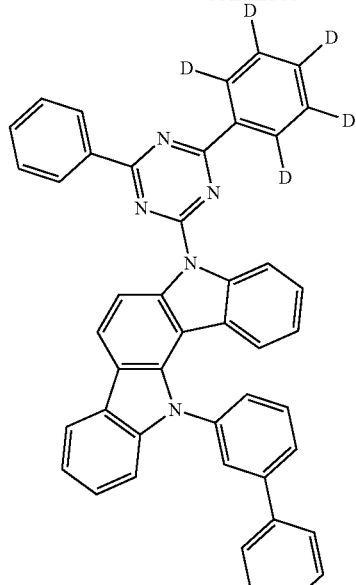
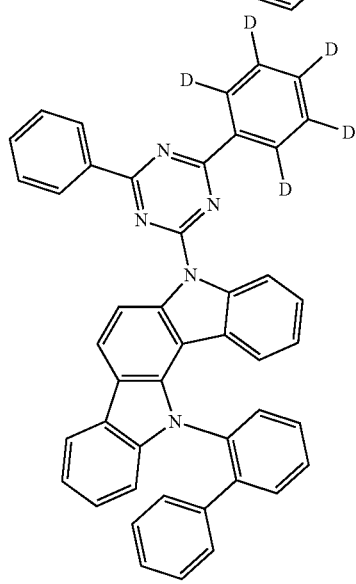
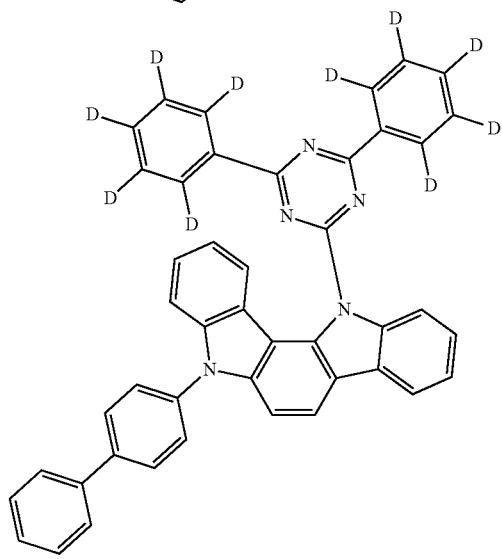

245
-continued
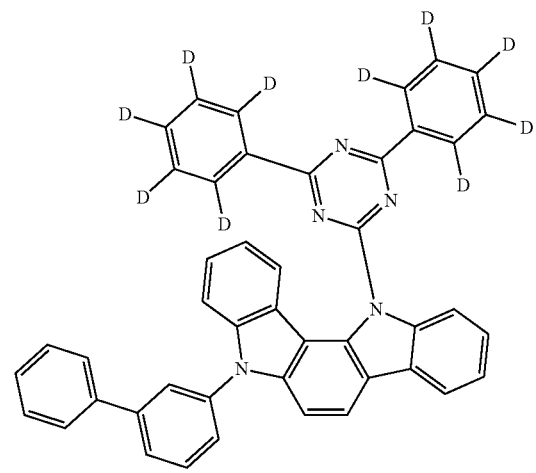
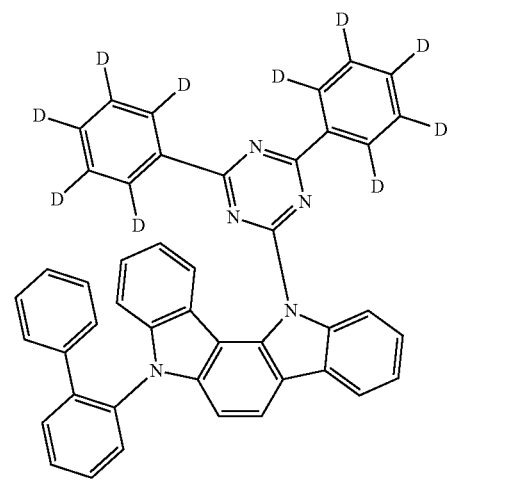
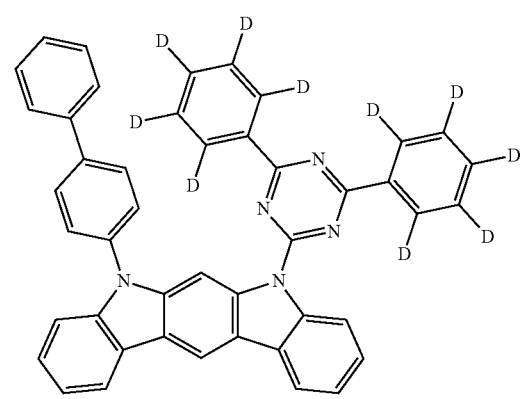
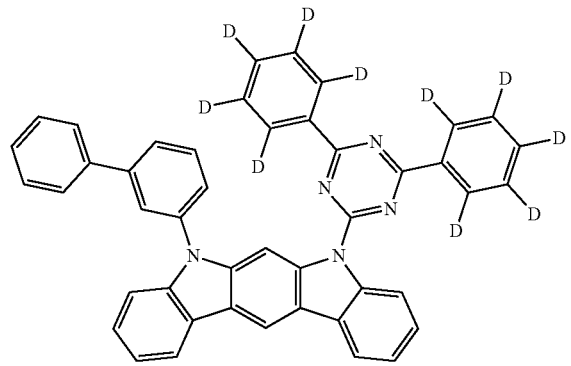
246
-continued
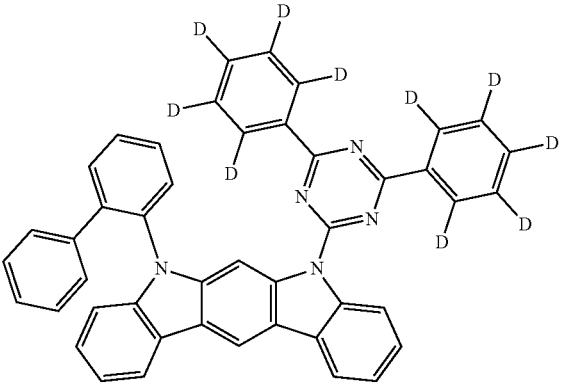
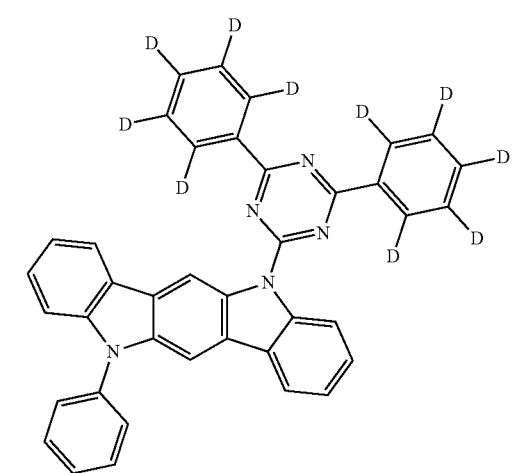
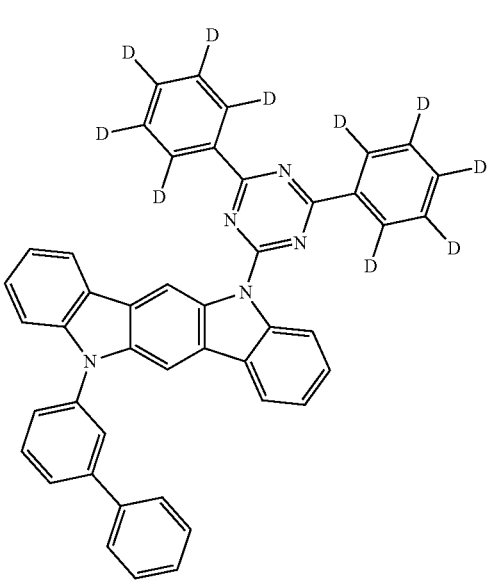

247
-continued
248
-continued
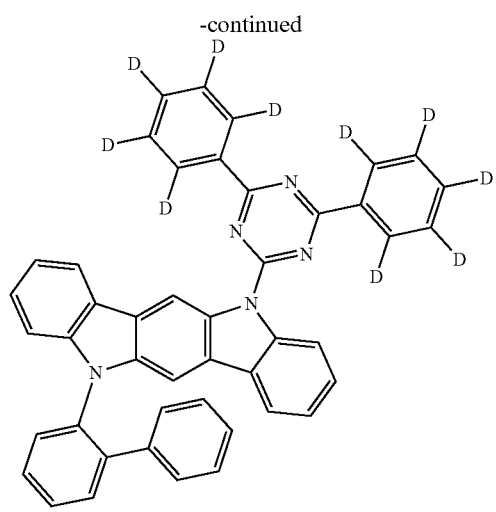
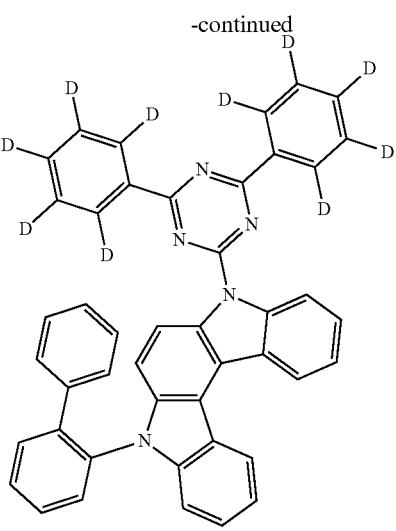
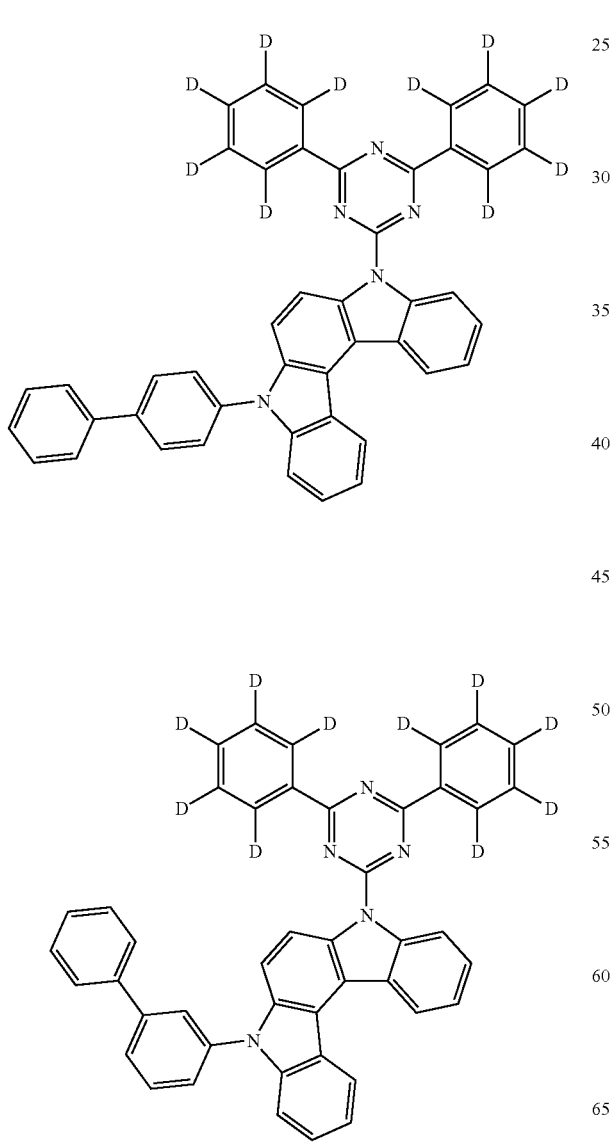
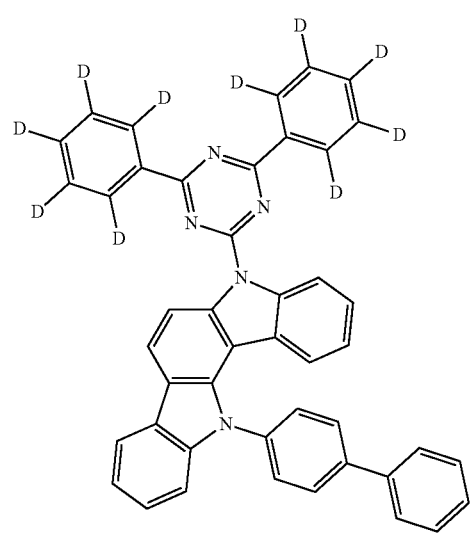
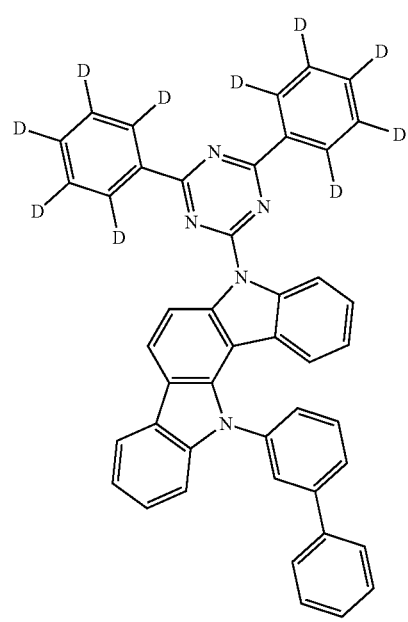

249
-continued
250
-continued
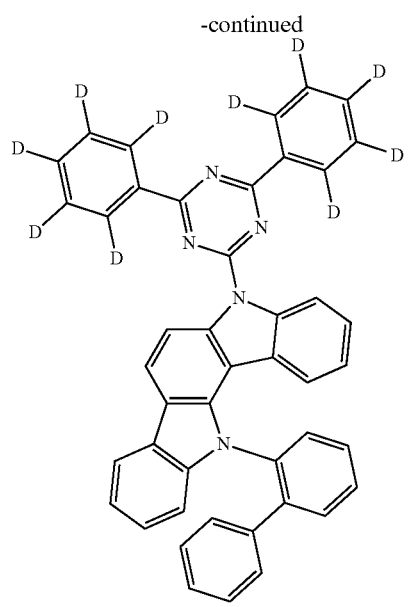
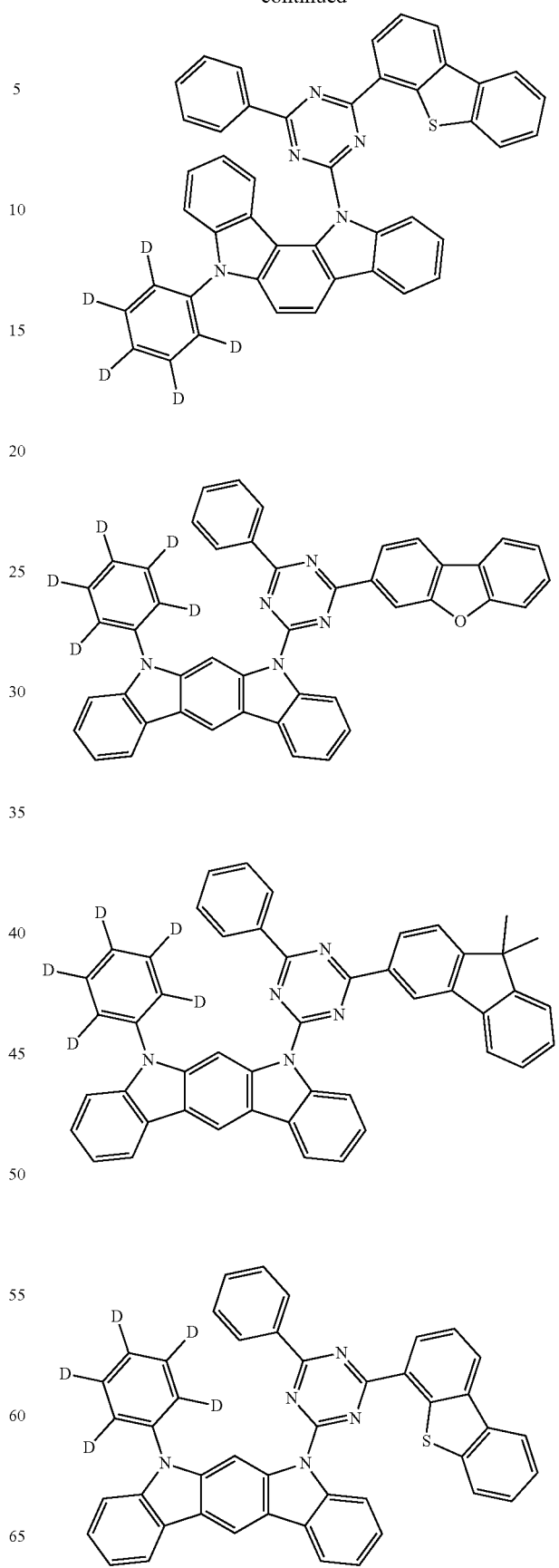

251
-continued
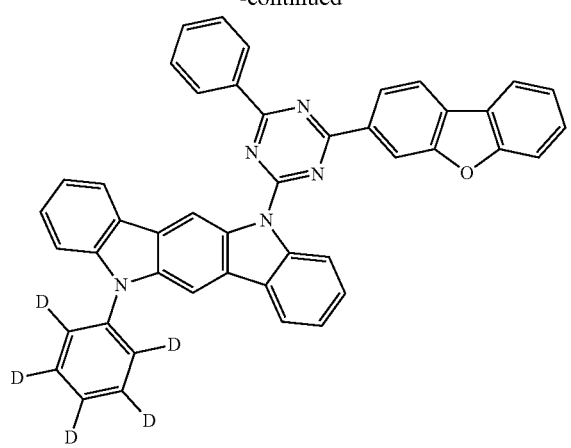
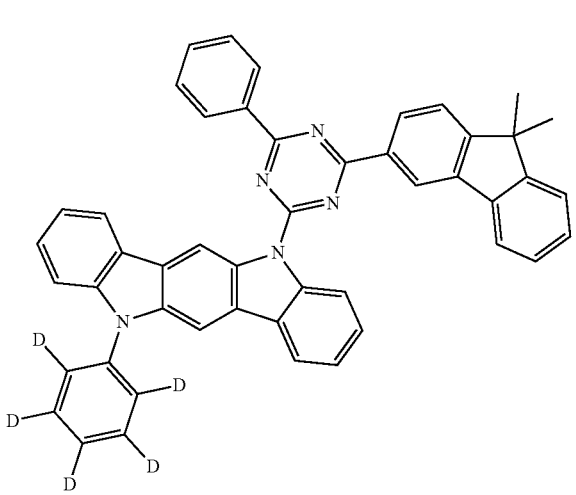
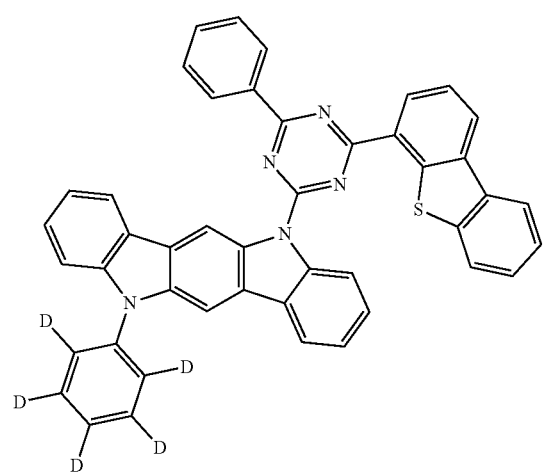
252
-continued
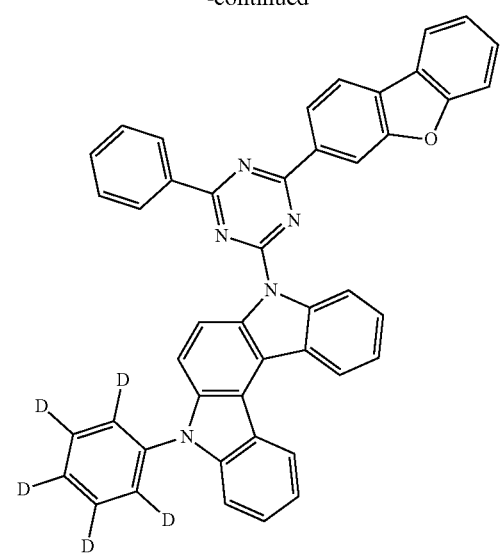
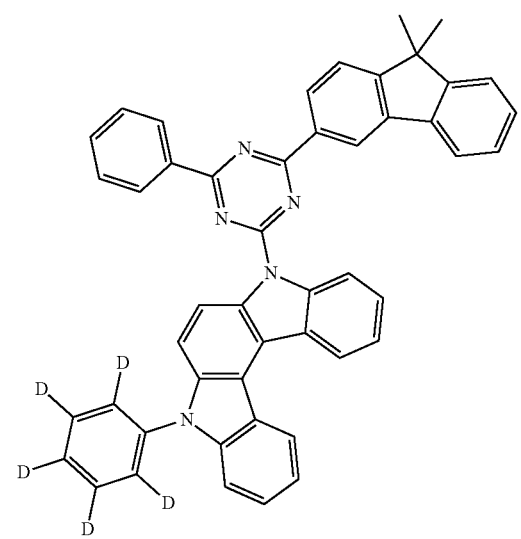
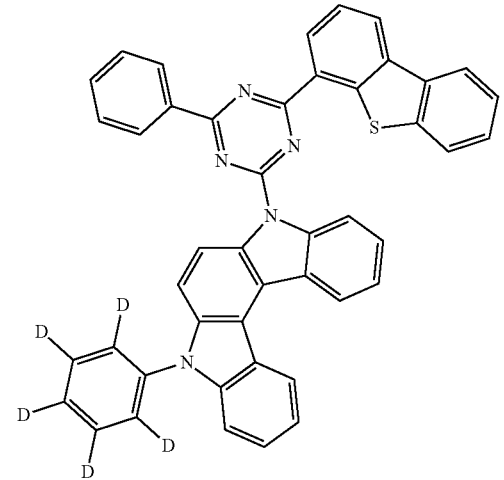

253
-continued
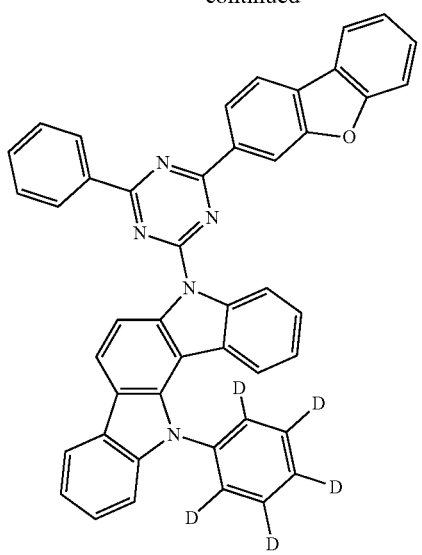
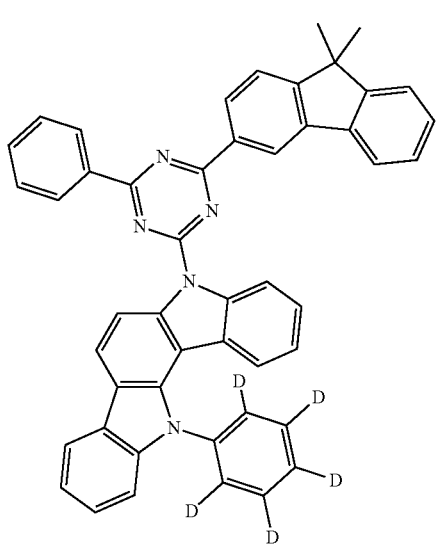
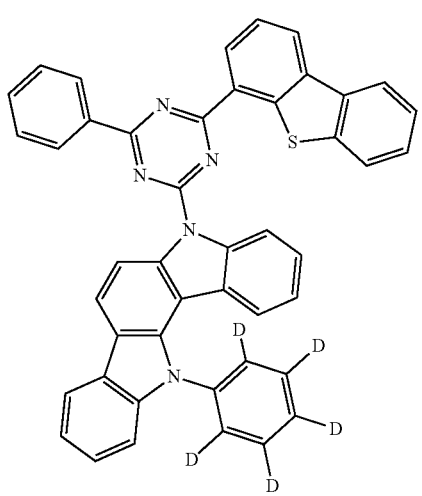
254
-continued
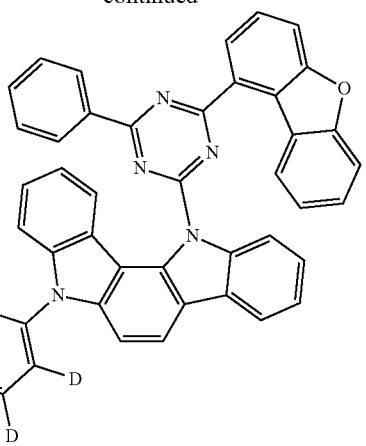
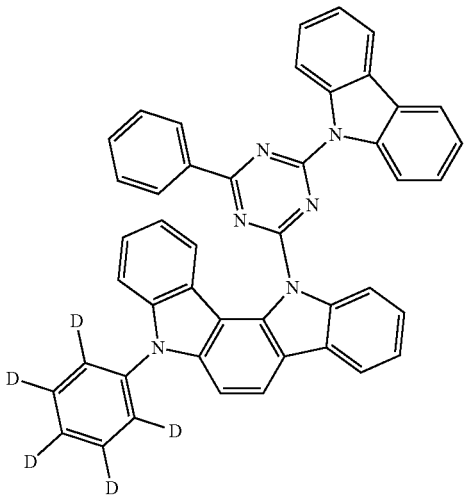
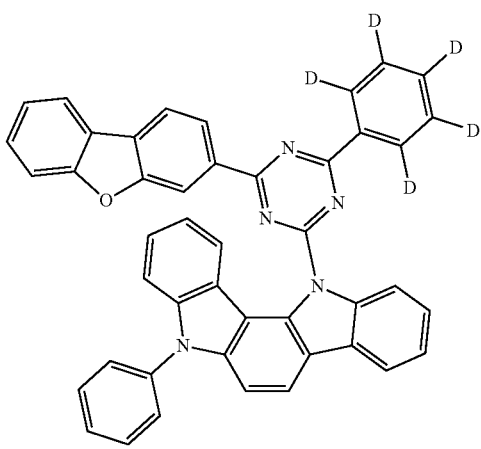

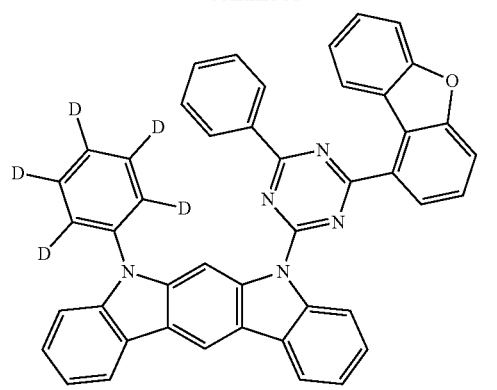
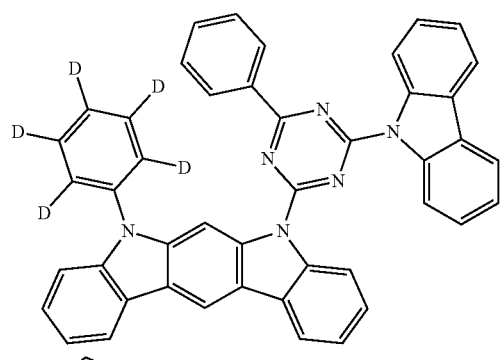
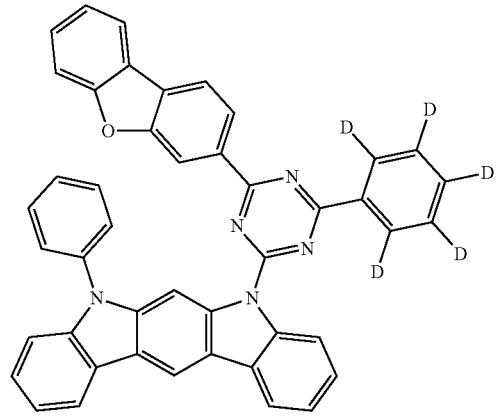
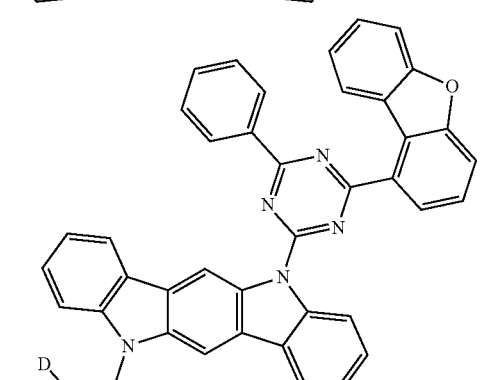
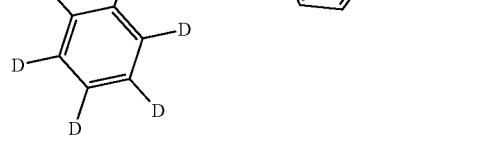
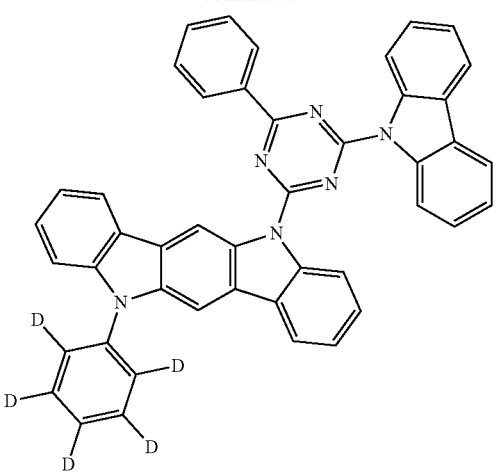
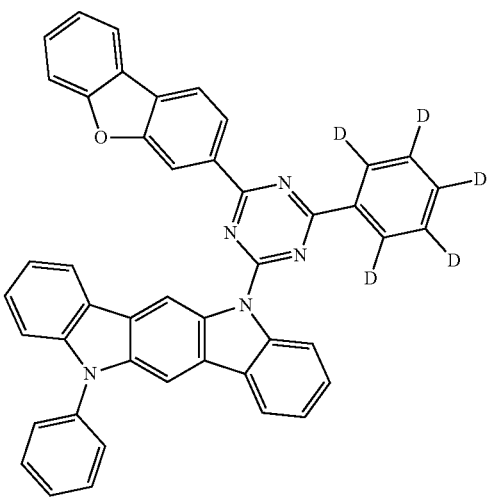
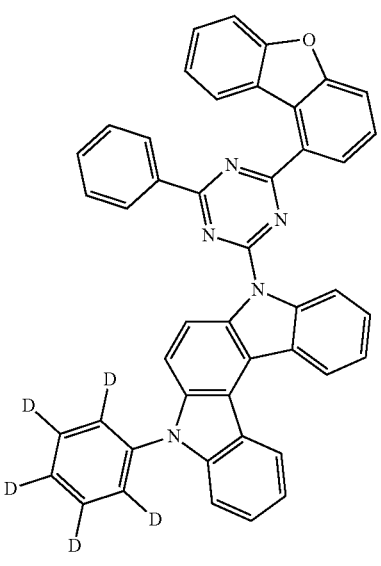

257
-continued
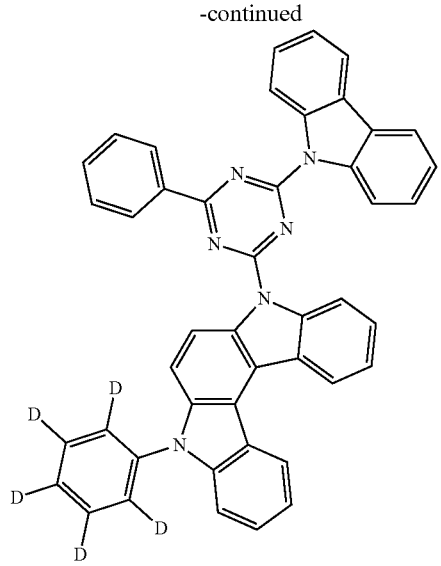
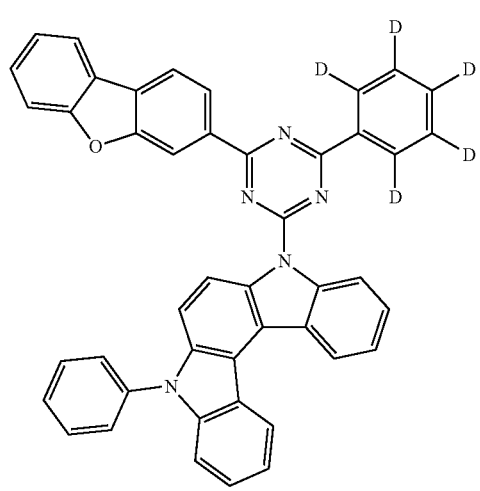
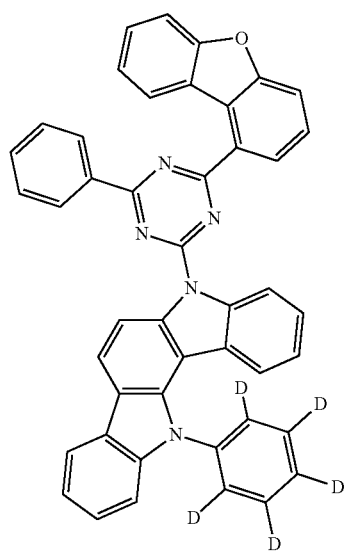
258
-continued
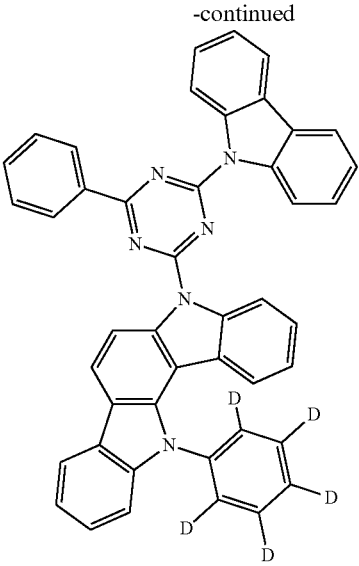
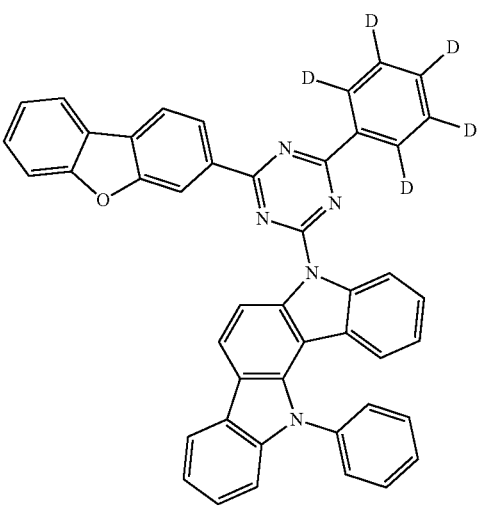
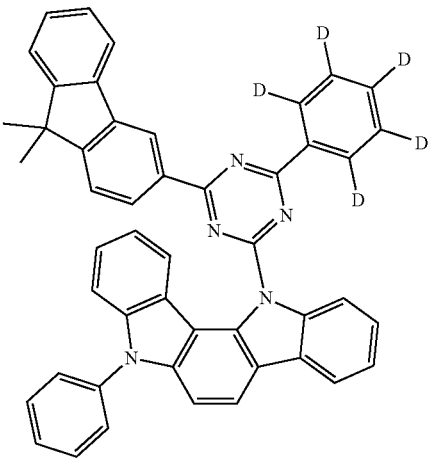

259
-continued
260
-continued
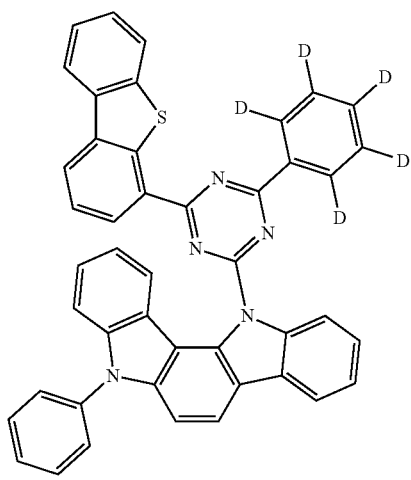
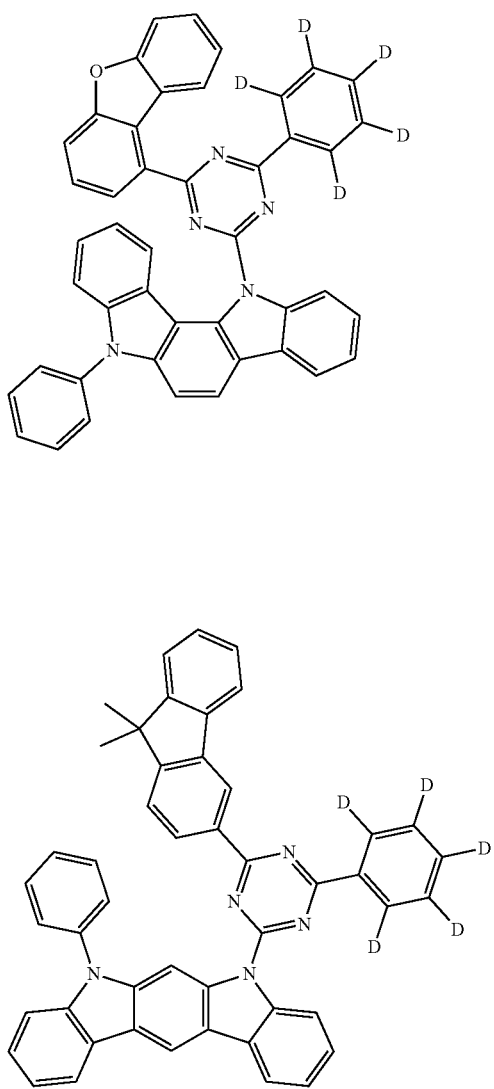
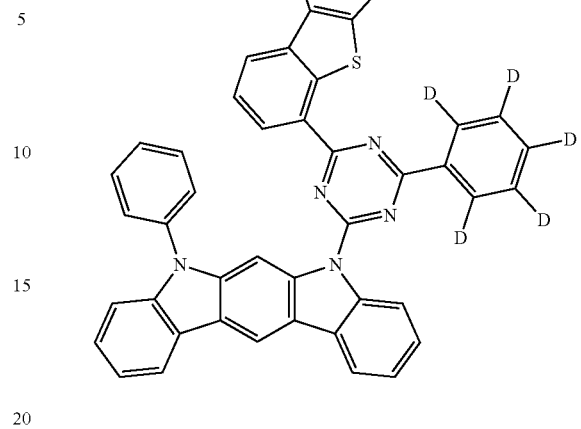
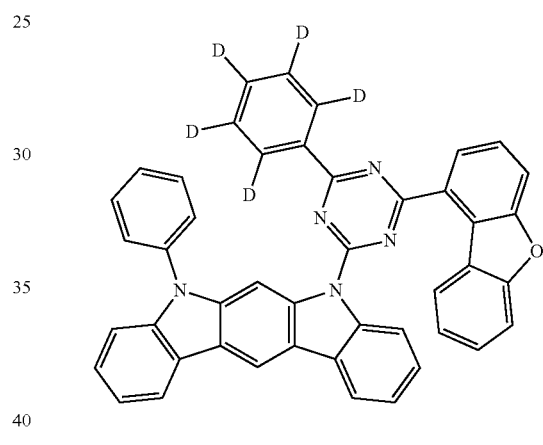
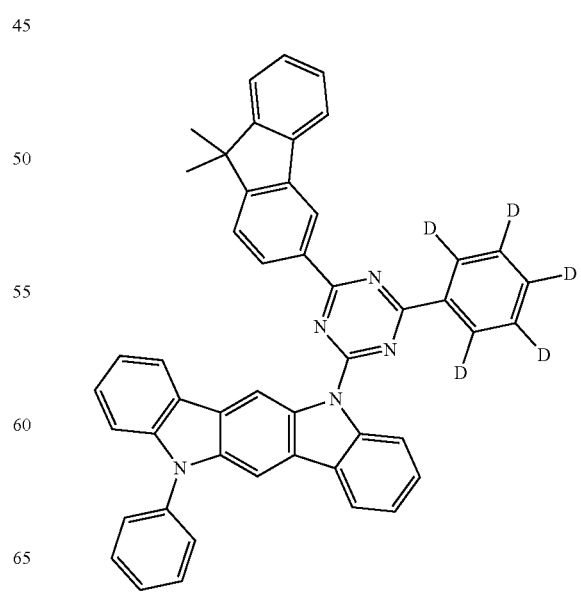

-continued
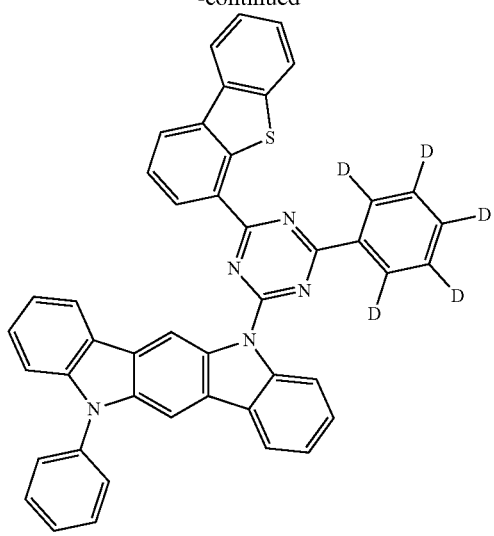
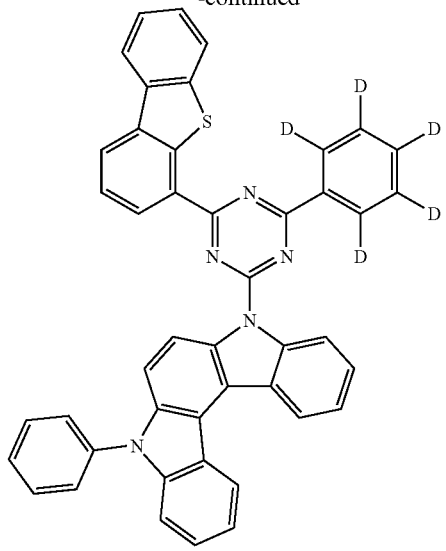
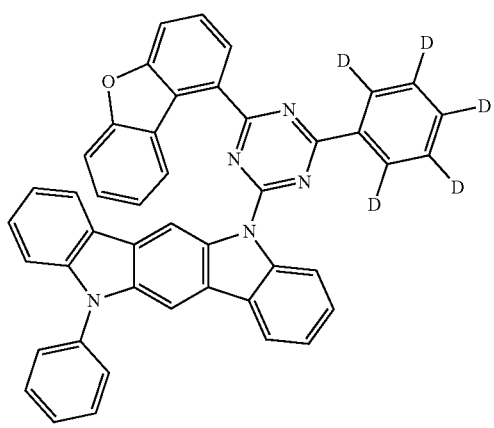
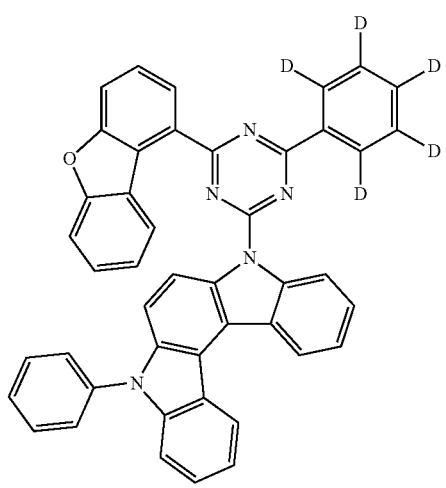
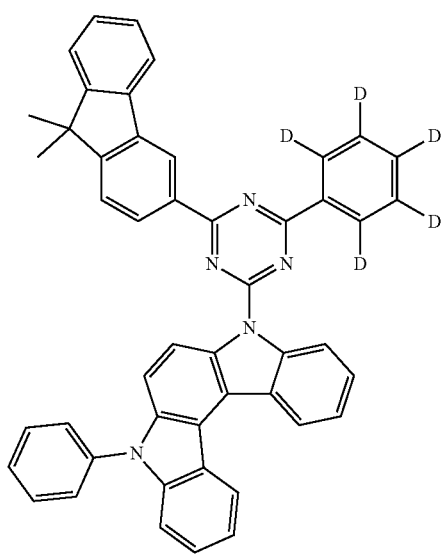
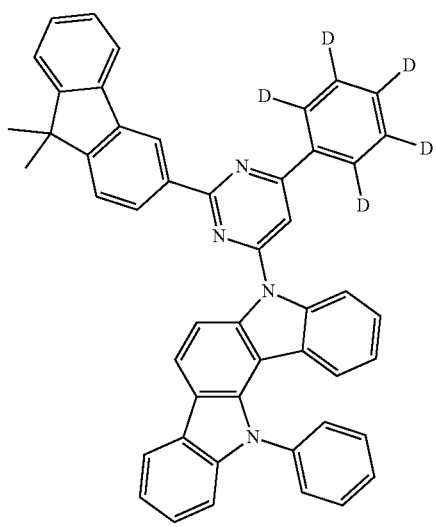

263
-continued
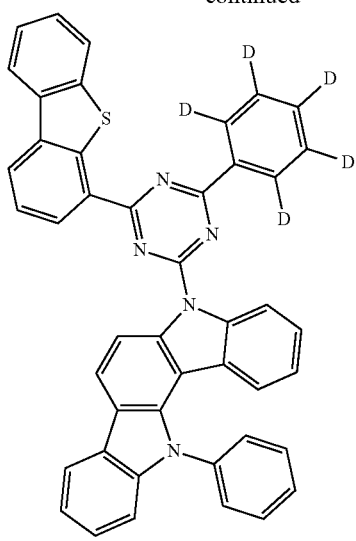
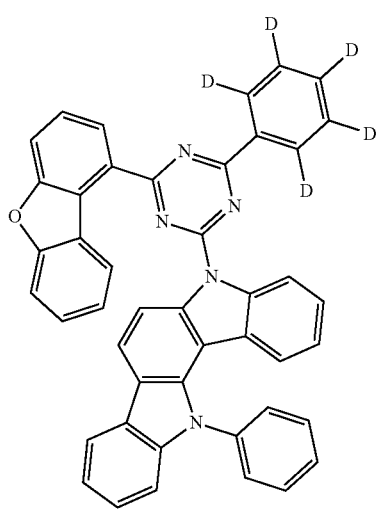
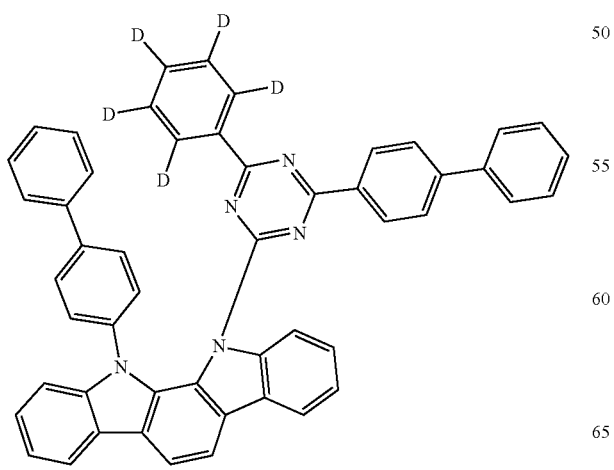
264
-continued
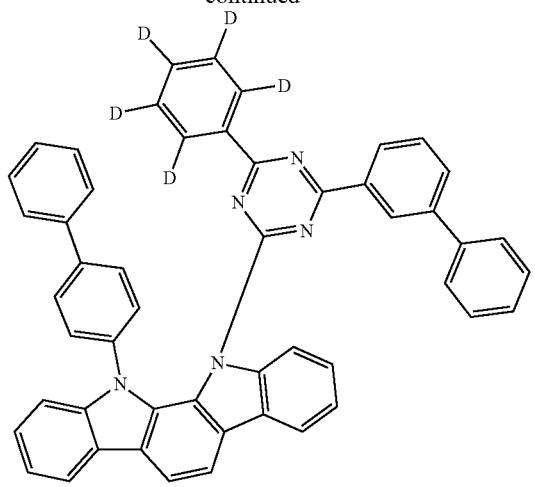
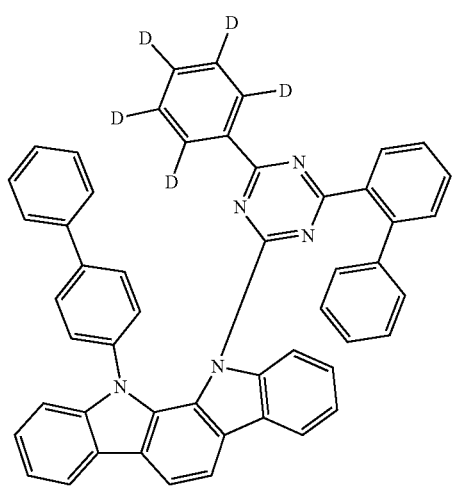
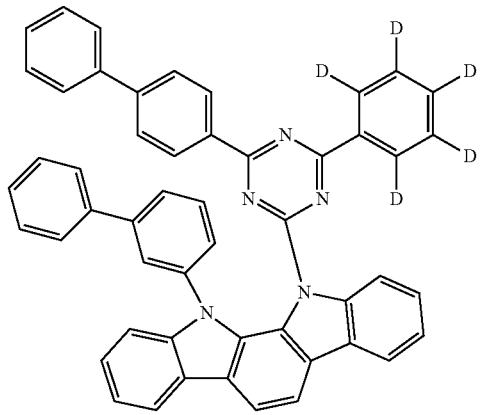

265
-continued
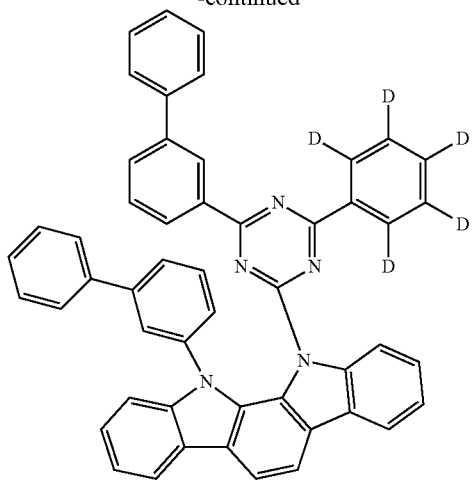
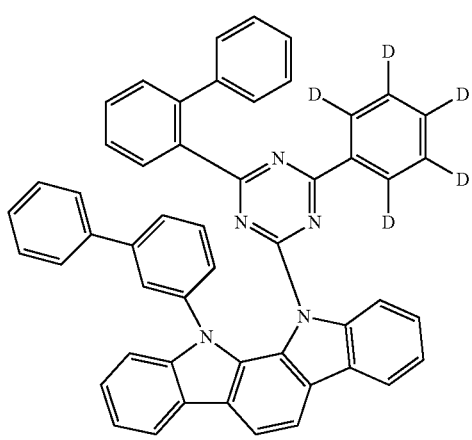
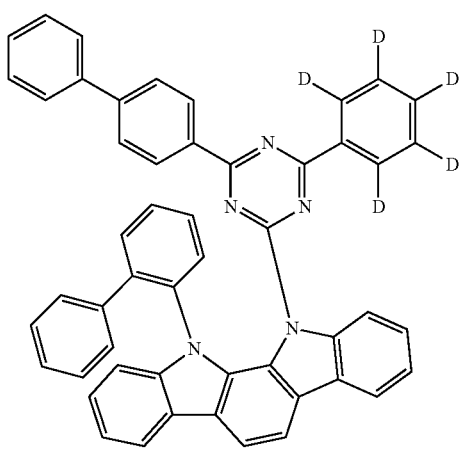
266
-continued
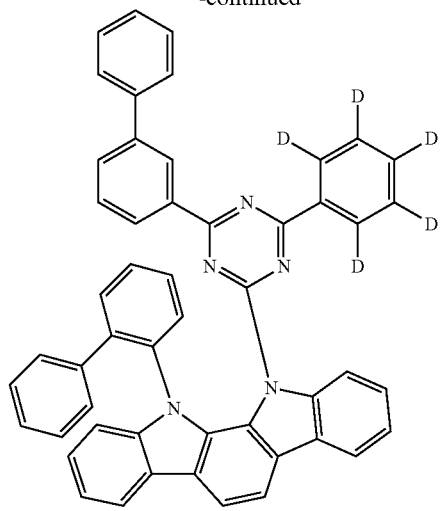
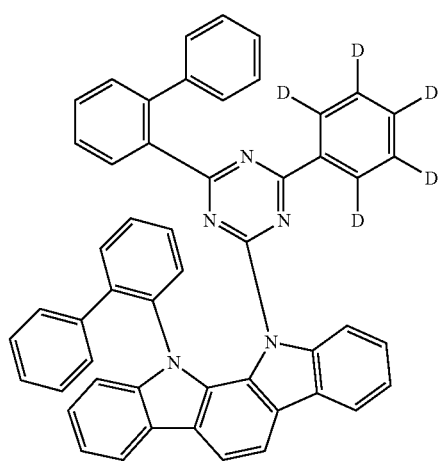
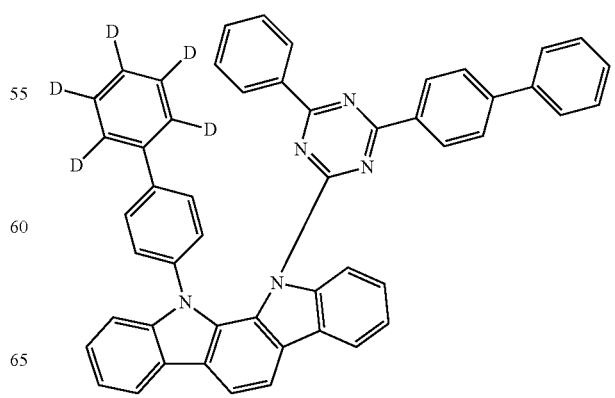

267
-continued
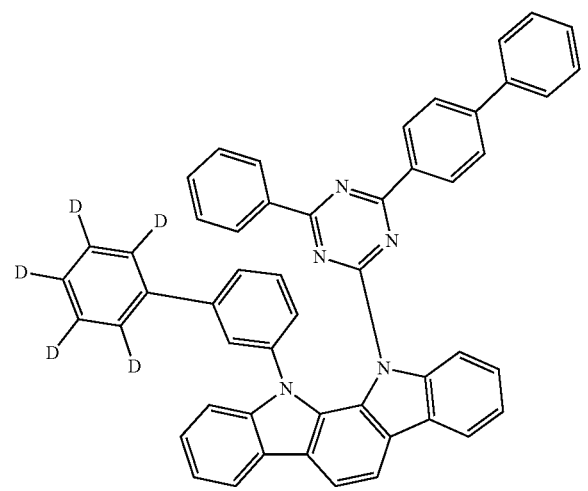
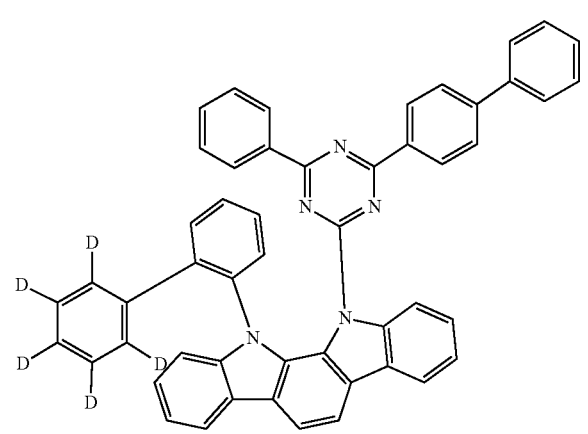
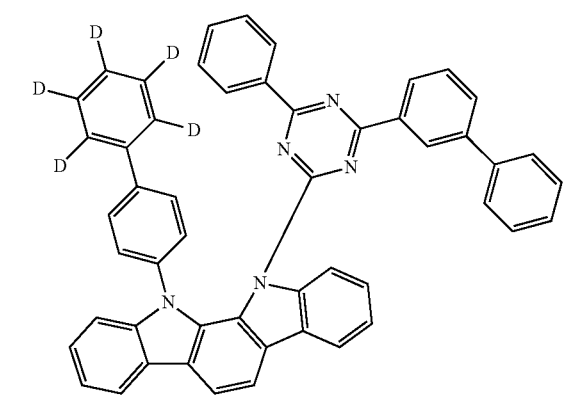
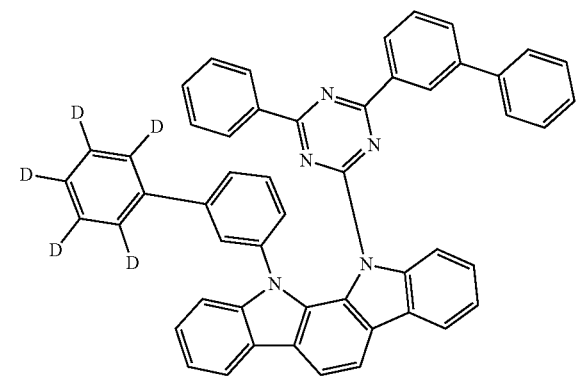
268
-continued
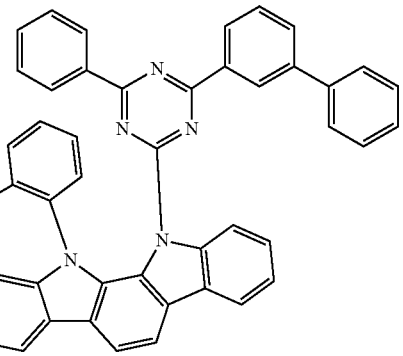
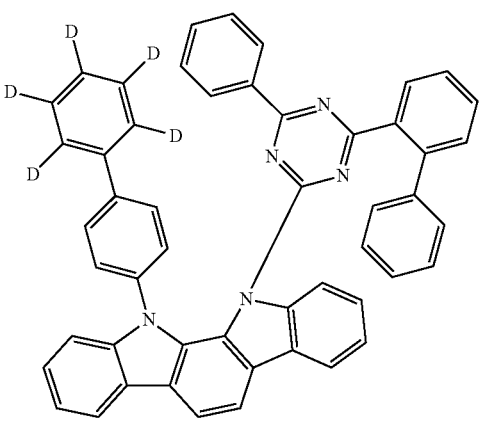
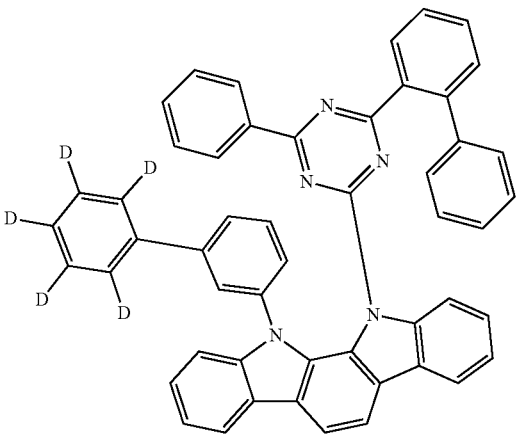
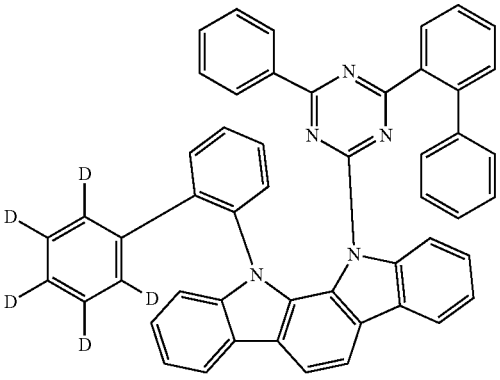

269
-continued
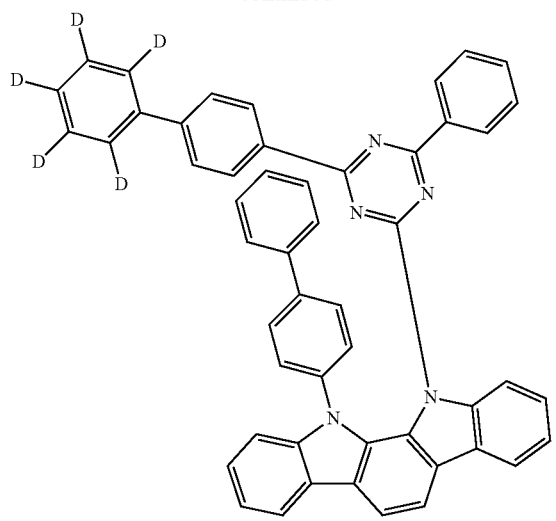
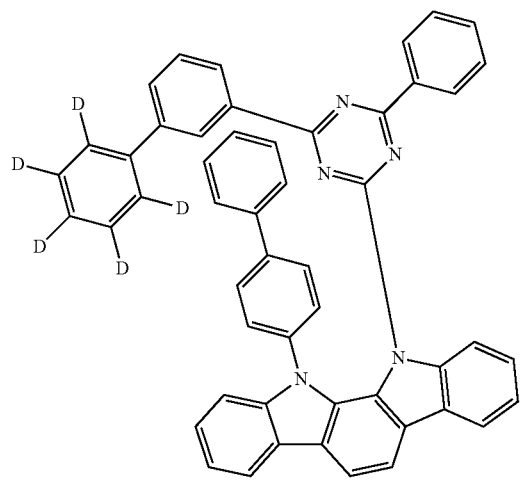
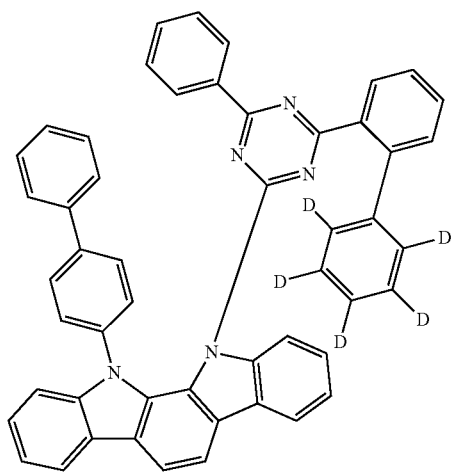
270
-continued
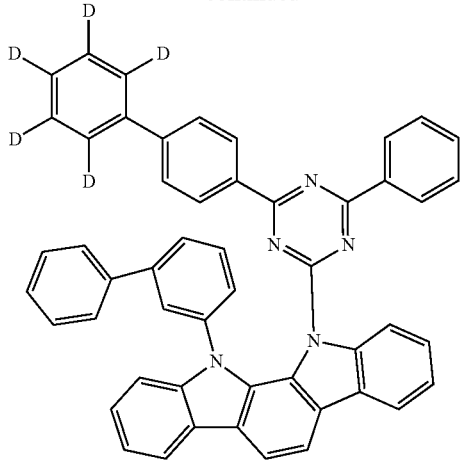
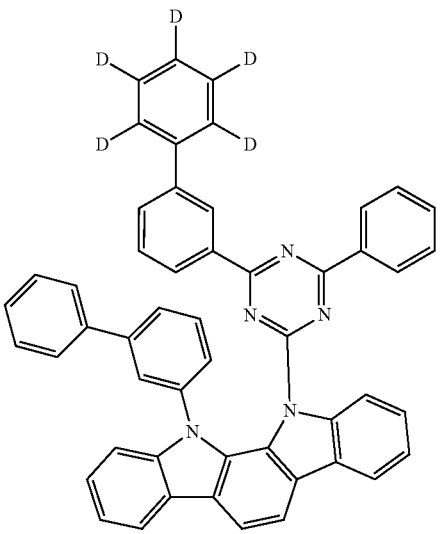
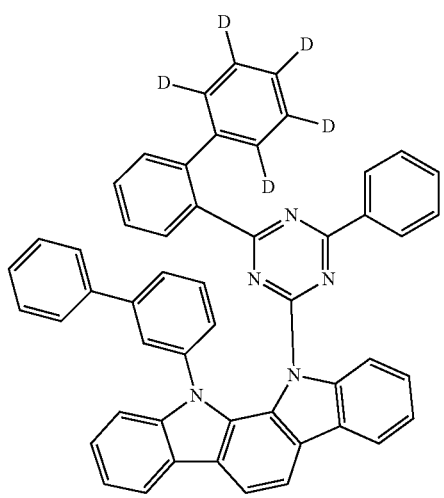

271
-continued
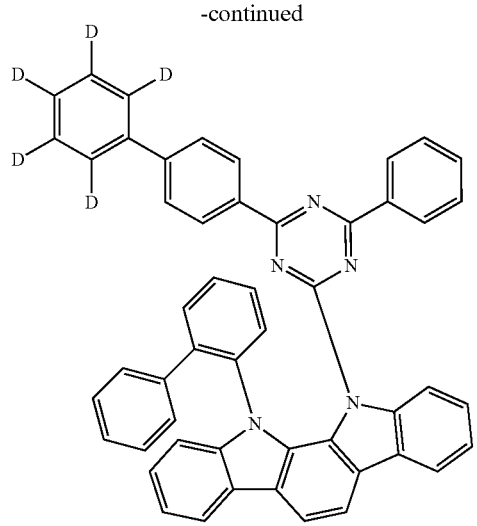
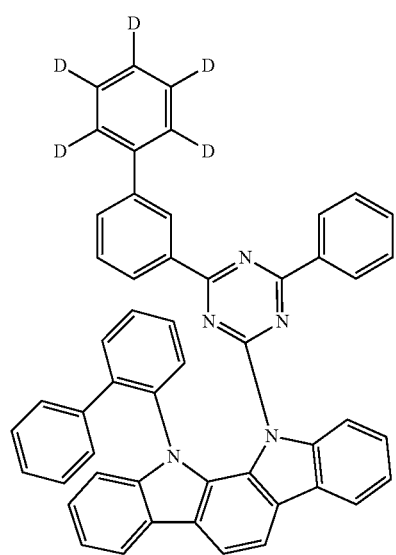
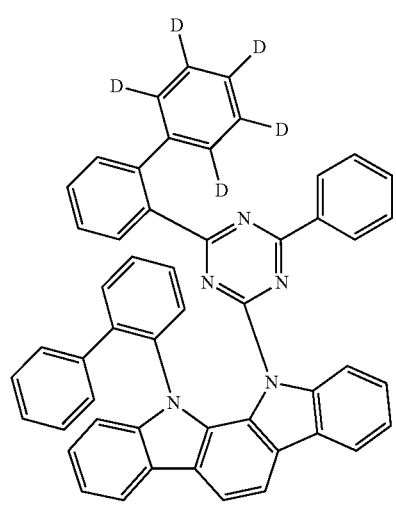
272
-continued
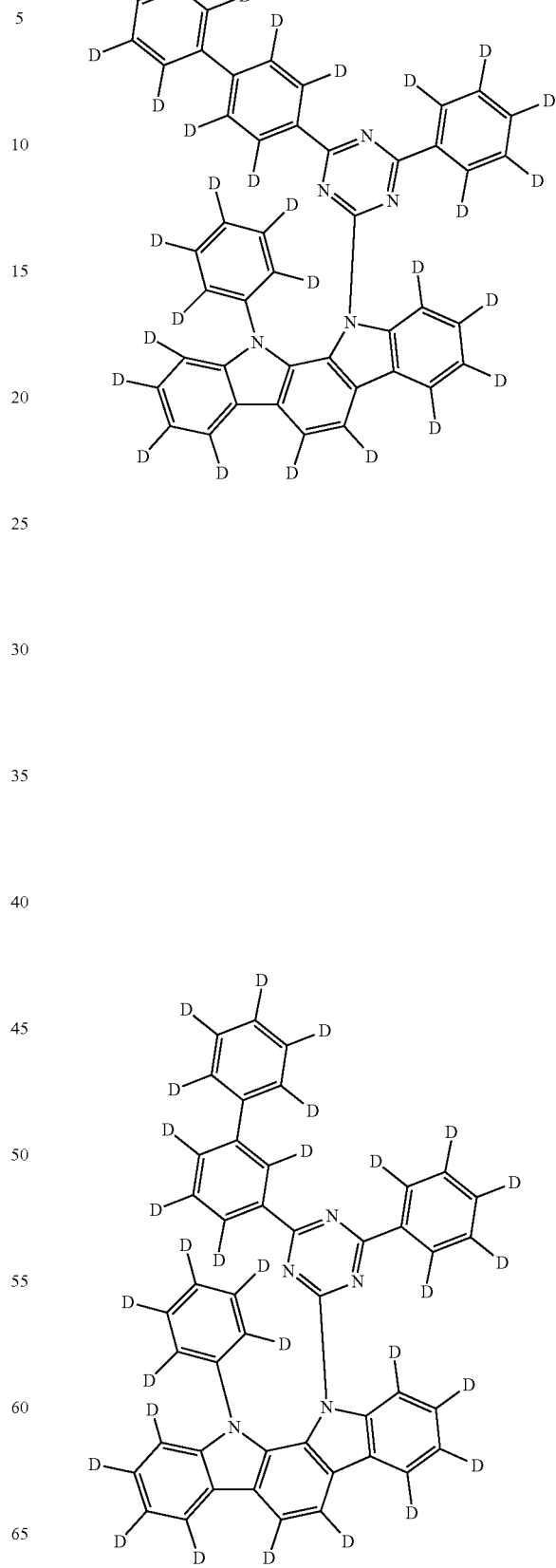

-continued
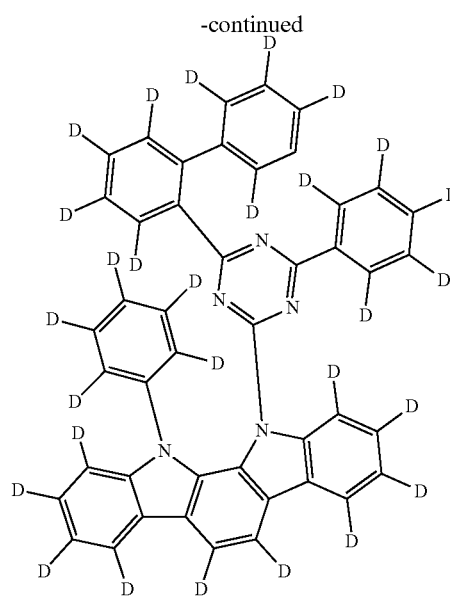
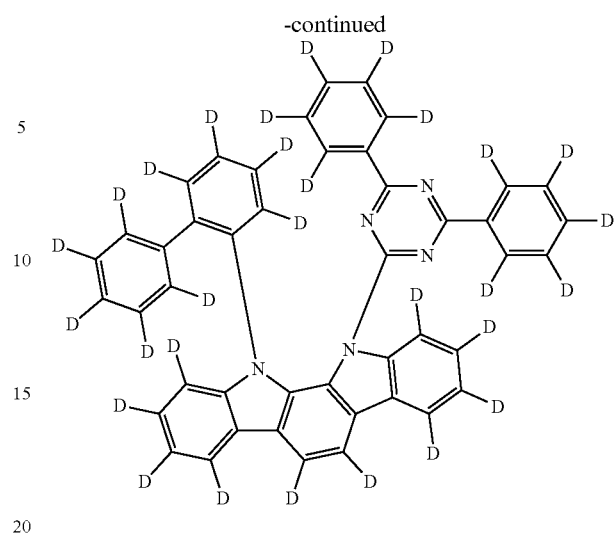
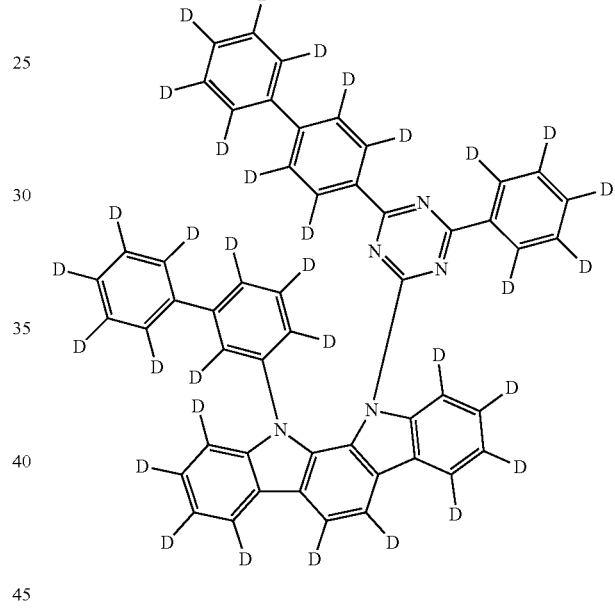
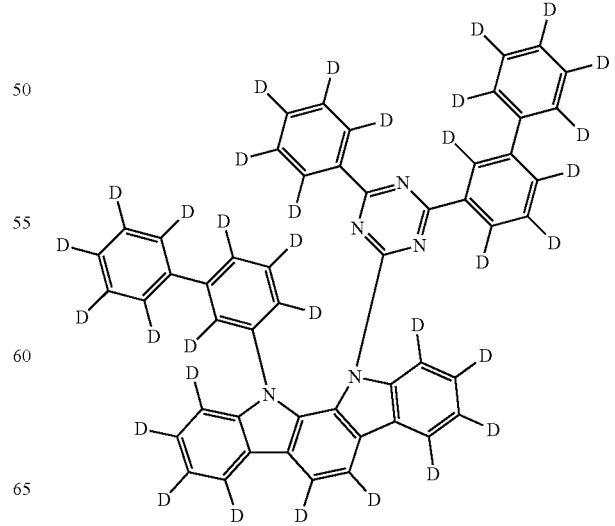

275
-continued
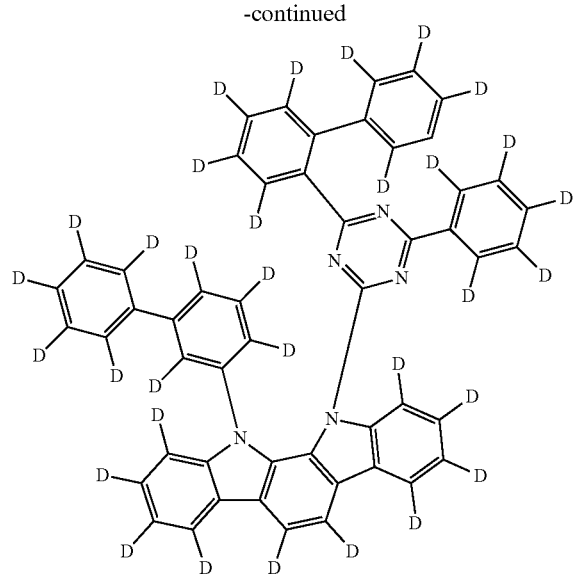
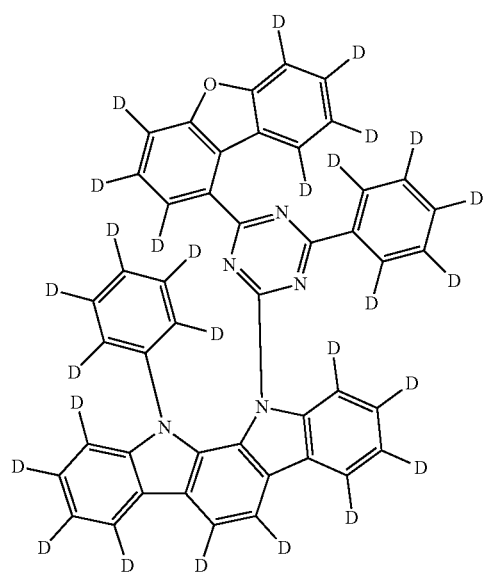
276
-continued
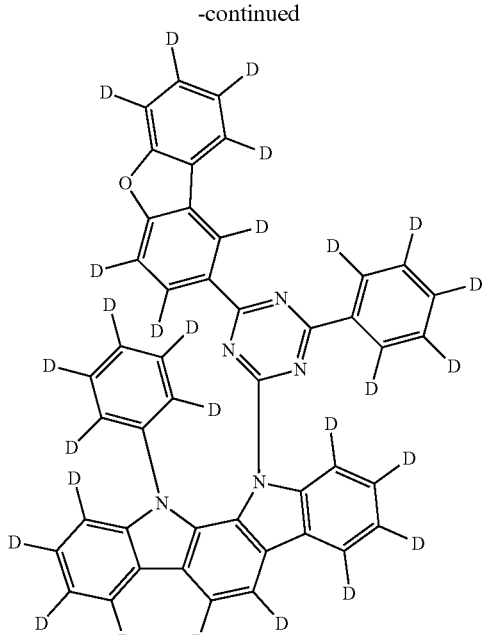
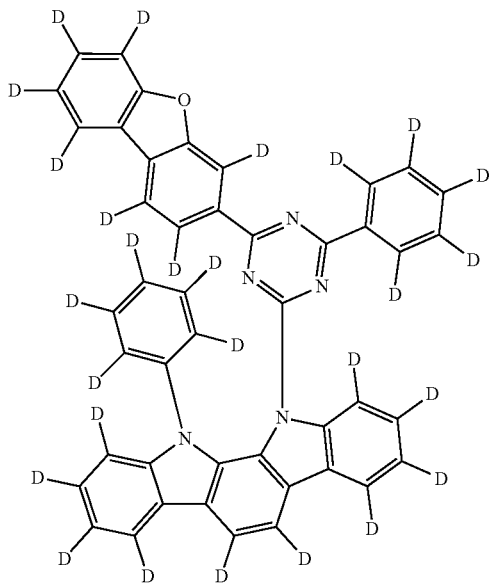

277
-continued
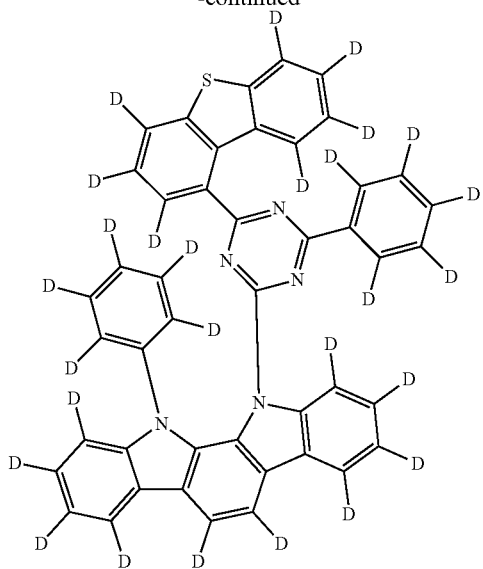
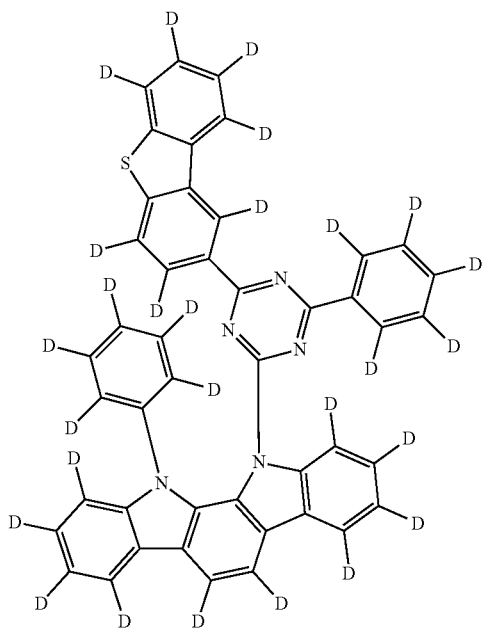
278
-continued
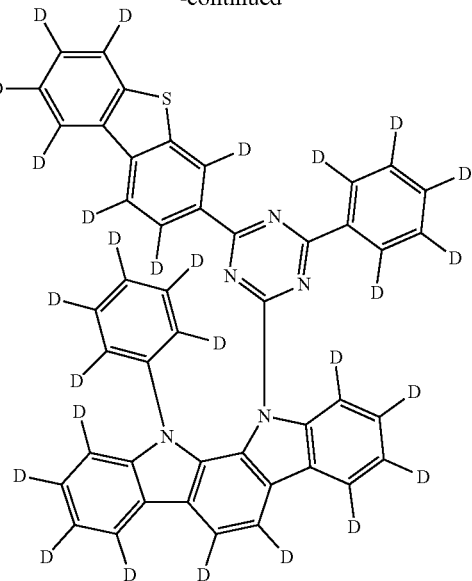
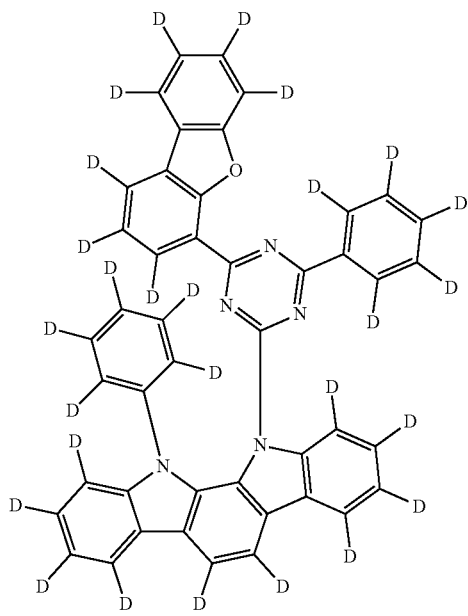

279
-continued
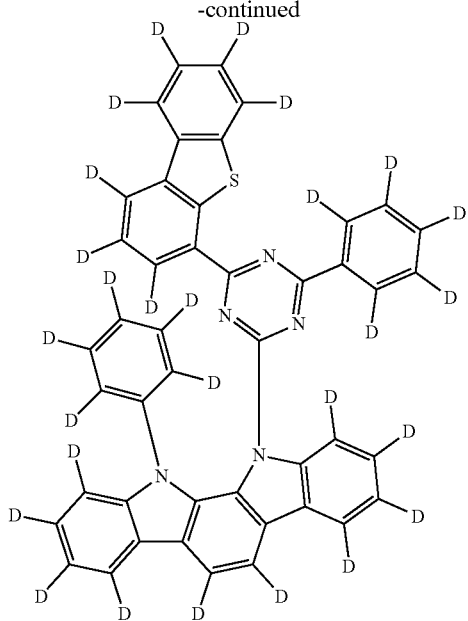
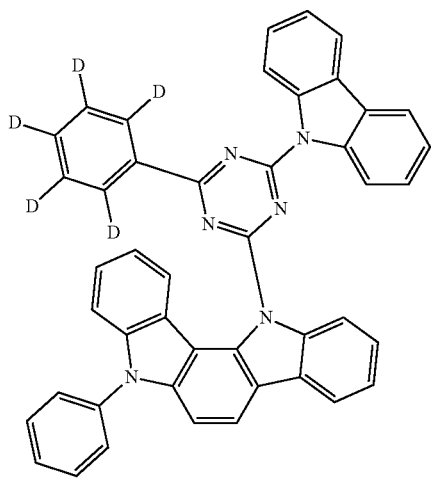
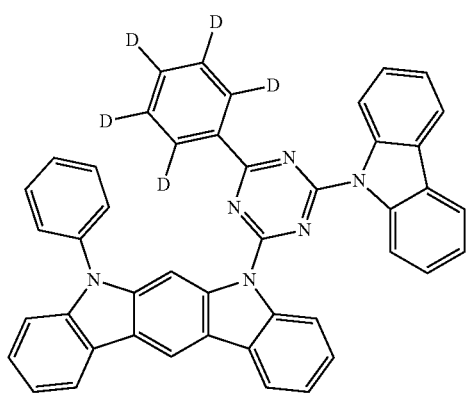
280
-continued
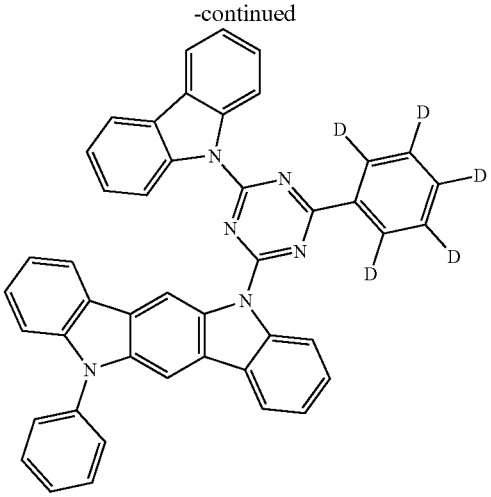
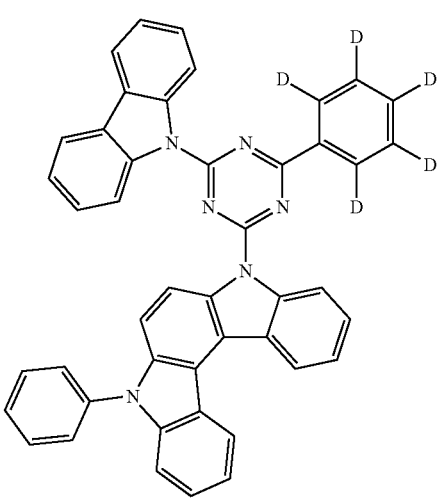
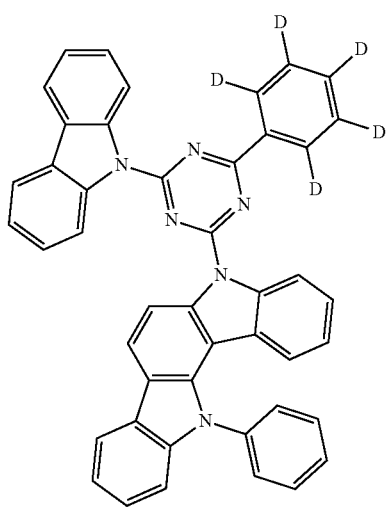

-continued

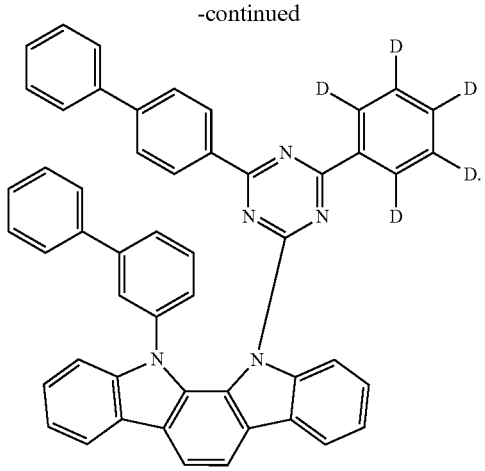

13. An organic light emitting device comprising:
a first electrode;
a second electrode disposed to face the first electrode; and
one or more organic material layers disposed between the first electrode and the second electrode,
wherein one or more layers of the organic material layers comprise the compound according to claim 1.

14. The organic light emitting device of claim 13, wherein the organic material layer comprising the compound is a light emitting layer.

15. The organic light emitting device of claim 14, wherein the light emitting layer further comprises a compound represented by Chemical Formula 3:

[Chemical Formula 3]

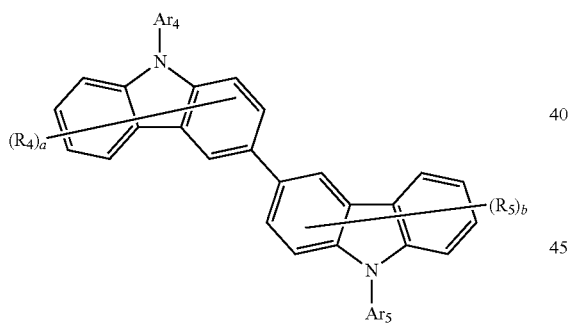

wherein, in Chemical Formula 3,
$Ar_4$ and $Ar_5$ are each independently a substituted or unsubstituted $C_{6-60}$ aryl group; or a substituted or unsubstituted $C_{2-60}$ heteroaryl group containing one or more heteroatoms selected from the group consisting of N, O and S,
$R_4$ and $R_5$ are each independently hydrogen; deuterium; halogen; cyano; nitro; amino; a substituted or unsubstituted $C_{1-60}$ alkyl group; a substituted or unsubstituted $C_{3-60}$ cycloalkyl group; a substituted or unsubstituted $C_{2-60}$ alkenyl group; a substituted or unsubstituted $C_{6-60}$ aryl group; or a substituted or unsubstituted $C_{2-60}$ heteroaryl group containing one or more heteroatoms selected from the group consisting of N, O and S, and
a and b are each independently an integer of 0 to 7.

16. The organic light emitting device of claim 15, wherein $Ar_4$ and $Ar_5$ are each independently a phenyl group; a biphenylyl group; a terphenylyl group; a naphthyl group; a dibenzofuranyl group; a dibenzothiophenyl group; or a 9,9-dimethylfluorenyl group.

17. The organic light emitting device of claim 15, wherein all $R_4$ and all $R_5$ are hydrogen.

18. The organic light emitting device of claim 15, wherein the compound represented by Chemical Formula 3 is any one selected from the group consisting of the following compounds:

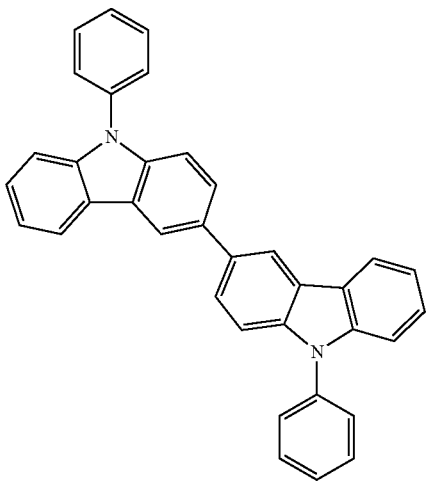

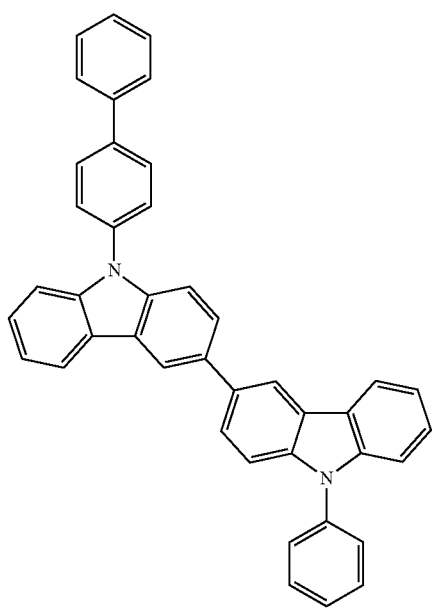

283
-continued
284
-continued
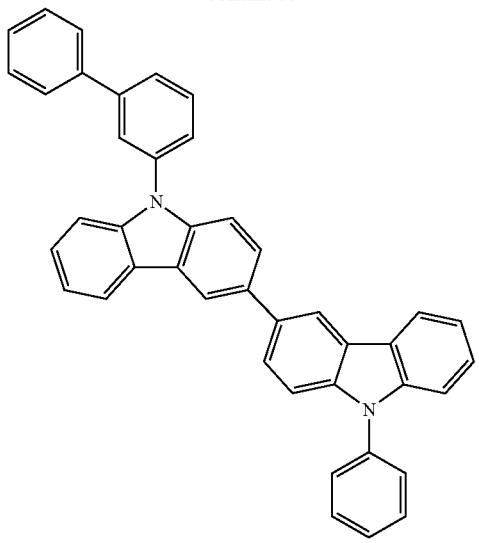
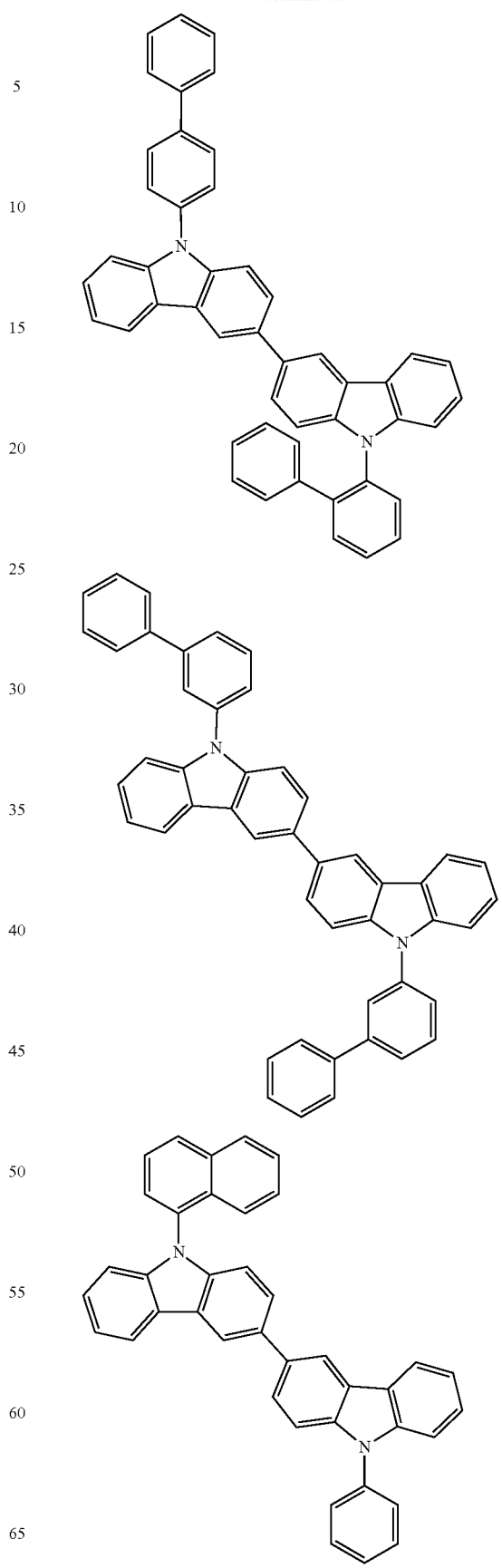

285
-continued
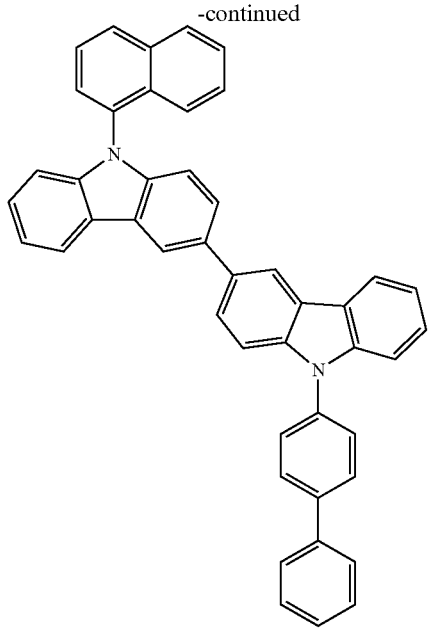
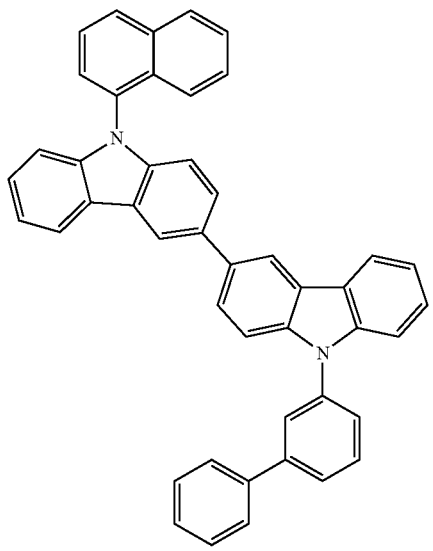
286
-continued
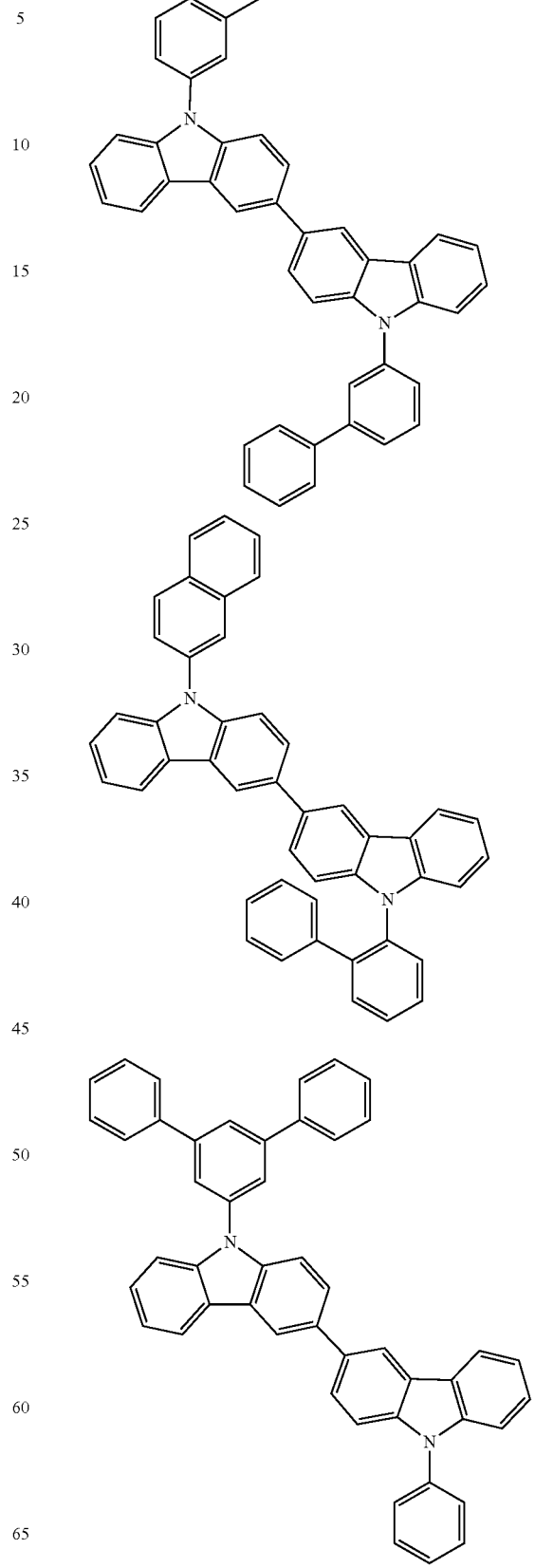

287
-continued
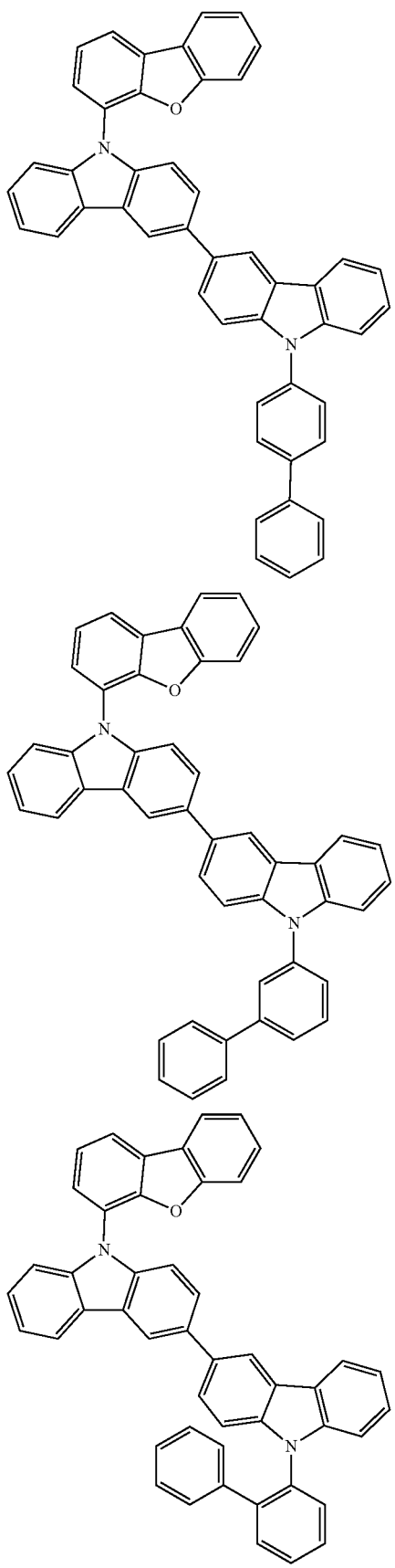
288
-continued
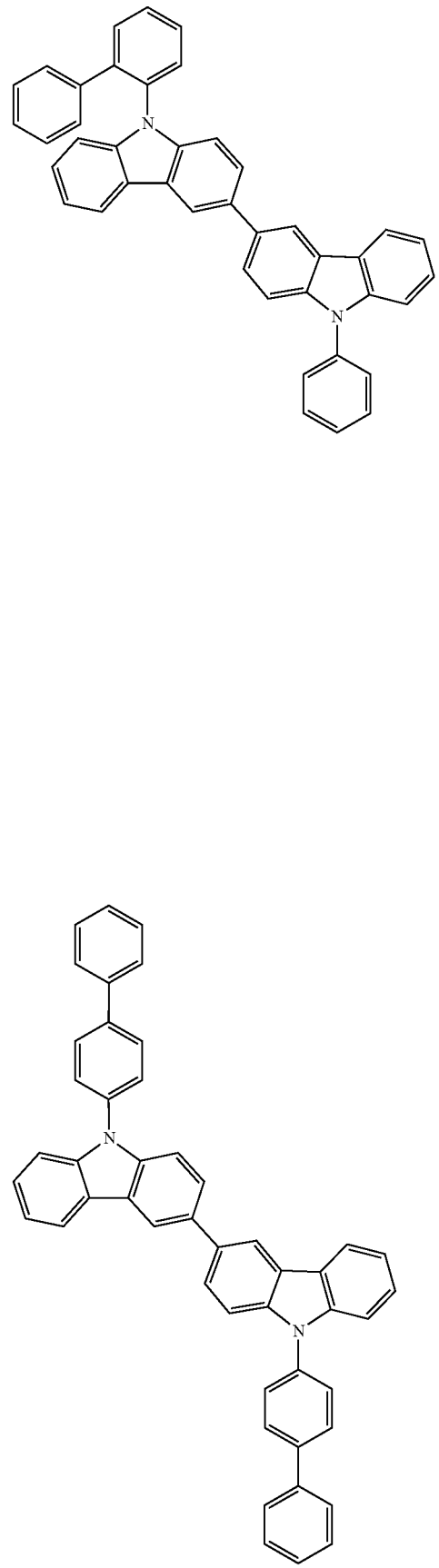

289
-continued
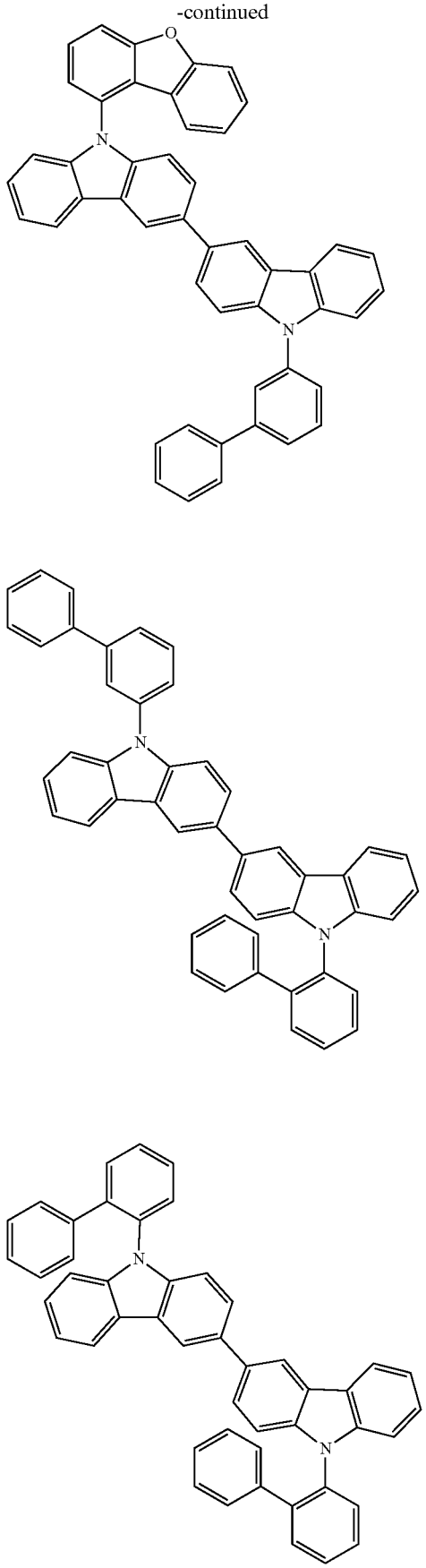
290
-continued
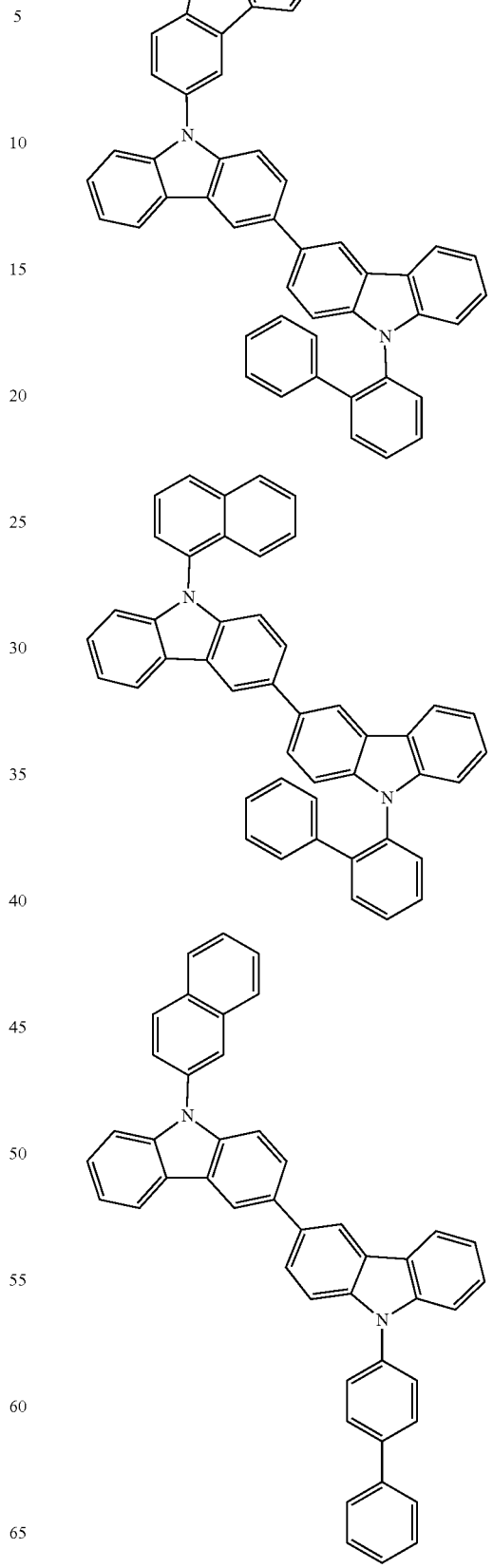

291
-continued
292
-continued
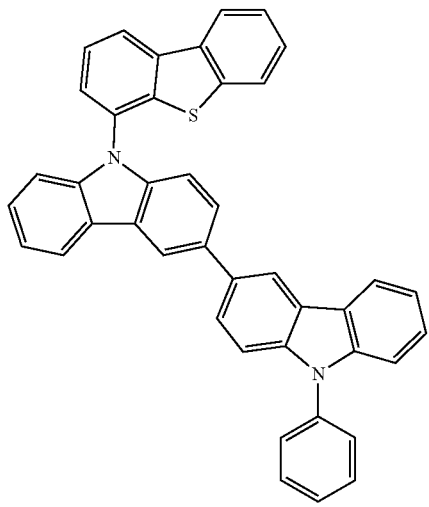
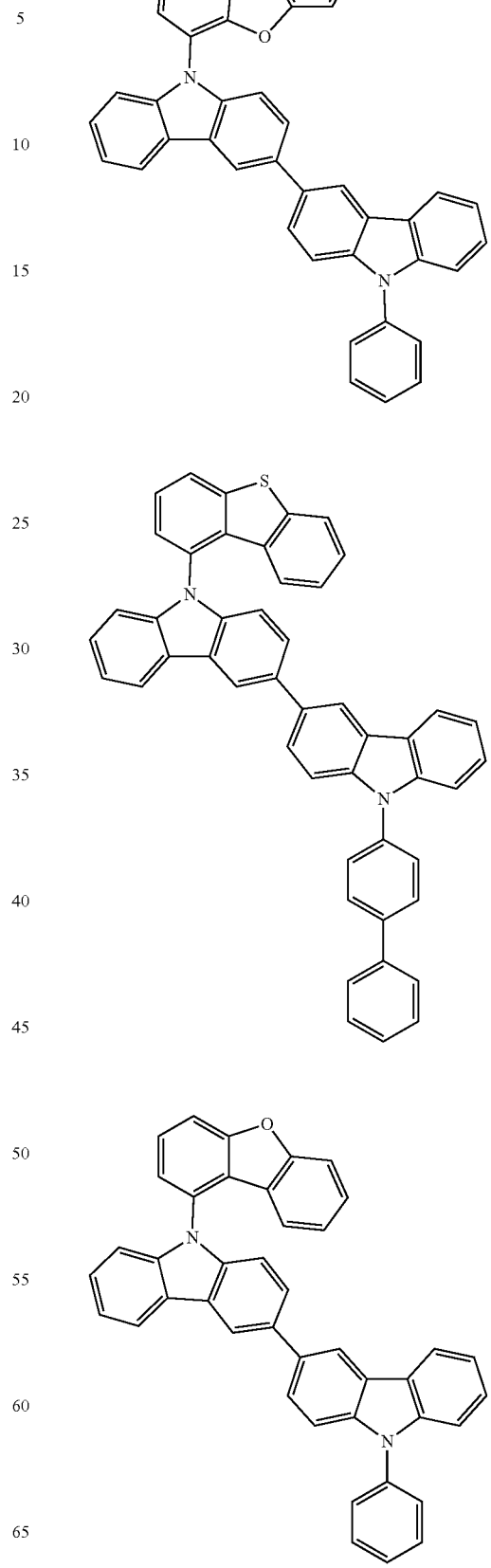

293
-continued
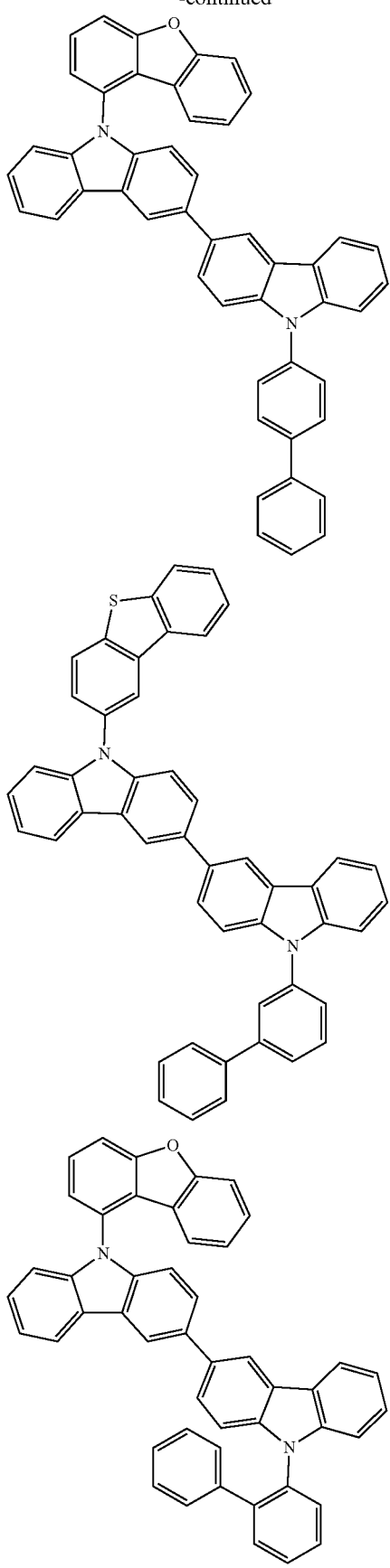
294
-continued
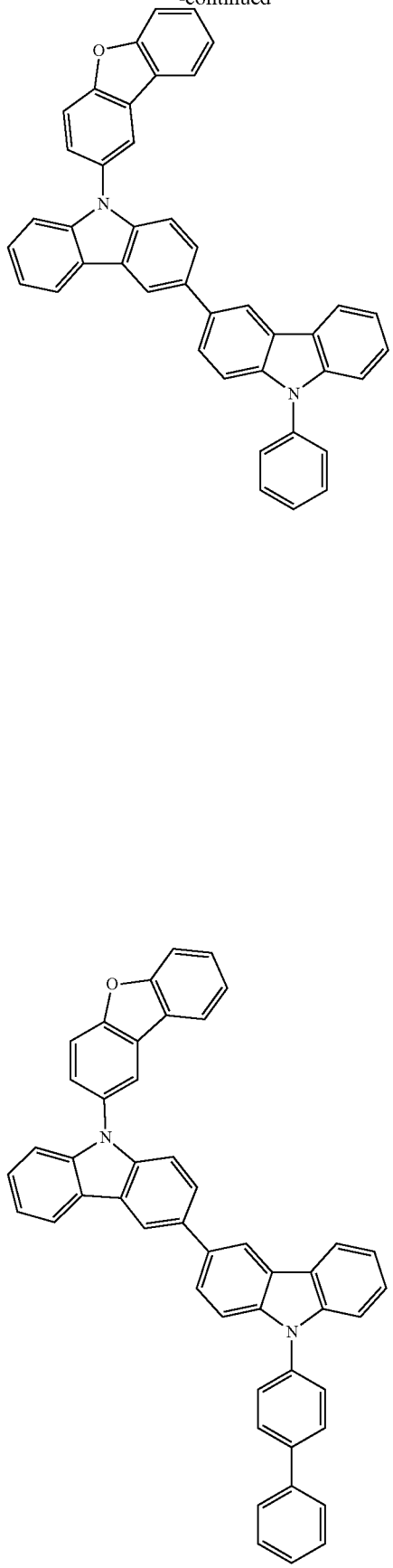

295
-continued
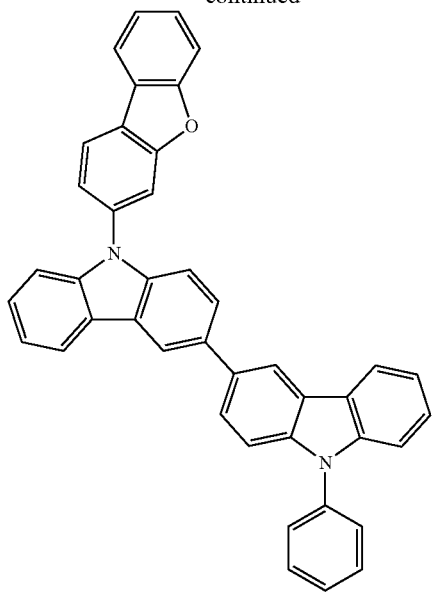
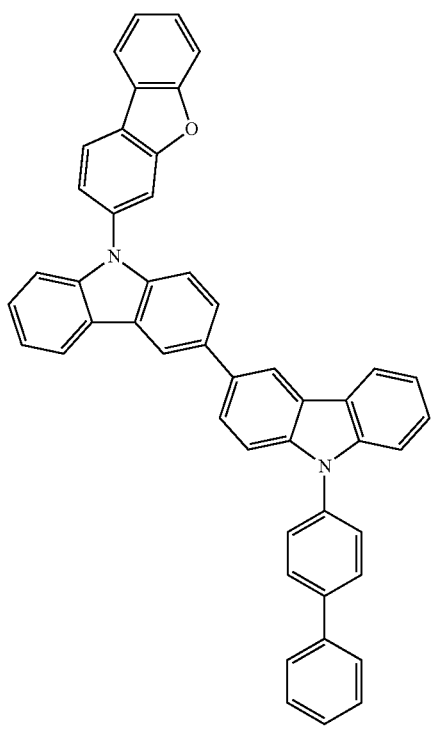
296
-continued
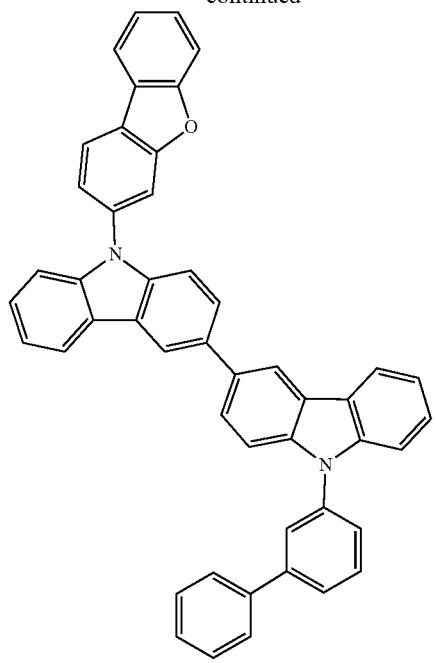
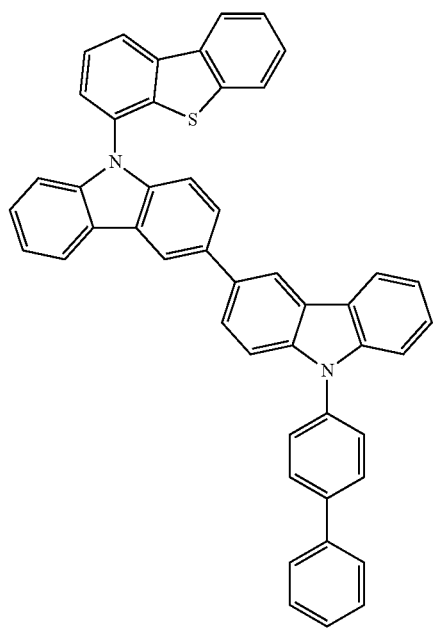

297
-continued
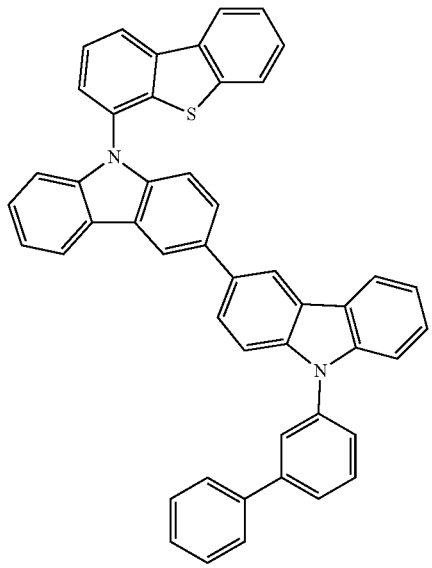
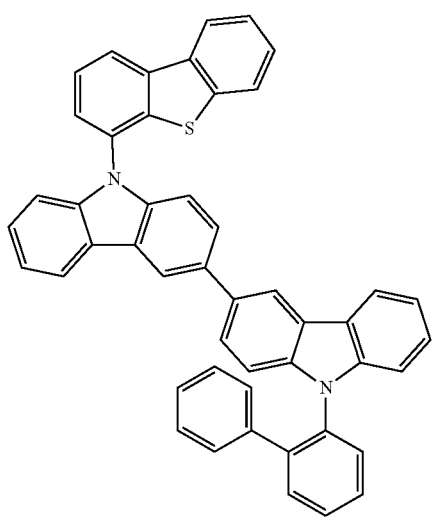
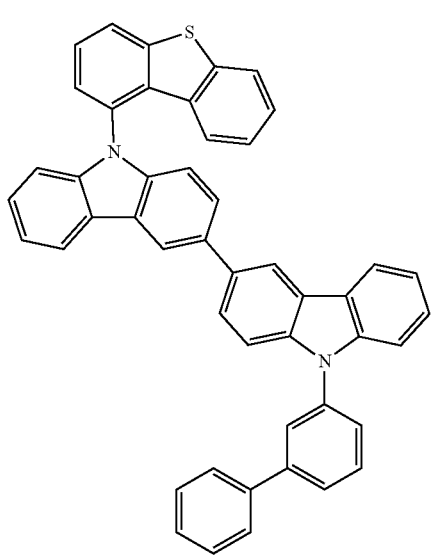
298
-continued
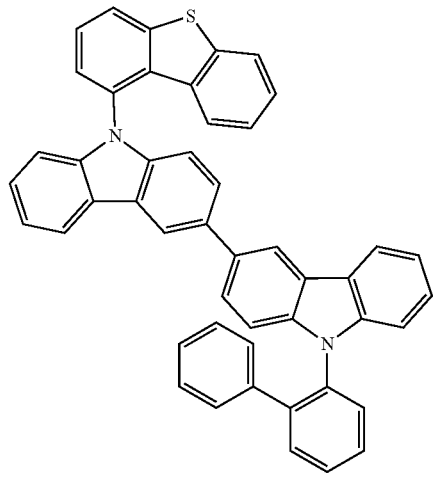
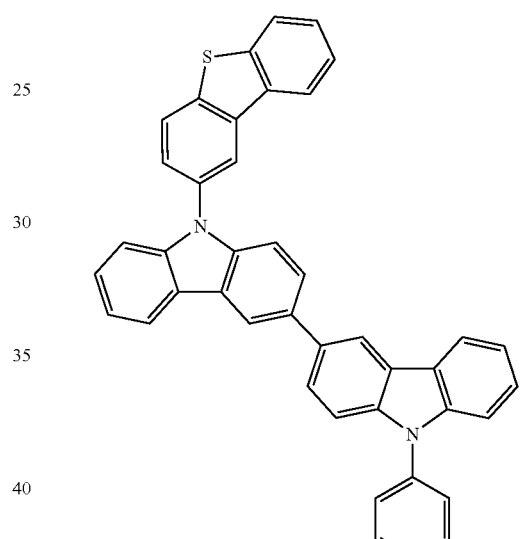
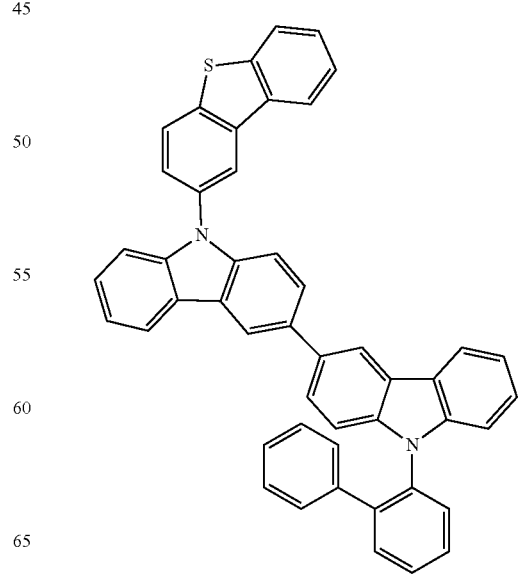

299
-continued
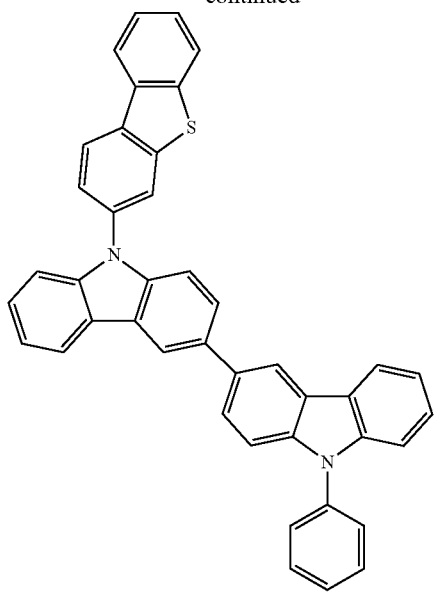
300
-continued
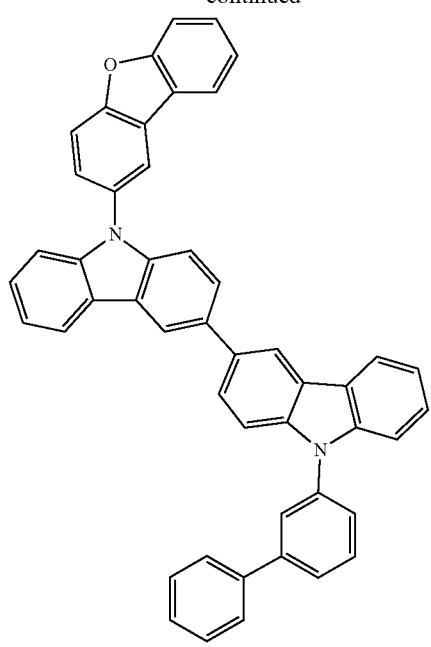
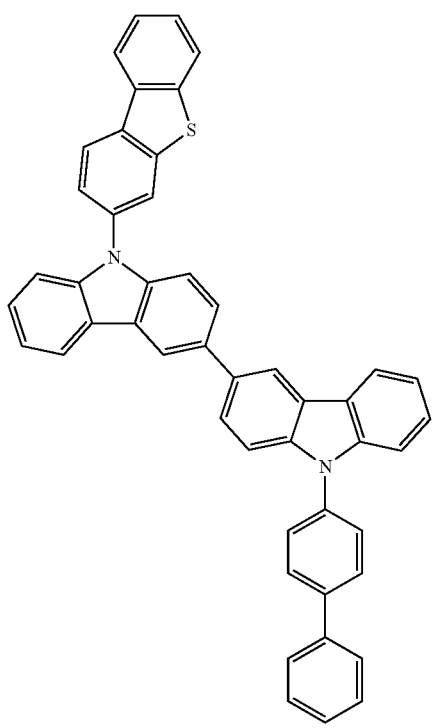
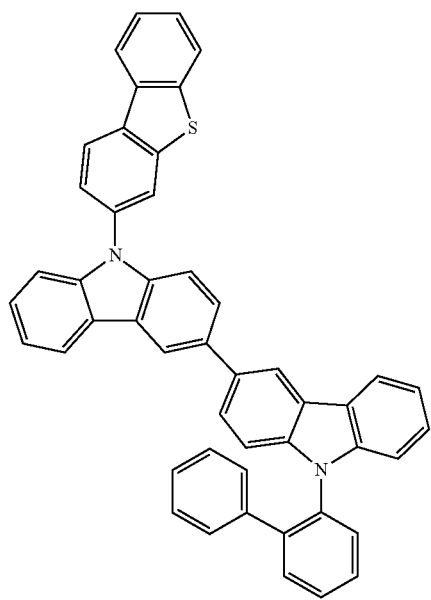

301
-continued
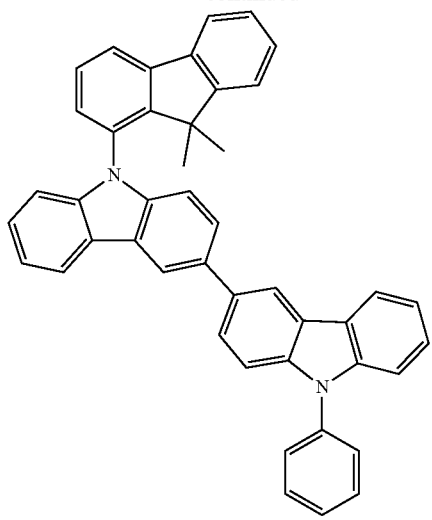
302
-continued
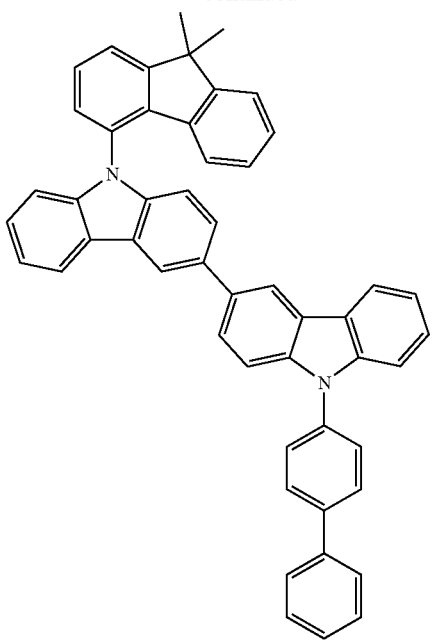
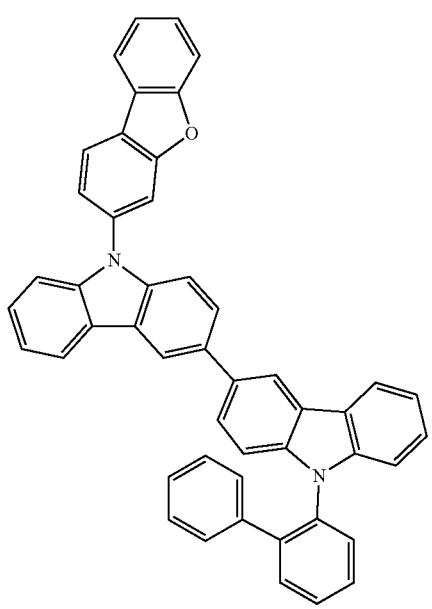
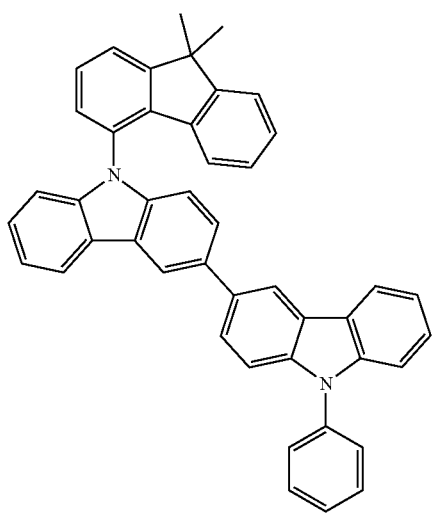
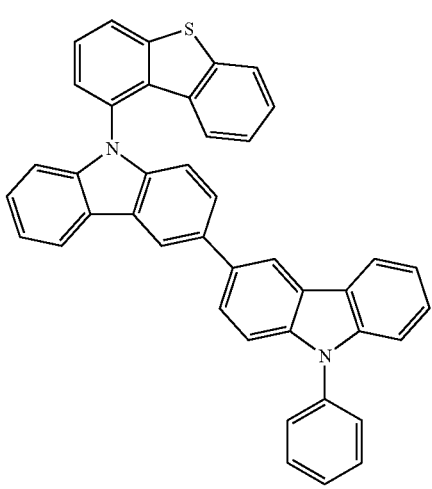

303
-continued
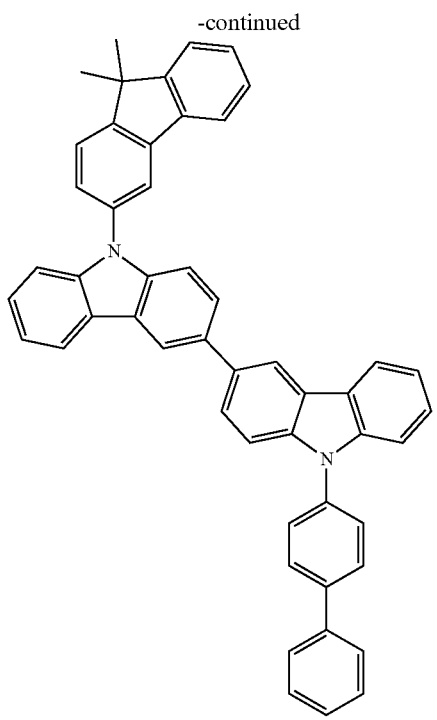
304
-continued
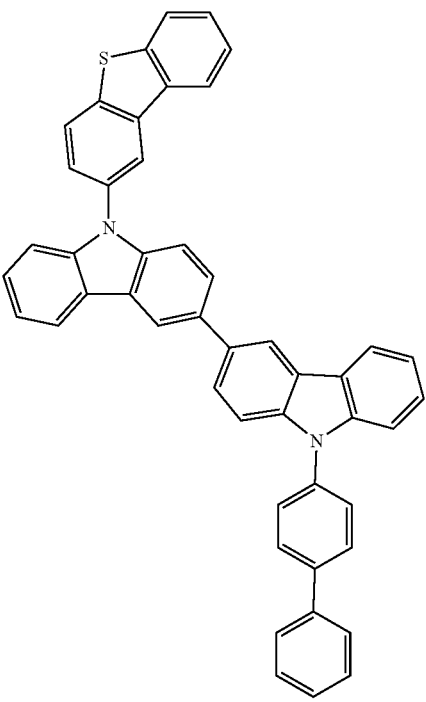
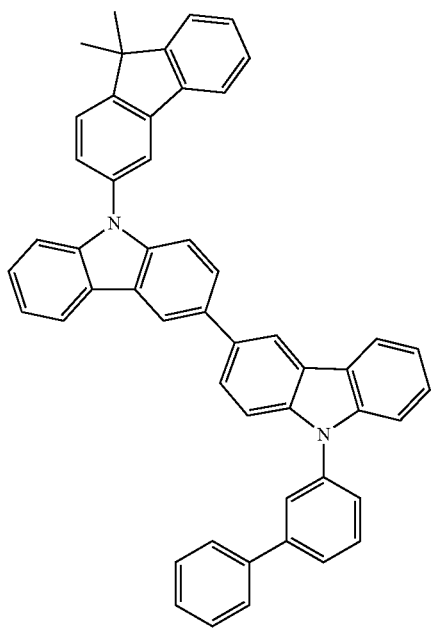

305
-continued
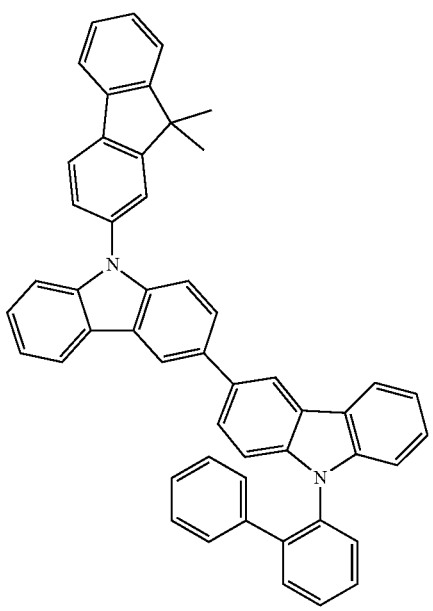
306
-continued
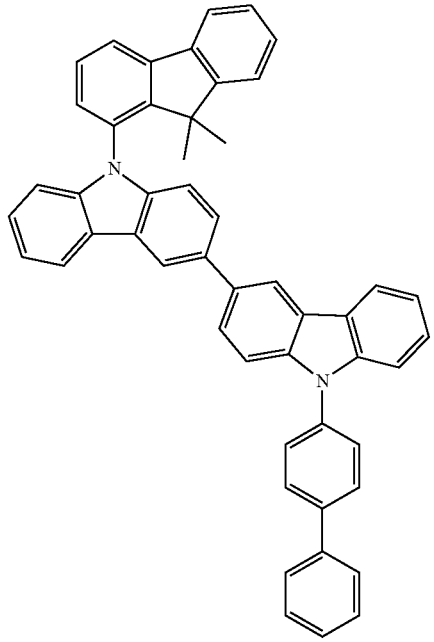
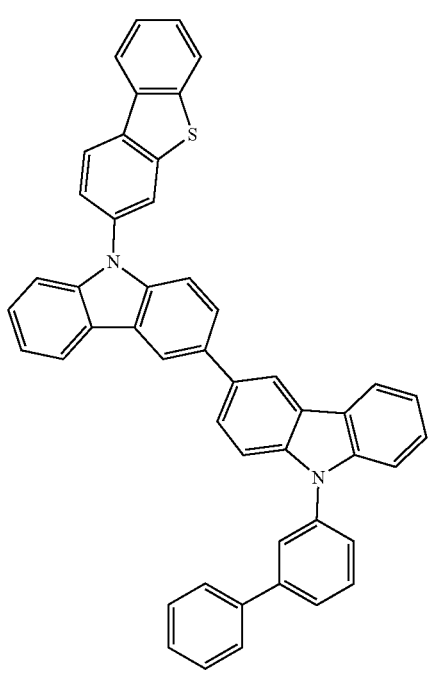
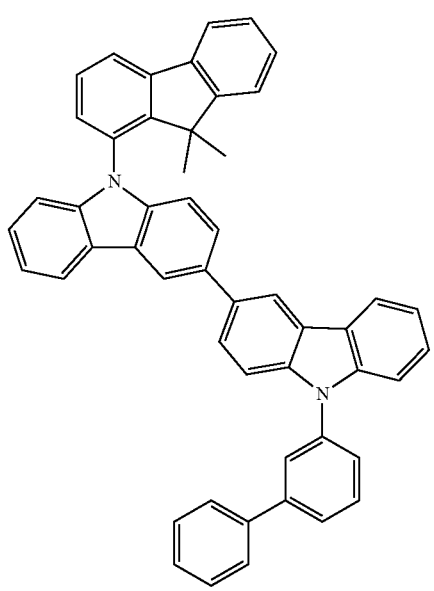

307
-continued
308
-continued
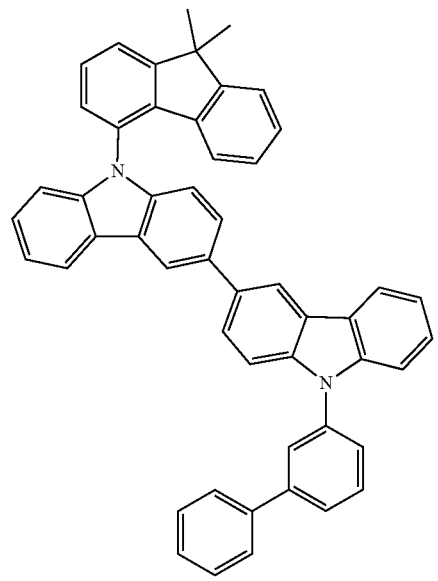
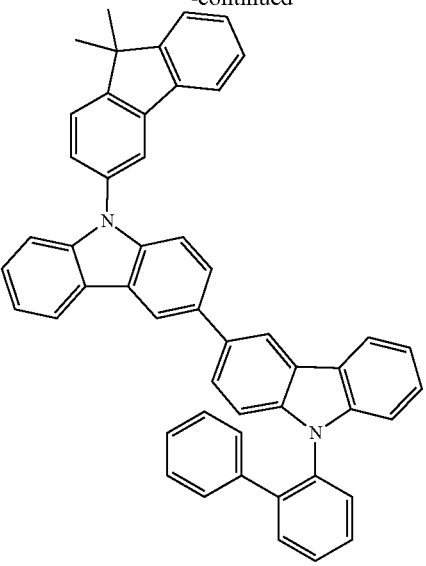

309
-continued
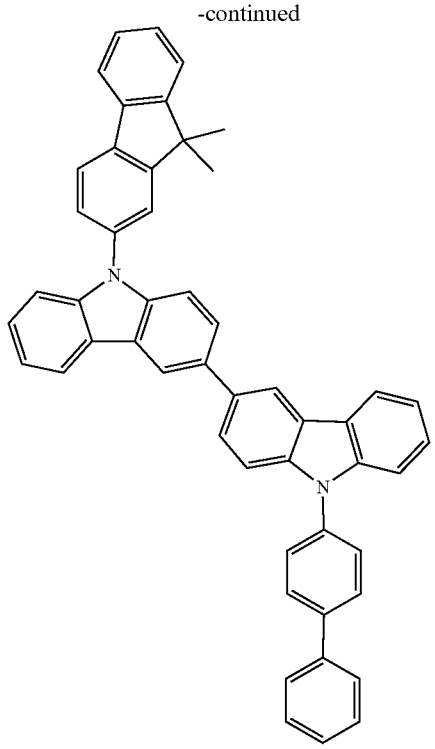
310
-continued
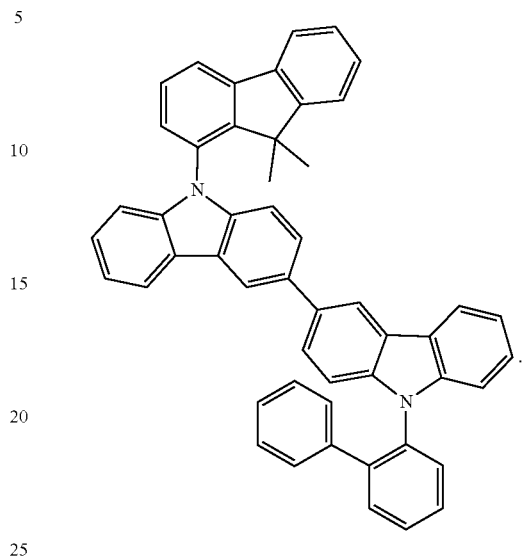
* * * * *